(12) United States Patent
Timms

(10) Patent No.: US 11,154,703 B2
(45) Date of Patent: Oct. 26, 2021

(54) HEART PUMP

(71) Applicant: BiVACOR Inc., Houston, TX (US)

(72) Inventor: Daniel Timms, Long Beach, CA (US)

(73) Assignee: BiVACOR Inc., Houston, TX (US)

( * ) Notice: Subject to any disclaimer, the term of this patent is extended or adjusted under 35 U.S.C. 154(b) by 0 days.

(21) Appl. No.: 16/709,458

(22) Filed: Dec. 10, 2019

(65) Prior Publication Data

US 2020/0222604 A1 Jul. 16, 2020

Related U.S. Application Data

(63) Continuation of application No. 16/028,945, filed on Jul. 6, 2018, now Pat. No. 10,543,301, which is a
(Continued)

(51) Int. Cl.
*A61M 60/82* (2021.01)
*A61M 60/205* (2021.01)
(Continued)

(52) U.S. Cl.
CPC .......... *A61M 60/82* (2021.01); *A61M 60/122* (2021.01); *A61M 60/148* (2021.01); *A61M 60/205* (2021.01); *A61M 60/419* (2021.01); *A61M 60/422* (2021.01); *A61M 60/50* (2021.01); *F04D 1/00* (2013.01);
(Continued)

(58) Field of Classification Search
CPC ...... A61M 1/101; A61M 1/1015; A61M 1/12; A61M 1/1031; A61M 1/1008; A61M 1/1036; A61M 1/1086; A61M 1/122; A61M 1/1017; A61M 2206/14; A61M 2206/20; A61M 2230/30; A61M 2206/04; A61M 2205/3334; A61M 2205/3365; F04D 1/00;
(Continued)

(56) References Cited

U.S. PATENT DOCUMENTS 2,700,343 A 1/1955 Pezzillo, Jr.
4,135,253 A 1/1979 Reich et al.
(Continued)

FOREIGN PATENT DOCUMENTS

CA 2638958 C 11/2011
CN 101873870 A 10/2010
(Continued)

OTHER PUBLICATIONS

Amano, et al., An ultrasonic actuator with multi-degree of freedom using bending and longitudinal vibrations of a single stator; IEEE Ultrason. Symp. Proc.; pp. 667-670; 1998.
(Continued)

*Primary Examiner* — Charles G Freay
(74) *Attorney, Agent, or Firm* — Goodwin Procter LLP

(57) ABSTRACT

A heart pump including: a housing forming a cavity including: at least one inlet aligned with an axis of the cavity; and, at least one outlet provided in a circumferential outer wall of the cavity; an impeller provided within the cavity, the impeller including vanes for urging fluid from the inlet to the outlet; and, a drive for rotating the impeller in the cavity and wherein a flow path through the pump has a minimal cross-sectional area of at least 50 mm².

14 Claims, 69 Drawing Sheets

Related U.S. Application Data continuation of application No. PCT/US2017/012503, filed on Jan. 6, 2017.

(60) Provisional application No. 62/275,754, filed on Jan. 6, 2016, provisional application No. 62/275,723, filed on Jan. 6, 2016, provisional application No. 62/275,744, filed on Jan. 6, 2016.

(51) Int. Cl.

| | |
|---|---|
| *F04D 29/048* | (2006.01) |
| *A61M 60/50* | (2021.01) |
| *A61M 60/122* | (2021.01) |
| *A61M 60/148* | (2021.01) |
| *A61M 60/419* | (2021.01) |
| *A61M 60/422* | (2021.01) |
| *F04D 1/00* | (2006.01) |
| *F04D 29/24* | (2006.01) |
| *F04D 29/42* | (2006.01) |

(52) U.S. Cl.
CPC ......... *F04D 29/048* (2013.01); *F04D 29/242* (2013.01); *F04D 29/4293* (2013.01); *A61M 2205/3334* (2013.01); *A61M 2205/3365* (2013.01); *A61M 2206/14* (2013.01); *A61M 2206/20* (2013.01); *A61M 2230/04* (2013.01); *A61M 2230/30* (2013.01)

(58) Field of Classification Search
CPC .. F04D 29/048; F04D 29/242; F04D 29/4293; A61F 2/24
See application file for complete search history.

(56) References Cited

U.S. PATENT DOCUMENTS

| | | | |
|---|---|---|---|
| 4,589,822 A | 5/1986 | Clausen et al. | |
| 5,041,934 A | 8/1991 | Stefansky | |
| 5,195,877 A | 3/1993 | Kletschka | |
| 5,290,227 A * | 3/1994 | Pasque | A61M 1/1081 417/356 |
| 5,306,295 A * | 4/1994 | Kolff | A61M 1/106 417/412 |
| 5,405,251 A * | 4/1995 | Sipin | F04D 13/0666 415/146 |
| 5,601,418 A | 2/1997 | Ohara et al. | |
| 5,613,935 A | 3/1997 | Jarvik | |
| 5,725,357 A | 3/1998 | Nakazeki et al. | |
| 5,840,070 A | 11/1998 | Wampler | |
| 5,851,174 A | 12/1998 | Jarvik et al. | |
| 5,890,883 A | 4/1999 | Golding et al. | |
| 5,928,131 A | 7/1999 | Prem | |
| 5,971,023 A | 10/1999 | Clague et al. | |
| 6,017,093 A | 1/2000 | Moser | |
| 6,017,903 A | 1/2000 | Slusher et al. | |
| 6,030,188 A * | 2/2000 | Nojiri | F16C 32/044 415/900 |
| 6,048,363 A | 4/2000 | Nagyszalanczy et al. | |
| 6,179,773 B1 | 1/2001 | Prem et al. | |
| 6,220,832 B1 | 4/2001 | Schob | |
| 6,227,797 B1 | 5/2001 | Watterson et al. | |
| 6,234,772 B1 | 5/2001 | Wampler et al. | |
| 6,264,635 B1 | 7/2001 | Wampler et al. | |
| 6,293,901 B1 | 9/2001 | Prem | |
| 6,312,443 B1 | 11/2001 | Stone | |
| 6,351,048 B1 | 2/2002 | Schob et al. | |
| 6,394,769 B1 | 5/2002 | Bearnson et al. | |
| 6,422,838 B1 * | 7/2002 | Sloteman | F04D 13/0666 415/101 |
| 6,527,698 B1 | 3/2003 | Kung et al. | |
| 6,547,530 B2 | 4/2003 | Ozaki et al. | |
| 6,575,717 B2 | 6/2003 | Ozaki et al. | |
| 6,589,030 B2 | 7/2003 | Ozaki | |
| 6,626,644 B2 | 9/2003 | Ozaki | |
| 6,638,011 B2 | 10/2003 | Woodard et al. | |
| 6,664,714 B2 | 12/2003 | Magnussen et al. | |
| 6,688,861 B2 * | 2/2004 | Wampler | H02K 41/03 417/423.7 |
| 6,690,101 B2 | 2/2004 | Magnussen et al. | |
| 6,717,311 B2 | 4/2004 | Locke | |
| 6,790,171 B1 | 9/2004 | Grundeman et al. | |
| 6,866,625 B1 | 3/2005 | Ayre et al. | |
| 6,870,304 B2 | 3/2005 | Magnussen et al. | |
| 7,229,474 B2 | 6/2007 | Hoffmann et al. | |
| 7,274,131 B2 | 9/2007 | Li et al. | |
| 7,435,059 B2 | 10/2008 | Smith et al. | |
| 7,439,652 B2 | 10/2008 | Ganor et al. | |
| 7,462,019 B1 | 12/2008 | Allarie et al. | |
| 7,476,077 B2 | 1/2009 | Woodard et al. | |
| 7,645,225 B2 | 1/2010 | Medvedev et al. | |
| 7,704,054 B2 * | 4/2010 | Horvath | F04D 29/042 417/213 |
| 7,914,436 B1 | 3/2011 | Kung | |
| 7,931,581 B2 | 4/2011 | Cohn | |
| 8,110,967 B2 | 2/2012 | Ting et al. | |
| 8,210,829 B2 | 7/2012 | Horvath et al. | |
| 8,226,373 B2 | 7/2012 | Yaegashi | |
| 8,506,471 B2 | 8/2013 | Bourque | |
| 8,551,163 B2 | 10/2013 | Aber et al. | |
| 8,613,696 B2 | 12/2013 | Medvedev et al. | |
| 8,632,449 B2 * | 1/2014 | Masuzawa | A61M 1/1086 600/17 |
| 8,636,638 B2 | 1/2014 | Timms | |
| 8,747,293 B2 | 6/2014 | Arndt et al. | |
| 8,834,345 B2 | 9/2014 | Yanai et al. | |
| 8,961,388 B2 | 2/2015 | Bourque | |
| 9,011,312 B2 | 4/2015 | Bourque | |
| 9,095,428 B2 | 8/2015 | Kabir et al. | |
| 9,371,826 B2 | 6/2016 | Yanai et al. | |
| 9,427,508 B2 | 8/2016 | Reyes et al. | |
| 9,433,717 B2 | 9/2016 | Bourque | |
| 9,492,601 B2 | 11/2016 | Casas et al. | |
| 9,511,179 B2 | 12/2016 | Casas et al. | |
| 9,512,852 B2 | 12/2016 | Wampler et al. | |
| 9,709,061 B2 | 7/2017 | Yanai et al. | |
| 9,801,988 B2 | 10/2017 | Bourque | |
| 9,901,666 B2 | 2/2018 | Cotter | |
| 10,077,777 B2 | 9/2018 | Horvath et al. | |
| 10,086,122 B2 | 10/2018 | Bourque | |
| 10,371,152 B2 * | 8/2019 | Yanai | A61M 1/1015 |
| 10,543,301 B2 * | 1/2020 | Timms | A61F 2/24 |
| 2002/0094281 A1 | 7/2002 | Khanwilkar et al. | |
| 2002/0109621 A1 | 8/2002 | Khair et al. | |
| 2003/0023131 A1 | 1/2003 | Antaki | |
| 2004/0267344 A1 | 12/2004 | Stett et al. | |
| 2005/0214131 A1 | 9/2005 | Miles et al. | |
| 2007/0249888 A1 | 10/2007 | Wu et al. | |
| 2007/0253842 A1 | 11/2007 | Horvath et al. | |
| 2010/0168848 A1 | 7/2010 | Horvath et al. | |
| 2011/0118537 A1 | 5/2011 | Wampler | |
| 2011/0118619 A1 | 5/2011 | Burton et al. | |
| 2011/0148253 A1 | 6/2011 | Friend et al. | |
| 2012/0245680 A1 | 9/2012 | Masuzawa et al. | |
| 2012/0253103 A1 | 10/2012 | Robert | |
| 2012/0289897 A1 | 11/2012 | Friend et al. | |
| 2014/0100413 A1 | 4/2014 | Casas et al. | |
| 2017/0340788 A1 | 11/2017 | Korakianitis et al. | |
| 2018/0185567 A1 | 7/2018 | Madhani et al. | |

FOREIGN PATENT DOCUMENTS

| | | |
|---|---|---|
| CN | 102458498 B | 6/2015 |
| CN | 102711862 B | 12/2015 |
| EP | 1065383 A1 | 1/2001 |
| EP | 1188453 A1 | 3/2002 |
| EP | 1273096 B1 | 11/2005 |
| EP | 1630897 A1 | 3/2006 |
| EP | 1674119 A1 | 6/2006 |
| EP | 1495773 A3 | 11/2006 |
| EP | 1721346 B1 | 10/2007 |
| EP | 2538086 A4 | 4/2015 |
| JP | 7255834 | 10/1995 |

(56) References Cited

FOREIGN PATENT DOCUMENTS

| | | |
|---|---|---|
| JP | 2001061957 A | 3/2001 |
| JP | 2001-224568 A | 8/2001 |
| JP | 2003-230547 A | 8/2003 |
| JP | 2004-61251 A | 2/2004 |
| JP | 2005-282675 A | 10/2005 |
| JP | 3930834 B2 | 6/2007 |
| JP | 2009-011767 A | 1/2009 |
| WO | WO-00/32256 A1 | 6/2000 |
| WO | WO-00/32257 A1 | 6/2000 |
| WO | WO-2002-053028 A8 | 12/2002 |
| WO | WO-2004-032738 A1 | 4/2004 |
| WO | WO-2004-043252 A1 | 5/2004 |
| WO | WO-2004-047636 A1 | 6/2004 |
| WO | WO-2004/098677 A1 | 11/2004 |
| WO | WO-2004-098389 A3 | 3/2005 |
| WO | WO-2006-053384 A1 | 5/2006 |
| WO | WO-2007-056493 A1 | 5/2007 |
| WO | WO-2007/084339 A3 | 1/2008 |
| WO | WO-2009/058726 A1 | 5/2009 |
| WO | WO-2010/118475 A1 | 10/2010 |
| WO | WO-2010-118476 A1 | 10/2010 |
| WO | WO-2011-026187 A1 | 3/2011 |
| WO | WO-2011-054545 A1 | 5/2011 |
| WO | WO-2013-033783 A1 | 3/2013 |
| WO | WO-2017-120453 A1 | 7/2017 |
| WO | WO-2017-120451 A3 | 8/2017 |
| WO | WO-2017/120449 A3 | 11/2017 |

OTHER PUBLICATIONS

Gaddum, Nicholas Richard, "Passive Control of a Bi-Ventricular Assist Device: An experimental and Numerical Investigation", (Thesis), Queensland University of Technology 2008, Ch. 3, sections 3.4.3.1, 3.4.3.4, 3.6 to 3.7 & Figs. 3-12 to 3-14, 3-16, 3-18, 3-23, 3-25 to 3-27, 3-35 to 3-36; Ch. 8, section 8.2.1.

Gouda et al.; A miniaturization of the multi-degree-of-freedom ultrasonic actuator using a small cylinder fixed on a substrate; Ultrasonics; 44 supp. 1; pp. e617-e620; Dec. 22, 2006.

Greatrex N. et al. 'Axial magnetic bearing . . . ', 2010, IEEE Transactions in Biomedical Eng', vol. 57(3), pp. 714-721.

Kanda et al. A micro ultrasonic motor using a micro-machined cylindrical bulk PZT transducer; Sensors and Actuators; 127; pp. 131-138; Dec. 19, 2009.

Kawano et al.; Application of a multi-DOF ultrasonic servomotor in an auditory tele-existence robot; IEEE Trans. Robotics; 21 (5); pp. 790-800; Oct. 2005.

Khoo et al.; Triple degree-of-freedom piezoelectric micromotor via flexural-axial coupled vibration; IEEE Transactions on ultrasonics, Ferroelectrics, and Frequency Control; 56(8); pp. 1716-1724; Aug. 2009.

Maslen E. et cl. 'Feedback Control Applications in Artificial Hearts . . .' 1998 IEEE Control Systems Mag, vol. 18(6), pp. 26-34.

Masuzawa T. et al., 'Magnetically Suspended Centrifugal . . . ' 2002, ASAIO Journal, pp. 437-442.

Masuzawa, T., H. Onuma, and Y. Okada, "Zero Power Control for Magnetically Suspended Artificial Heart." Jido Seigyo Rengo Koenkai Koen Ronbunshu, 2004. 47: p. 322.

Masuzawa, Toru et al., "An Ultradurable and Compact Rotary Blood Pump with a Magnetically Suspended Impeller in the Radial Direction", Artificial Organs, vol. 25, Issue 5, 2001, pp. 395-399, Abstract; Suspension system (pp. 396-397); Discussion (p. 398); Figs. 1-6.

Masuzawa, Toru et al., "Magnetically Suspended Centrifugal Blood Pump with an Axially Levitated Motor", Artificial Organs, vol. 27, Issue 7, 2003, pp. 631-638 Abstract; axially levitated motor (pp. 632-633); Motor design and experimental set-up (pp. 633-634); levitation performance (pp. 634-635); Discussion (pp. 636-638); Figs. 1, 3-5, 8 and 13.

Masuzawa, Toru et al., "Magnetically Suspended Rotary Blood Pump with Radial Type Combined Motor-Bearing", Artificial Organs, vol. 24, Issue 6, 2000, pp. 468-474, Abstract; Suspension control (pp. 468-469); Prototype of the magnetically suspended centrifugal pump (pp. 469-470); Discussion (p. 471); Figs. 1-6.

Morita, et al.; A cylindrical micro ultrasonic motor using PZT thin film deposited by single process hydrothermal method (Ø2.4 mm, L=10 mm stator transducer); IEEE Trans. Ferroelectr. Freq. Contrl; 45(5); pp. 1178-1187; Sep. 1998.

Niwano, et al.; An active dummy head driven by a multi-degree-of-freedom ultrasonic actuator; WCU Conf. Proc. 1597; 2003.

Park, et al.; Study on multi-DOF ultrasonic actuator for laparoscopic instrument; JSME int. J.; 47(2); pp. 574-581; 2004.

Rogers; A diameter 300 μm bragg reflector for acoustic isolation of resonant micro-actuators; J. Micromech. Microeng. 21 (4 ); pp. 1-4; Apr. 2011.

Rogers; Piezoelectric ultrasonic micro-motor system for minimally invasive surgery—the intellimotor; AIP Conf. Proc. 1433 pp. 705-708; 2012.

Rogers; Three degree-of-freedom piezoelectric ultrasonic micro-motor with a major diameter of 350 μm; J. Micromech. Microeng. ;20(12); pp. 1-5; Dec. 2010.

Satoshi Ueno et al., "Characteristics of axial force and rotating torque and their control of permanent magnet type axial gap self-bearing motor", Electrical Engineering in Japan, vol. 132, Issue 1, 2000, pp. 81-91 (whole document).

Sin, D.C et al., "Blood flow in a double output centrifugal artificial heart pump as a biventricular assist device", ANZIAM J. 48 (CTAC2006), Feb. 27, 2008, pp. C949-C962, Materials and Method section (pp. C952-C955); Figures 2-4.

Takemura et al.; Characterstics of an ultrasonic motor capable of generating a multi-degrees of freedom motion; Proc. IEEE int. Conf, on Robotics and Automation; vol. 4; pp. 3660-3665; Apr. 2000.

Takemura et al.; Control of multi-dof ultrasonic actuator for dexterous surgical instrument; Journal of Sound and Vibration; 311; pp. 652-666; Nov. 26, 2007.

Timms, D.L., "Design, Development and Evaluation of Centrifugal Type Ventricular Assist Devices", (Thesis), Queensland University of Technology, 2005 Ch. 4, sections 4.4.4-3 BiLVAD and 4.4.4 Bi-VAD & Figure 4-20 to 4-21; Ch. 5—VAD Experimental Evaluation; Ch. 6, VAD Summary & Figures 6-1 to 6-8.

Wajchman et al.; An ultrasonic piezoelectric motor utilizing axial-torsional coupling in a pretwisted non-circular cross-sectioned primatic beam; IEEE Transactions of Ultrasonics, Ferroelectrics, and Frequency Control; 55(4); pp. 832-840; Apr. 2008.

Watson Peizoelectric ultrasonic micro/milli-scale actuators; Sensors Actuators; 152; pp. 219-233; Apr. 2, 2009.

Sonune, et al,, "Performance Investigation of Centrifugal Pump By Varying Blade Angles of the Impeller-A" IJCET INPRESSO Special Issue—7 (Mar. 2017), pp. 399-401.

"Blade Design", Design of Hydraulic components, pp. 352-357.

Gulich, Centrifugal pumps 2nd Ed (2010), pp. 352-357.

\* cited by examiner

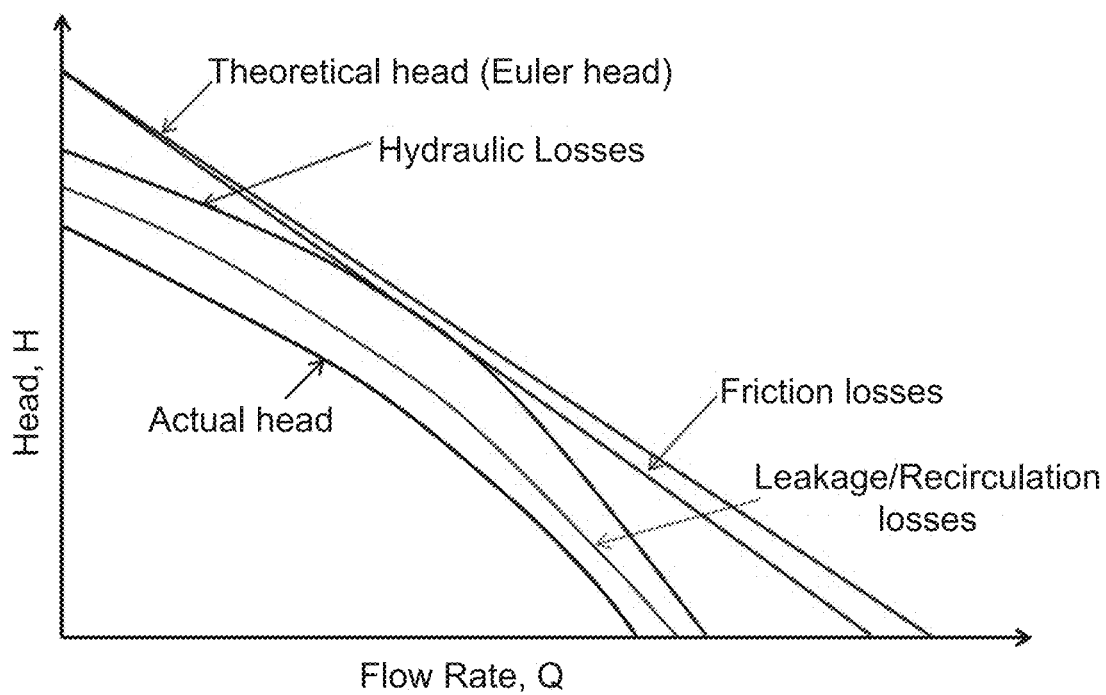
Fig. 4C
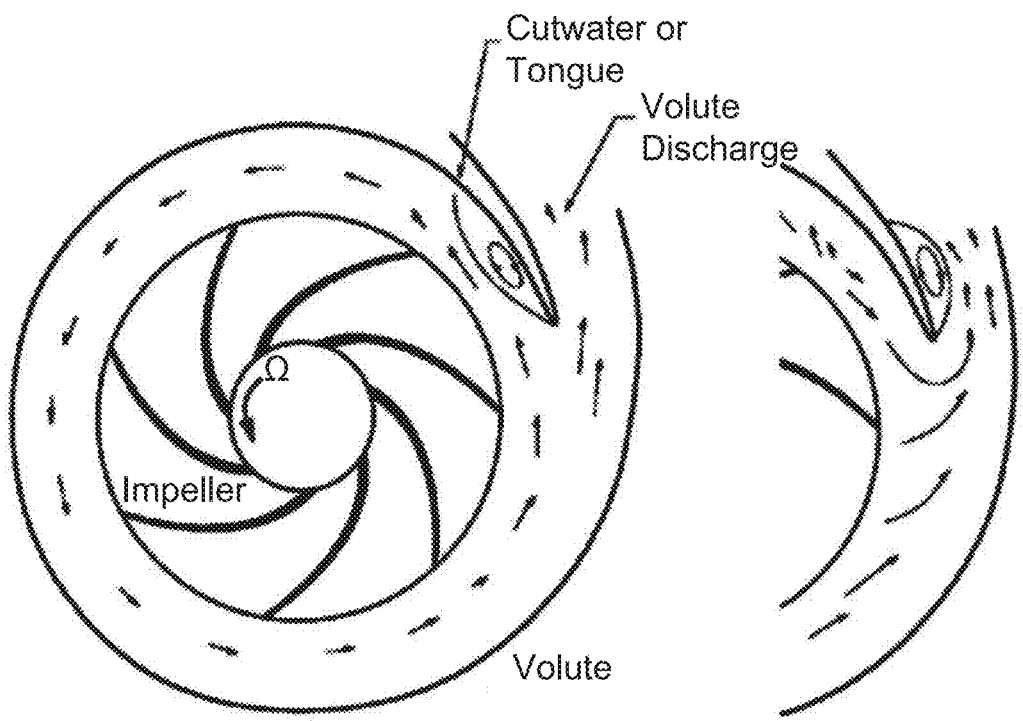
Fig. 4D      Fig. 4E

→(LV1452)　→(LV1454)　→(LV1526)　→(LV1528)
→(LV1535)　—(LV1538)　—(LV1542)　—(LV1544)
→BIVACOR V1 →(LV1453)　—(LV1525)　—(LV1527)
—(LV1534)　→(LV1536)　—(LV1541)　—(LV1543)
—(LV1532)

—(LV1452)　—(LV1454)　—(LV1428)
→(LV1534)　—(LV1536)　—(LV1540)
→(LV1542)　　(LV1544)
—(LV1453)　→(LV1427)　—(LV1452)
→(LV1535)　—(LV1538)　→(LV1541)
→(LV1543)　—(LV1545)

HEART PUMP

RELATED APPLICATIONS

This application claims the benefit of priority under 35 U.S.C. § 120 to U.S. patent application Ser. No. 16/028,945 entitled "Heart Pump," filed on Jul. 6, 2018 which claims the benefit of priority under 35 U.S.C. § 120 to International Patent Application No. PCT/US2017/012503 entitled "Heart Pump," filed on Jan. 6, 2017 which claims priority under 35 U.S.C. § 119 to U.S. Provisional Patent Application No. 62/275,754 entitled "Heart Pump," filed on Jan. 6, 2016; U.S. Provisional Patent Application No. 62/275,723 entitled "Heart Pump Impeller Rotational Speed Control," filed on Jan. 6, 2016; and U.S. Provisional Patent Application No. 62/275,744 entitled "Heart Pump With Impeller Axial Position Control," filed on Jan. 6, 2016, the contents of all of which are incorporated herein by reference in their entireties.

BACKGROUND OF THE INVENTION

The present invention relates to a heart pump and in particular to a heart pump including improved flow characteristics.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

The use of rotary impeller based mechanical pumps to treat heart failure is increasing as the general population ages and the number of donor organs for heart transplantation remains limited. Devices can be used to bridge a patient to heart transplant, to recovery, or indeed as a destination alternative. They can be configured to assist the heart in its function, or replace it entirely.

WO2004098677 and WO2006053384A1 each describe a double sided impeller that rotates at a common speed, with each side of the impeller respectively configured for left and right heart support. This effectively introduces an inherent problem regarding the ability to independently control and thus balance the outflow from the left and right sides of the device, i.e. an increase in impeller rotational speed with produce a corresponding increase in outflow from both cavities.

WO2006053384A1 addressed this issue by introducing the ability to axially displace the rotating impeller within the cavity so as to simultaneously alter the relative efficiencies of each side of the device. However, when the control method used to achieve this axial displacement is active, such pumps require the use of feedback signals from pressure sensors and the like to actively control and maintain a desired set axial location. This method of control would inherently consume excessive amounts of electrical power and introduce issues relating to the long term reliability of blood contacting sensors.

U.S. Pat. No. 8,636,638 describes a controller for a heart pump that determines movement of an impeller within a cavity in a first axial direction, the cavity including at least one inlet and at least one outlet, and the impeller including vanes for urging fluid from the inlet to the outlet, causing a magnetic bearing to move the impeller in a second axial direction opposite the first axial direction, the magnetic bearing including at least one coil for controlling an axial position of the impeller within the cavity, determining an indicator indicative of the power used by the magnetic bearing and causing the magnetic bearing to control the axial position of the impeller in accordance with the indicator to thereby control a fluid flow between the inlet and the outlet.

U.S. Pat. No. 7,435,059 describes a system for pumping blood to assist or assume the cardiac function of a patient is characterized by a blood pump that exhibits a steep pump curve such that only small changes in pump flow occur for large changes in differential pressure across the pump. The pump therefore exhibits flow-limiting characteristics to protect the physiological system against harmful flow rates. Pump flow may also be limited by controlling the current provided to a driver from a power supply or by suitable restrictions within or external to the pump housing.

The natural heart continuously balances systemic and pulmonary flow through ventricular interdependence and the Frank-Starling mechanism. This mechanism relates directly to the pressure sensitivity of the heart, and is an important feature to enable the heart to balance left and right blood flow and thus pressure in the face of alterations in patient state, such as postural changes, coughing, straining/Valsalva and transitions to exercise. It also effectively accommodates for the natural flow imbalance created by the bronchial circulation, which shunts blood from the aorta back to the pulmonary venous network. When the heart fails, the Frank-Starling mechanism and thus this pressure sensitivity is compromised.

Mechanical circulatory support is an effective means to restore blood flow to the circulatory system in the case of a failing heart, however current blood pumps do not exhibit the same pressure sensitivity as the native or even failing heart. This support can be in the form of a ventricular assistance device (VAD), whereby the device assist the function of one or more of the failing ventricles, or complete replacement of the ventricles with a total artificial heart (TAH).

Reduced pressure sensitivity results in the potential for flow and thus pressure imbalance in the systemic and pulmonary circulations. High inflow (venous) pressures caused by a hypo functioning side of the heart/device can result in the accumulation of fluid in interstitial spaces (oedema). Should this occur in the pulmonary venous network, efficient gas exchange in the lungs may be impacted. When it occurs in the systemic venous network, liver and kidney failure can result.

Low inflow (venous) pressures resulting from a hyper functioning side of the heart/device can lead to vessel wall collapse, leading to an increase in resistance for blood to enter the device, and ultimately a reduction or indeed cessation of forward flow from the device. Conversely, a hyper functioning pump may also raise arterial pressure to levels that may predispose the patient to haemorrhagic stroke or other hypertensive related complications.

In the case of single ventricular assistance (VAD), usually left sided (LVAD), the native ventricles remains with varying degree of Frank-Starling mechanism intact and thus varying degrees of pressure sensitivity remain in the left and right ventricle, from normal to compromised. A normal right heart can assist with flow balance, however a more pressure sensitive left device assisting the left heart will result in greater changes in device outflow for changes in patient state, and thus both a higher sustained cardiac output during exercise and faster return to flow balance, mitigating the requirement for changes in device rotational speed.

In instances whereby the two failing ventricles are completely removed for the implantation of a total artificial heart (TAH), the device itself must reproduce the Frank-Starling mechanism and thus pressure sensitivity and ultimately correct imbalances in flow.

Traditional wisdom has been to produce a pump that has optimum operating efficiency at a typical flow rate for a subject, which typically corresponds to a flow rate of about five to six litres per minute, thereby minimising the power consumed by the pump. Additionally, it is typical to design pumps having a relatively low flow sensitivity to preload, as described for example in U.S. Pat. No. 7,435,059, so that the pump exhibits flow-limiting characteristics to protect the physiological system against harmful flow rates or pressures.

Such configurations result in a heart pump having a steep pump curve which is a plot of the flow rate against head pressure across the pump (the difference between the inlet and outlet pressures), for a given impeller rotational speed. This shows that a large change in pressures is required in order to cause a change in flow rate through the pump thereby providing the aforementioned flow-limiting characteristics.

In such an arrangement, it may be necessary to vary the rotational speed of the impeller to thereby control pump outflow, in order to account for changes in pressures within the subject's circulatory system. However, such control systems may require information regarding the physiological state of the subject, such as blood pressures or flow rates, in order to function correctly. This requires the use of complex sensing techniques and/or implanted sensors, which are undesirable, and in many cases makes assumptions regarding at least some parameters, such as blood viscosity, meaning they can be inaccurate. As a result, many existing heart pumps have only a limited ability to accommodate physiological changes, meaning the subjects are often restricted in terms of activities they are able to perform.

Flow path areas tend to influence the resistance of fluid to flow through the pump and thus outflow pressure sensitivity, with larger areas generally considered to create flatter pump curves.

However larger areas also tend to assist with device biocompatibility. Larger areas between the rotating impeller and the stationary casing result in lower shear stresses levels in this region and thus reduced red blood cell lysis (haemolysis). However larger flow path areas are also suggested to reduce the incidence of vonWillebrand factor (vWF) degradation. Degradation of this molecule can lead to impaired ability for blood to clot, thus raising the risk of bleeding complications.

Finally, another major complication with currently implanted rotary blood pumps is device failure due to pump thrombosis. A clot either formed in low flow regions within the device, or formed in the circulatory system and ingested into the device, may lodge in the impeller blades or small clearances around the rotating impeller, causing the device to stop. These small clearances are often found at the site of a contact bearing or hydrodynamic bearing. Thus, selecting impeller blades that have large separations between them, and implementing a maglev system that widens the surrounding clearances, may reduce the incidence of pump thrombosis. This has particular relevance to the right circulation, whereby emboli originating from the deep veins may enter into the right sided impeller. Hence large clearances and large flow paths may assist in allowing such emboli to pass unimpeded through the device, to be filtered by the small capillaries in the pulmonary network.

SUMMARY OF THE PRESENT INVENTION

In one broad form an aspect of the present invention seeks to provide a heart pump including: a housing forming a cavity including: at least one inlet aligned with an axis of the cavity; and, at least one outlet provided in a circumferential outer wall of the cavity; an impeller provided within the cavity, the impeller including vanes for urging fluid from the inlet to the outlet; and, a drive for rotating the impeller in the cavity and wherein a flow path through the pump has a minimal cross-sectional area of at least 50 mm$^2$.

In one embodiment a flow path through the heart pump has a cross-sectional area throughout the entire pump that is at least one of: at least 75 mm$^2$; at least 100 mm$^2$; at least 125 mm$^2$; at least 140 mm$^2$; at least 150 mm$^2$; at least 200 mm$^2$; and, up to 300 mm$^2$.

In one embodiment the pump has a performance curve having a gradient of less than −20% over a defined flow range such that a change in pressure of 10 mmHg across the pump causes a change in flow rate of at least 2 LPM, the defined flow range being between at least one of 5 LPM to 8 LPM; 3 LPM to 12 LPM; and, 3 LPM to 15 LPM.

In one embodiment the pump generates a pressure head that is at least one of: for a pump that provides at least partial left ventricular function: between 60 mmHg and 100 mmHg at 6 LPM; between 70 mmHg and 90 mmHg at 6 LPM; and, approximately 80 mmHg at 6 LPM; and, for a pump that provides at least partial right ventricular function: between 10 mmHg and 30 mmHg at 6 LPM; between 15 mmHg and 25 mmHg at 6 LPM; and, approximately 20 mmHg at 6 LPM.

In one embodiment the heart pump provides at least partial left ventricular function.

In one embodiment the heart pump has a pump performance curve having a gradient less than at least one of: −25%; −30%; −35%; −40%; −100% −200%; and, −500%.

In one embodiment an axial position of the impeller within the cavity controls in part a flow of fluid from the inlet to the outlet, and wherein a change in axial position of 200 μm causes at least one of: a change in flow rate of at least one of: at least 1 LPM; at least 2 LPM; less than 4 LPM; and, between 2 LPM and 3 LPM; and, a change in flow pressure of at least one of: at least 5 mmHg; at least 10 mmHg; at least 15 mmHg; at least 20 mmHg; at least 25 mmHg; at least 30 mmHg; at least 35 mmHg; and, at least 40 mmHg.

In one embodiment the outlet at least one of: has a throat area of at least one of: at least 60 mm$^2$; at least 80 mm$^2$; at least 120 mm$^2$; between 60 mm$^2$ and 250 mm$^2$; between 120 mm$^2$ and 160 mm$^2$; between 140 mm$^2$ and 160 mm$^2$; between 140 mm$^2$ and 250 mm$^2$; between 130 mm$^2$ and 150 mm$^2$; approximately 140 mm$^2$; and, approximately 150 mm$^2$; has a substantially rectangular cross-sectional shape and a width to height aspect ratio of at least one of: between 1:2 and 2:1; between 1:1 and 2:1; between 1:1 and 1.8:1; between 1.1:1 and 1.6:1; and, approximately 1.4:1; and, defines a cutwater angle of at least one of: between 0° and 70°; between 30° and 50°; between 40° and 45°; between 35° and 45°; between 45° and 50°; between 0° and 60°; and approximately 45°.

In one embodiment the impeller has at least one of: a vane height of at least one of: at least 1.5 mm; less than 5 mm; between 1.5 mm and 3 mm; between 1.7 mm and 2.3 mm; between 1.8 mm and 2.2 mm; and, between 1.9 mm and 2.1 mm; and, approximately 2 mm; and, a vane inlet angle of at least one of: less than 90°; greater than 60°; between 70° and 90°; between 82° and 86°; and, approximately 84°; and, a vane outlet angle of at least one of: less than 60°; greater than 20°; between 30° and 50°; between 35° and 45°; between 38° and 42°; and, approximately 40°.

In one embodiment the impeller includes at least one of: a number of primary vanes, the primary vanes having an inner diameter of at least one of: larger than a diameter of an inflow port; at least 10 mm; less than 40 mm; between 20 mm and 40 mm; between 25 mm and 35 mm; and, approximately 25-30 mm; a number of secondary vanes, the secondary vanes having an inner diameter of at least one of: at least 20 mm; less than 40 mm; between 30 mm and 40 mm; and, approximately 35 mm; and, an outer vane diameter of at least one of: at least 20 mm; less than 60 mm; between 45 mm and 55 mm; between 48 mm and 52 mm; and, approximately 50 mm.

In one embodiment the primary vanes having an outer thickness of at least one of: at least 5 mm; less than 20 mm; between 6 mm and 15 mm; between 7 mm and 8 mm; and, approximately 7.5 mm.

In one embodiment the impeller includes at least one of: an equal number of primary and secondary vanes; at least three primary and secondary vanes; less than six primary and secondary vanes; and, four primary and four secondary vanes.

In one embodiment in a region of an outlet volute the cavity has at least one of: a base circle diameter of at least one of: at least 40 mm; at least 50 mm; less than 100 mm; less than 80 mm; between 50 mm and 74 mm; between 54 mm and 64 mm; and, approximately 60 mm; and, an outer wall diameter of at least one of: at least 50 mm; less than 100 mm; less than 80 mm; between 50 mm and 80 mm; between 65 mm and 76 mm; and, approximately 71 mm.

In one embodiment the housing includes a split volute.

In one embodiment over the defined flow range the volute generates a maximum radial force of less than at least one of 1.2 N, 1.0 N and 0.85 N, and wherein the defined flow range is at least one of: 5 LPM to 8 LPM; 3 LPM to 12 LPM; and, 3 LPM to 15 LPM.

In one embodiment the heart pump provides at least partial right ventricular function.

In one embodiment the heart pump has a pump performance curve having a gradient less than at least one of: −30%; −35%; −40%; −75%; −100%; and, −150%.

In one embodiment an axial position of the impeller within the cavity controls in part a flow of fluid from the inlet to the outlet, and wherein a change in axial position of 200 µm causes at least one of: a change in flow rate of at least one of: at least 0.2 LPM; at least 0.5 LPM; less than 2 LPM; and, between 0.5 LPM and 1.5 LPM; and, a change in flow pressure of at least one of: at least 1 mmHg; at least 2 mmHg; at least 5 mmHg; and, at least 10 mmHg.

In one embodiment the outlet at least one of: has a throat area of at least one of: at least 100 mm$^2$; at least 130 mm$^2$; between 130 mm$^2$ and 250 mm$^2$; between 130 mm$^2$ and 230 mm$^2$; between 170 mm$^2$ and 210 mm$^2$; between 140 mm$^2$ and 200 mm$^2$; between 140 mm$^2$ and 210 mm$^2$; between 150 mm$^2$ and 200 mm$^2$. approximately 233 mm$^2$; approximately 175 mm$^2$; and, approximately 150 mm$^2$; has a substantially rectangular cross-sectional shape outlet and a width to height aspect ratio of at least one of: between 1:3 and 1:1; and, approximately 0.45-0.65:1; and, a width of between 8 mm and 12 mm; and, defines a cutwater angle that is at least one of: between 90° and 180°; between 90° and 135°; between 0° and 90°; between 45° and 90°; between 45° and 135°; between 60° and 80°; and approximately 70°.

In one embodiment the impeller has at least one of: a vane height of at least one of: at least 10 mm; less than 30 mm; between 10 mm and 25 mm; between 15 mm and 20 mm; between 17 mm and 18 mm; and, approximately 17.5 mm; a vane inlet angle of at least one of: greater than 60°; less than 115°; between 80° and 100°; and, approximately 90°; and, a vane outlet angle of at least one of: greater than 60°; less than 115°; between 80° and 100°; approximately 72° and, approximately 90°.

In one embodiment the impeller includes: a number of primary vanes, the primary vanes having an inner diameter of at least one of: at least 10 mm; less than 25 mm; between 10 mm and 20 mm; between 14 mm and 18 mm; and, 16 mm; a number of secondary vanes, the secondary vanes having an inner diameter of at least one of: at least 10 mm; less than 25 mm; between 15 mm and 25 mm; between 18 mm and 20 mm; and, approximately 19 mm; and, an outer vane diameter of at least one of: at least 15 mm; less than 40 mm; between 20 mm and 30 mm; between 22 mm and 27 mm; and, approximately 24 mm; and approximately 25 mm.

In one embodiment the primary vanes at least one of: have a thickness of at least one of: at least 0.5 mm; less than 3.0 mm; between 0.75 mm and 2.5 mm; and, 1.5 mm; and, have a filleted edge of between 0.25 mm and 1.14 mm.

In one embodiment the impeller includes at least one of: an equal number of primary and secondary vanes; between three and five primary vanes; four primary vanes; between three and six secondary vanes; four secondary vanes; and, four primary vanes and four secondary vanes.

In one embodiment the inlet has a diameter of at least one of: at least 10 mm; at least 15 mm; less than 30 mm; less than 25 mm; between 18 mm and 22 mm; and, approximately 19 mm to 20 mm.

In one embodiment the cavity has a diameter of a least one of: at least 20 mm; at least 25 mm; less than 40 mm; less than 30 mm; between 27 mm and 29 mm; and, approximately 28 mm.

In one embodiment the impeller includes a rotor having a height of at least one of: at least 5 mm; less than 15 mm; between 6 mm and 13 mm; and, between 8 mm and 11 mm; and, approximately 10 mm.

In one embodiment the rotor has an outer circumferential wall spaced from an inner cavity wall by at least one of: an average distance of at least 2 mm; an average distance of less than 8 mm; an average distance of less than 5 mm; and, an average distance of approximately 4 mm.

In one embodiment the impeller includes first and second sets of vanes provided on a rotor body, the rotor being positioned within the cavity to define: a first cavity portion having a first inlet and a first outlet, the first set of vanes being provided within the first cavity portion so as to define a first pump that provides at least partial left ventricular function; and, a second cavity portion having a second inlet and a second outlet, the second set of vanes being provided within the second cavity portion so as to define a second pump that provides at least partial right ventricular function.

In one embodiment the heart pump is a total artificial heart.

In one embodiment the axial position of the impeller determines a separation between each set of vanes and a respective housing surface, the separation being used to control the fluid flows from the inlets to the outlets.

In one embodiment the first and second pumps have respective pump performance curve having different gradients so that a change in rotational speed of the pump causes a change in the relative flows of the first and second pumps.

In one embodiment the first and second pumps have a design pressure ratio at 6 LPM of 3.5-4.5:1.

In one embodiment the first and second pumps have an axial pressure sensitivity of at least one of: at least 20 mmHg/mm; and, approximately 60 mmHg/mm.

In one embodiment the first and second pumps have a change in design pressure ratio at 6 LPM of 3.25-4.75:1.

In one embodiment the drive includes: a number of circumferentially spaced permanent magnets mounted in the rotor of the impeller, adjacent magnets having opposing polarities; and, at least one drive coil that in use generates a magnetic field that cooperates with the magnetic material allowing the impeller to be rotated.

In one embodiment the housing and impeller cooperate to provide a shunt flow path between the first and second cavity portions, the shunt flow path having a cross-sectional area that is at least one of: at least 15 mm$^2$; no greater than 50 mm$^2$; between 20-50 mm$^2$; and, approximately 25 mm$^2$.

In one embodiment the shunt flow path cross-sectional area is adjustable by controlling an axial position of the impeller within the cavity.

In one embodiment the pump includes a magnetic bearing for controlling an axial position of the impeller within the cavity.

In one embodiment the magnetic bearing includes: first and second annular magnetic bearing members mounted within and proximate a face of the rotor, the first magnetic bearing member being outwardly of the second magnetic bearing member; a number of circumferentially spaced substantially U-shaped bearing stators mounted in the housing proximate a second end of the cavity, each U-shaped bearing stator having first and second bearing stator legs substantially radially aligned with the first and second magnetic bearing members respectively; and, at least one bearing coil on each bearing stator that generates a magnetic field that cooperates with the magnetic bearing members to thereby at least one of: control an axial position of the impeller; and, at least partially restrain radial movement of the impeller.

In one embodiment the drive is positioned at a first end of the cavity and the magnetic bearing is positioned at a second end of the cavity.

In one broad form an aspect of the present invention seeks to provide a heart pump including: a housing forming a cavity including: a first cavity portion having a first inlet aligned with an axis of the first cavity portion and a first outlet provided in a circumferential outer wall of the first cavity portion; and, a second cavity portion having a second inlet aligned with an axis of the second cavity portion and a second outlet provided in a circumferential outer wall of the second cavity portion; and, an impeller provided within the cavity, the impeller including: a first set of vanes being provided within the first cavity portion so as to define a first pump that provides at least partial left ventricular function; and, a second set of vanes being provided within the second cavity portion so as to define a second pump that provides at least partial right ventricular function; and, a drive for rotating the impeller in the cavity and wherein the first and second pumps define a respective flow path through the pump, each flow path having a minimal cross-sectional area of at least 50 mm$^2$.

In one embodiment the first and second pumps have at least one of: a design pressure ratio at 6 LPM of 3.5-4.5:1; an axial pressure sensitivity of at least one of: at least 20 mmHg/mm; and, approximately 60 mmHg/mm.

In one broad form an aspect of the present invention seeks to provide a heart pump including: a housing forming a cavity including: at least one inlet aligned with an axis of the cavity; and, at least one outlet provided in a circumferential outer wall of the housing; an impeller provided within the cavity, the impeller including vanes for urging fluid from the inlet radially outwardly to the outlet; and, a drive for rotating the impeller in the cavity and wherein the pump includes at least one of: improved outflow pressure sensitivity (OPS); improved axial pressure sensitivity (APS); reduced radial hydraulic forces; emboli tolerance; and, improved passive flow balancing.

In one broad form an aspect of the present invention seeks to provide a heart pump including: a housing forming a cavity including: at least one inlet aligned with an axis of the cavity; and, at least one outlet provided in a circumferential outer wall of the cavity; an impeller provided within the cavity, the impeller including vanes for urging fluid from the inlet to the outlet; and, a drive for rotating the impeller in the cavity and wherein the pump has a performance curve having a gradient of less than −20% over a defined flow range such that a change in pressure of 10 mmHg across the pump causes a change in flow rate of at least 2 LPM, the defined flow range being between at least one of 5 LPM to 8 LPM; 3 LPM to 12 LPM; and, 3 LPM to 15 LPM.

In one broad form an aspect of the present invention seeks to provide a method of operating a biventricular heart pump during implantation, the method including: connecting the heart pump to the pulmonary and systemic circulatory systems; blocking a left pump outflow to the system circulatory system; operating the pump so that blood flow recirculates through the lungs with blood flow received from the lungs via a left pump inlet being shunted to a right pump via a left/right shunt flow path so that blood is supplied to the lungs via a right pump outlet; once the lungs are perfused, unblocking the left pump outflow so that blood flows through the pulmonary and systemic circulatory systems.

In one embodiment the method includes: initially operating the pump at at least one of: a rotational speed of between 1000 RPM and 1250 RPM; and, a blood flow rate though the lungs is approximately 0.5 LPM; and, increasing the rotational speed of the pump until at least one of: the rotational speed is approximately 1800 RPM; and, the blood flow rate though the lungs increases to approximately 1.5-2 LPM.

In one embodiment the method includes: pumping blood through the lungs until at least one of: for between 5 minutes and 10 minutes; and, until lung resistance reduces; and, unblocking the left pump outflow to the system circulatory system.

It will be appreciated that the broad forms of the invention and their respective features can be used in conjunction and/or independently, and reference to separate broad forms in not intended to be limiting.

BRIEF DESCRIPTION OF THE DRAWINGS

Various examples and embodiments of the present invention will now be described with reference to the accompanying drawings, in which:—

FIG. 4C is a graph showing an example of factors contributing to a pump curve;

FIG. 4D is a schematic diagram of an example of blood recirculation at a pump outlet;

FIG. 4E is a schematic diagram of an example of the effect of angle of incidence on blood flow through a pump outlet;

FIG. 6ZA is a graph showing an example of left pump axial sensitivity for different impeller vane configurations;

FIG. 6ZB is a graph showing an example of left pump curve for example thrust bearing configurations;

FIG. 6ZC is a graph showing an example of left pump pressure displacement for different impeller vane configurations;

FIG. 11H is a graph illustrating a pump curve for the impeller configuration of FIG. 11G;

FIG. 11I is a schematic plan view of a fifth specific example impeller configuration;

FIG. 11J is a graph illustrating a pump curve for the impeller configuration of FIG. 11I;

FIG. 11K is a schematic plan view of a sixth specific example impeller configuration;

FIG. 11L is a graph illustrating a pump curve for the impeller configuration of FIG. 11K;

FIG. 12A is a schematic perspective view of an example of a single VAD heart pump;

FIG. 12B is a schematic cutaway side view of the heart pump of FIG. 12A;

FIG. 12C is a schematic cutaway plan view of the heart pump of FIG. 12A;

FIG. 12D is a schematic perspective view of the impeller of the heart pump of FIG. 12A;

FIG. 12E is a schematic perspective view of the magnetic bearing of the heart pump of FIG. 12A;

FIG. 12F is a schematic cutaway perspective view of the impeller of FIG. 12A;

FIG. 13A is a graph illustrating changes in drive speed during an implantation process;

Figure 13A:
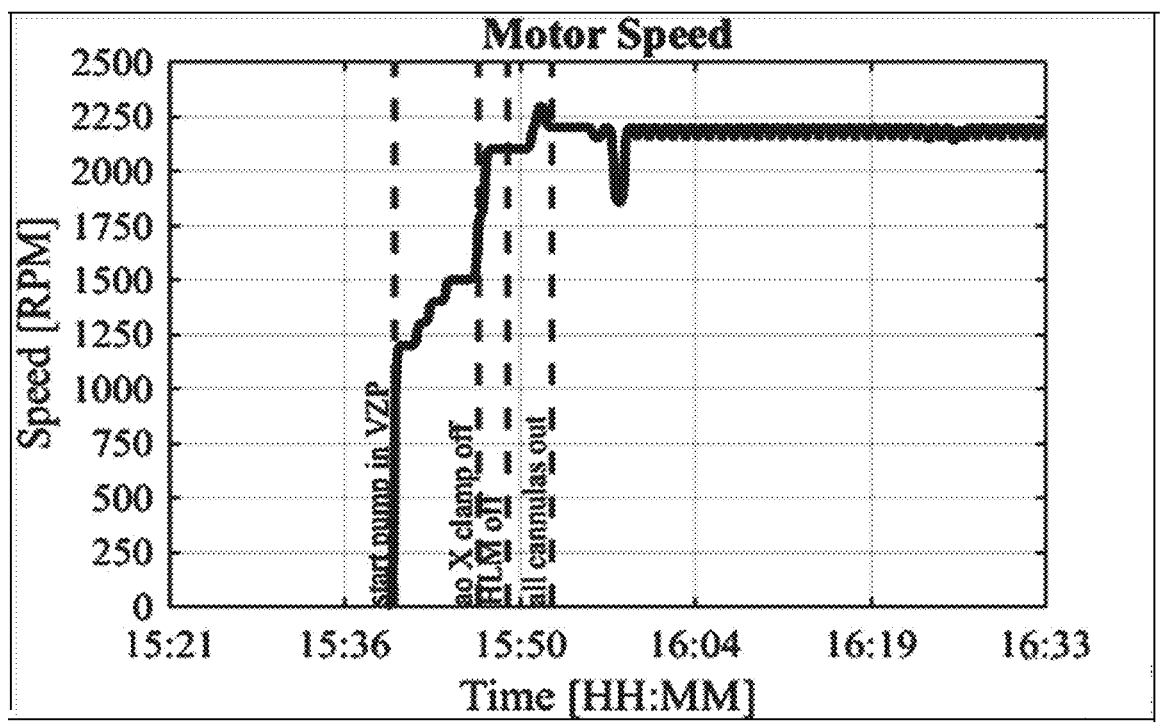
Figure 13B:
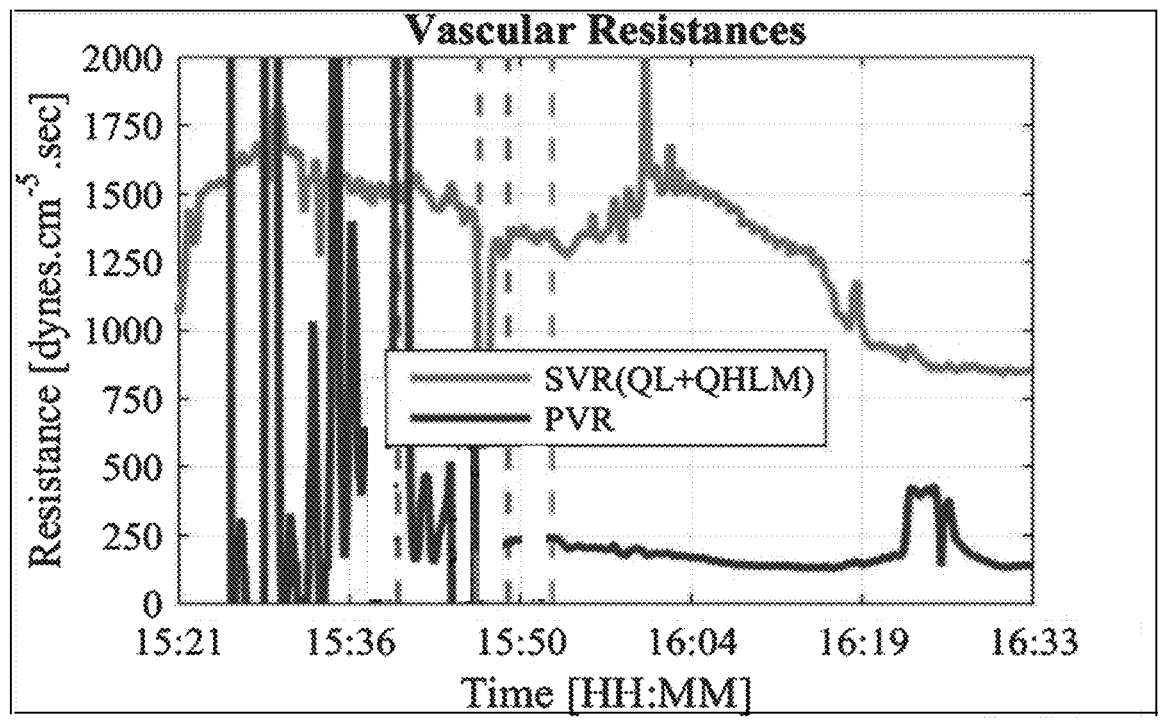
Figure 13C:
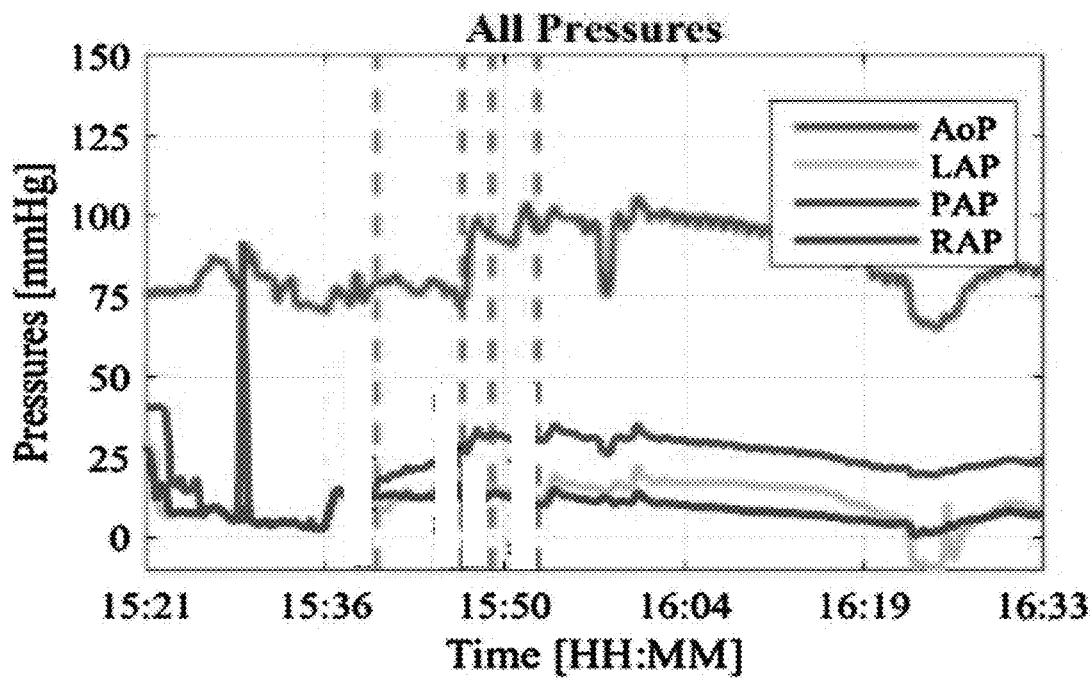
Figure 13D:
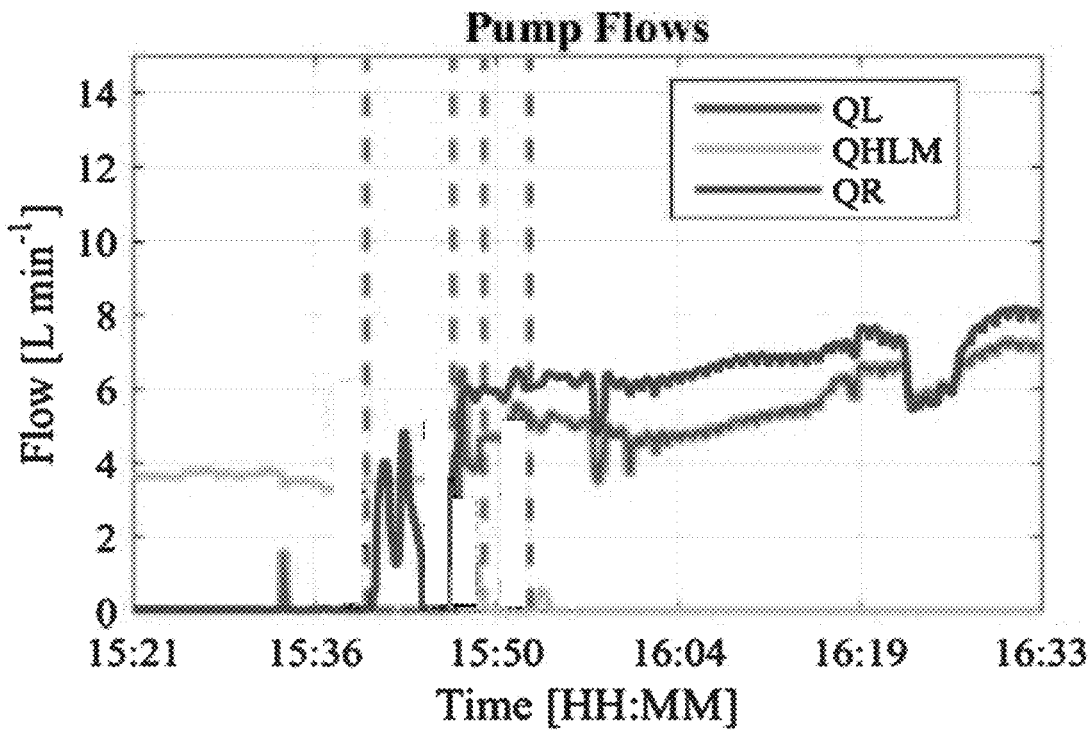

FIG. 13B is a graph illustrating changes in vascular resistance during an implantation process;

FIG. 13C is a graph illustrating changes in blood pressures during an implantation process; and, FIG. 13D is a graph illustrating changes in pump flows during an implantation process.

DETAILED DESCRIPTION OF THE PREFERRED EMBODIMENTS

An example of a heart pump will now be described with reference to FIGS. 1A to 1D, FIGS. 2A to 2I and FIGS. 3A to 3D.

In this example the heart pump is a biventricular device which can operate either as a ventricular assist device to assist function of left and right ventricles of a subject's heart, or alternatively as a total artificial heart. It will be appreciated however that whilst reference is made to a biventricular device this is not essential, and alternatively the principles described herein could equally be applied to single ventricular assist devices or any other form of blood pump.

In this example, the heart pump 100 includes a housing 110 defining a cavity 115. The housing can be of any suitable form but typically includes a main body 110.1, left and right end caps 110.2, 110.3 which connect to the main body 110.1, as well as an end plate 110.4 positioned between the main body 110.1 and left end cap 110.2. The housing can be made of any suitable biocompatible material, and can be made of titanium, a polymer or the like.

The housing 110 includes two inlets 111, 113, for connection to the left atrium/pulmonary vein and right atrium/vena cava, or left and right ventricles, and two outlets 112, 114 for connection to the aorta and pulmonary artery, respectively. Whilst two inlets and outlets are shown, it will be appreciated that this is in the context of a biventricular device, and that a single inlet and outlet can be used for a single ventricular device.

The heart pump 100 includes an impeller 120 provided within the cavity 115. The impeller 120 includes a rotor 121 having vanes mounted thereon for urging fluid from the inlet to the outlet upon rotation of the impeller 120. In this example, as the heart pump 100 is a biventricular device, the impeller includes two sets of vanes 122, 123 each of which is used for urging fluid from a respective inlet 111, 113 to a respective outlet 112, 114. In this example, the rotor 121 is positioned within the cavity 115 to effectively divide the cavity into first and second cavity portions, each having a respective inlet and outlet, thereby allowing each to function as a respective pump.

Figure 1A:
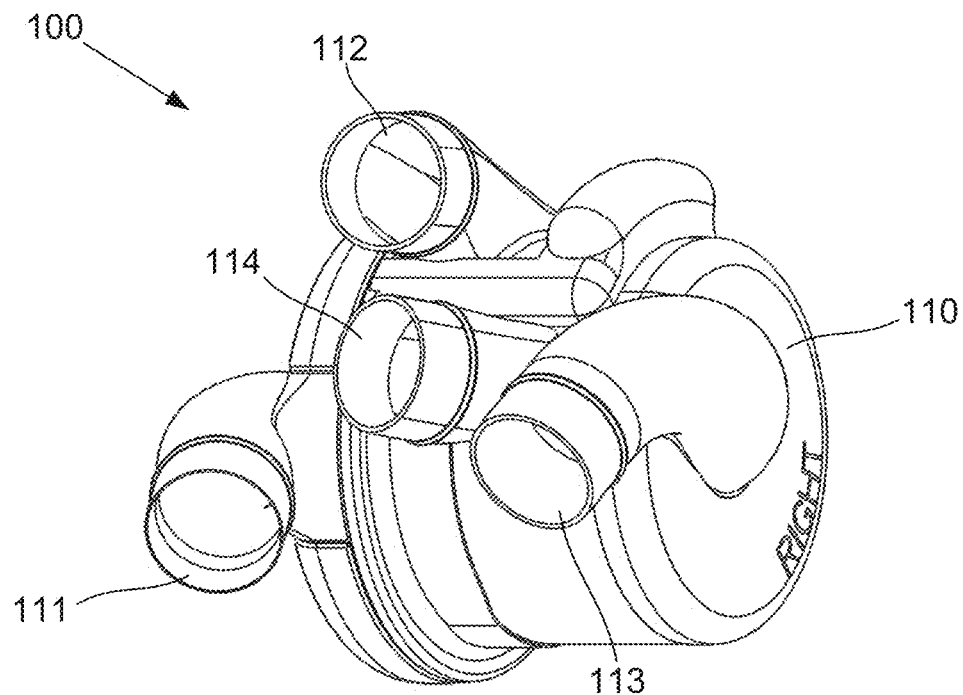
FIG. 1A is a schematic perspective view of an example of a heart pump.
Figure 1B:
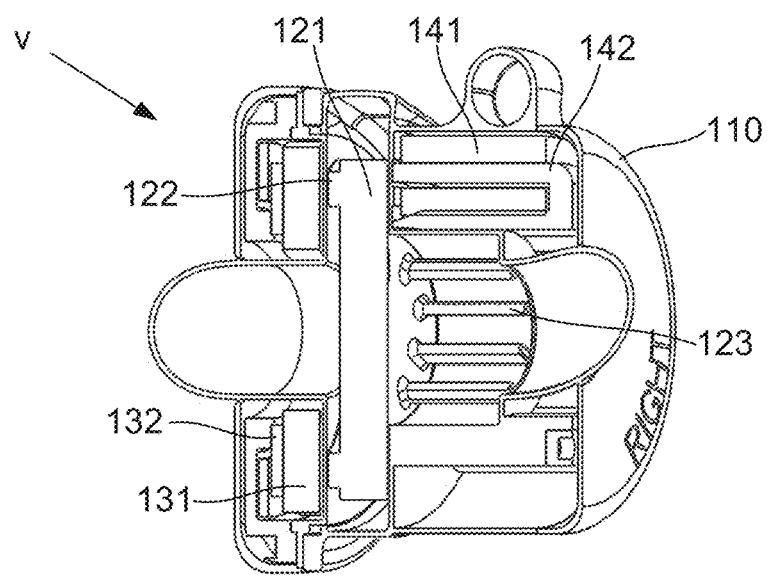
FIG. 1B is a schematic cutaway view of the heart pump of FIG. 1A.
Figure 1C:
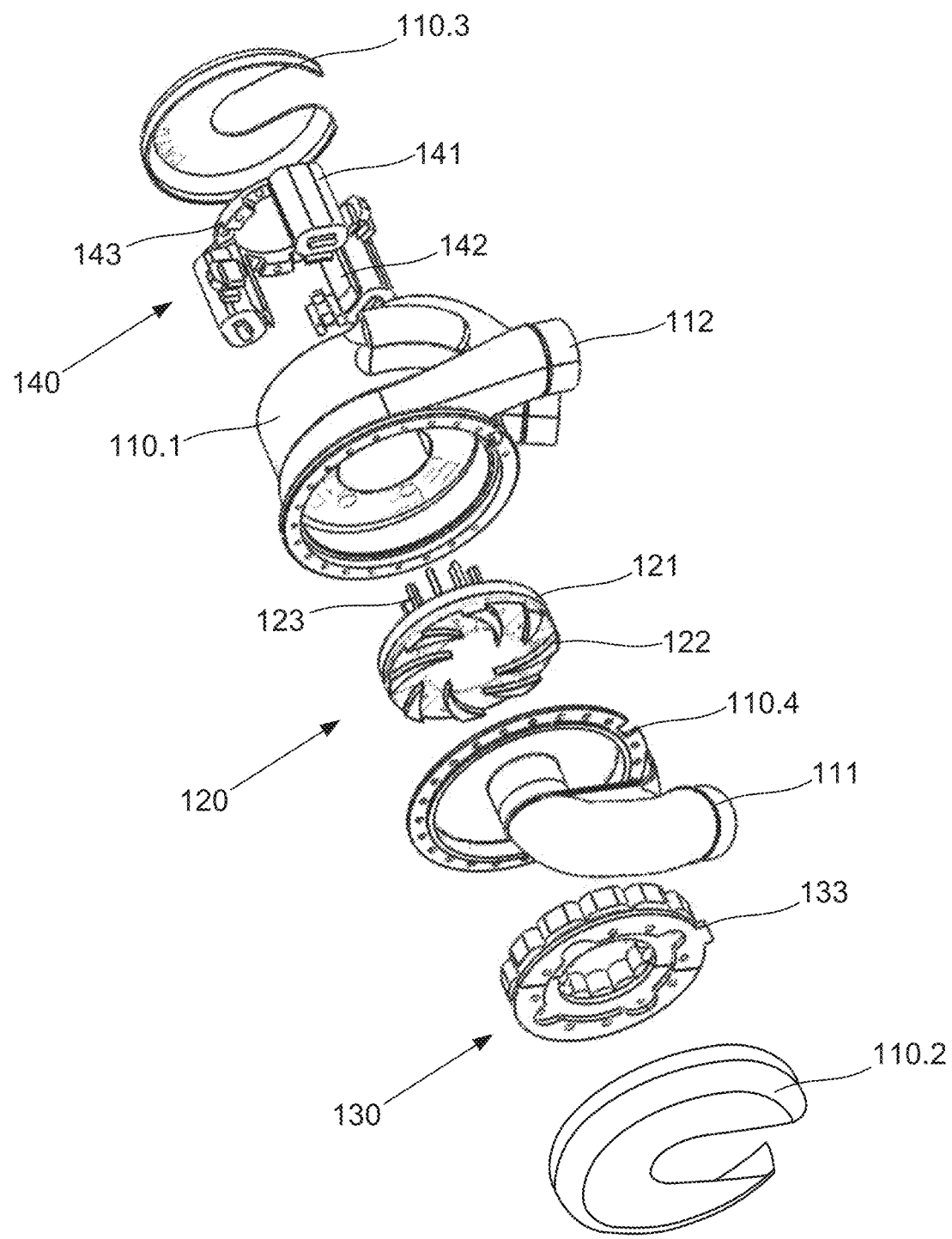
FIG. 1C is a schematic perspective exploded view of the heart pump of FIG. 1A.

Thus, in the current example, the vanes 122 are used to urge fluid from the inlet 111 to the outlet 112, with this being provided on the left-hand side of the pump in the orientation shown in FIG. 1B, and operating to provide left-ventricular function, whilst the vanes 123 urge fluid from the inlet 113 to the outlet 114 and act to provide right-ventricular function. In this context the first and second cavity portions are generally referred to as left and right cavities, and in conjunction with the impeller 120 provide left and right pumps, respectively. It will be appreciated that in this regard, the terms left and right refer to the intended ventricular function of the cavities as opposed to the particular orientation of the pump in the Figures, which is used for illustrative purposes only.

As shown in FIGS. 3A to 3D, the vanes 122, 123 have different profiles, which provide different flow characteristics for the left and right hand pumps, as will be described in more detail below. In particular, in this example, the left hand vanes 122 are flared outwardly, thickening towards an outer circumferential edge of the rotor 121, as well as being swept so as to be angled away from a direction of rotation of the impeller, as shown by the arrow R. However, this is not always the case, and for example, for an LVAD the left hand vanes are radially straight and thin, similar to the right sided vanes described below. In contrast, the right hand vanes 123 are generally straight and of a constant thickness, extending radially towards, but without meeting, an edge of the rotor perpendicularly. The impact on these arrangements and the particular dimensions of the vanes 122, 123 and rotor 121 will be described in more detail below.

The heart pump 100 further includes a drive 130 that rotates the impeller 120 within the cavity 115. The drive 130 can be of any appropriate form but typically includes a number of coils 131, each wound on a respective stator 132, supported by a mounting 133, allowing the drive 130 to be coupled to the housing 110. The drive cooperates with magnetic material 134 mounted in the rotor 121, with the magnetic material being in the form of a number of circumferentially spaced permanent drive magnets arranged proximate an outer circumferential edge of the rotor 121 and proximate a face of the rotor 121 facing the drive coils 131.

Figure 2A:
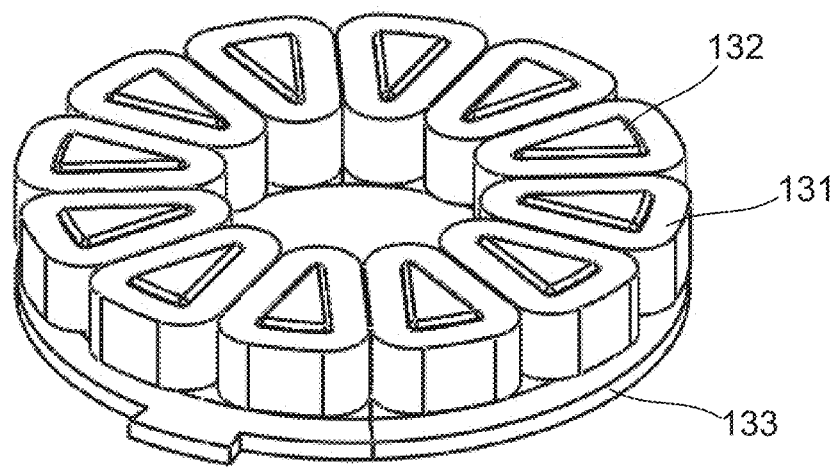
FIG. 2A is a schematic perspective top side view of an example of a drive magnet configuration.
Figure 2B:
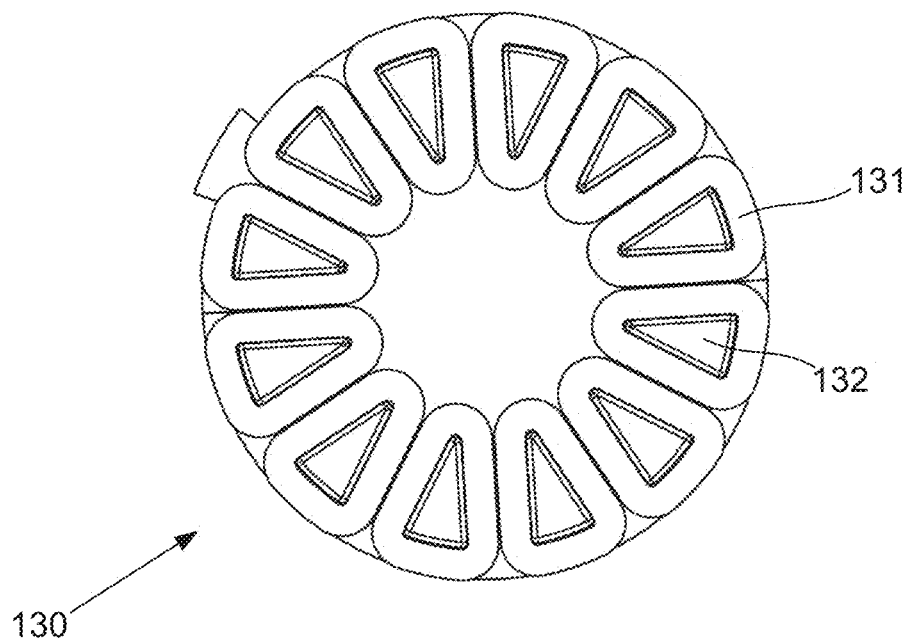
FIG. 2B is a schematic plan view of the drive magnet configuration of FIG. 2A.
Figure 2C:
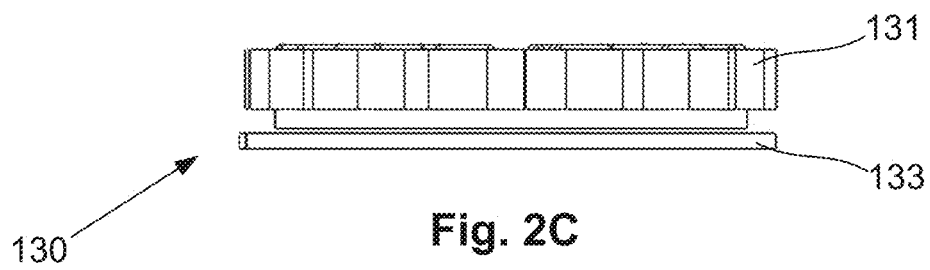
FIG. 2C is a schematic side view of the drive magnet configuration of FIG. 2A.
Figure 2D:
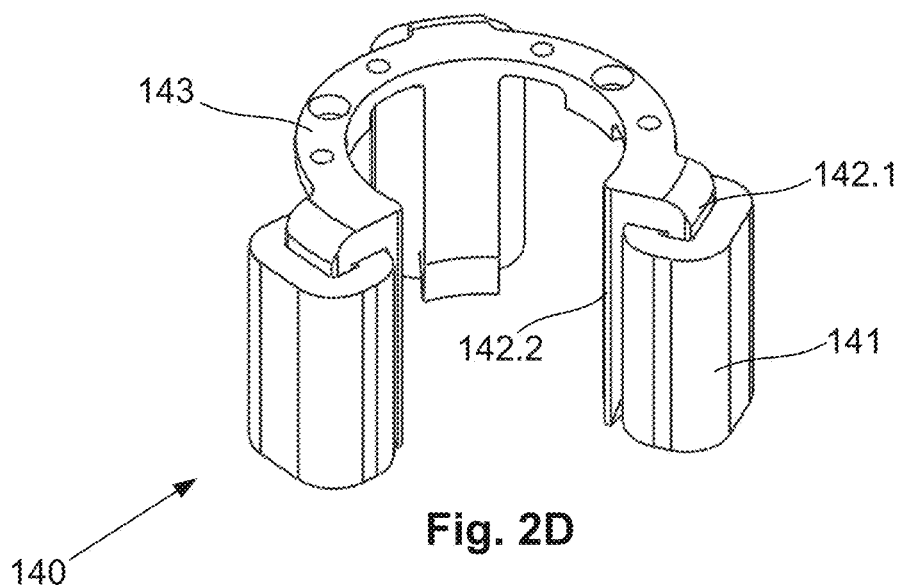
FIG. 2D is a schematic perspective top side view of a bearing magnet configuration.
Figure 2E:
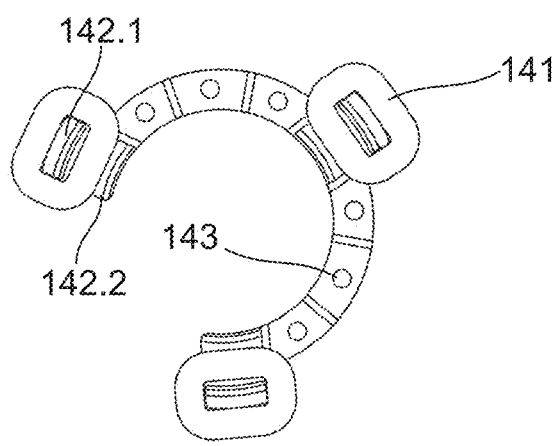
FIG. 2E is a schematic underside view of the bearing magnet configuration of FIG. 2D.
Figure 2F:
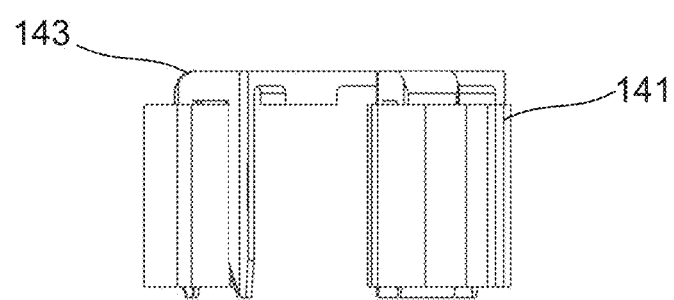
FIG. 2F is a schematic side view of the bearing magnet configuration of FIG. 2D.

An example drive magnet configuration is shown in more detail in FIGS. 2A to 2C. In this example, the coils 131 and stators 132 are wedge shaped and circumferentially spaced around the mounting 133, so as to provide twelve electromagnets radially aligned with the drive magnets 134 in the rotor 121. The drive magnets 134 are arcuate shaped rare earth magnets, circumferentially spaced proximate an outer circumferential edge of the rotor 121, and mounted on a soft iron rotor drive yoke 135.

The heart pump 100 can further include a magnetic bearing 140 including at least one bearing coil 141 which cooperates with bearing magnetic material mounted in the rotor 121 to thereby control an axial position of the impeller 120 within the cavity 115. In one particular example, shown in more detail in FIGS. 2D to 2F, the magnetic bearing includes three bearing coils 141, each of which is mounted on a first leg 142.1 of respective U-shaped stators 142, with a second leg 142.2 being positioned radially inwardly of the first leg 142.1. The stators 142 are mounted to a support 143 and circumferentially spaced 120° apart around the housing so that the first and second legs 142.1, 142.2 align with respective bearing magnetic material, such as bearing magnets 144, 145, allowing an axial position of the impeller 120 to be controlled.

The bearing magnetic material typically includes first and second annular magnetic bearing members mounted within and proximate a face of the rotor, the first magnetic bearing member being provided radially outwardly of the second magnetic bearing member. In one particular example, the first bearing magnet material 144 includes an annular soft iron material that can be integrally formed with the annular yoke, or an annular permanent magnet 144 mounted on the yoke, and mounted in the rotor, proximate an outer circumferential edge of the rotor 121. The second bearing magnetic material is an annular permanent bearing magnet 145 mounted radially inwardly of the first bearing member 144, so that the first and second bearing members 144, 145 align with respective legs 142.1, 142.2 of the stators 142. It will be appreciated the annular members could include a plurality of individual elements, such as individual circumferentially spaced magnets or ferromagnetic elements. Additionally, the use of a magnetic bearing may not be required and can be replaced by a static physical bearing, or the like.

Figure 1D:
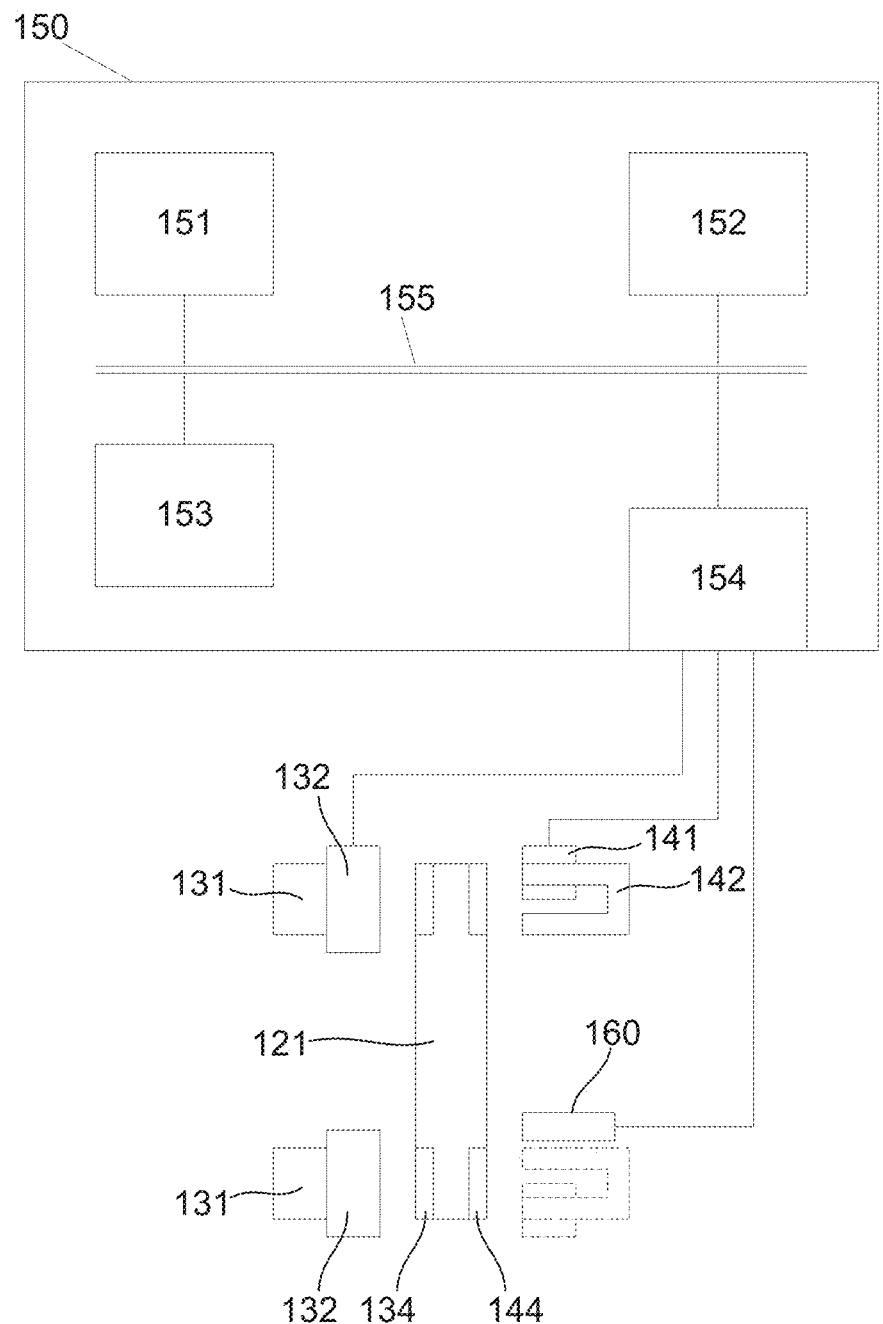
FIG. 1D is a schematic diagram of an example of a control system for the heart pump of FIG. 1A.
Figure 2G:
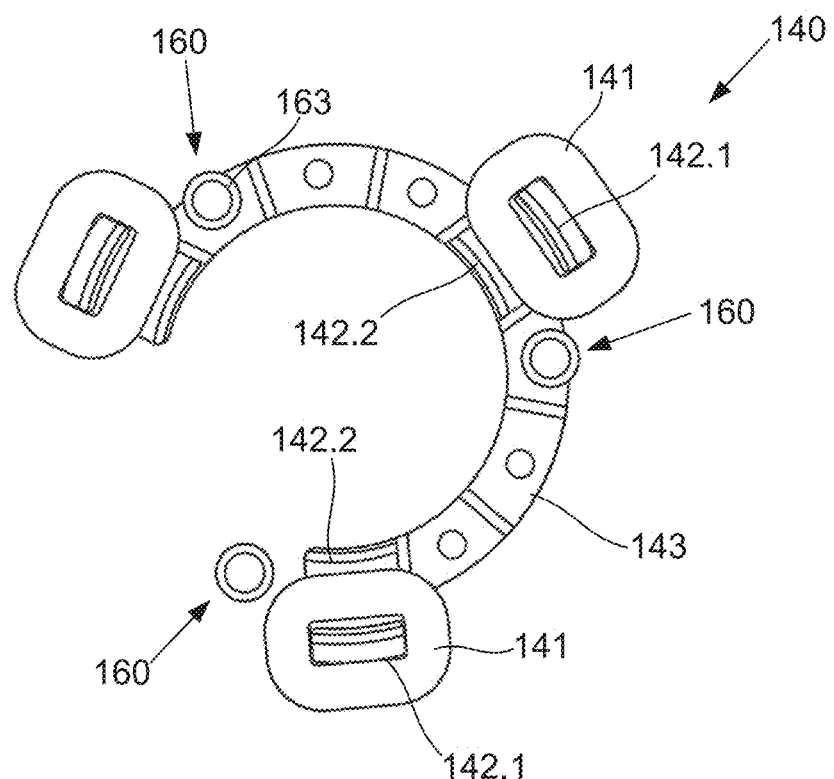
FIG. 2G is a schematic underside view of the bearing magnet arrangement of FIG. 2D with an eddy current sensor.
Figure 2H:
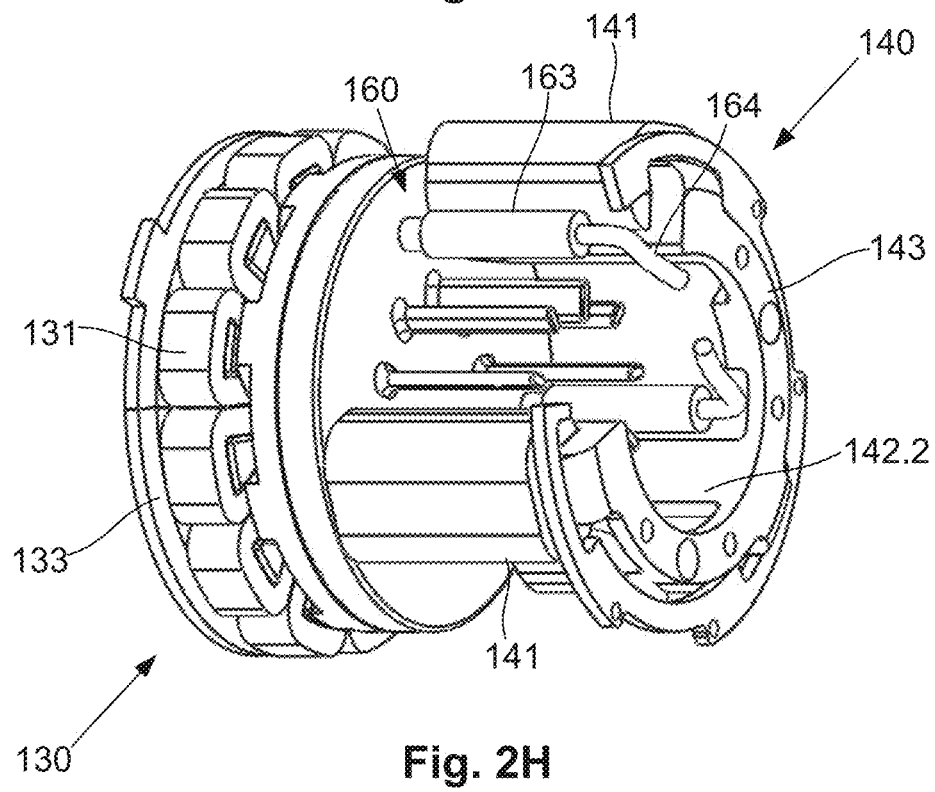
FIG. 2H is a schematic perspective top side view of the bearing and drive magnet configurations of FIGS. 2A and 2D together with the eddy current sensor.
Figure 2I:
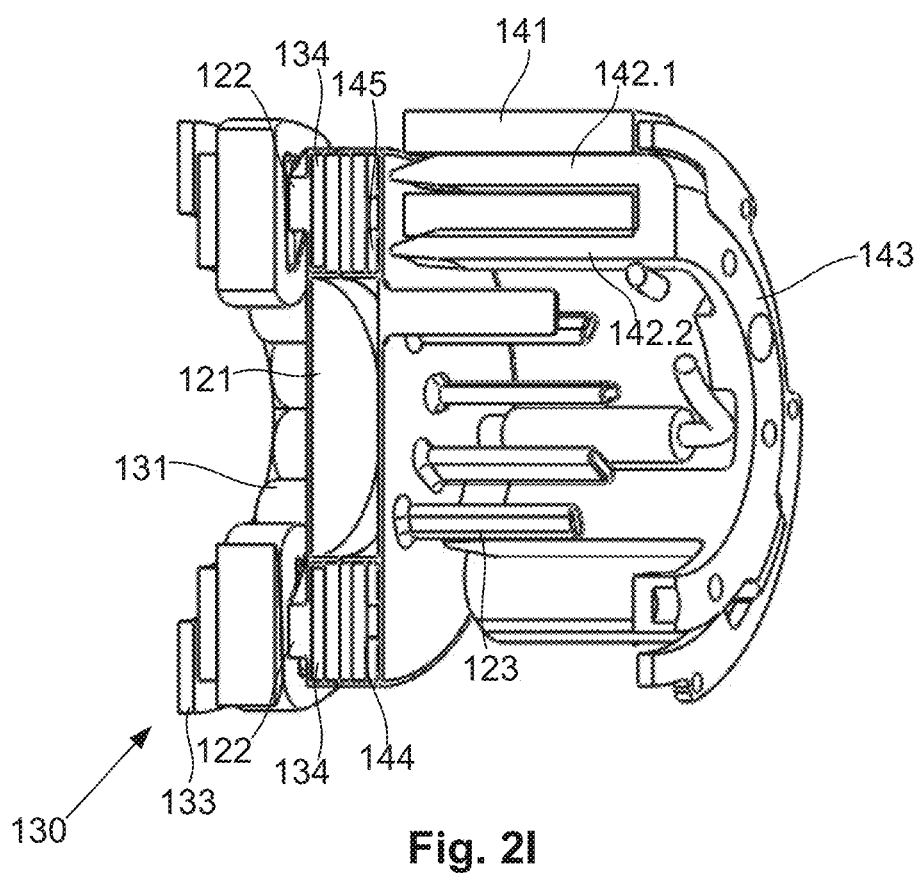
FIG. 2I is a schematic perspective cutaway view of the arrangement of FIG. 2H.
Figure 3A:
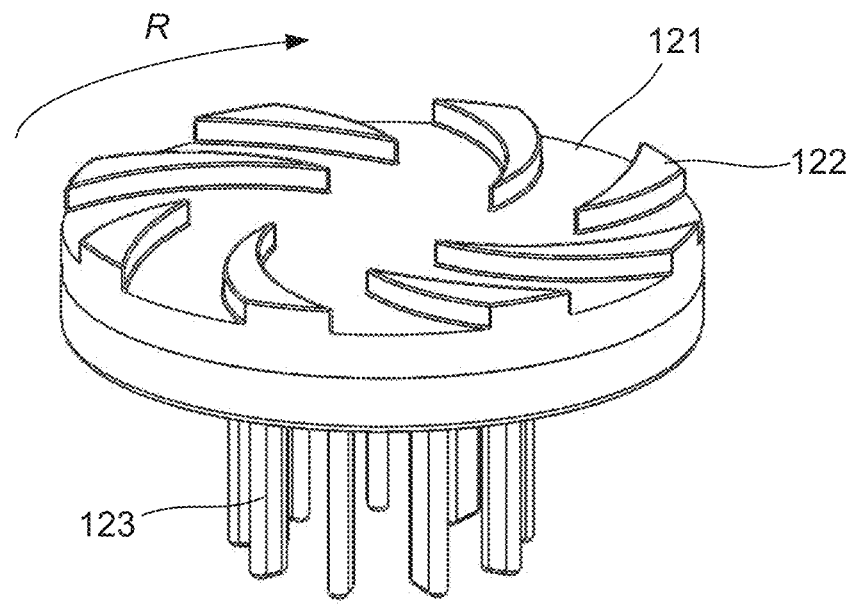
FIG. 3A is a schematic perspective view of an example impeller from the left pump side.
Figure 3B:
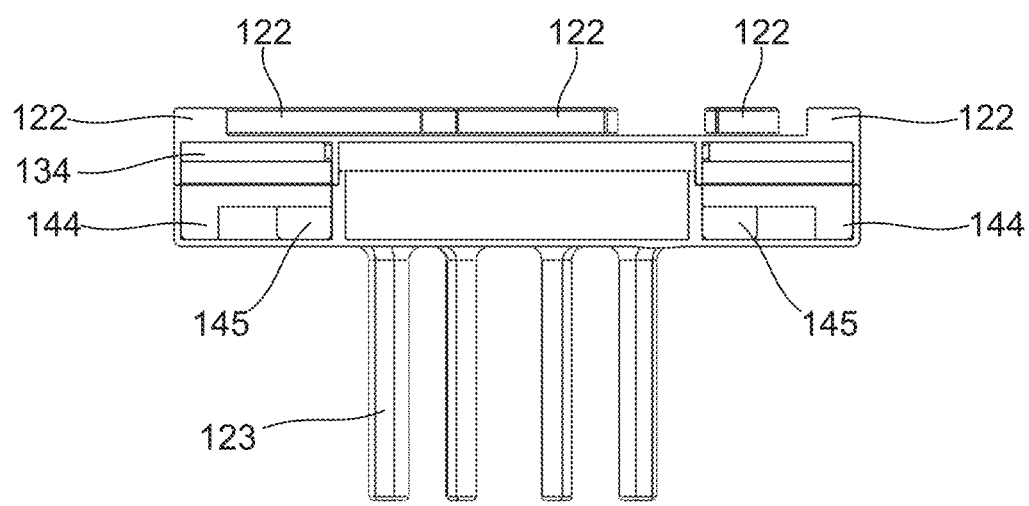
FIG. 3B is a schematic cut through view of the impeller of FIG. 3A.
Figure 3C:
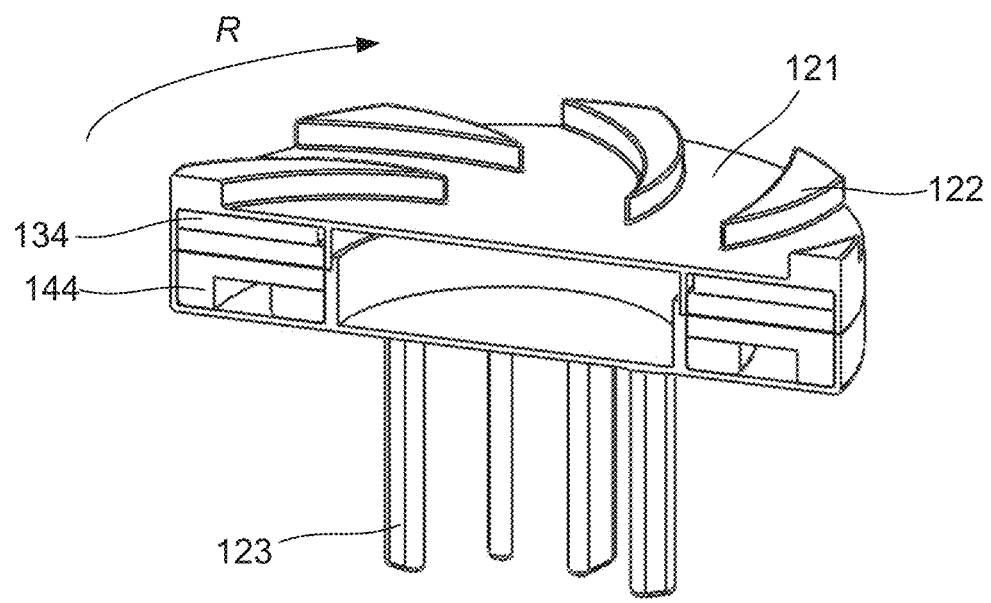
FIG. 3C is a schematic perspective cut through view of the impeller of FIG. 3A.
Figure 3D:
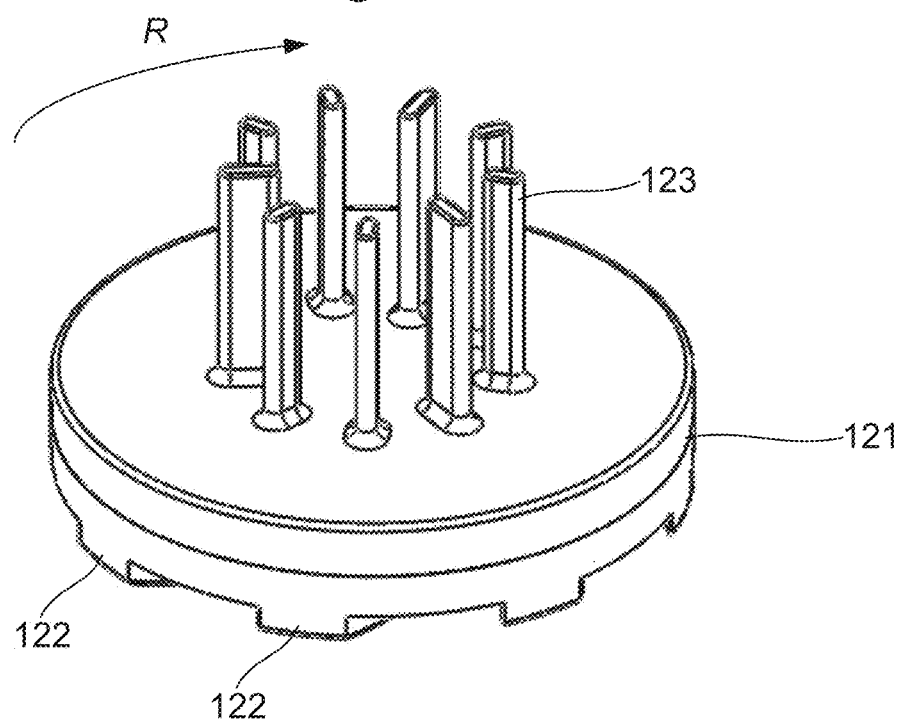
FIG. 3D is a schematic perspective view of the impeller of FIG. 3A from the right pump side.

The drive 130 and magnetic bearing 140 are mounted at opposing ends of the housing 110 so that the drive and bearing 130, 140 are provided proximate opposing surfaces of the rotor 121 as shown for example in FIG. 1D, and FIGS. 2H and 2I. In the current example the drive 130 is mounted adjacent the left pump, whilst the bearing 140 is mounted adjacent the right pump, although the opposite configuration is contemplated. The depicted arrangement has a number of benefits.

Firstly, the inherent attractive magnetic forces between the drive and rotor and the bearing and rotor can be configured to substantially balance when the rotor is provided at a balance point at a normal operating speed, which may for example by approximately at a center of the cavity under conditions of normal flow.

For example, this arrangement can be configured so that the magnetic forces inherent between the drive 130 and impeller 120, and between the magnetic bearing 140 and impeller 120 are matched at an impeller balance position within the cavity, which corresponds to a desired position of the impeller under conditions of normal flow. This minimises the bearing current required to maintain the position of the impeller 120 within the cavity, hence reducing the amount power required to operate, and in particular drive and axially position the impeller.

Additionally, as well as having the magnetic forces balance, the forces generated by the drive and bearing can also be configured to provide a desired degree of axial and radial stiffness. In this regard, the stiffness is a measure of the deflection of the impeller 120 from a balance position in response to an external force. In one example, it is desirable to maximise the radial stiffness so as to maintain the impeller radially centralised within the cavity and to stop the impeller touching the inner circumferential wall of the cavity. Conversely, as the axial position of the impeller 120 can be used for flow control, and in particular to allow for passive and/or active response to changes in hemodynamic parameters, a low degree of axial stiffness is preferred. Accordingly, the passive magnetic forces can be configured to assist in meeting these requirements, as will be described in more detail below.

A further benefit of the above described arrangement, in the context of BiVAD applications, is that it allows the greater size of the magnetic bearing to be accommodated by the smaller size of the right pump cavity. In particular, this allows a gap between a bearing stator and bearing magnets to be minimized, as no vanes are located in this gap (as opposed to the left side where vanes are located in the magnetic airgap between the drive and the rotor), as will be described in more detail below. However, it will be appreciated that this limits an outer diameter of the right pump and thus achievable pressure generation at a given rotational speed, although for right pumps this is generally not an issue given their lower flow requirements than the left pump. The apparatus further includes a controller 150 which, in use, is coupled to a sensor 160 and the drive and bearing coils 131, 141. The sensor 160 senses an axial position of the impeller 120 within the cavity 115 and can be of appropriate form.

In the example of FIGS. 2G to 2I eddy current sensors 160 are used including three sensors, each having a coil mounted in a housing 163, circumferentially spaced and aligned with the inner leg 142.2 of the magnetic bearing stators 142. The coil is aligned with a rotor shell/target mounted radially inwardly of a first bearing magnet 144, so as to generate a field therein, with variations in the field being detected to determine the separation of the sensor 160 and the shell/target, and hence the rotor 121. However, it will be appreciated that other suitable sensors can be used, such as reluctance sensors or the like, in which case the first permanent magnet 144 might be replaced with ferromagnetic material, depending on the sensor/bearing requirements.

In use the controller 150 is adapted to monitor signals from the position sensor 160 and then control the current supplied to the drive coils 131 to control rotation of the impeller and to the bearing coils 141 to control the axial position of the impeller 120. Thus, the impeller 120 is acted upon by the fluid pressures in the housing 110, which create a net hydraulic force on the impeller 120. Forces acting on the impeller 120 are compensated for by the magnetic bearing, with the controller 150 operating to control the amount of current supplied to the electromagnets in the bearing to thereby maintain the position of the impeller 120. As such, the current used by the magnetic bearing system has a direct correlation to the forces and pressures acting on the impeller 120. In this manner, changes to the inlet and outlet pressures can be detected through the magnetic bearing signals in real-time.

The controller 150 can also be adapted to provide speed control functionality, altering the rotational speed of the impeller, for example depending on factors such as fluid pressures within the pump.

The controller 150 can be of any suitable form but typically includes an electronic processing device 151, an optional memory 152, and an interface 154 for connecting to the heart pump, each of which are interconnected by a bus 155, or other similar arrangement. The electronic processing device can be any form of electronic processing device capable of interpreting signals and causing the drive and bearing to be controlled, such as a microprocessor, microchip processor, logic gate configuration, firmware optionally associated with implementing logic such as an FPGA (Field Programmable Gate Array), or any other electronic device, system or arrangement.

The controller can also implement separate control functionality, for example separate modules, to thereby control the bearing and drive.

An optional external interface 153 may be provided allowing for interaction with the controller 150. In the event that the controller is positioned outside the body this could include an I/O device 153 such as a touch screen or the like, whereas if positioned inside the body this would typically be in the form of a wireless communications module allowing communication with an external control device.

The above described heart pump is an example of a heart pump that can operate as a bi-ventricular assist device, providing ventricular assistance to the left and right ventricles, or could act as a total artificial heart, allowing functionality of the left and right ventricles to be replaced completely. Similar arrangements can also be provided corresponding to the left or right side pumps only, to thereby provide left or right ventricular assist devices.

A number of features of a specific example will now be described. In this regard, as previously mentioned, the particular design of the pump can have an impact on performance characteristics of the heart pump, so selection of appropriate design features can be used to provide desired flow characteristics.

Examples of desirable flow characteristics include:
Improved outflow pressure sensitivity (OPS) so that the magnitude of flow rates are dependent and sensitive to changes in inflow-outflow pressure differential, so that greater variations in outflow during alterations in patient physiological state (exercise, posture change) can be obtained at a constant impeller rotational speed;
Improved axial pressure sensitivity (APS) so that, particularly for the left pump, flow rates and pressure differentials are dependent on impeller axial position so that the flow is adjusted as the impeller moves axially within the cavity, which can automatically compensate for and balance pressure variations within the subject's circulatory system;
Reduced radial hydraulic forces below 1.2 N over the entire a flow range of 5-8 LPM and more typically 3-12 LPM or even 3-15 LPM, to allowing the radial position of the impeller to be passively maintained closer to the axis of rotation;
Emboli tolerant pump using large impeller flow paths and clearance gaps to mitigate the potential growth or lodgement of thrombus in the pump. In particular, to allow emboli that may originate in the systemic venous system to pass through the right impeller to then be filtered by the pulmonary network; and,
Improved passive left/right flow balancing through the use of an appropriate left/right design pressure ratio, high outflow pressure sensitivity (particularly right sided) and axial pressure sensitivity (due to impeller movement) to alter the left/right design pressure ratio in real-time at a given rotational speed.

In one example, above characteristics are achieved at least in part using a heart pump with a housing forming a cavity 115 having at least one inlet 111, 113 aligned with an axis of the cavity and at least one outlet 112, 114 provided in a circumferential outer wall of the cavity 115. The heart pump further includes an impeller 120 provided within the cavity, the impeller including vanes 122, 123 for urging fluid from the inlet 111, 113 radially outwardly to the outlet 112, 114, a drive 130 for rotating the impeller 120 in the cavity 115.

The pump is further arranged to define a flow path through the pump that has a minimal cross-sectional area of at least 50 mm$^2$. In this regard, the term cross-sectional area will be understood to refer to an area defined perpendicularly to the vector of the fluid velocity of the blood flow through the pump.

The cross-sectional area is typically achieved through appropriate configuration of the inlet, outlet and impeller, such as the impeller vane configuration. Providing a flow path of at least 50 mm$^2$ provides a number of advantages.

For example, this sizing more closely mimics the cross-sectional area of the human circulatory system, making the heart pump more effective from a biocompatibility perspective. In this regard, the human circulatory system, and in particular the heart valves, for an adult typically has a minimum cross-sectional area of 300 mm$^2$, and handles instantaneous flow rates of up to 25 Liters per min (LPM), leading to a flow velocity of up to 1.4 m/s. As the heart pump typically operates over a range of 2 LPM to 8 LPM, and up to 12 LPM during exercise, this leads to a typical flow velocity through the pump of 0.6 m/s to 4 m/s. While this is high at an upper end of the range, this is still significantly improved over traditional heart pumps, which can have a flow path of less than 20 mm$^2$, leading to a velocity of up to 10 m/s. Thus, this represents a significant improvement over traditional arrangements.

Furthermore, in practical scenarios, the cross-sectional area can be increased to 100 mm$^2$, with patients typically not exercising and hence requiring less than 8 LPM, leading to an upper limit on the blood flow velocity of 1.3 m/s, typical of normal human blood flow.

Additionally, the increased cross-sectional area of the flow path inherently leads to an emboli tolerant pump, mitigating the potential growth or lodgement of thrombus in the pump. Additionally, the large cross-sectional areas lead to improved outflow pressure sensitivity (OPS) due to reduced flow induced resistive losses, and reduced radial hydraulic forces. This can also assist with improved passive left/right flow balancing in BiVAD/TAH applications, although it will be appreciated that other advantages are also applicable in LVAD applications.

In one example, the heart pump further includes a magnetic bearing 140 for controlling an axial position of the impeller 120. However, it will be appreciated that benefits can also be obtained in non-magnetically levitated impeller configurations, such as hydraulically suspended impellers, or shaft mounted impellers.

Whilst the cross-sectional area of the flow path is at least 50 mm$^2$, it can be at least 75 mm$^2$; at least 100 mm$^2$, at least 125 mm$^2$, at least 140 mm$^2$, at least 150 mm$^2$, at least 200 mm$^2$, and up to 300 mm$^2$.

In one example, the heart pump is configured to provide a pump having a pump curve having a gradient of less than −20% over a defined flow range, such that a change in pressure of 10 mmHg across the pump causes a change in flow rate of at least 2 litres per minute (LPM), the defined flow range being between 5 LPM and 8 LPM and more typically between 3 LPM and 12 LPM or 15 LPM.

Such a gradient can be achieved for a pump that generates a pressure head that is, for a left ventricular pump, between 60 mmHg and 100 mmHg at 6 LPM, between 70 mmHg and 90 mmHg at 6 LPM and more typically approximately 80 mmHg at 6 LPM, whereas for a right ventricular pump, this can be between 10 mmHg and 30 mmHg at 6 LPM, between 15 mmHg and 25 mmHg at 6 LPM and more typically approximately 20 mmHg at 6 LPM.

Figure 4A:
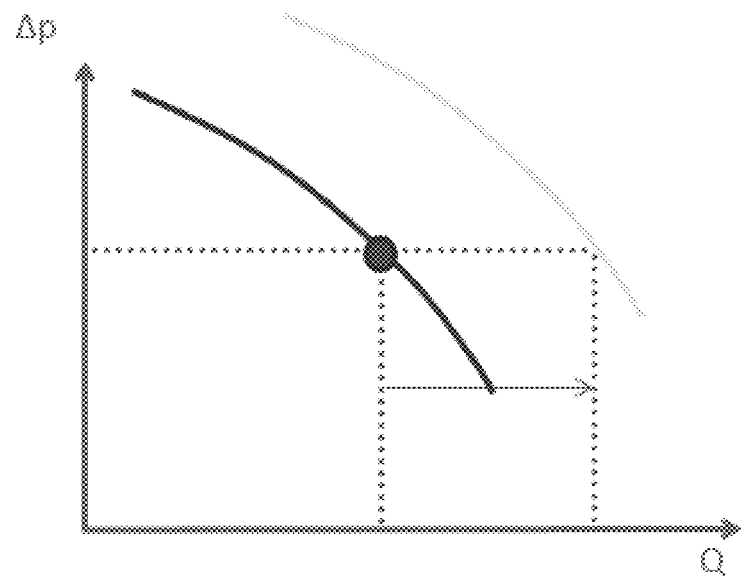
FIG. 4A is a graph showing an example of a performance for a heart pump with relatively low flow sensitivity.
Figure 4B:
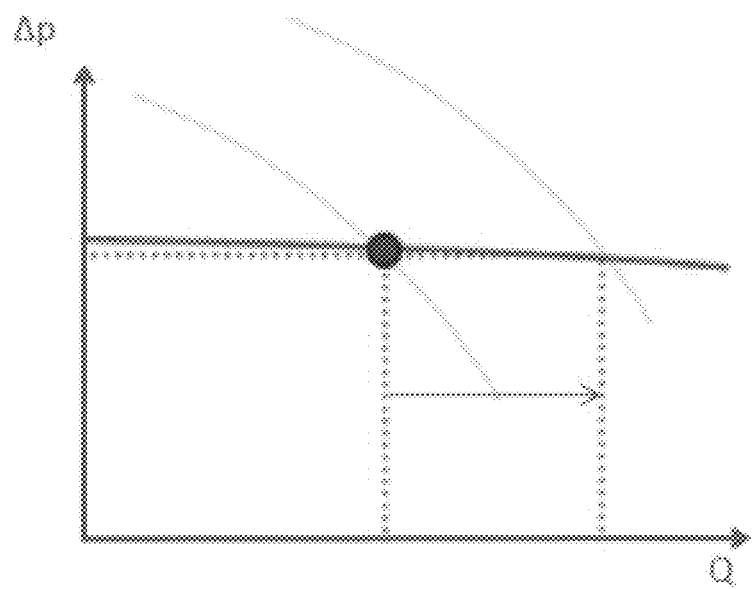
FIG. 4B is a graph showing an example of a performance for a heart pump with relatively high flow sensitivity.

Thus, a heart pump is provided that has a pump curve with a much lower gradient than traditional pumps, as shown for example in FIG. 4B, versus the conventional heart pump gradient shown in FIG. 4A. As a result, the heart pump demonstrates high flow sensitivity, so that even minor pressure variations caused by changes in physiological state (outflow resistances) of the subject result in a high change in flow rate through the pump, which in turn provides a correction mechanism to ensure that flow rates are suitable from a physiological perspective.

For example, if pressures at the left pump inlet 111 increase (due to a reduced upstream pulmonary resistance), this results in a higher flow through the left pump, thereby returning the pressure at the pump inlet 111 to a normal level. Thus, a highly sensitive left and/or right pump will maximize outflow at a constant rotational speed during increased patient activity (exercise). Additionally, in the case of a biventricular device, this can also help maintain left/right flow balance over a wider and more extreme range of physiological imbalances (posture change/Valsalva), by allowing the flow rate through the left and right pumps to adapt solely on the basis of pressures.

Thus, this allows a more pressure sensitive heart pump to be provided, which can maintain balanced flow and provides more cardiac output over a wider range of patient daily activities at a constant rotational pump speed.

In one example, when the heart pump provides at least partial left ventricular function, the heart pump can have a pump curve having a gradient less than at least one of −25%, −30%, −35% and more typically −40%, but can be up to −200% or even −500%. In the case of a right pump, the pump curve can have a gradient less than at least one of −30%, −35%, −40%, −75%, −100% and more typically 150%, but can be up to −200% or even −500%. Thus, in one example biventricular device, the left and right pumps can have different pump curves, which can further assist in flow balancing. However, this is not intended to be limiting and a range of different pump curve characteristics can be used. For example, whilst the above gradient values are particularly suited for a total artificial heart scenario, if the pump is being used as a single VAD, such as an LVAD or RVAD, a gradient can be up to −200% or even up to −500%.

In this regard, it should be noted that the pump curve refers to the measured pressure from the inlet to the impeller to the outlet of the impeller. In practice, the shape (straight or bent/curved) and diameter of the inlet and outlet pipe/cannula will also affect this pump curve, but this is not accounted for in the explanation above. Thus the above gradient values are in respect of fluid flow from the inlet to the outlet of the pump, and are independent of connection of the pump to the subject's body.

The sensitivity to changes in outflow due to pressure variations on the heart pump is related to the pump curve of the pump, which incorporates various losses (friction, hydraulic, leakage/recirculation) which are in turn dependent on design parameters of the impeller/volute, including the characteristic resistance, throat area, volute angle, vane angles, vane numbers, vane dimensions, or the like.

It should be noted that, as will be described in more detail below, these design parameters also have an impact on other aspects of pump operation, and in particular, parameters suitable for ensuring a high axial flow sensitivity can also have a number of other beneficial effects.

For example, this can help ensure that the heart pump provides greater sensitivity to pressure generated due to alterations in axial position of the impeller 120. Additionally, parameters that contribute to an improved pump curve can result in low radial hydraulic forces over the range of intended outflow, which enables suspension support in a radial direction by passive reluctance restoration forces generated by an axial magnetic bearing, without requiring additional stabilisation, such as the use of a hydrodynamic journal bearing, which can have adverse physiological and hemocompatible consequences.

Consequently, this configuration allows for large gaps to surround the circumference of the impeller (typically 2-4 mm) which results in low shear stress and thus improved biocompatibility. Additionally, when combined with large axial gaps (250 to 350 µm and typically 300 µm), a significant amount of washout flow between the cavities can occur. In the TAH application, this results in a shunt of oxygenated blood from the high pressure left cavity to the low pressure right cavity. The degree of shunt flow is not considered clinically significant, however measures can be used to attenuate the magnitude of flow, such as the inclusion of fins or vanes or spiral groove bearings to oppose shunt flow. For the LVAD application, a large hole located in the centre of the impeller will direct this leakage flow back into the main flow path. In both cases, this leakage flow is effective in providing washout of these clearance gaps, thus reducing the potential for stagnant flow and consequent thrombus formation.

In one specific example, the ability to shunt flow from the left to the right pump can have significant benefits during installation of the pump, as will be described in more detail below.

Parameters that contribute to an improved pump curve also typically lead to large passages through the impeller vanes (at a range of 120 mm$^2$-300 mm$^2$ and typically with a minimum of 150 mm$^2$ on the left and at a range of 500 mm$^2$-1500 mm$^2$ and typically with a minimum of 650 mm$^2$ on the right) used to reduce the characteristic resistance of the flow path and also allows for the passing of emboli through the pump. This is of particular importance for any emboli originating in the systemic venous system to pass unimpeded through the right side of the device, to then be filtered by the arterioles in the pulmonary network of the lungs. Furthermore, these large areas greater than 120 mm$^2$ may reduce the incidence of vonWillebrand factor degradation, due to lower fluid velocity and thus shear stress at maximal flow rates.

Specific examples of configurations will now be described.

Improved Outflow Pressure Sensitivity (OPS)

The pump curve for a heart pump is dependent on a wide range of different factors, as shown for example in FIG. 4C. In particular, each pump has theoretical performance characteristics defined by Euler's equation, which are derived from angular momentum considerations based on the design of the impeller vanes, as indicated by the Euler-line. Deviation from this theoretical performance results from factors such as:

leakage resulting from flow between impeller vanes and the walls of the impeller cavity;
friction between the bloodflow and walls of the pump;
recirculation between the cutwater and the impeller as shown in FIG. 4D;
recirculation within the outlet volute/throat area leading to impeded flow as shown in FIG. 4E;
inlet port diameter and thus fluid recirculation, particularly at flows below the best efficiency point (BEP);
volute throat magnitude (area) and aspect ratio (Width× Height)
impeller eye diameter (ID1);
the use of secondary splitter vanes;
impeller vane number and fluid entrance/exit area; and,
angle of flow incidence entering the impeller vanes and interacting with the volute cutwater tongue.

Accordingly, by controlling parameters of the physical construction that can influence these factors, this can be used to configure a desired pump curve, and in turn a high degree of outflow pressure sensitivity. In one particular example, a desired pump curve is obtained by reducing friction losses by increasing the throat area, altering the vane outlet angle and increasing recirculation losses at low flows while reducing recirculation losses at high flows.

Each of these will now be considered individually, although it will be appreciated that there is some interaction between the individual pump parameters and each factor, which leads to constraints on the selection of each parameter. Accordingly, in practice the pump parameters must be considered collectively, and reference to each factor individually is for the purpose of illustration only.

Friction Losses

Friction losses increase with flow rate due to viscous boundary layer production and increased effective blockage throughout the flow path. Reducing the ratio of boundary layer thicknesses to the main flow path area created by flow areas interacting with the relatively viscous fluid (blood) within the device reduces characteristic resistance/blockages to flow, especially at high flows. This may be achieved by increasing the cross-sectional area of flow paths through the heart pump.

Figure 5A:
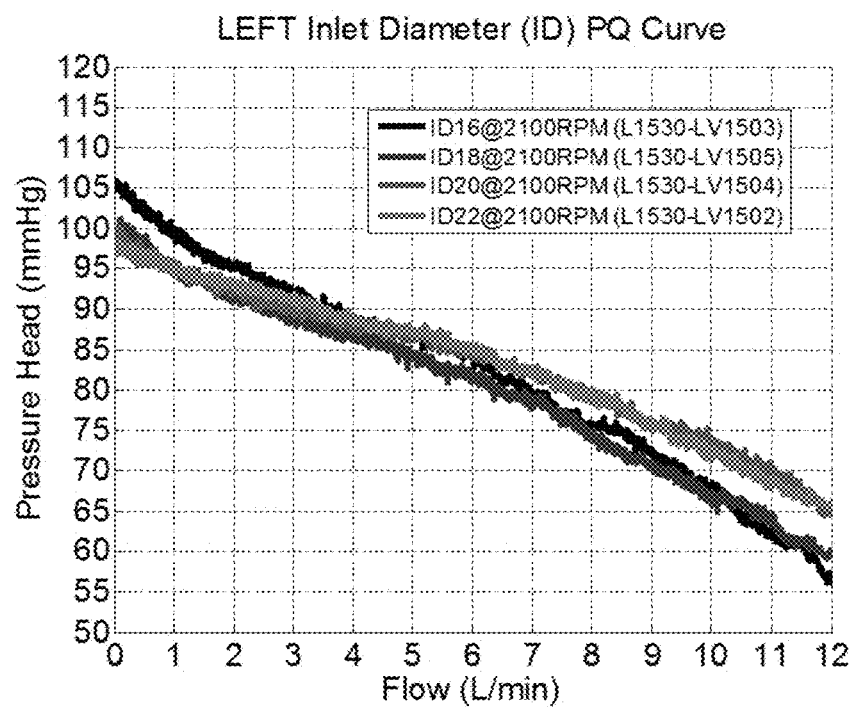
FIG. 5A is a graph illustrating the effect of left pump inlet diameter on the left pump curve.
Figure 5B:
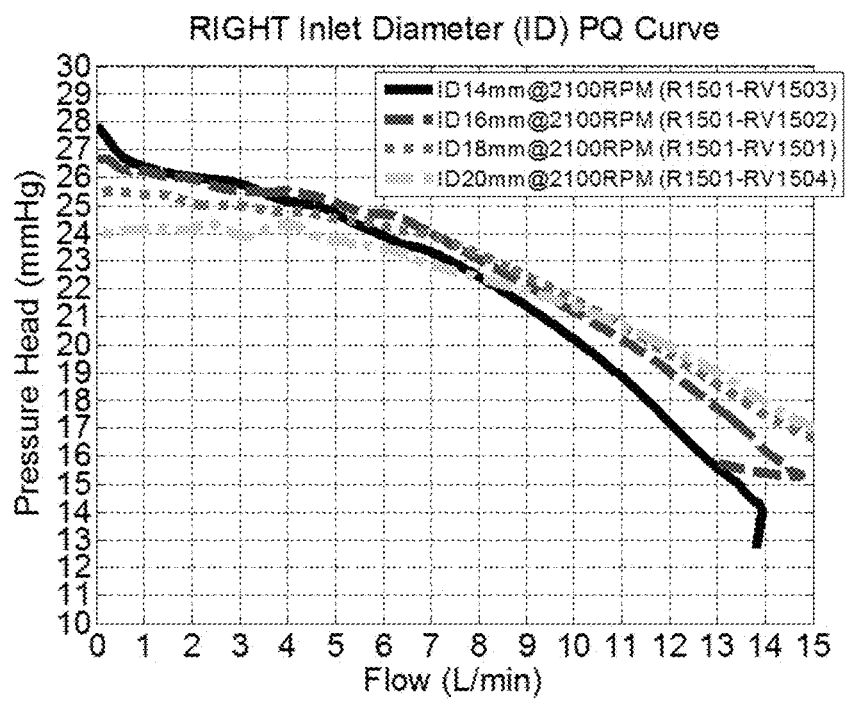
FIG. 5B is a graph illustrating the effect of right pump inlet diameter on the right pump curve.

Increasing the cross-sectional area of flow paths through the heart pump can be achieved by increasing the cross-sectional area/diameter D1 of the inlets 111, 113. In this regard, as inlet diameter increases, shutoff pressure decreases due to additional recirculation losses at the inlet. However at high flows, friction losses are reduced with increasing inlet diameter, leading to a flatter pump curve. It should be noted that the inlet diameter that affects recirculation is the diameter of the port as it enters the pump cavity, and hence as blood flows onto the impeller. In other words this is the inlet diameter downstream of the connection to the cannula or cuff that attaches to the body and any bend in the inlet, which can be of any diameter. Examples of this are shown in FIGS. 5A and 5B, which show example left and right hand pump curves for a range of different inlet diameters ID. For example, for the right hand pump, increasing the inlet diameter ID by 2 mm drops the shutoff pressure by ~1.3 mmHg and reduces the gradient by 0.1 mmHg/LPM.

This effect has limited influence above 20 mm, so in one example, the inlet has a diameter of at least one of at least 10 mm, at least 15 mm, less than 30 mm, less than 25 mm, between 18 mm and 22 mm and more typically approximately 18 mm to 20 mm. This contrasts to traditional arrangements in which smaller diameters, such as 9-10 mm or lower, are used. It will also be appreciated that different inlet diameters may be used for the left and right pumps respectively.

Figures 5C, 5D:
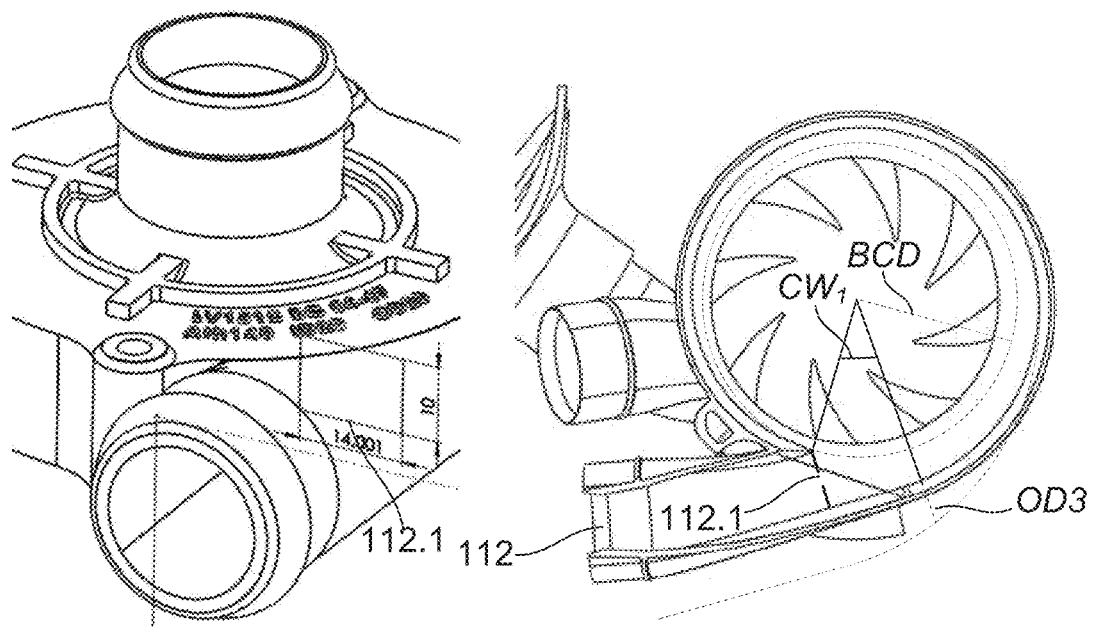
FIG. 5C is a schematic cut-away end view of an example of a left pump volute outlet throat area.
FIG. 5D is a schematic cut-away plan view of an example of a left pump volute outlet throat.
Figures 5E, 5F:
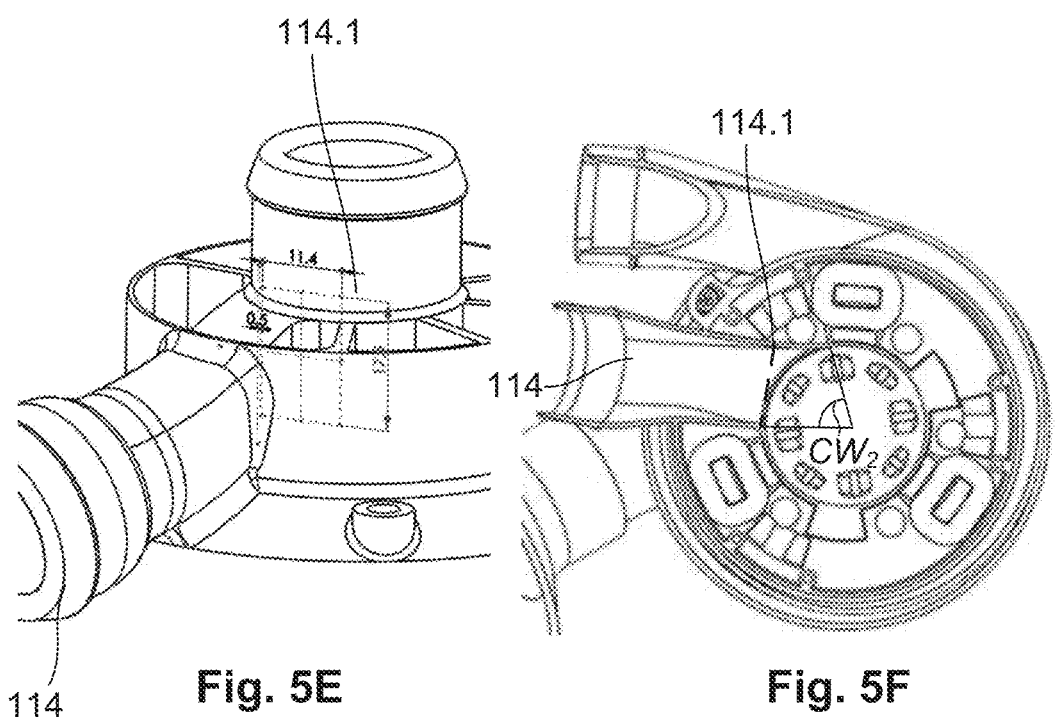
FIG. 5E is a schematic perspective view of an example of a right pump volute outlet throat area.
FIG. 5F is a schematic cut-away plan view of an example of a right pump volute outlet throat.
Figure 5G:
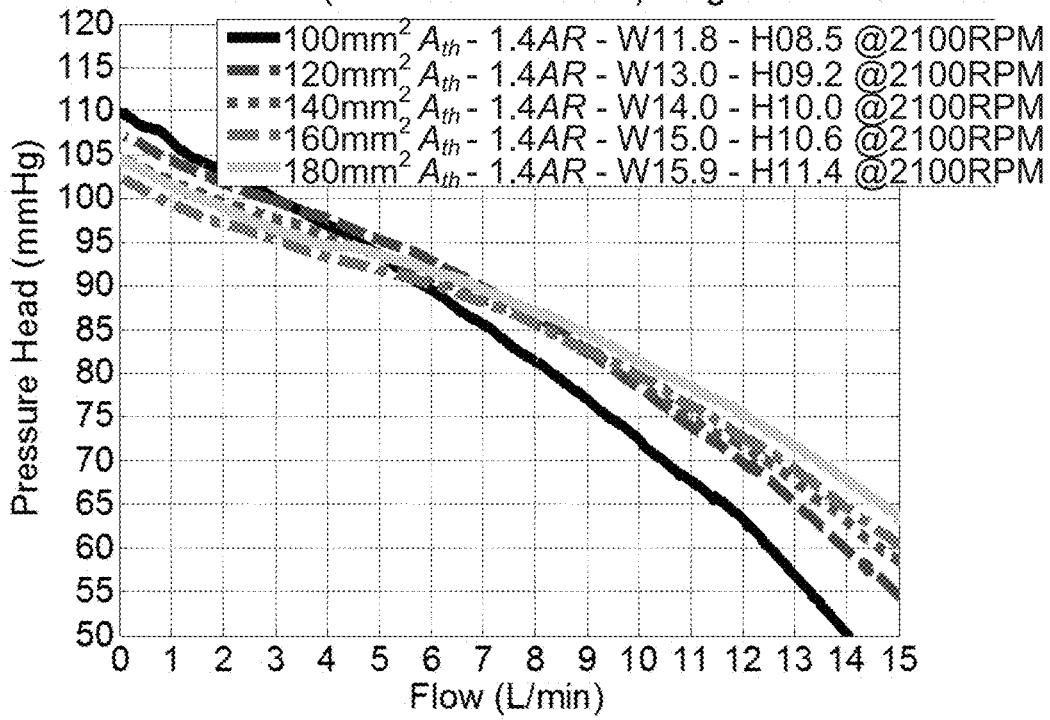
FIG. 5G is a graph showing an example of changes in left pump curve for different outlet throat areas.
Figure 5H:
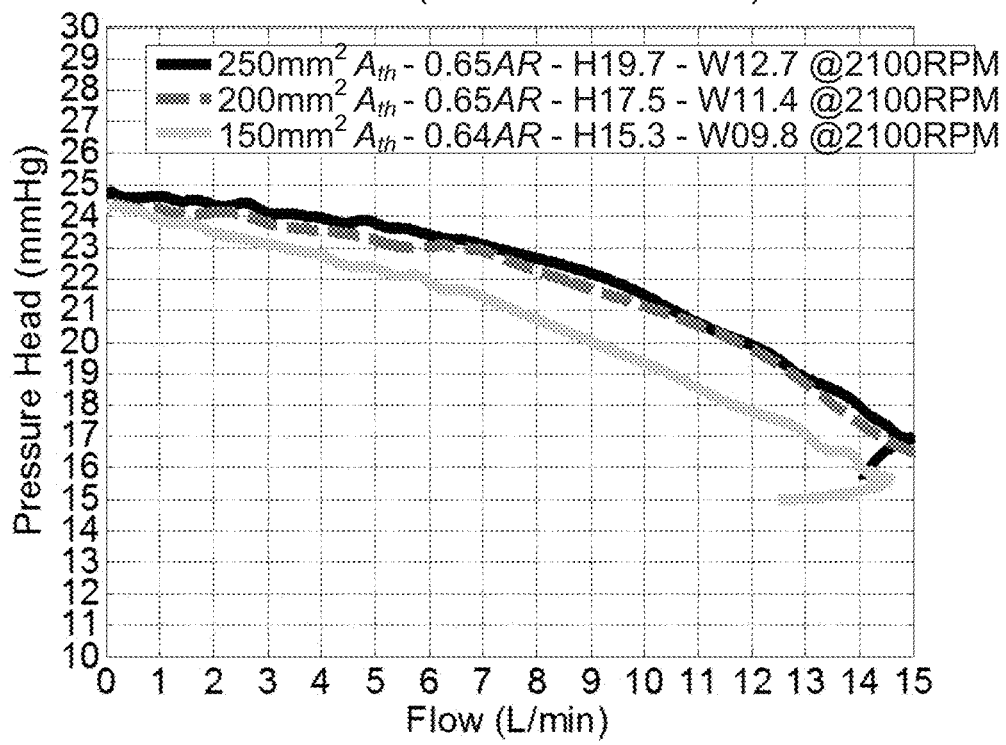
FIG. 5H is a graph showing an example of changes in right pump curve for different outlet throat areas.

Additionally, throat area $A_{th}$ of the throats 112.1, 114.1 of the left and right pump outlets 112, 114, shown in FIGS. 5C and 5D and 5E and 5F, respectively can be increased in order to maximise pressure at higher outflows from the pump at a given impeller rotational speed. In a rotary blood pump, the throat area is traditionally less than 60 mm$^2$, which corresponds to creating a best efficiency (design) point (BEP) at 5-6 LPM. A number of different throat areas were trialed, and a graph showing examples of different pump curves for different throat areas with the same impeller configuration is shown in FIGS. 5G and 5H for the left and right pumps respectively. For these examples the aspect ratio (width vs height) of the throat is kept constant.

In this case, for the left pump, shutoff pressure increases as throat area Ath and width (W) decreases, leading to a slightly steeper curve. In this instance, it is apparent that flow above 9 LPM starts to choke if the throat area is below 120 mm$^2$, but performs similarly at greater areas, with limited benefit being seen at areas above 140 mm$^2$.

In contrast, for the right pump, reducing the throat area $A_{th}$ causes the flow to choke below 200 mm$^2$, with significantly reduced performance at 150 mm$^2$ due in part to the smaller vane height. Limited benefit is seen above 200 mm$^2$, suggesting that an optimum lies around this value for outlet throat area for the right hand pump.

These results highlight that a larger throat area has a flatter pump curve. As the throat area becomes larger, greater fluid deceleration at this region results at flows below BEP<1, as well as more of a recirculation volume and so more static pressure energy is converted into kinetic energy. Whilst a smaller throat area reduces this effect, it creates more fluid acceleration (which reduces static pressure) and thus turbulence and blockage at higher flows above BEP. These effects were observed up until 140 mm$^2$ on the left and 200 mm$^2$ on the right, above which only marginal alterations in the performance curve were observed. Accordingly, whilst a larger throat area provides a flatter curve, this needs to be balanced by efficiency and radial hydraulic force generation considerations as described later.

Accordingly, in one example, for a left pump, the outlet 112 has an area of at least one of at least 60 mm$^2$, at least 80 mm$^2$, at least 120 mm$^2$, between 60 mm$^2$ and 250 mm$^2$, between 120 mm$^2$ and 160 mm$^2$, between 140 mm$^2$ and 160 mm$^2$, between 140 mm$^2$ and 250 mm$^2$, between 130 mm$^2$ and 150 mm$^2$, and approximately 140 mm$^2$ or 150 mm$^2$. In the case of a right pump, the outlet 114 has an area of at least one of at least 100 mm$^2$, at least 130 mm$^2$, between 130 mm$^2$ and 250 mm$^2$, between 130 mm$^2$ and 230 mm$^2$, between 170 mm$^2$ and 210 mm$^2$, between 150 mm$^2$ and 200 mm$^2$, between 170 mm$^2$ and 210 mm$^2$, between 175 mm$^2$ and 200 mm$^2$, approximately 233 mm$^2$, 200 mm$^2$ or 150 mm$^2$. The choice of a larger right pump throat area than left assists in producing a more OPS right pump than left pump. That is to say, the throat area Ath of the right pump should be larger than that of the left, in general.

In addition to an absolute throat area, an aspect ratio of the outlet and in particular the ratio of width to height, also has an impact on flow through the outlet. In this regard, a higher throat area with a larger height has a greater length of cutwater tongue, which can in turn lead to separation eddies due to incidence mismatch having a greater impact on flow blockage.

Figure 5I:
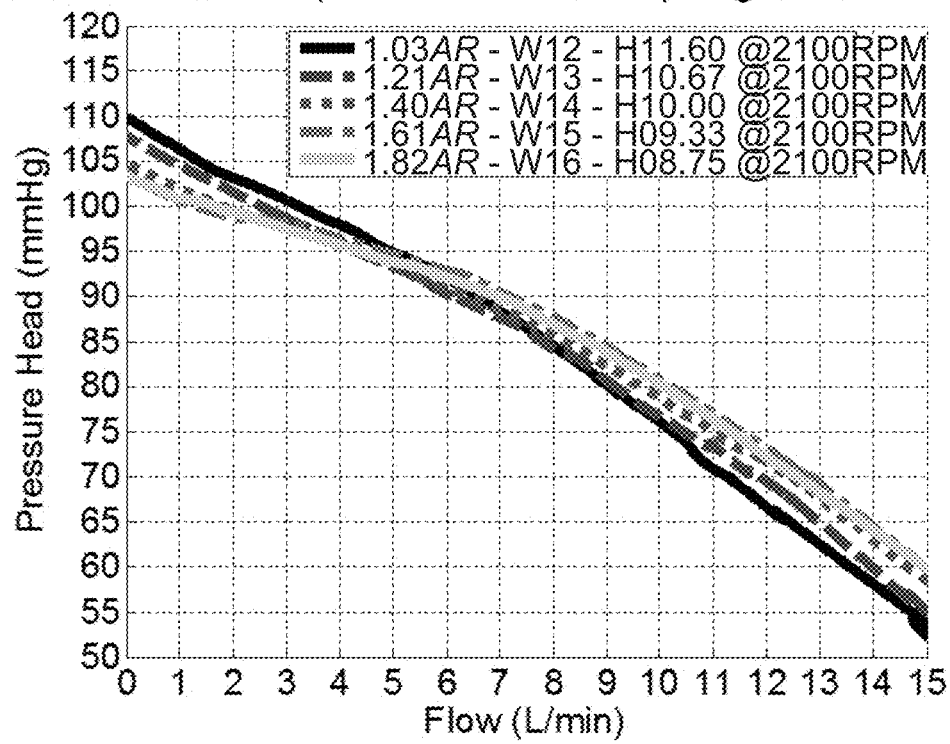
FIG. 5I is a graph showing an example of changes in left pump curve for different outlet throat aspect ratios.
Figure 5J:
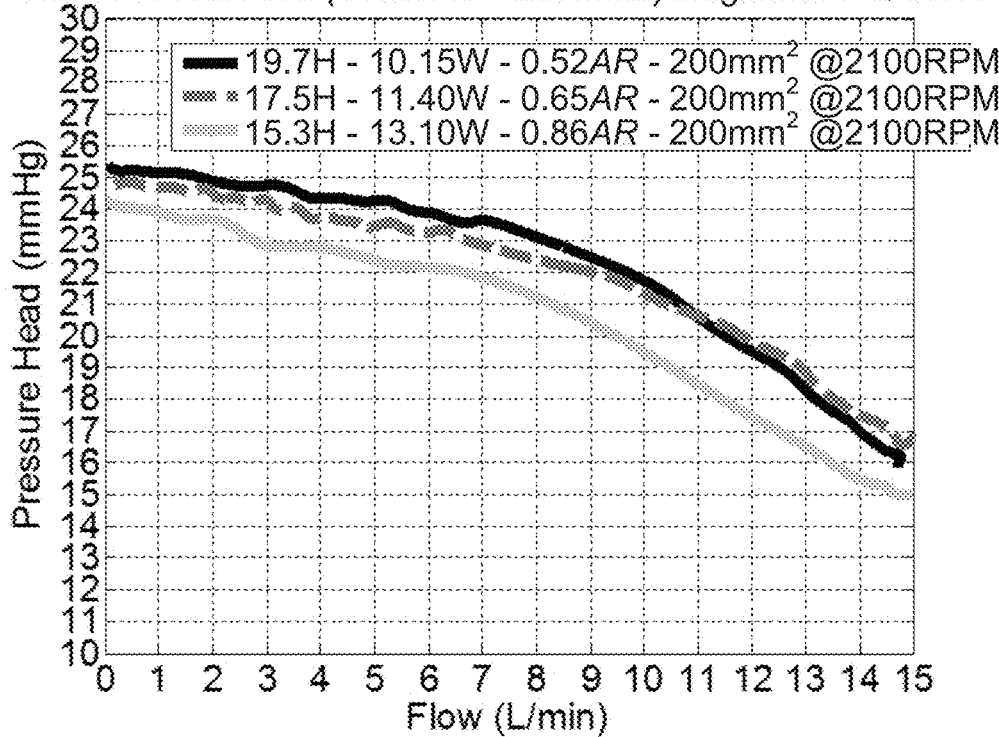
FIG. 5J is a graph showing an example of changes in right pump curve for different outlet throat aspect ratios.

Examples of the impact of change in throat aspect ratio, for a fixed throat area, are shown in FIGS. 5I and 5J for the left and right pump respectively.

As can be observed in FIG. 5I, maintaining the same throat area but altering the aspect ratio (W:H) alters the shape of the performance curve, with a larger aspect ratio generally producing flatter pump curves in the case of the left pump, which has a spiral volute. A larger aspect ratio (AR) is characterised as locating the outer wall of the throat area at a larger outer wall diameter (OD3). Since the location of the cutwater is unchanged (54 mm) at the base circle diameter (BCD), the volute spiral angle is thus increased to make the transition around the impeller circumference, and was between 1.7° and 3.4° for this aspect ratio range. A larger volute angle is generally more favourable to match the fluid off-flow discharge angle created by the flow exiting the impeller at high flows (higher meridional radial flow velocity at the same impeller rotational tangential velocity) thus reducing the level of incidence mismatch at high flows and thus maintaining pressure. This fluid off-flow discharge angle is approximately 4.5°-11.5° for flows between 3-12 LPM@2100 RPM for an impeller with a 20-90° outflow vane angle ($\beta_2$).

The reduced throat area height also reduces the cutwater wall height, and thus volume of separation downstream of the cutwater tongue at these higher flows, and thus reduced influence of throat blockage by this cutwater/flow velocity incidence mismatch. At part (significantly reduced) flows, the volute angle and thus flow incidence has a larger mismatch, which causes more recirculation volume upstream the cutwater tongue (between the impeller and the cutwater) as well as at the outer wall of the throat, leading to retarded pressure generation. Reducing the throat area width (and consequently the volute angle) by reducing the diameter of the outer wall OD3 maintains pressure at part flows hence steepening the curve and exhibiting a larger shutoff pressure. The reduction in volute angle in this case matches the off-flow angle at part flows better, and thus reduces the separation and thus recirculation volume at both the cutwater and volute outer wall at part flows. It was found that increasing the AR>1.4-1.6 had minimal effect on creating a flatter pump performance curve.

In the case of the right volute of the right pump, it is a concentric/circular volute, hence the volute angle is always 0°. As shown in FIG. 5J, as the throat area width increases, shutoff pressure decreases and the curve is flatter. This observation breaks down as the aspect ratio AR>0.65, whereby the height (and corresponding vane height) is reduced below 17.5 mm which reduces the ability for the impeller to create pressure over all flow rates. Therefore widths lower than 11.40 mm start to choke flow >11 LPM, whilst at widths higher than 11.40 mm (and corresponding height reduced) head pressure suffers. Hence, an aspect ratio AR of −0.65 is ideal for a 200 mm² throat area $A_{th}$.

A number of different throat areas and geometries were trialed, and results are shown in FIGS. 5K to 5N, with the throat area geometry being expressed as a width and height. In these cases, the throat area Ath was varied and either width or height was kept constant.

Figure 5K:
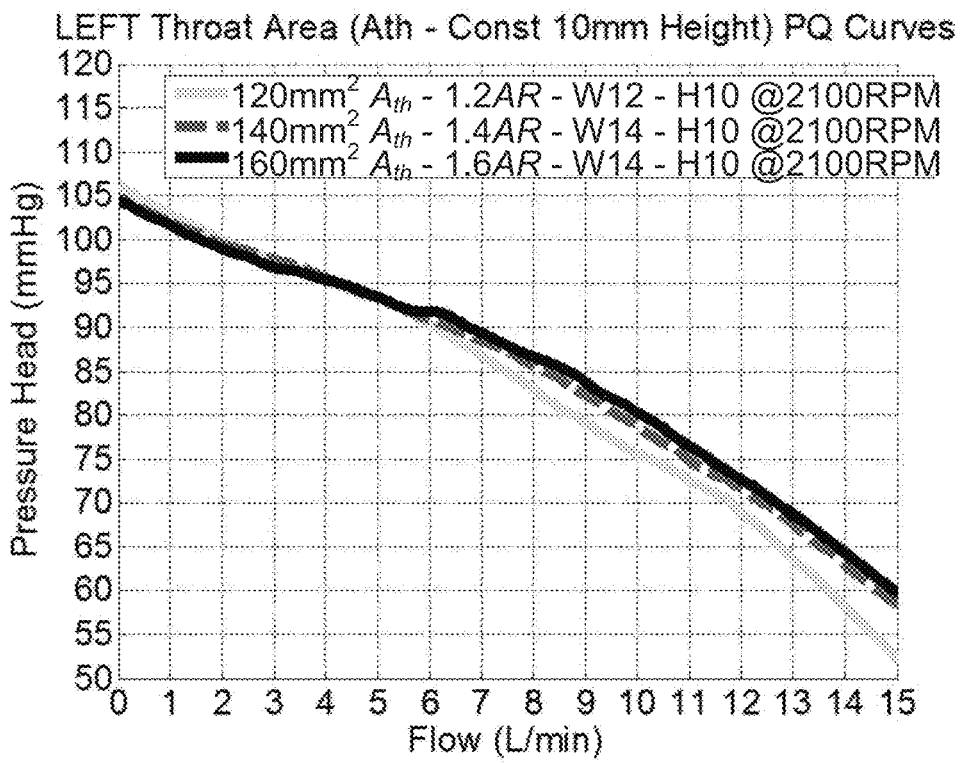
FIG. 5K is a graph showing an example of changes in left pump curve for different outlet throat areas for a constant throat height.
Figure 5L:
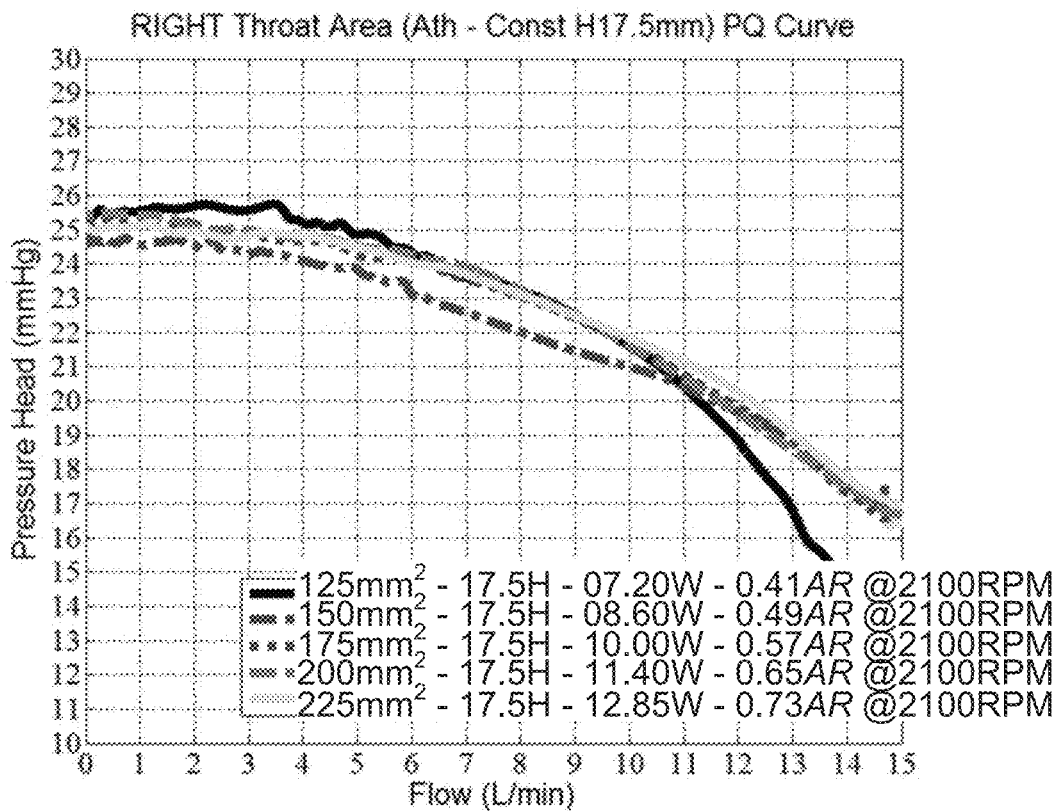
FIG. 5L is a graph showing an example of changes in right pump curve for different outlet throat areas for a constant throat height.
Figure 5M:
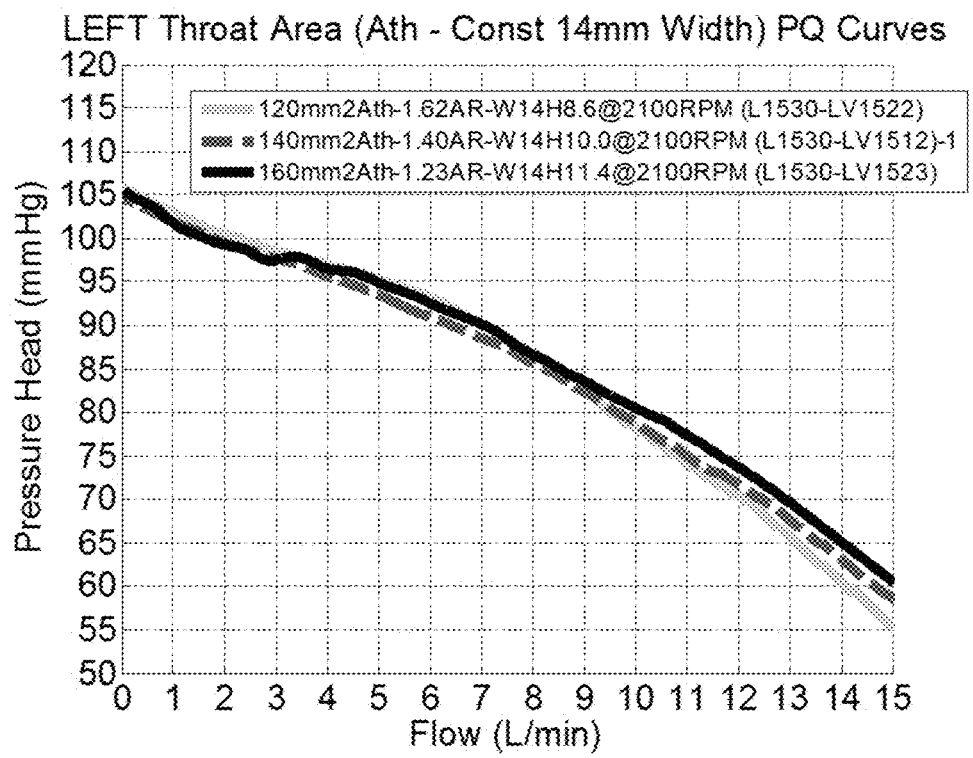
FIG. 5M is a graph showing an example of changes in left pump curve for different outlet throat areas for a constant throat width.

For the left pump, as shown in FIGS. 5K and 5M, increasing the volute outer diameter and hence the throat area width (and thus volute angle) whilst maintaining throat height retards the ability to generate pressure at part flows due to the greater degree of separation of recirculating fluid at both the cutwater tongue and outer wall of the throat. Resistance to flow is reduced at high flows, leading to a flatter curve as width and throat area $A_{th}$ is increased. A marginal difference was observed for a throat area $A_{th}$ above 140 mm² for the left pump.

Figure 5N:
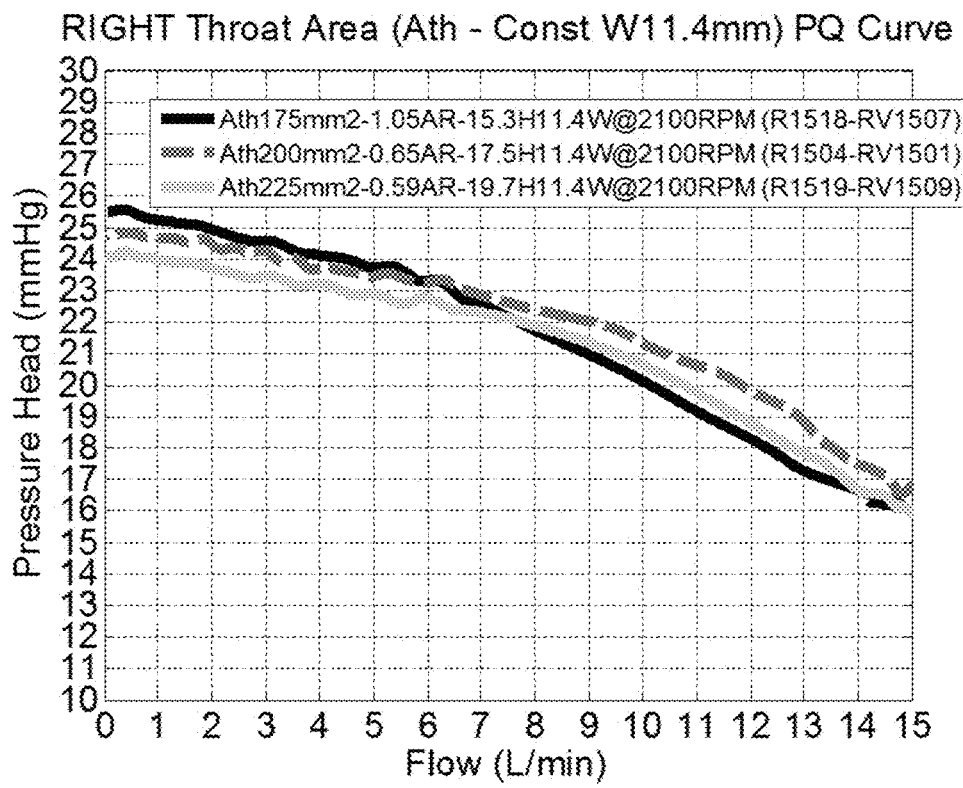
FIG. 5N is a graph showing an example of changes in right pump curve for different outlet throat areas for a constant throat width.

For the right pump, shown in FIGS. 5L and 5N, a similar observation was made, whereby performance did not alter much between all throat areas $A_{th}$ when height was maintained at 17.5 mm until below 150 mm². Hence allowing for a smaller throat area $A_{th}$ of 150 mm²-175 mm² for the right pump, results in a 8.6 mm-10 mm throat width. This in turn assists in passing the right pump outlet between the magnetic bearing components, which can in turn have a larger size.

In contrast, increasing the throat area $A_{th}$ by maintaining the width (and thus volute angle) and increasing the height had a more pronounced effect on pressure generation and pump curve gradient.

For the left pump, identical shut off pressures were generated at each throat area $A_{th}$, however increasing the throat area $A_{th}$ leads to an increase in generated pressure at high flows due to reduced resistance and thus results in a flatter pump curve. For the right impeller, shutoff pressure was found to decrease as throat area $A_{th}$ increased by increasing height and maintaining width, whilst more pressure was generated at high flows, due to a reduction in resistance. Detrimental performance was observed when increasing the throat area $A_{th}$ above 200 mm² and corresponding to a height above 17.5 mm.

Finally, for a constant throat area of 140 mm², a number of different left pump throat area locations were trialed, with the throat area location being expressed in relation to an inner (base circle diameter—BCD) and outer throat area wall diameter (OD3), compared to the pump cavity as a whole.

Figure 5O:
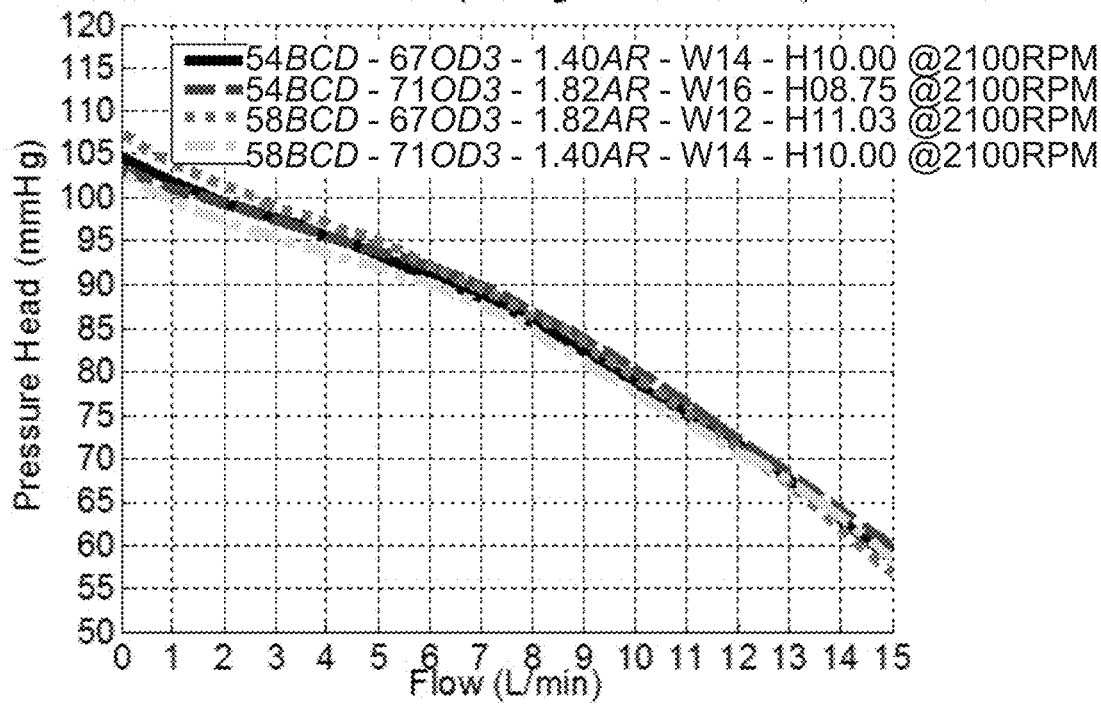
FIG. 5O is a graph showing an example of changes in left pump curve for different outlet throat radial position.

As shown in FIG. 5O, each arrangement has a generally similar gradient, particularly at high flows. However as already observed, as the throat width W reduced, shutoff pressure increased leading to a steeper gradient. Maintaining the throat width (and thus volute angle) by increasing both the base circle diameter BCD and outer wall diameter OD3 resulted in similar pressure generation at high flow, but retarded pressure generation at part flows. Since a larger base circle diameter BCD increases recirculation area between the cutwater and the impeller, flow does not need to decelerate as much at part flows, hence less kinetic energy is converted to pressure. Since the width W is the same, the amount of recirculation adjacent the throat outer wall is similar, so the reduction in pressure is due to the cutwater recirculation.

Increasing the base circle diameter from 54 mm to 58 mm whilst maintaining the outer wall diameter at 71 mm (thus reducing both width and volute angle but increasing height) reduces the generation of pressure at part flows due an increase in the recirculation area downstream of the cutwater.

The larger base circle diameter BCD allows for fluid to recirculate past the cutwater with a lower velocity at part flows (but still higher velocity than that in the throat area) and thus less acceleration, hence less pressure losses (meaning lower radial force at part flows, as described later) and thus more pressure generated at shut off. However this means the pump curve is slightly steeper.

Increasing the outer wall diameter OD3 from 67 mm to 71 mm whilst maintaining the BCD slightly improves pressure generation at high flows. Additionally, increasing the outer wall diameter OD3 helps to generate this pressure at high flows due to the larger volute angle created and hence closer match to the impeller off flow angle at high flows.

The width was therefore determined as a major contributing factor for altering the pump curve gradient, with larger widths returning flatter curves. Coupling this with larger base circle diameter BCD further reduced pressure generation at part flows and thus flatten the curve further.

Taking the above into account, for a left hand pump, the outlet 112 typically has a substantially rectangular cross-sectional shape and a width to height aspect ratio of at least one of between 1:2 and 2:1, between 1:1 and 2:1, between 1:1 and 1.8:1, between 1.1:1 and 1.6:1 and approximately 1.4:1. The base circle diameter at the throat is typically at least one of at least 50 mm, less than 100 mm, less than 80 mm, between 50 mm and 74 mm, between 54 mm and 64 mm, and approximately 60 mm. The outer wall diameter at the throat is typically at least one of at least 40 mm, less than 100 mm, less than 80 mm, between 50 mm and 80 mm, between 65 mm and 76 mm, and approximately 71 mm. It will be appreciated that these values are in respect of a 50 mm rotor, and that smaller diameters would be required for smaller diameter rotors. Thus, in general the base circle diameter at the throat is between 108% and 125% of the rotor diameter and the outer wall diameter is between 130% and 160% of the rotor diameter.

In one preferred example, for the left pump the throat aspect ratio (width:height) is at least 1.4:1, the throat area is at least 150 mm², the base circle diameter is not greater than 120% of the rotor diameter and the outer wall diameter is at least 130% of the rotor diameter.

In one example, for a right hand pump, the outlet 114 typically has a substantially rectangular cross-sectional shape and a width to height aspect ratio of at least one of between 1:3 and 1:1 and approximately 0.45-0.65:1. The cavity typically has a diameter of a least one of at least 20 mm, at least 25 mm, less than 40 mm, less than 30 mm, between 27 mm and 29 mm and, approximately 28 mm. These values are in respect of a 24 mm-25 mm diameter rotor, so that the right cavity diameter is approximately 112%-116% of the cavity diameter.

In one preferred example, for the right pump, the throat aspect ratio (width:height) is between 0.45:1 and 0.65:1, the throat height is about 17.5 mm, the throat area is at least 150 mm², and more typically about 175 mm², and the base circle diameter is about 28 mm. The larger the BCD, the more space for rotor radial displacement before potential touchdown, however the least space for magnetic bearing components, hence an optimum of 28 mm was reached for this embodiment.

Figure 5P:
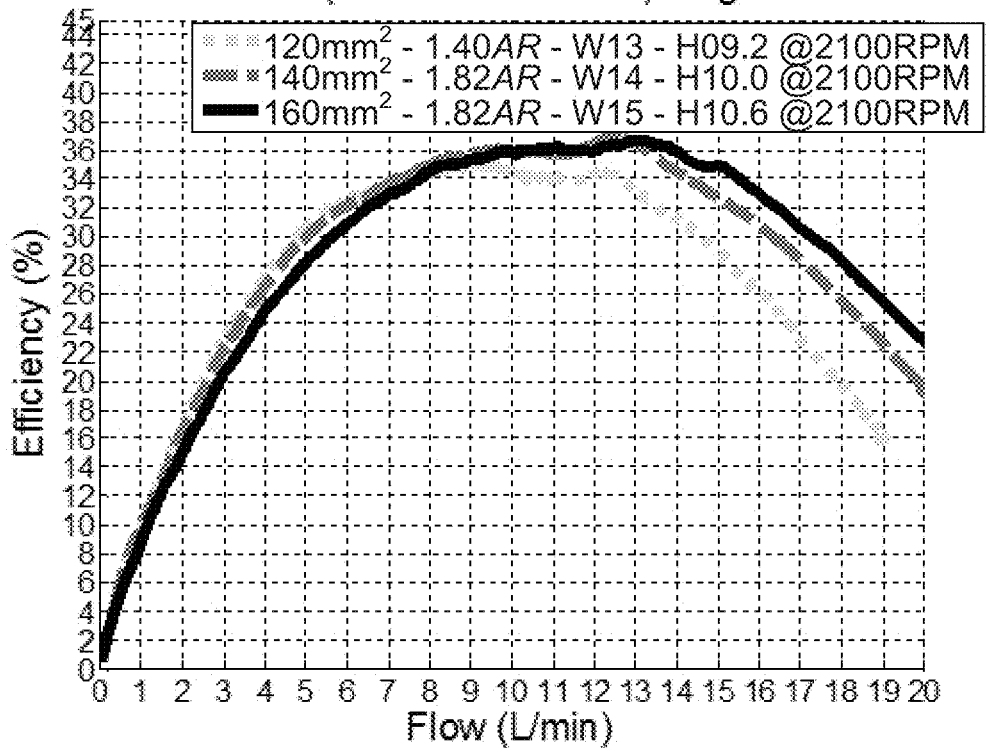
FIG. 5P is a graph showing an example of changes in left pump efficiency for different outlet throat areas for a constant throat aspect ratio.

Choosing the best efficiency point BEP to be at the higher end of the expected operating range (9-12 LPM), as shown in FIG. 5P, by selecting a larger throat area maintains a flatter curve for the intended operating range of 3-12 LPM, which is counter to traditional arrangements in which the BEP is typically set at mean blood flows for the subject of about 5-6 LPM, corresponding to a resting condition, thereby minimising the average energy usage over the entire operating flow range.

It should be noted that whilst the configurations that produce the flatter curves may cause recirculation eddies at low flows, these can be counteracted with regular impeller speed modulations to increase flow to at least BEP flow each cycle to completely wash out any recirculation eddies.

Figure 6A:
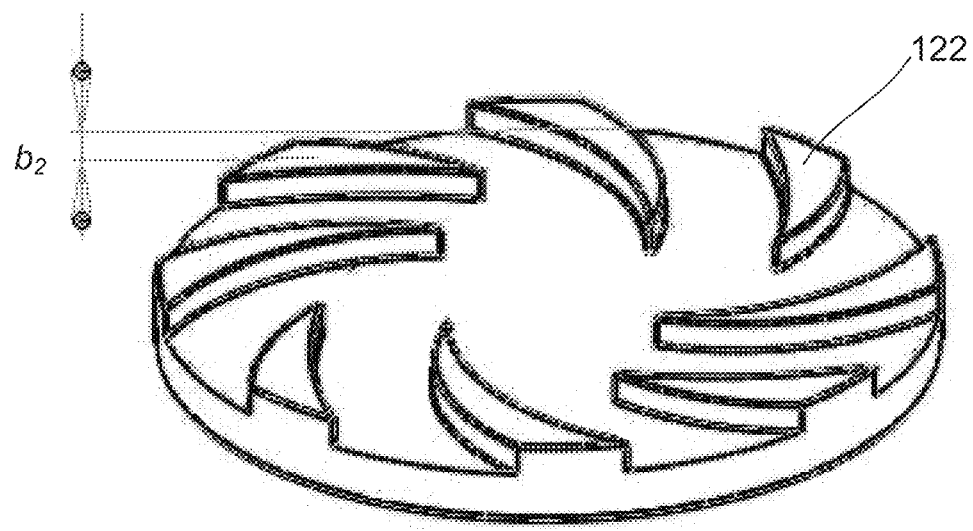
FIG. 6A is a schematic perspective view of an example of the left side impeller showing a vane height.
Figure 6B:
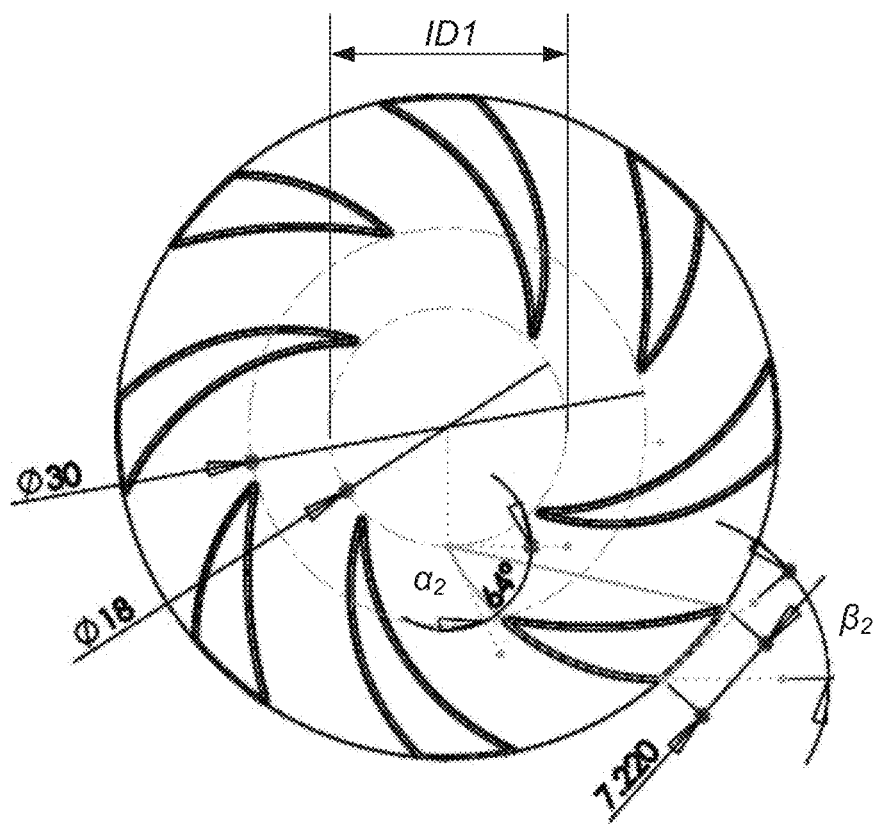
FIG. 6B is a schematic plan view of the left side impeller of FIG. 6A showing vane dimensions.
Figure 6C:
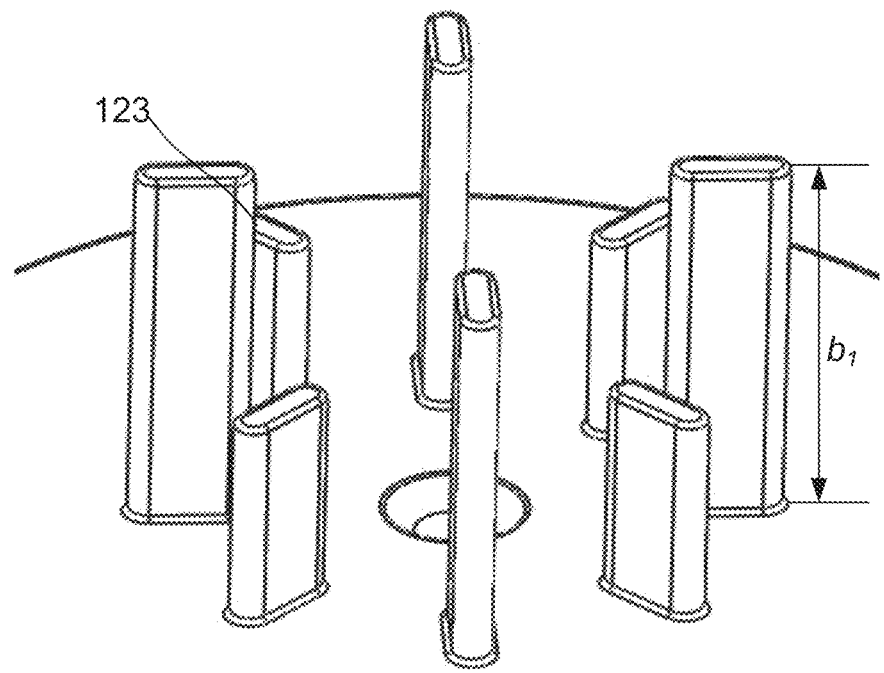
FIG. 6C is a schematic perspective view of an example of the right side impeller showing a vane height.
Figure 6D:
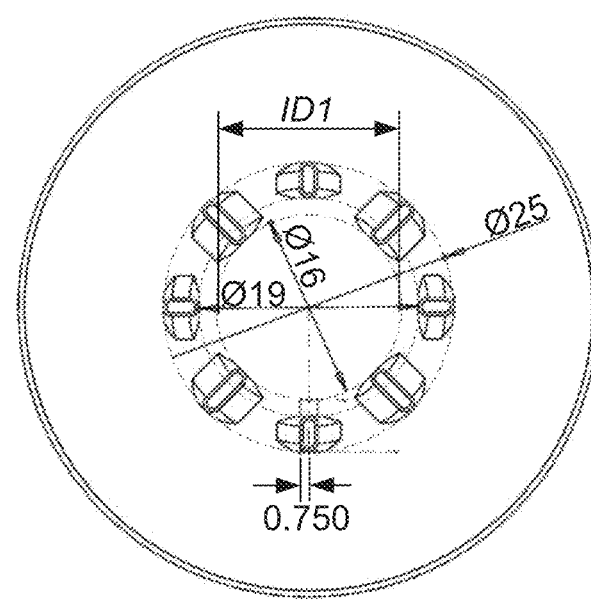
FIG. 6D is a schematic plan view of the left side impeller of FIG. 6C showing vane dimensions.

Additionally, the cross-sectional flow area through the pump is influenced by the impeller inner eye diameter ID1 of the impeller, shown for the left and right hand pumps in FIGS. 6B and 6D respectively, and vane height, shown as $b_2$ and $b_1$ in FIGS. 6A and 6C, for the left and right pumps, respectively. In general, a larger inner diameter for a given vane height results in a larger cross-sectional area flow path. Similarly, a larger vane height for a given impeller inner eye diameter ID1 results in a larger cross-sectional area flow path. Increasing the flow path area generally reduces resistance and produces a greater efficiency for the same rotational speed.

Figure 6E:
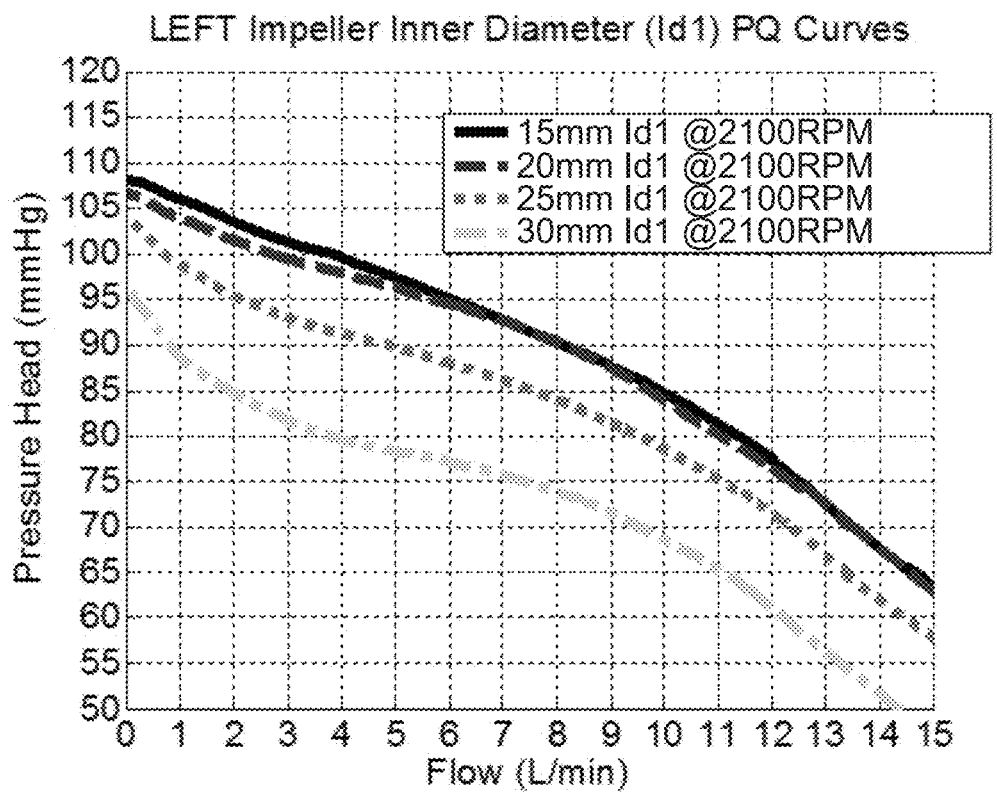
FIG. 6E is a graph showing an example of left pump curves for different impeller eye diameters.
Figure 6F:
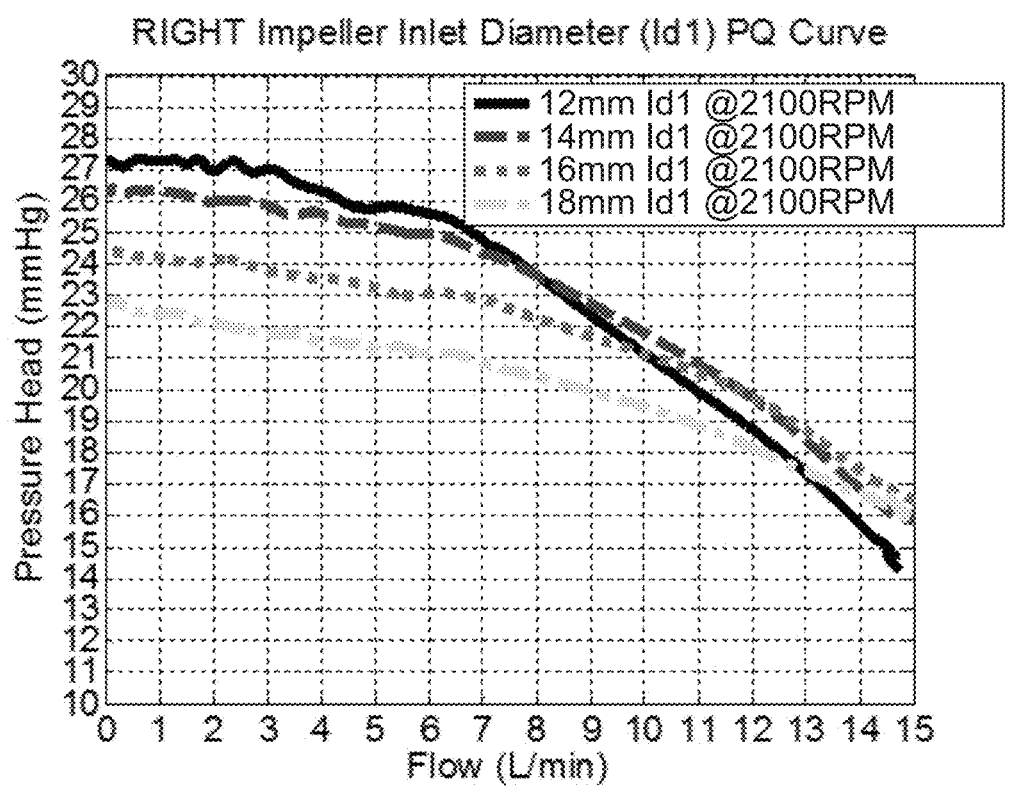
FIG. 6F is a graph showing an example of right pump curves for different impeller eye diameters.

An example of the impact of impeller inner eye diameter ID1 will now be described with reference to FIGS. 6E and 6F.

Increasing the inner eye diameter for a given vane height results in a larger flow path area and reduced resistance to flow (especially high flow) but at the expense of a reduction in Euler pressure generation at a given RPM (Stepanoff, A. J. 1957). That is, a larger diameter increases vane circumferential velocity $u_1$ at the inner diameter and the flow area is greater and hence meridonial inlet velocity $c_{m1}$ is lower, thus reducing the theoretical head over all flows. However this has a greater influence at lower flows, whereby the fluid inlet velocity is larger since the meridonial inlet velocity $c_{m1}$ is smaller, but impeller circumferential velocity to is the same (and vane inlet angle $\beta_1$ is fixed). Hence the shutoff pressure is lower and pump curve is flatter at low flows. Furthermore, the inlet vane incidence mismatch is greater at larger diameters due to this larger circumferential velocity, leading to a rapid reduction in pressure generation as soon as forward flow begins to develop. For the purpose of these experiments, the inlet vane angle $\beta_j$ was kept constant at 64°, thus at these larger diameters, the mismatch of incidence angle effectively replicates a larger inlet angle (at a smaller diameter) and as such greater mismatch especially at low flows. As flow rate increases, the incidence mismatch decreases, hence pressure is generated and the pump curve becomes flatter. Pressure generation is also maintained at high flows with increasing ID1 due to the larger inlet flow areas and hence lower flow resistance.

In this regard, an impeller eye diameter ID1 of 20 mm, for a vane height of 2 mm gives a fluid inlet area through the vanes of 125.6 mm². In contrast, for a 25 mm-30 mm impeller eye diameter ID1, the area becomes 157 mm²-188.4 mm² respectively.

Increasing the impeller inner diameter ID1 is most effective at both flattening the pump curve and also reducing the pressure generation at a given rotational speed. This characteristic is observed whenever the impeller inlet diameter ID1 exceeds the pump inlet diameter D1, and can be utilised to great effect when attempting to create the preferred left/right design pressure ratio. Furthermore, the resultant larger impeller inlet area provides an easier passage for systemic venous emboli to pass, and also reduces flow velocities and thus shear stresses in this region.

Accordingly, a preferred impeller eye diameter ID1 for the left pump is in the region of 25-30 mm (for an inlet port diameter of 20 mm), but may be up to 40 mm and as little as 10 mm.

For the right pump, increasing the impeller eye diameter ID1 results in a reduction of shutoff pressure, whilst reducing below 14 mm chokes flows above 6 LPM, resulting in a steep curve at high flows (flow at the outer circumference enters the top of the spinning vanes).

Accordingly, for the right pump the impeller eye diameter ID1 is typically selected to be 16-18 mm (for an inlet port diameter of 18 mm), but can be as low as 10 mm and as high as 20 mm.

Figure 6G:
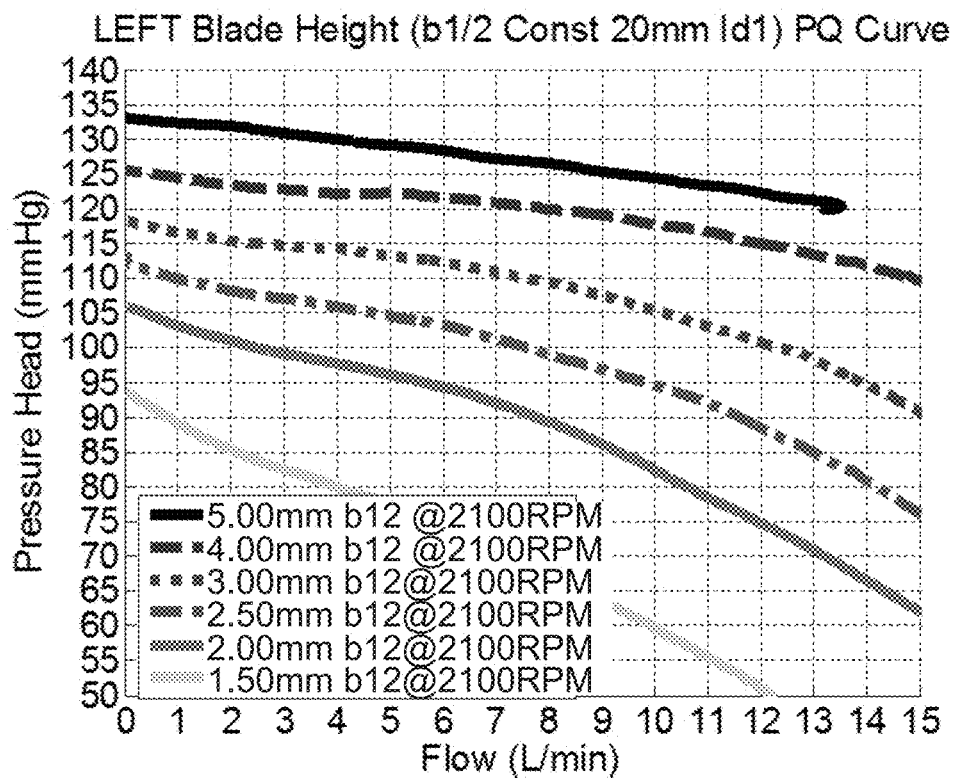
FIG. 6G is a graph showing an example of left pump curves for different impeller left vane heights.
Figure 6H:
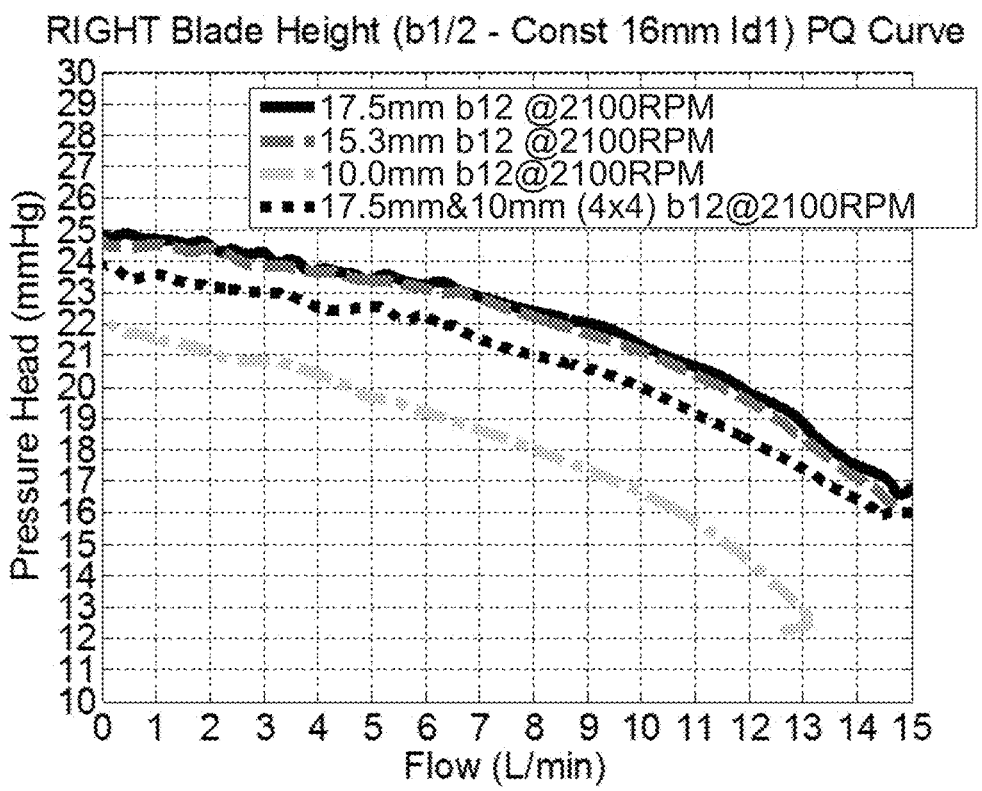
FIG. 6H is a graph showing an example of left pump curves for different impeller right vane heights.

An example of the impact of vane height will now be described with reference to FIGS. 6G and 6H, which show pump curves for different vane heights for the left and right pump respectively.

Figure 6I:
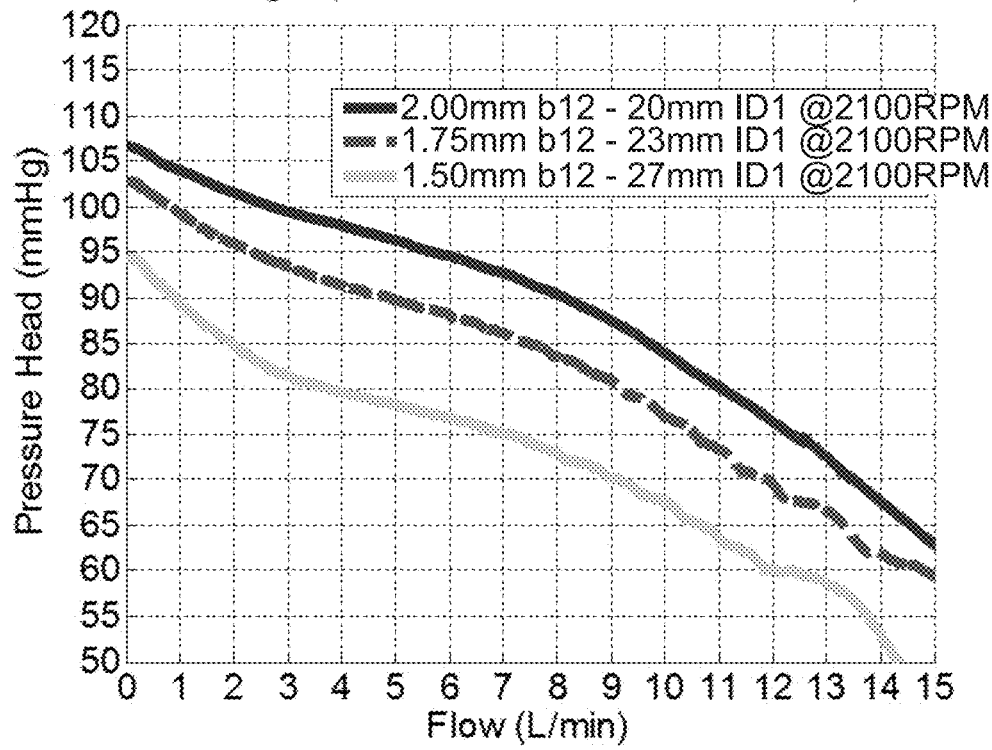
FIG. 6I is a graph showing an example of left pump curves for different impeller left vane heights with constant inflow area.

Increasing the impeller vane height (whilst maintaining impeller inlet diameter) results in a larger flow path area and reduced resistance to flow (especially high flow), without the consequent reduction in Euler pressure generation. In fact, the reduction in meridonial inlet velocity $c_{m1}$ caused by increasing the vane height assists in developing pressure by reducing the '$u_1 \times c_{u1}$' term of the Euler equation. Hence, as can be seen in FIGS. 6H and 6I, increasing vane height also raises pressure over all flow rates. The reduced radial flow velocity caused by an increased height also exacerbates the inlet vane angle mismatch, particularly at low flows, thus also contributing to a flatter pump curve.

Major changes to the gradient were observed in the left impeller when height is reduced below 2.0 mm, thus this vane heights are in a suitable range for the left side TAH application due to its pressure generation being in the range required to produce the designed left/right design pressure ratio. A 4.0 mm vane height suits the VAD application since only minor changes in gradient were observed with larger heights. These larger heights require a special motor design to maintain high efficient operation at relatively large magnetic airgaps. A vane height of 15-17.5 mm is suitable for the right side TAH application. Since minor performance improvements were observed with larger heights, a 15 mm height allows venous emboli to pass the top of the vanes.

Additionally, as shown in FIG. 6I, by increasing the impeller eye diameter ID1 and reducing the vane height to maintain an inlet area of 125 mm$^2$ and outlet area of 194 mm$^2$, the effect of flow choking for heights smaller than 2.0 mm is mitigated, hence all PQ curve gradients are similar at high flows. As already observed, a larger impeller eye diameter reduces the overall Euler pressure, especially at low flows, leading to a flatter pump curve.

In general terms, pressure at high flows can be raised by increasing the vane height and thus reducing resistance to flow, and pressure at low flows can be reduced by increasing the impeller inner diameter to values larger than the inlet port diameter, thus leading to a flatter pump curve. However, it should also be noted that an increased vane height reduces the axial pressure sensitivity (especially when the impeller eye diameter ID1 is maintained), as will be described in more detail below.

As axial pressure sensitivity is more important for the left hand pump in the TAH application, the resulting vane height is significantly reduced. Consequently, for the left pump for the TAH application, the vane height is at least 1.0 mm, but less than 5 mm, between 1.3 mm and 3 mm, between 1.5 mm and 2.5 mm, between 1.7 mm and 2.3 mm and approximately 2.0 mm In contrast for the right pump has a vane height of at least one of at least 10 mm, less than 30 mm, between 15 mm and 20 mm, between 17 mm and 18 mm and approximately 17.5 mm Impeller Inlet/Outlet Vane Angle/Volute Cutwater Angle Losses due to flow vector and impeller vane/volute cutwater incidence angle mismatch is minimal at the BEP, which results in minimal recirculation and eddies in the vicinity of the inlet vanes and cutwater, as shown in FIG. 4D, which increase above and below BEP. Blockage due to incidence separation at the impeller inlet occurs at flows either side of the flow rate and impeller speed for which they are designed. Blockage and separation at the cutwater tongue increases above BEP as fluid separates downstream of the cutwater, hence contributing to a reduced effective throat area, greater fluid acceleration and thus reduced pressure generation. A larger volute cutwater angle will increase the flow rate for which downstream separation will occur at the cutwater, whilst at the same time, will increase the separation upstream of the cutwater at lower flows below the design point. Both of these effects lead to a flatter pump curve as seen above (larger aspect ratio and thus larger volute angle leads to a flatter curve). Vane outlet angle affects also pressure generation as flow rate increases, and thus pump curve gradient, since $V_{m2}$ increases for a larger flow and thus $c_{u2}'$ reduces, leading to a lower Euler pressure. This characteristic is even more pronounced as outlet angle is reduced, meaning that the pump curve gradient steepens as outlet angle reduces.

Selection of the impeller vane inlet angle alters the gradient of the pump curve due to separation and blockage mentioned above. Furthermore, the higher the vane inlet angle, the larger the $c_{u1}'$, and thus the lower the Euler pressure that is generated (Stepanoff, A J., 1957), particularly at low flows since the incidence on the inlet angle is most deviated from the design flow for a larger angle. However the larger the angle, the reduced resistance to flow through the pump, which dominates.

Figure 6J:
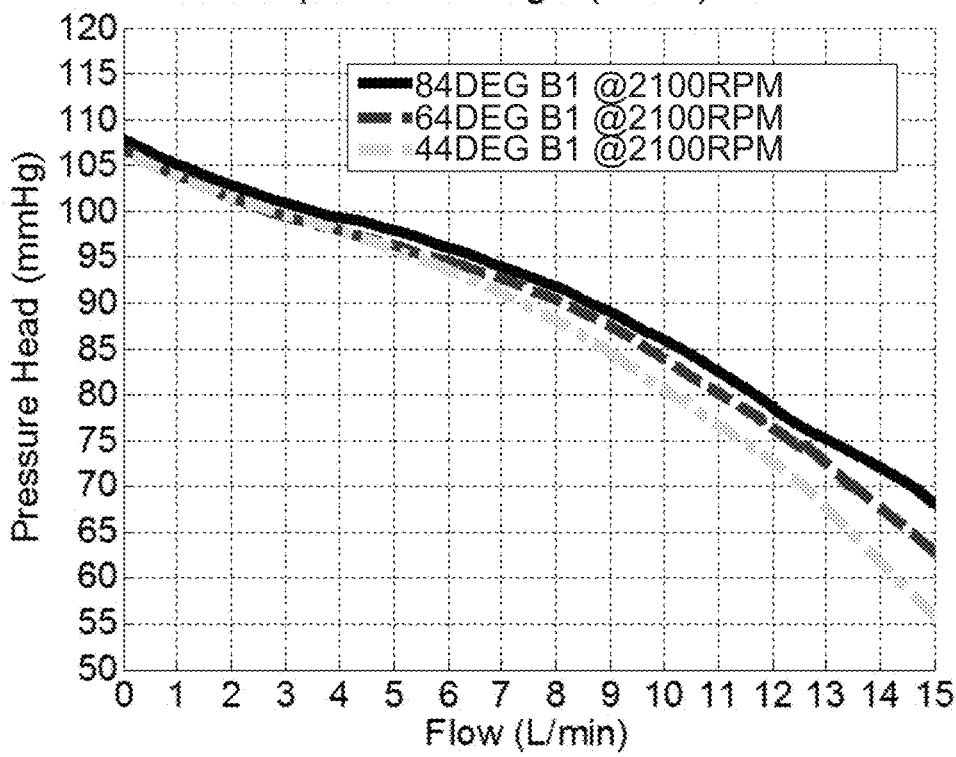
FIG. 6J is a graph showing an example of left pump curves for different impeller left vane inlet angles.

An example of the impact of vane inlet angle on the left pump is shown in FIG. 6J. From this it is apparent that increasing the vane inlet angle from 64° to 84° creates marginally more pressure over all flows, and a flatter curve, due to reduced resistance, especially at higher flows above 4 LPM. A smaller inlet angle appears to choke flow after 4 LPM due to excessive flow path blockage due to a mismatched incidence angle which creates a steeper pump curve.

To utilize the effect of inlet angle on shaping the pump curve to be flatter, the left pump vanes have an inlet angle of at least one of less than 90°, greater than 60°, between 80° and 90°, between 82° and 86° and approximately 84°.

Figure 6K:
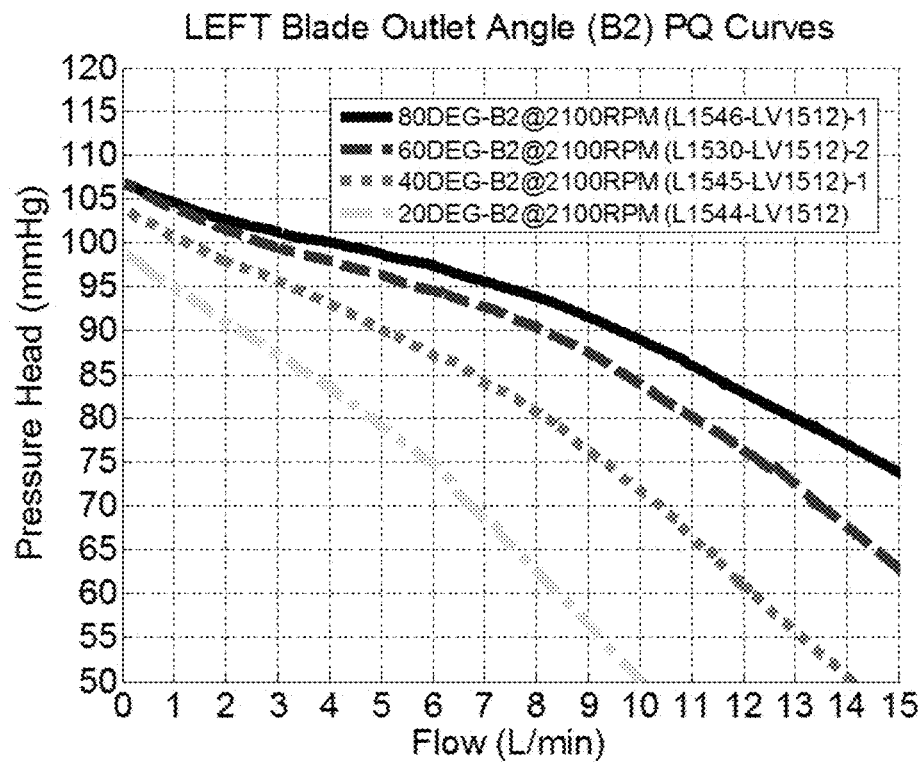
FIG. 6K is a graph showing an example of left pump curves for different impeller left vane outlet angles.

For reasons explained above, a larger outlet vane angle leads to a flatter pump curve gradient. An example of this effect of left vane outlet angle $\beta_2$ is shown in FIG. 6K.

Figure 6L:
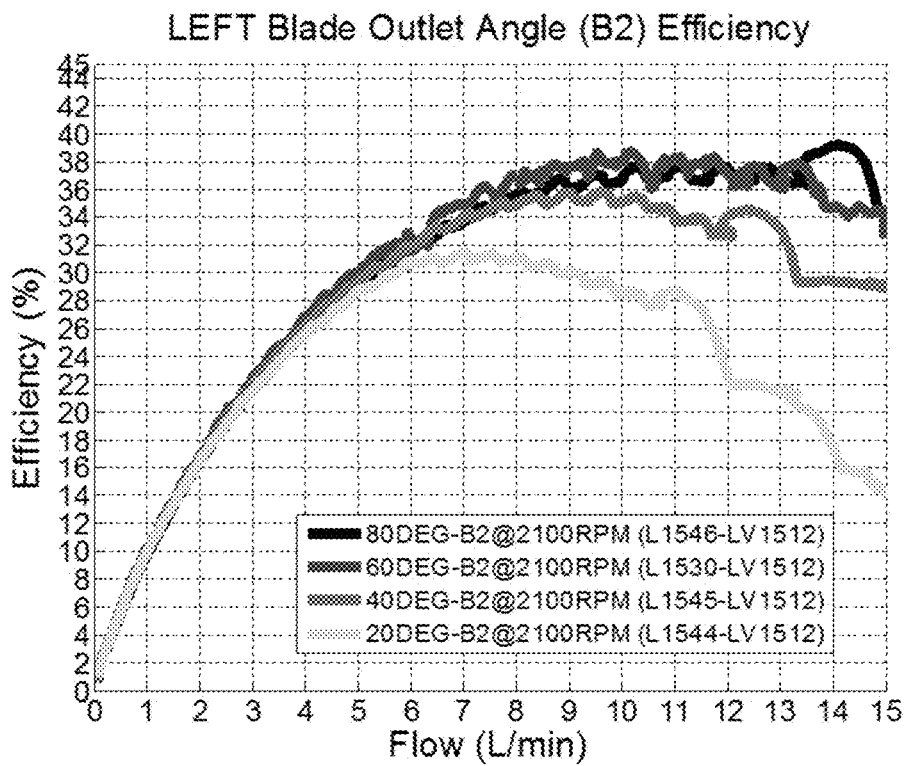
FIG. 6L is a graph showing an example of left pump efficiency for different impeller left vane outlet angles.

For a set vane height of 2.0 mm and thus for impeller inlet and outlet flow passages of 125 mm$^2$ and 194 mm$^2$ respectively, reducing vane outlet angle significantly disrupts pressure generation and thus steepens the PQ curve gradient. The difference between 80° (−2 mmHg/LPM) and 60° (−2.5 mmHg/LPM) in terms of gradient between 5-10 LPM is however, minimal. Efficiency is also comparable as shown in FIG. 6L. Performance and efficiency of the 20° vane impeller is worse than the other configurations, however this result is indicative of an axial gap above the vane tips of 500 μm. When this gap is reduced to 100 μm, the shutoff pressure and efficiency is comparable, albeit at a steep gradient. This drastic alteration in performance returns an amplified APS.

Figure 6M:
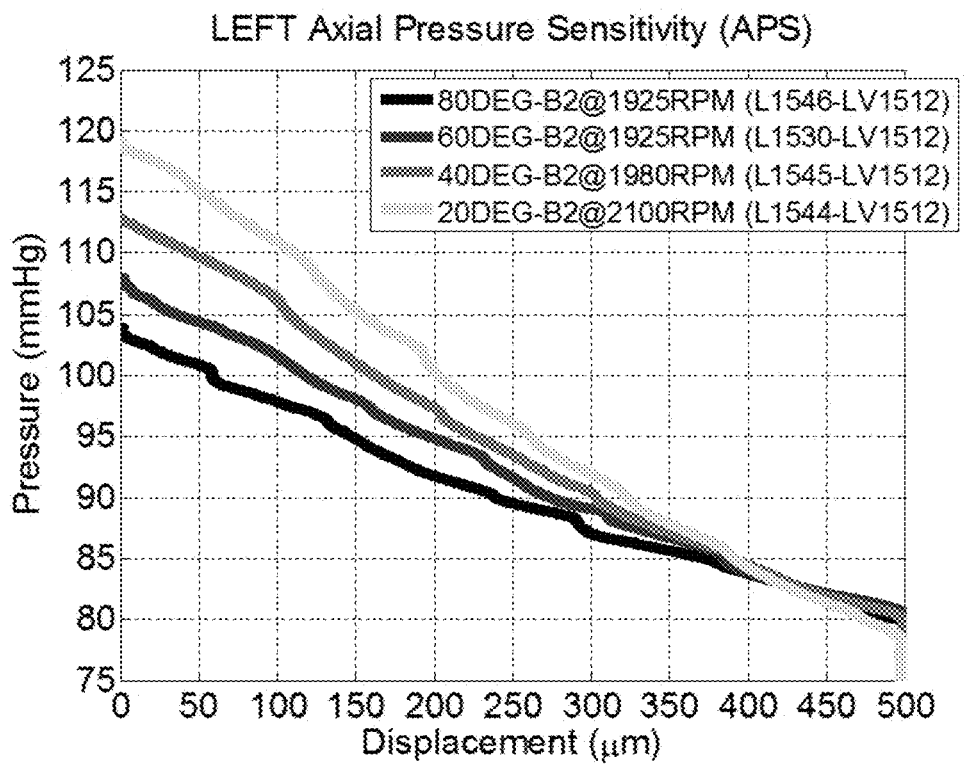
FIG. 6M is a graph showing an example of left pump axial pressure sensitivity curves for different impeller left vane outlet angles.

The axial pressure sensitivity is shown in FIG. 6M, which shows that the generated pressure is reduced by 3 mmHG for 60° vanes@6 LPM, so 80° outlet angle should be selected for flattest curve. The 20° vanes create the highest axial pressure sensitivity over the 500 μm range, which can be explained by the additional leakage transiting over the impeller vanes causing an opposition to the main forward flow.

Thus, this demonstrates that increasing vane angle $\beta_2$ flattens the pump curve and increases efficiency at a 500 μm gap but decreases axial pressure sensitivity. Accordingly, for the left hand pump, where some axial pressure responsiveness is desirable, the impeller has a vane outlet angle of at least one of less than 60°, greater than 20°, between 30° and 50°, between 35° and 45°, between 38° and 42° and approximately 40°.

Figure 6N:
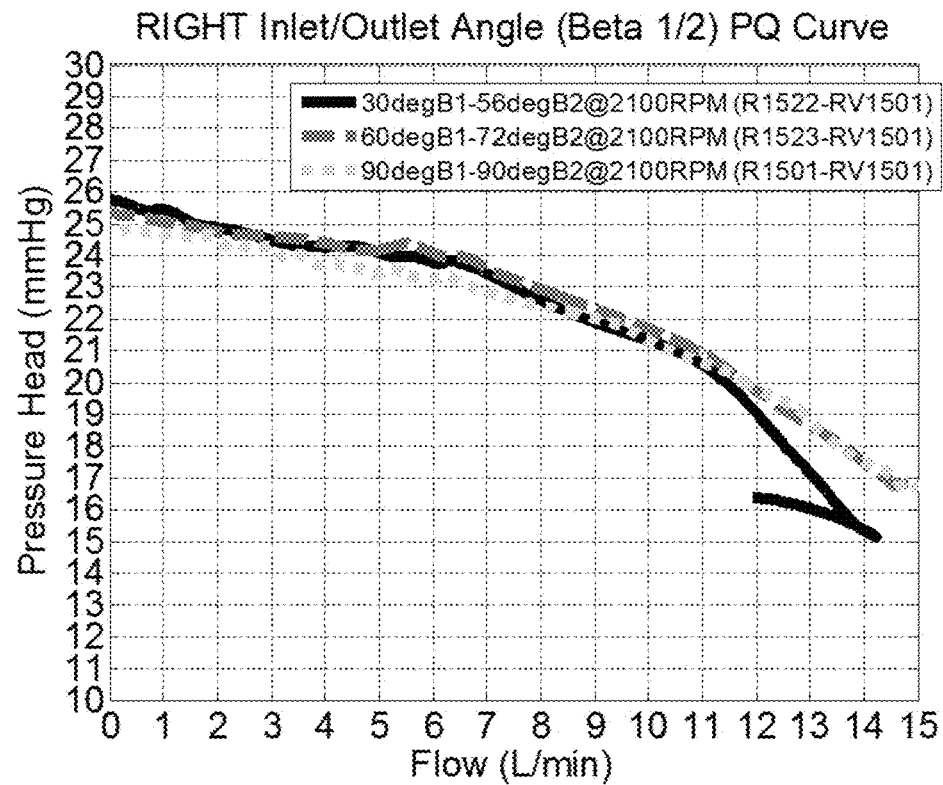
FIG. 6N is a graph showing an example of right pump curves for different impeller right vane inlet/outlet angles.

An example of the impact of vane inlet angle on the right pump is shown in FIG. 6N. The lower the vane inlet/outlet angle, the higher the shutoff pressure and lower the maximum flow pressure. The arrangement with a 60° inlet angle and 72° vane outlet angle creates 0.5 mmHg more pressure@6 LPM and otherwise performs very similar to an impeller with 90° inlet and outlet angles and thus an acceptable vane inlet angle would be between 60°-90° for the right pump.

Thus, in contrast, for the right hand side impeller, a greater pressure sensitivity and thus flatter pump curve is desired whilst axial pressure sensitivity is less required, hence vane angle, and in particular both inlet and outlet vane angle are maximised. Accordingly, the right side impeller has a vane inlet angle $\beta_1$ of at least one of greater than 75°, less than 115°, between 80° and 100° and approximately 90° and a vane outlet angle $\beta_2$ of at least one of greater than 75°, less than 115°, between 80° and 100°; and approximately 90°.

It will also be appreciated from the above that the cutwater angle can heavily influence flow within the pump and hence the shape of the pump curve. In one example, for the right pump, the cutwater angle CW$_2$ shown in FIG. 5F is at least one of between 90° and 180°; between 90° and 135°; between 0° and 90°; between 45° and 90°; between 45° and 135°; between 60° and 80°; and approximately 70°. In one example, for the left pump, the cutwater angle CW$_1$ shown in FIG. 5D is at least one of between 0° and 70°; between 30° and 50°; between 40° and 45°; between 35° and 45°; between 45° and 50°; between 0° and 60°; and approximately 45°.

Impeller Recirculation/Slip

Figure 6O:
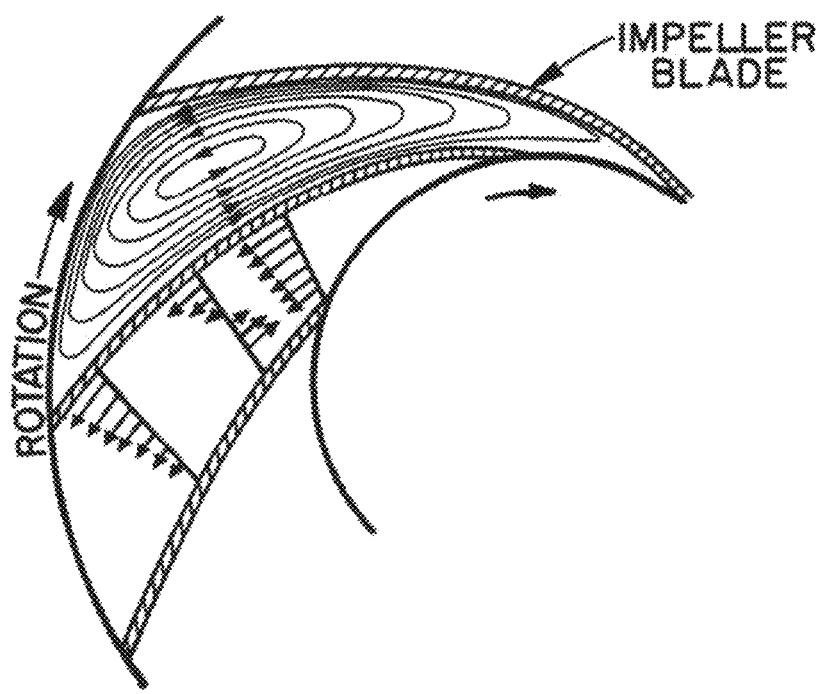
FIG. 6O is a schematic diagram showing flow recirculation behind an impeller.

Impeller recirculation/slip arises due to recirculating flow between the high pressure leading face of the impeller vane and the low pressure training edge of the next vane, creating a relative eddy, as shown in FIG. 6O, resulting in a decrease in pumping efficiency and hence flow.

Vane Number

Figure 6P:
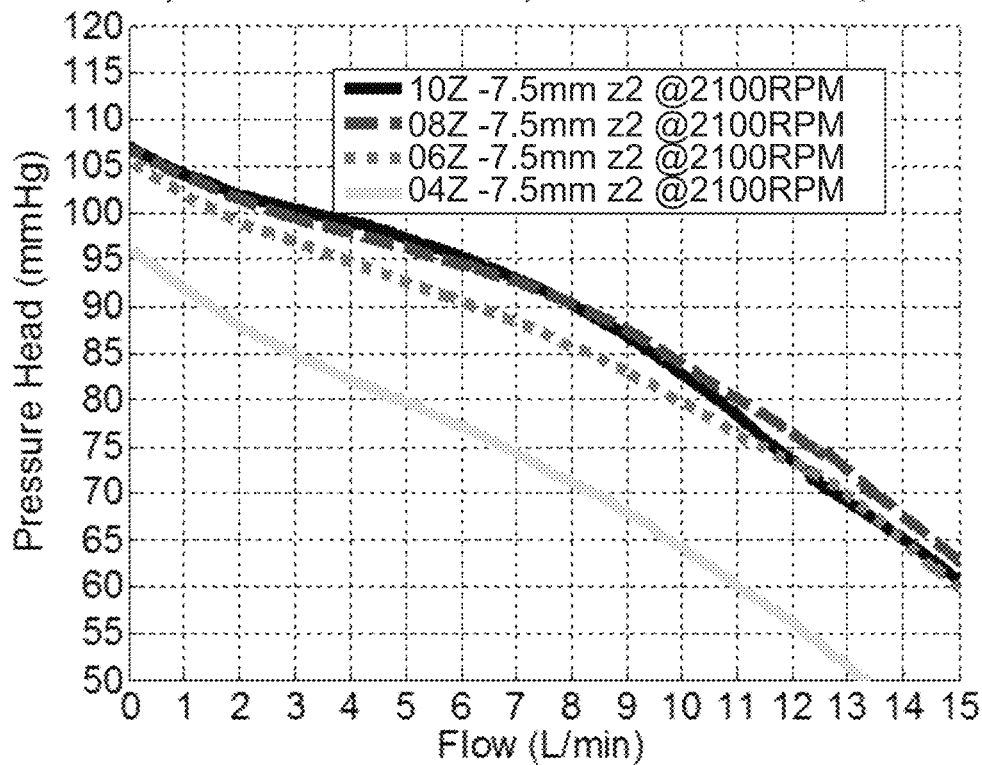
FIG. 6P is a graph showing an example of left pump curves for different numbers of impeller vanes.
Figure 6Q:
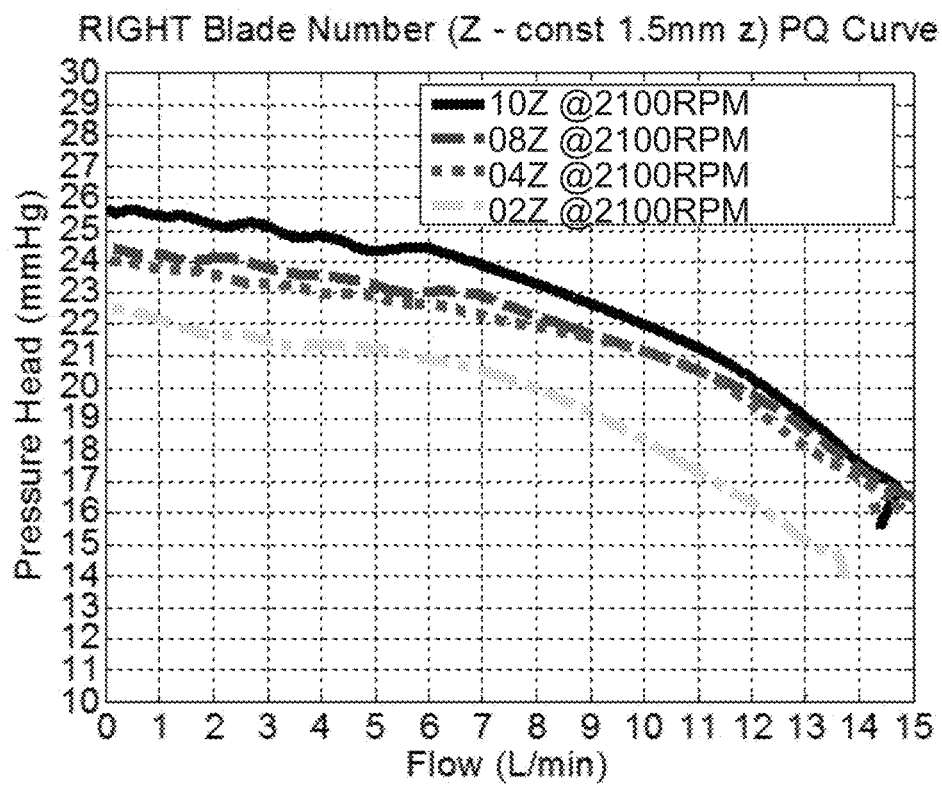
FIG. 6Q is a graph showing an example of right pump curves for different numbers of impeller vanes.

Impeller recirculation/slip depends on the physical barrier provided by the vanes. The number of vanes can lead to an alteration of impeller recirculation/slip magnitude. Examples of this are shown for the left and right pumps in FIGS. 6P and 6Q, respectively.

For the left pump, when the vane width is maintained and more vanes are added, the effect on P/Q and efficiency of adding more vanes than eight is not significant. However, pressure (at 500 μm) suffers when less than eight vanes are used, and is significantly disrupted when less than six vanes are used. Although more vanes provide more pressure generation, this is offset by the increased flow resistance caused by blockage, especially at high flows.

For the right pump six vanes and eight vanes perform similarly, whilst four vanes have poor performance. Increasing the number of vanes to ten increases pressure generated at 6 LPM by ~1 mmHg but max flow pressure is the same as six and eight (thus the gradient is steeper)

Thus the larger the vane number, the greater the pressure generation, leading to a flatter pump curve when impeller outlet area is maintained (by altering the outlet vane thickness $z_2$). However when the area is not maintained, as shown in FIG. 6R, the pressure generating benefits of additional vanes are offset by the increased resistance caused by a reduction in impeller exit area, especially as flow increases.

Figure 6R:
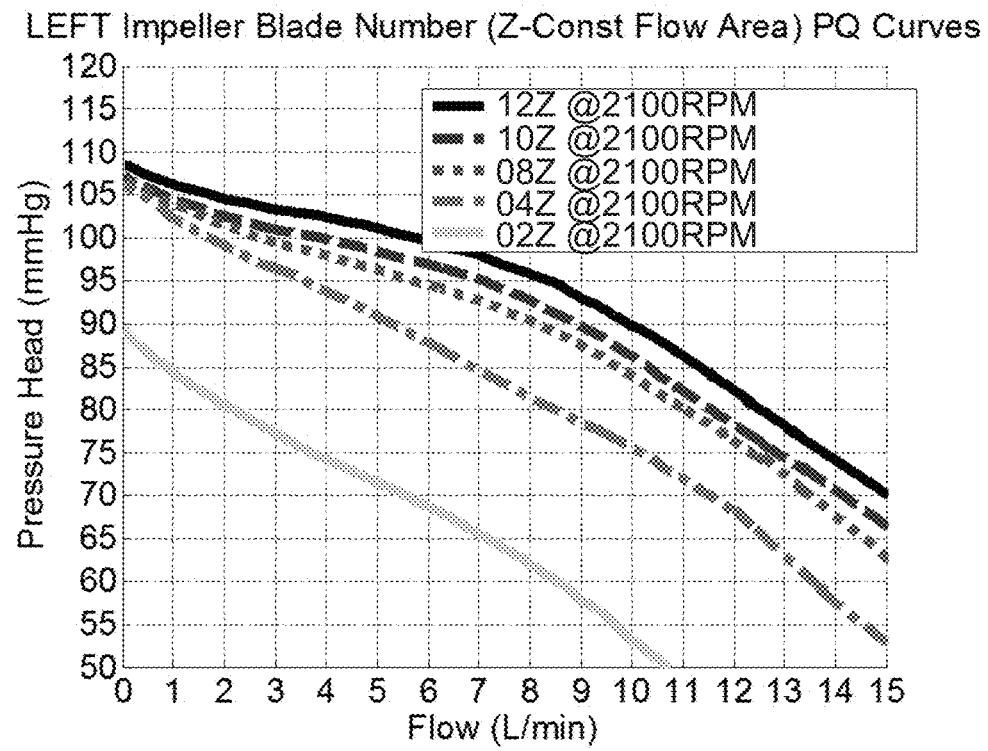
FIG. 6R is a graph showing an example of left pump curves for different numbers of impeller vanes and different vane thicknesses.

In the example of FIG. 6R, maintaining the exit flow path area at 194 mm$^2$ (by altering the vane exit width z) whilst altering the vane number had significant impact. However the larger vane number reduces the individual surface area of each vane and thus may compromise the performance of any thrust bearing. Efficiency was comparable for eight-twelve vanes. The most number of vanes (twelve) generated the highest pressure overall with the flattest gradient (although gradient was similar with eight-twelve vanes from 5-12 LPM). Accordingly, in one example, eight vanes are used to drop pressure by ~6 mmHg for the same speed and allow sufficient surface area for a backup thrust bearing.

Figure 6S:
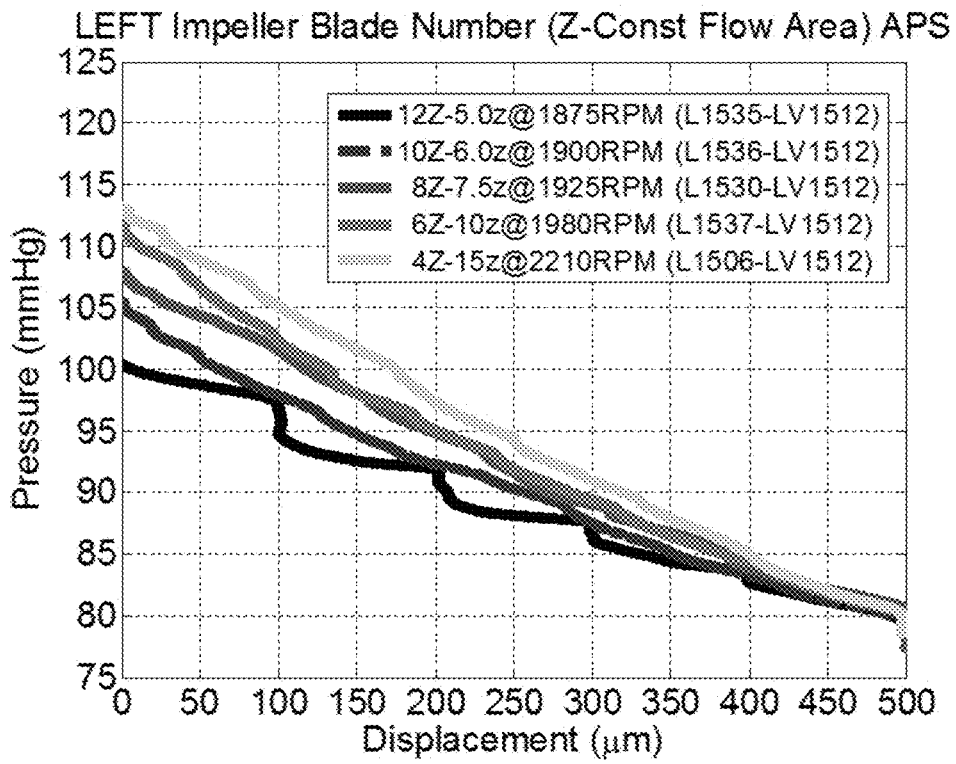
FIG. 6S is a graph showing an example of left pump axial pressure sensitivity for different numbers of impeller vanes.
Figure 6T:
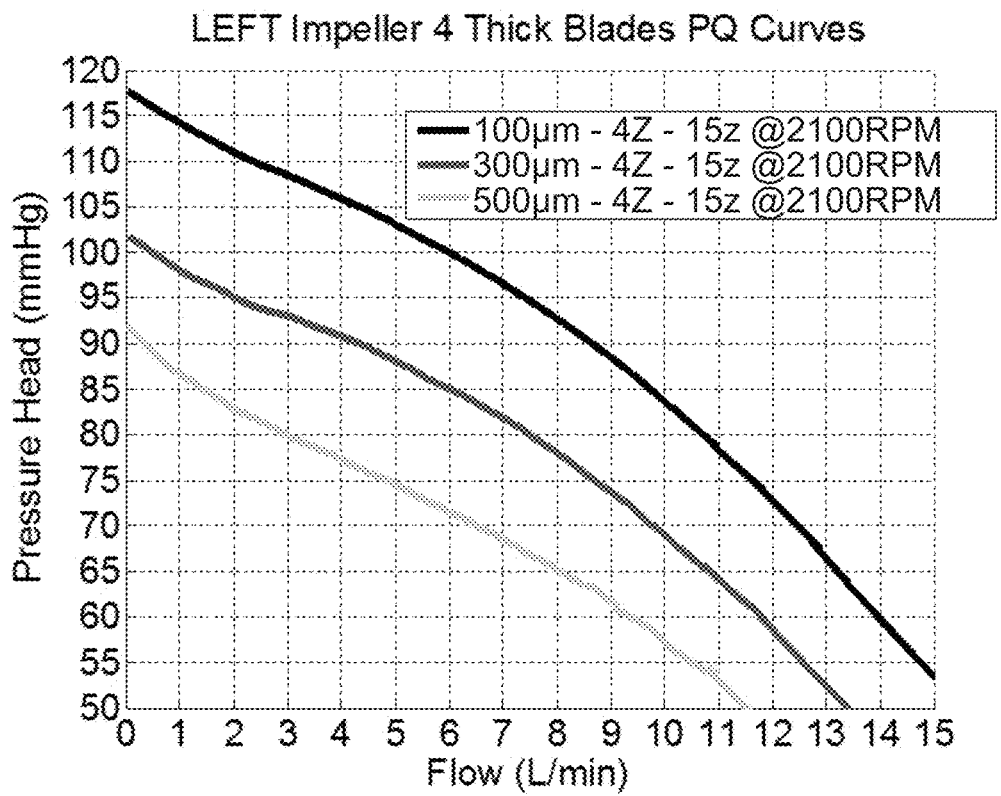
FIG. 6T is a graph showing an example of left pump curves for different axial impeller positions.

These relative changes in left impeller performance were observed with a 500 μm axial gap between the casing and the tip of the vanes. When the axial gap is reduced to 100 μm, the lower vane number impeller had a similar shutoff pressure to the larger vane number impeller (albeit at a steeper pressure gradient as flow increased due to the impeller slip). The relationship between pressure and axial gap is shown in FIGS. 6S and 6T. As such, as described in detail later, the axial pressure sensitivity of a lower number of vanes (four) is higher and is preferred for the TAH application, since performance can be altered by varying the axial gap and gradient flattened by selecting a larger outlet angle.

Impeller recirculation/slip depends on the physical barrier provided by the vanes, and hence the tall vanes 123 on the right hand side of the impeller significantly reduce impeller recirculation/slip.

Whilst a larger number of vanes can lead to a further decrease in impeller recirculation/slip, this can reduce the cross-sectional flow path available to blood traversing the pump, and so accordingly secondary vanes can be provided, the secondary vanes having an increased inner diameter, so that the flow path cross-sectional area is not reduced and thus resistance to flow not increased, whilst the effective barrier provided by the impellers is increased.

Figure 6U:
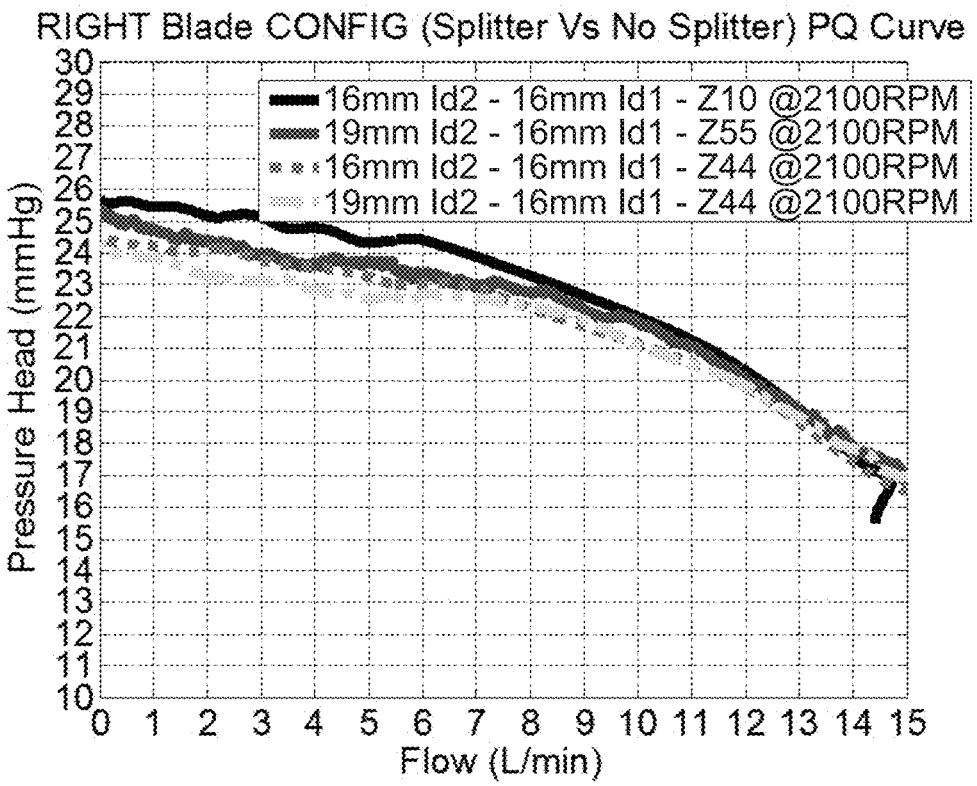
FIG. 6U is a graph showing an example of right pump curves for different numbers of primary and secondary impeller vanes.

An example of this for the right pump is shown in FIG. 6U. In this example, half of the primary vanes that start at a diameter (16 mm) are replaced with secondary vanes that begin at a larger diameter (19 mm). This interrupts pressure generation at flow <8 LPM, which leads to a flatter pump curve between 5-8 LPM. Flow above 12 LPM is choked less and pressure at higher flows is slightly higher. Increasing the number of vanes from eight to ten increases pressure generation by 1 mmHg@6 LPM but with a slightly steeper gradient. The flattest curve is produced by a four primary four secondary vane configuration. This gradient is comparable to an 18 mm impeller eye diameter ID1 arrangement, but with a >1 mmHg pressure generation, which helps to achieve the desired left/right design pressure ratio at a greater overall pump efficiency.

However, the reduced resistance path provided by the alteration of primary to secondary vanes (with a larger inner diameter) is offset by the reduced effective vane area imparting energy on the fluid (vane loading/length). Thus whilst the addition of the splitter vanes results in a slightly flatter curve at high flows, this comes at the expense of a reduced pressure generation over all flows.

Figure 6V:
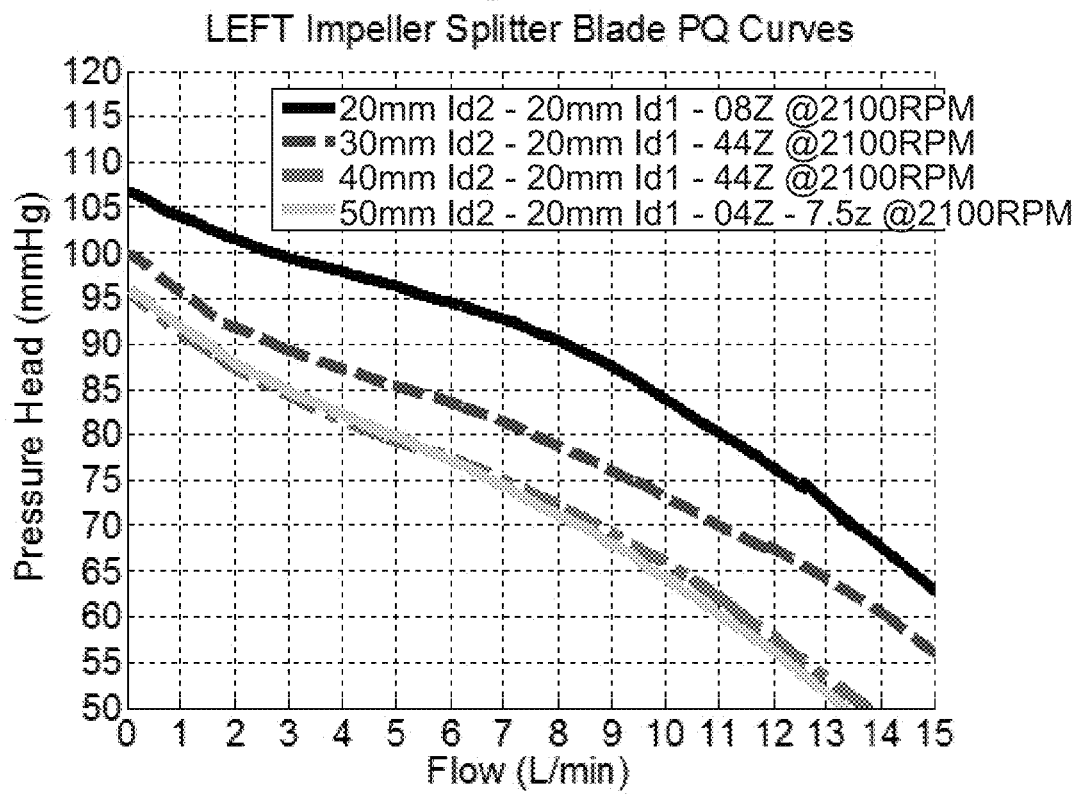
FIG. 6V is a graph showing an example of left pump curves for different primary and secondary impeller vane configurations.

The effect of the inner diameter of the secondary impeller vanes will now be described. As shown in the example of FIG. 6V, which shows pump curves for the left pump, adding secondary vanes reduces the pressure generated over the whole flow range due to a reduced Euler pressure generation by the split vanes at a larger diameter, and in particular reduces the pressure by 12 mmHg@6 LPM. This is a similar observation from increasing the impeller eye diameter ID1 of all vanes, and relates to the reduced vane loading. Thus, using splitter vanes can be considered as a means to reduce the pressure generation of the left impeller into the range targeted for a suitable TAH left/right design pressure ratio, whilst maximising OPS.

Adding a set secondary vanes having an inner eye diameter ID2 of 30 mm flattens the pump curve gradient especially above 8 LPM due to reduced blockage. Using an eye diameter ID2 greater than 30 mm adversely affects pressure generation and gradient. Accordingly, in one example, the preferred approach is to use a four primary four secondary vane configuration with a secondary vane eye diameter of up to 30 mm.

Figure 6W:
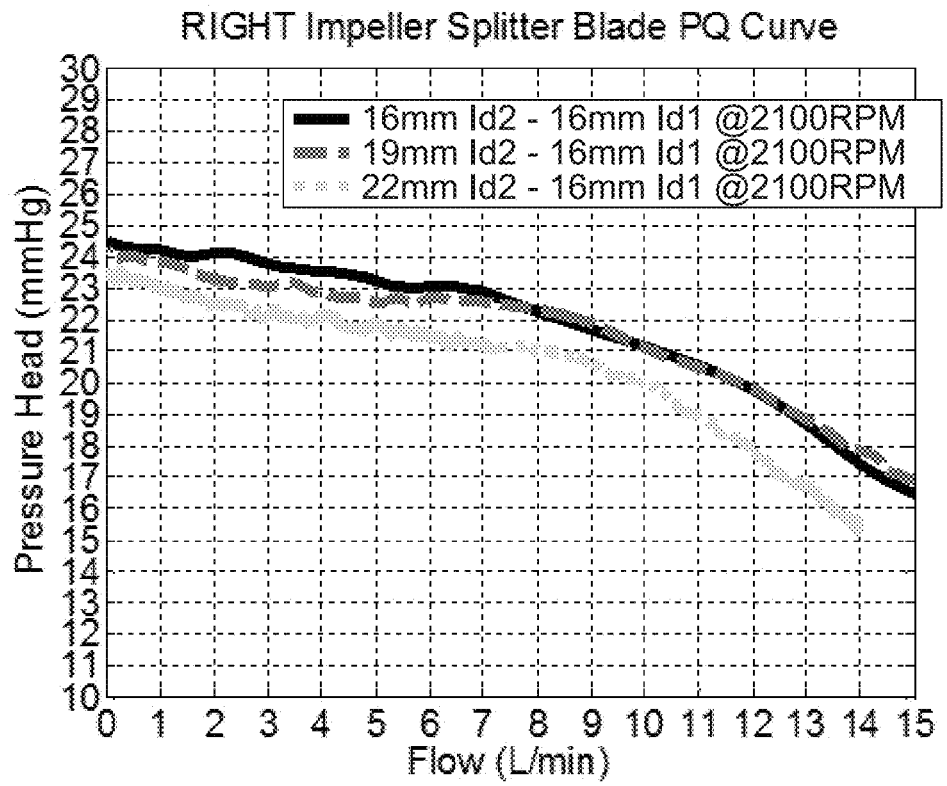
FIG. 6W is a graph showing an example of right pump curves for different primary and secondary impeller vane configurations.

In the case of the right pump, as shown in FIG. 6W, adding secondary vanes with an eye diameter of 19 mm reduces pressure at low flows leading to a marginally flatter pump curve, but pressure generated at 6 LPM is comparable. A secondary vane with an inner eye diameter of 22 mm reduces pressure over all flows (approaching performance of four vanes only) but does not raise the gradient and as such is not preferred.

Figure 6X:
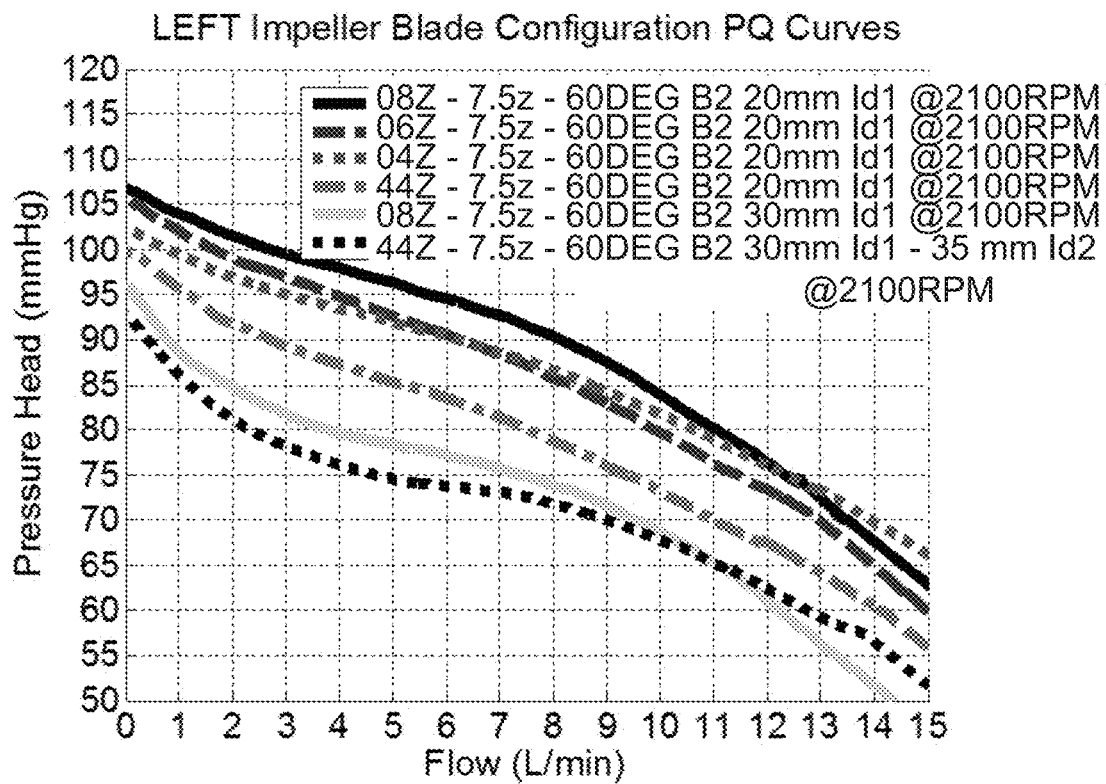
FIG. 6X is a graph showing an example of left pump curves for different primary and secondary impeller vane configurations.
Figure 6Y:
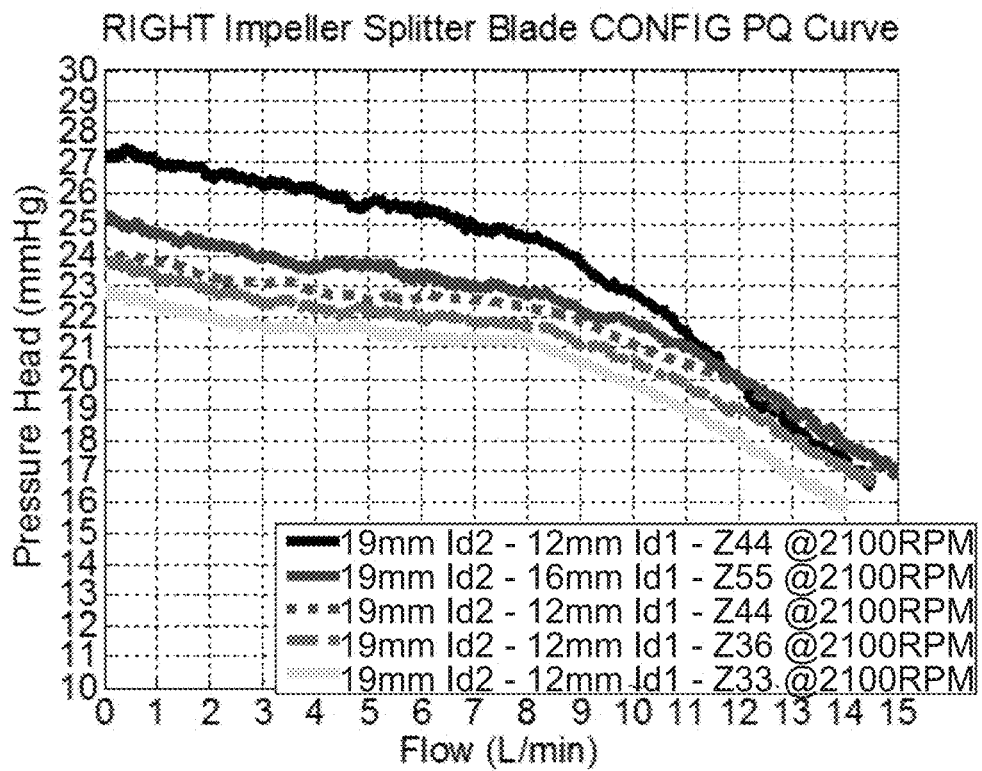
FIG. 6Y is a graph showing an example of right pump curves for different primary and secondary impeller vane configurations.

The vane configuration (number, inner diameter etc) and outlet angle $\beta_2$ also have an impact on flow as will now be described with reference to FIGS. 6X and 6Y.

In the case of the left pump, eight full vanes at 60° outlet angle having an impeller eye diameter of 20 mm, created 10 mmHg more pressure @ 6 LPM than four primary and four secondary vanes. The effect of the four primary and four secondary vanes is to reduce pressure generation due to the increased diameter of the split vanes and thus reduced Euler head generation by these vanes.

It was observed that six full vanes at 80° vane outlet angle $\beta_2$ create a pump curve of similar pressure and gradient to eight vanes at 60° vane outlet angle $\beta_2$, however the latter starts to choke flow >8 LPM and hence the six vane gradient is flatter in this region. Therefore it is generally preferred to reduce the vane number and increase the vane outlet angle $\beta_2$ rather than utilizing splitter vanes for the left pump. It can be understood that splitter vanes may be utilized to reduce the design pressure generation at a given rotational speed, whilst not compromising gradient, which occurs when vane number alone is reduced.

The flattest pump curve and thus greatest OPS for the left impeller of the TAH application is obtained for the eight vanes having 80° vane outlet angle $\beta_2$ with an impeller eye diameter of 30 mm, thus, in one example, an impeller eye diameter ID1 of 30 mm and splitter ID2 of 35 mm is used in conjunction with an 84° vane inlet angle $\beta_1$ and 80° vane outlet angle $\beta_2$ to reduce pressure generation to a range suitable for the targeted left/right pressure ratio whilst creating the flattest pump curve.

In the case of the right pump, reducing the inner diameter of the primary vanes to 12 mm increases shutoff pressure, but steepens the curve from 8 LPM as flow is choked entering the impeller eye. Adding an extra primary and secondary vane, to use a five primary and five second vane configuration raises pressure by 1 mm over all flows and maintains gradient, whilst removing a primary and secondary vane to use a four primary and four second vane configuration reduces pressure by 1 mm over all flows but maintains gradient. Finally, removing one primary vane and adding two to use a three primary and six second vane configuration reduces pressure by 0.5 mm over all flows but maintains gradient. In general, it is preferred to reduce the number of vanes to increase the fluid passage between the vanes to allow emboli to pass unimpeded. In one example, a four primary and four second vane configuration is used with impeller eye diameter ID1 of 16 mm and 19 mm respectively.

For the left hand pump, the impeller typically includes a number of primary vanes having an inner diameter of at least one of at least 10 mm, less than 40 mm, between 15 mm and 35 mm, between 25 mm and 35 mm and, approximately 25-30 mm, a number of secondary vanes, the secondary vanes having an inner diameter of at least one of at least 20 mm, less than 40 mm, between 30 mm and 40 mm, and, approximately 35 mm and an outer vane diameter of at least one of at least 20 mm, less than 60 mm, between 45 mm and 55 mm, between 48 mm and 52 mm, and approximately 50 mm. The impeller can includes an equal number of primary and secondary vanes, at least three primary and secondary vanes, less than six primary and secondary vanes, and more typically four primary and four secondary vanes.

For the right hand pump, the impeller includes a number of primary vanes, the primary vanes having an inner diameter of at least one of at least 10 mm, less than 25 mm, between 10 mm and 20 mm, between 14 mm and 18 mm and, approximately 16 mm, a number of secondary vanes, the secondary vanes having an inner diameter of at least one of at least 10 mm, less than 25 mm, between 15 mm and 25 mm, between 18 mm and 20 mm, and approximately 19 mm and an outer vane diameter of at least one of at least 15 mm, less than 40 mm, between 20 mm and 30 mm, between 22 mm and 27 mm, and approximately 24 mm or approximately 25 mm. The impeller typically includes an equal number of primary and secondary vanes, between three and five primary vanes, and more typically four primary vanes, between three and six secondary vanes and more typically four secondary vanes. The lower the number of vanes, whilst still optimising performance, allows for a larger fluid passage and thus more area for any possible deep vein thrombus emboli to pass unobstructed through the right impeller.

In addition, a further reduction in impeller recirculation/slip can be achieved by increasing the vane thickness, particularly towards the outer circumferential edge of the impeller. This is not required for the right hand side, due to the vane height. However, this is beneficial for the left hand side, so that the vanes thicken towards the outer circumferential edge of the impeller, resulting in an outer edge thickness of at least 5 mm, less than 20 mm, between 6 mm and 14 mm, between 7 mm and 8 mm and approximately 7.5 mm for an eight vane impeller. In contrast, for the right hand pump, the vanes have an outer (and substantially constant) thickness of at least one of at least 0.5 mm, less than 3.0 mm, between 0.75 mm and 2 mm, and 1.5 mm Too thin and fatigue cracking may occur at the base of the long struts. For this reason, a suitable fillet connection from the strut to the rotor base should be utilised.

An example of the impact of impeller vane thickness for the left pump will now be described with reference to FIGS. 6Z and 6ZA.

Figure 6Z:
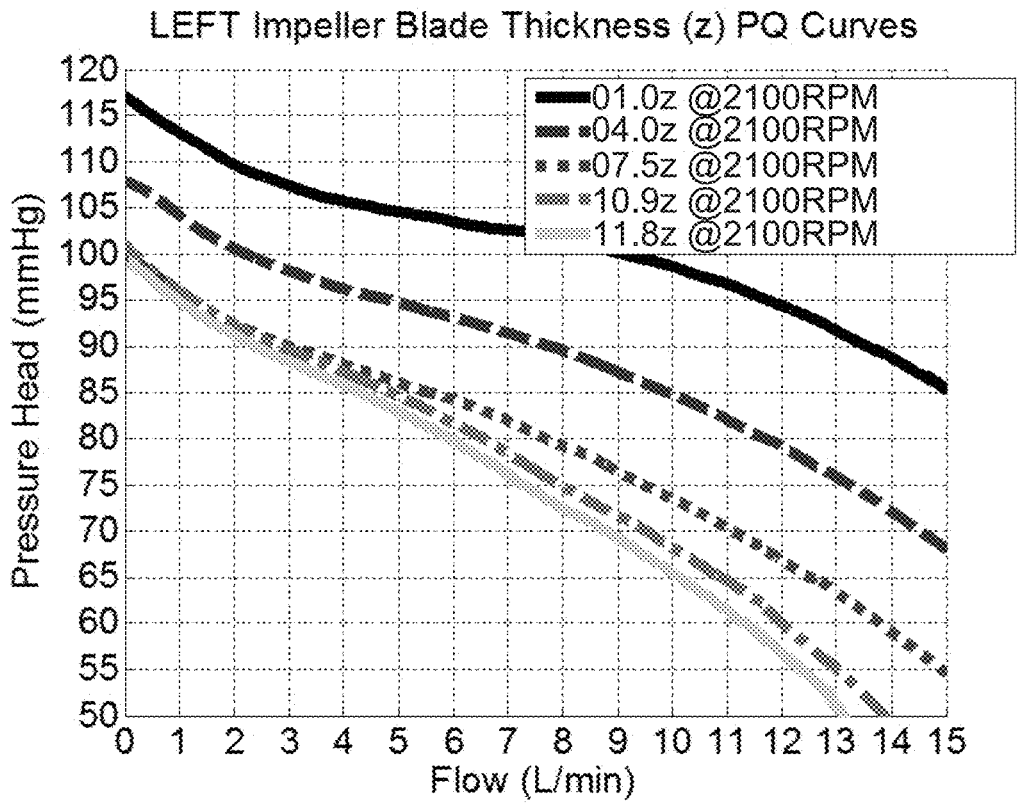
FIG. 6Z is a graph showing an example of left pump curves for different impeller vane thicknesses.
Figure 6Z:
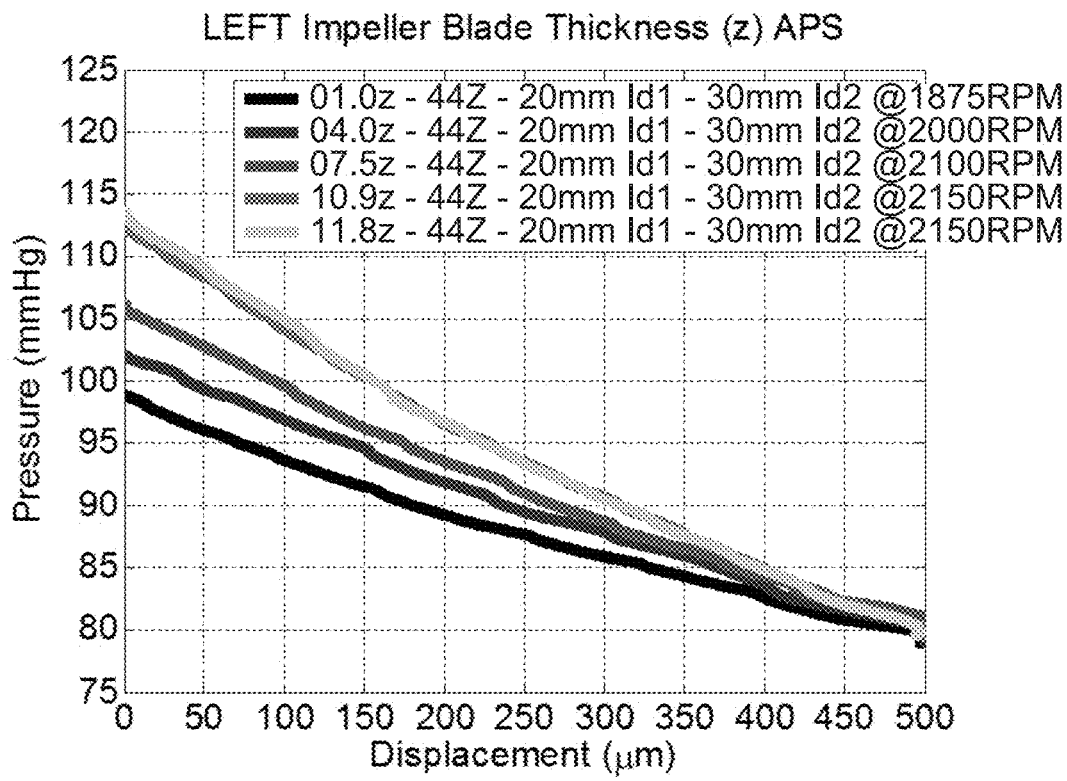
Figure 6Z:
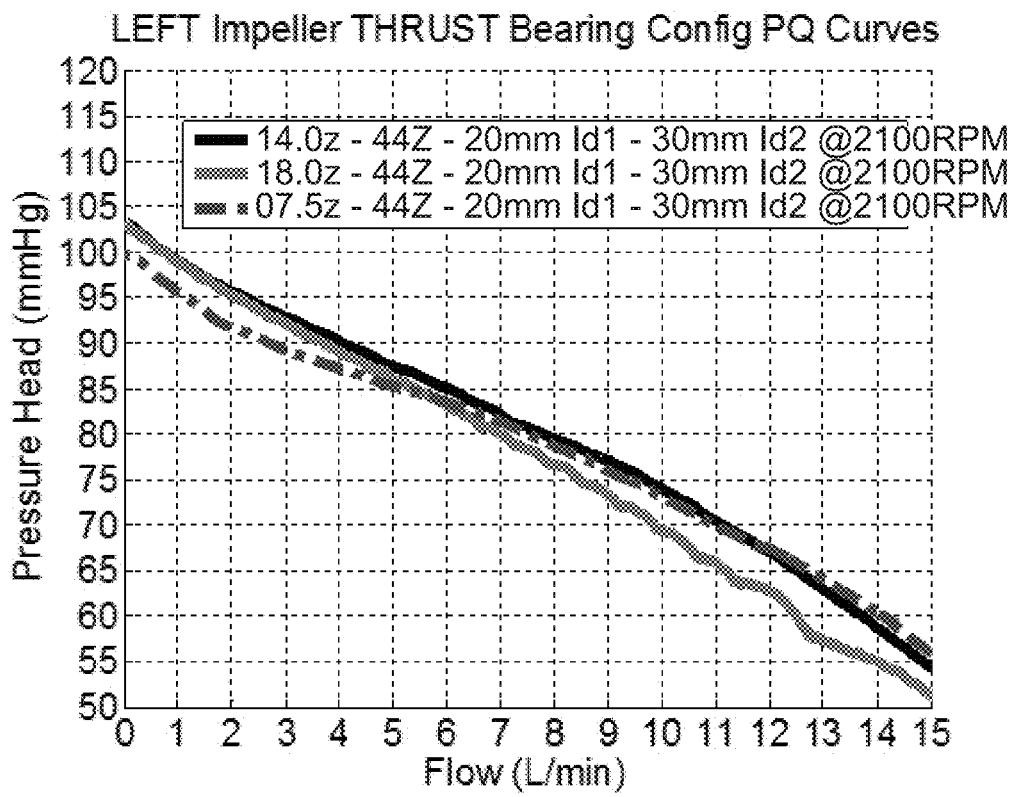
Figure 6Z:
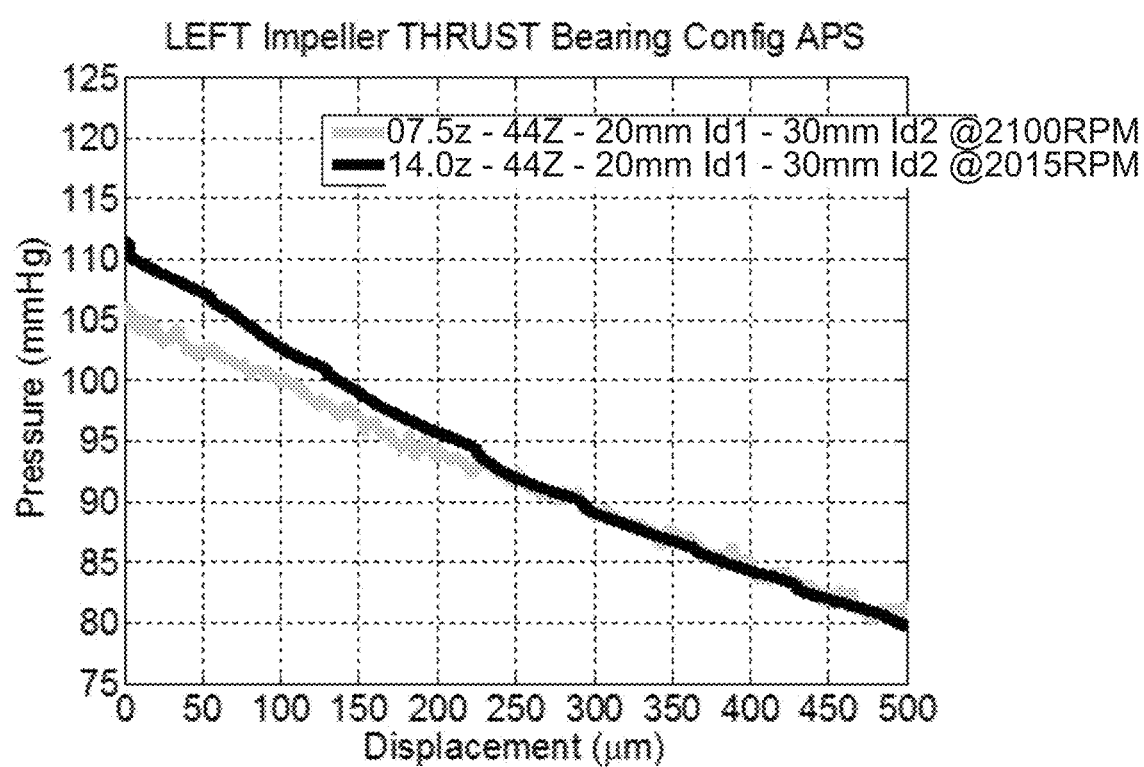

As shown in FIG. 6Z, a change in vane width has a significant effect on efficiency and pressure gradient. For example a 1 mm vane outer width results in a pump curve gradient of −1.5 mmHg/LPM while 4 mm and 7.5 mm widths result in a −2 mmHg/LPM gradient and >7.5 mm width has a gradient of −3.5 to −4 mmHg/LPM. Based on this 7.5 mm is acceptable to allow a lower pressure generation (<20 mmHg) at 2100 RPM.

Turning now to FIG. 6ZA, this shows that the change in vane width has an effect on axial pressure sensitivity. The improvement for a vane width of greater than 10.9 mm is marginal, suggesting that the vane thickness should be at least 10.9 mm for an impeller with eight vanes if APS is to be maximised.

Thus, increasing vane thickness at the outer circumference has the added benefit of increasing axial pressure sensitivity. However an additional benefit of a thicker vane is for the inclusion of a backup hydrodynamic thrust bearing configured to act between the left impeller vanes and the flat left casing face between the rotor and the motor. Such a hydrodynamic bearing would not be in functional operation until the impeller approached the left casing wall. This may occur during an excessive shock force, or in the unlikely event that the magnetic bearing suspension ceases operation. In such cases, the motor would cause the impeller to continue to rotate, and the hydrodynamic bearing would provide non-contact suspension, until such time as the magnetic bearing can be restored.

Whilst the 7.5 mm vane thickness discussed is sufficient, a thicker vane would result in a larger hydrodynamic bearing surface area, but at the expense of more resistance to flow and thus a steeper pump curve. To mitigate this issue, the secondary vane thickness can be reduced (to 1.0 mm), which allows the primary vane to increase to 14 mm before significantly impacting flow resistance. Further, the primary and second vane impeller eye diameter ID1, ID2, of 25 mm, 40 mm respectively, can be made to start at a larger diameter to take advantage of this feature and reduce the pressure generated, particularly at low flows, to match the targeted left/right design pressure ratio and return a flatter pump curve.

Example thrust bearing configurations will now be described with reference to FIG. 6ZB and FIG. 6ZC.

These examples highlight thickening the four primary vanes from 7.5 mm to 14 mm and reducing the four secondary vanes from 7.5 mm to 1.0 mm results in a 3 mmHg greater generation of pressure at shutoff. The gradient from 5-10 LPM reduced from 2 mmHg/LPM to −2.5 mmHg/LPM. Increasing the primary vanes further to 18 mm started to choke flow off the impeller and thus steepened the gradient to −3 mmHg/LPM. It is therefore acceptable to thicken primary vanes to 14 mm and reduce secondary to 1.0 mm to trade −0.5 mmHg/LPM gradient for a larger and more efficient thrust pad.

Whilst the addition of the splitter vanes helps to improve OPS, it comes at the expense of a reduced APS. To improve this optimisation of OPS and APS, the splitter vanes can be removed and the four primary vanes thickened to 15 mm or 18 mm. The inner eye diameter ID1 is increased to 30 mm which both reduces pressure generation (particularly at low flows) and improves OPS. Outlet vane angle is increased to 80° and inlet increased to 84° to further restore the OPS. Vane height could also be increased to 2.5 mm.

Results of the above described configurations are shown in FIGS. 7A to 7G.

Figure 7B:
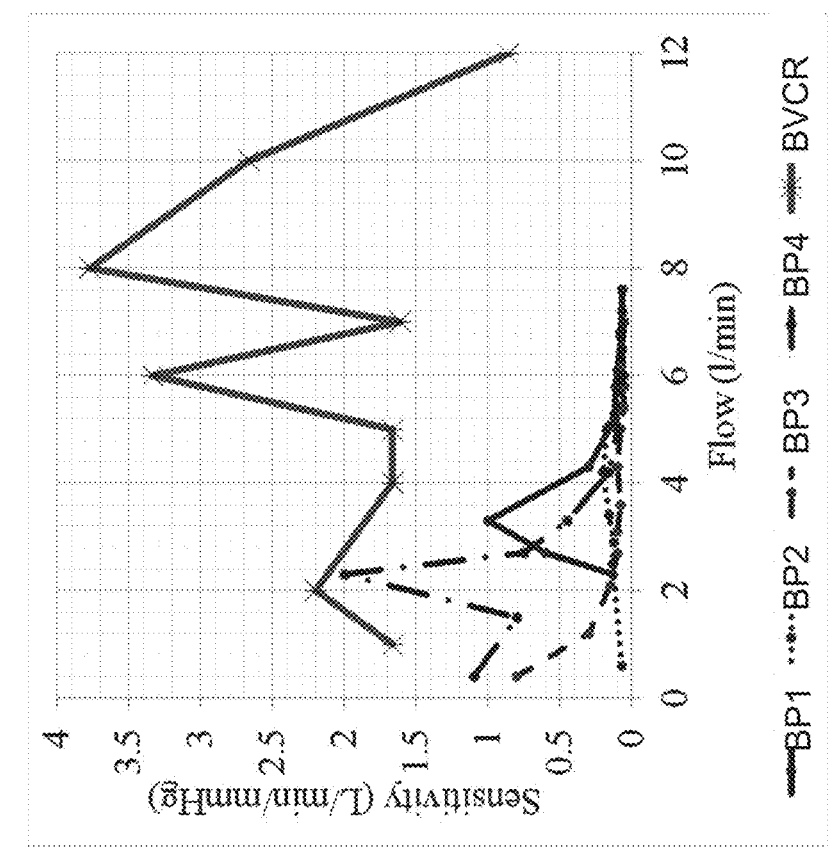
FIG. 7B is a graph showing flow sensitivity for the heart pumps of FIG. 7A.
Figure 7A:
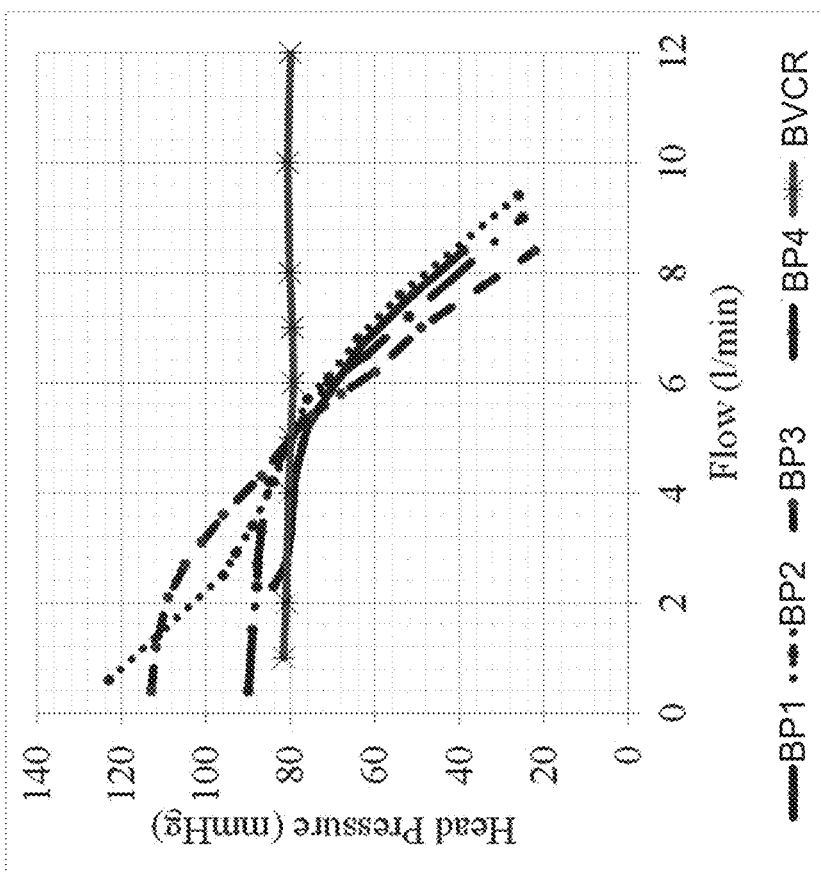
FIG. 7A is a graph showing example pump curves for a number of different heart pumps.

In particular, a heart pump created in accordance with the above described arrangements, denoted as BVCR in FIG. 7A, provides good outflow pressure sensitivity up to and above 3.5 LPM/mmHg over the defined operation range of 5-12 LPM, whereas traditional rotary blood pumps BP1, BP2, BP3, BP4 maintain approximately 0.1 LPM/mmHg over this range. In particular, the gradients are BP1=80−46/3=−11.33 mmHg/LPM, BP2=−10.6 mmHg/LPM, BP3=−17.3 mmHg/LPM and BP4=−13 3 mmHg/LPM, whereas in the described configuration, the pressure gradient is slightly positive from 5-8 LPM.

Figure 7C:
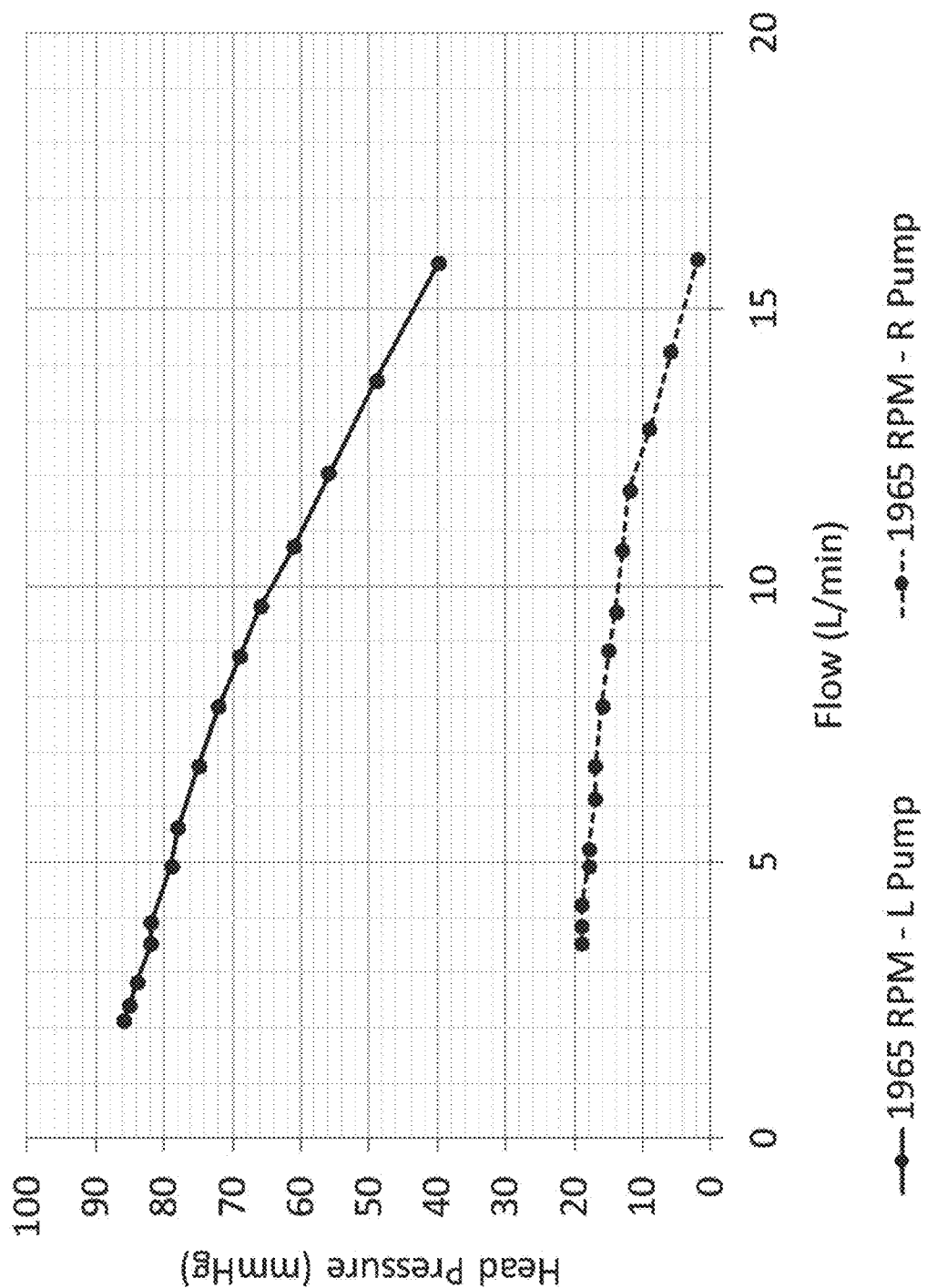
FIG. 7C is a graph showing pump curves for the left and right pumps for an example heart pump.

As also shown in FIG. 7C, the above described configuration further results in a significantly different pump curve between the left and right pumps, for example due to different vane configurations, which as previously indicated can assist in providing differential flow control based solely on pressure variations.

Figure 7D:
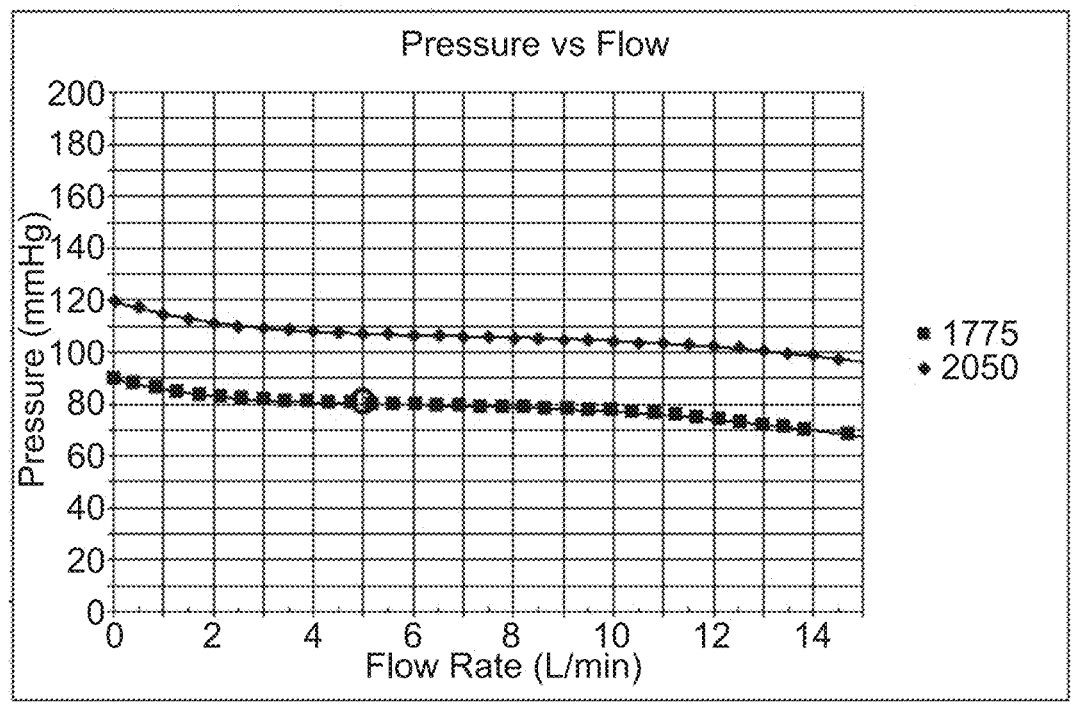
FIG. 7D is a graph showing an example of changes in pump curve at different rotational speeds.

FIG. 7D highlights how the pump curve gradient is consistent at different rotational speeds, helping to maximize the degree of control that can be maintained. Under these conditions, the gradient between 5-10 LPM is around −0.25-0.33 mmHg/LPM. A peak hydraulic efficiency of 57% occurs at 12 LPM, with an efficiency at 7.5 LPM of 55%, meaning there is little decrease in efficiency below BEP, so that overall energy usage is not majorly impacted.

Figure 7E:
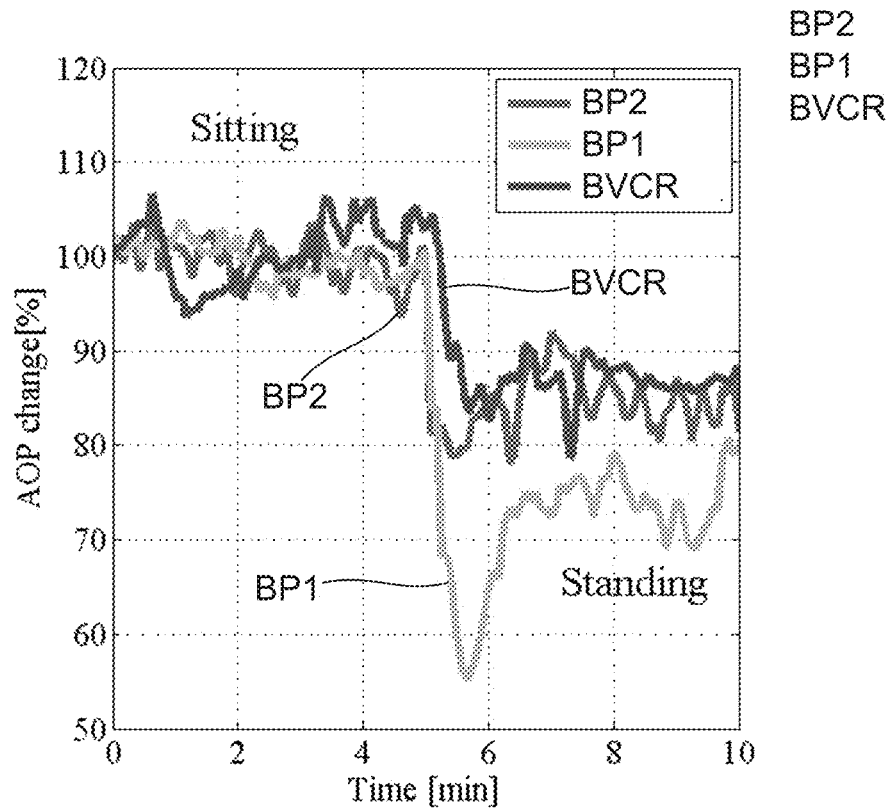
FIG. 7E is a graph of an example of the response of the heart pumps of FIG. 7A to a standing event.

The beneficial effect of the greater outflow pressure sensitivity is highlighted with respect to a change in posture (standing event), in which a subject goes from an at rest sitting condition, to standing. As shown in FIG. 7E, an initial reduction of arterial pressure by just 15% was observed for BVCR compared to up to 40% for other rotary blood pump designs BP1, BP2. Thus, the above described arrangement can help prevent excessive drops in blood pressure caused by the onset of activity, helping prevent lightheadedness, dizziness or the like.

Figure 7F:
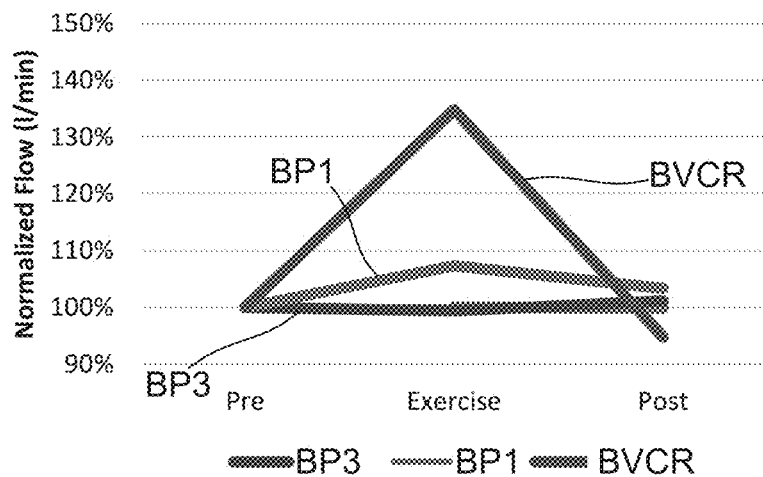
FIG. 7F is a graph of an example of the response of the heart pumps of FIG. 7A to exercise.

Further, FIG. 7F shows how an increase of outflow by 35% was observed in-vivo during a transition to exercise of a cow with a heart pump on a treadmill, compared to 2-8% for other rotary blood pump designs. This was achieved without additional control of the heart pumping, meaning the pump is automatically compensating for physiological changes without requiring additional control of rotational speed.

Figure 7G:
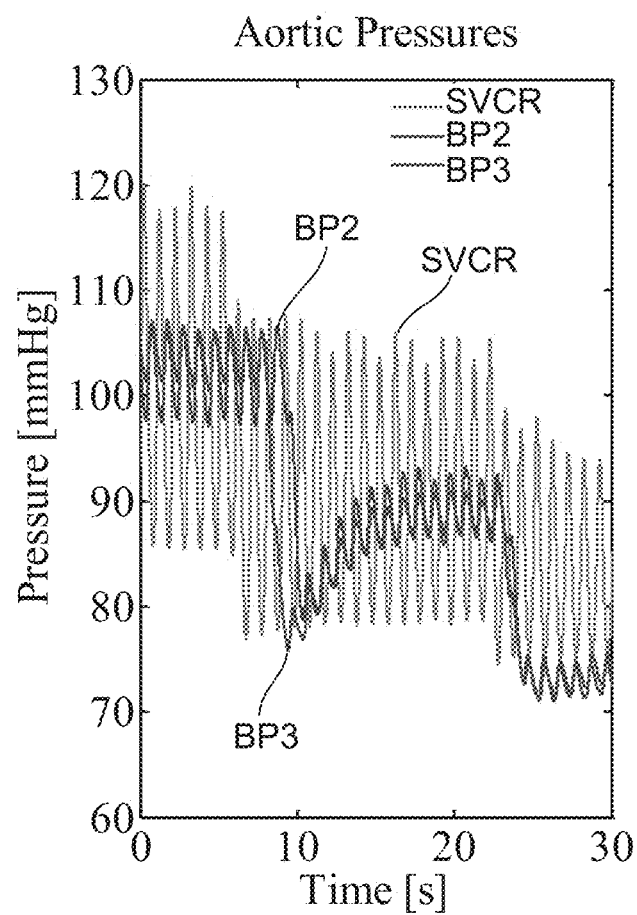
FIG. 7G is a graph showing examples of variations in aortic pressures for different pumps.

A further beneficial effect is observable in the pressures shown in FIG. 7G. In a single VAD application SVCR, the transmitted pulsatility of the native heart is better preserved. In an MCL experiment, the natural pulse pressure was preserved to 35 mmHg in comparison to just 5-10 mmHg in previous rotary blood pump designs. When an exercise/stand-up condition was simulated (by a reduction in SVR), MAP dropped by just 15 mmHg as opposed to 25-30 mmHg in the previous designs, which provides a greater tolerance to orthostatic hypotension. Importantly, diastolic pressure is lowered allowing arterial vessels vital relaxation time, which may reduce the incidence of hemorrhagic stroke, vascular malformations and gastrointestinal bleeding.

Accordingly, it is apparent that the use of a high outflow sensitivity to inflow pressure can significantly improve the ability of the heart pump to accommodate natural pressure changes within a subject, and that this can be achieved through the selection of appropriate parameters, including increasing flow path cross-sectional area to reduce friction, selection of an optimum vane angles, and configuring the impeller to reduce impeller recirculation/leakage.

Improved Axial Pressure Sensitivity (APS)

As previously mentioned, it is useful to maximise axial pressure sensitivity to allow for flow to be adjusted based on the relative axial position of the impeller within the cavity. This allows for an expanded range of left/right design pressure ratio at a given rotational speed. In this regard, the axial pressure sensitivity is largely dependent on the amount of leakage between the impeller vanes and the cavity housing, and so accordingly, the axial pressure sensitivity is largely dependent on the impeller vane parameters and in particular the vane outlet angle, the vane thickness, vane number, and the vane height.

Some leakage is desirable as its alteration contributes to axial pressure sensitivity, in particular by allowing the amount of leakage to be controlled by adjusting a clearance between the vane and housing.

Vane Outlet Angle

The lower the outlet vane angle is, the more pressure sensitivity is observed due to the inwardly radial component of flow passing over the top of the vane, between the vane and the housing, which acts to oppose the main forward flow.

Figure 8A:
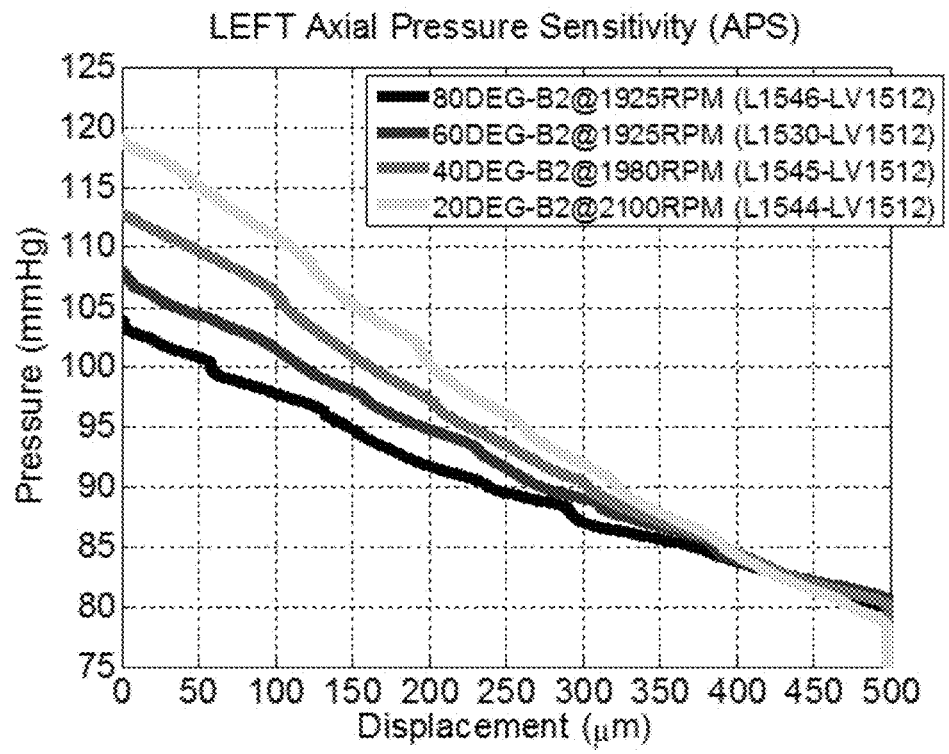
FIG. 8A is a graph showing examples of pressure variations based on impeller axial position for different vane outlet angles.

The most influential factor for BTG ΔP sensitivity was found to be the vane outlet angle $\beta_2$, as shown by the graph of FIG. 8A.

A backward swept curved vane of 20° has almost double the pressure sensitivity than straighter radial vanes. This may be explained by the breakdown of velocity components of the leakage flow over the vanes. A pure radial vane exhibits a circumferential velocity vector alone, whilst a backward swept vane produces a velocity component in the inward radial direction, opposing forward flow through the impeller.

Vane Thickness

The thickness of the vane contributes to resistance to flow over the vane as the vane approaches the casing, with a thicker vane increasing friction to flow, and reducing the ability for blood to flow over the vane, hence resulting in enhanced axial pressure sensitivity.

Figure 8B:
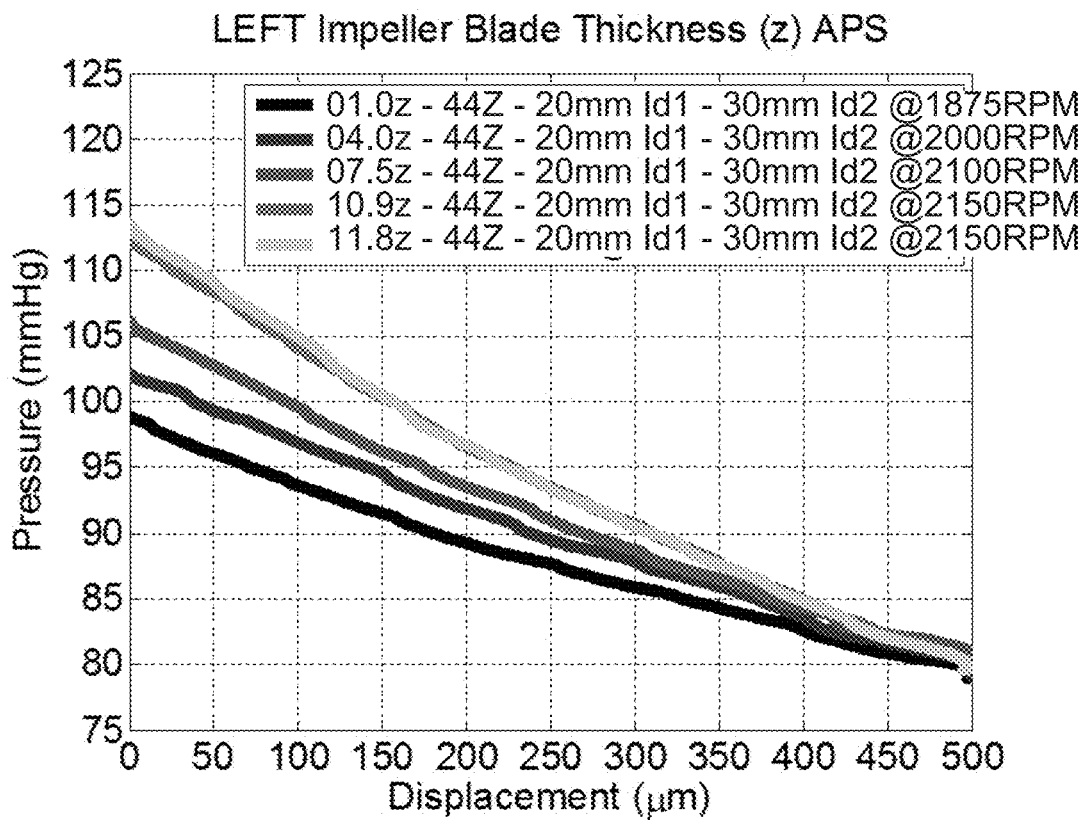
FIG. 8B is a graph showing examples of pressure variations based on impeller axial position for different vane thicknesses.

Thus, a change in vane width has an effect on axial pressure sensitivity as shown in FIG. 8B. However, an increase in vane thickness only leads to a minor increase in sensitivity for a vane thickness over 10.9 mm. Consequently, the axial thickness of the outer edge of the vanes can be selected to be 10.9 mm if the vane thickness is to be otherwise minimised whilst maintaining increased axial sensitivity, but otherwise any thicker vane can be used.

Vane Number

Figure 8C:
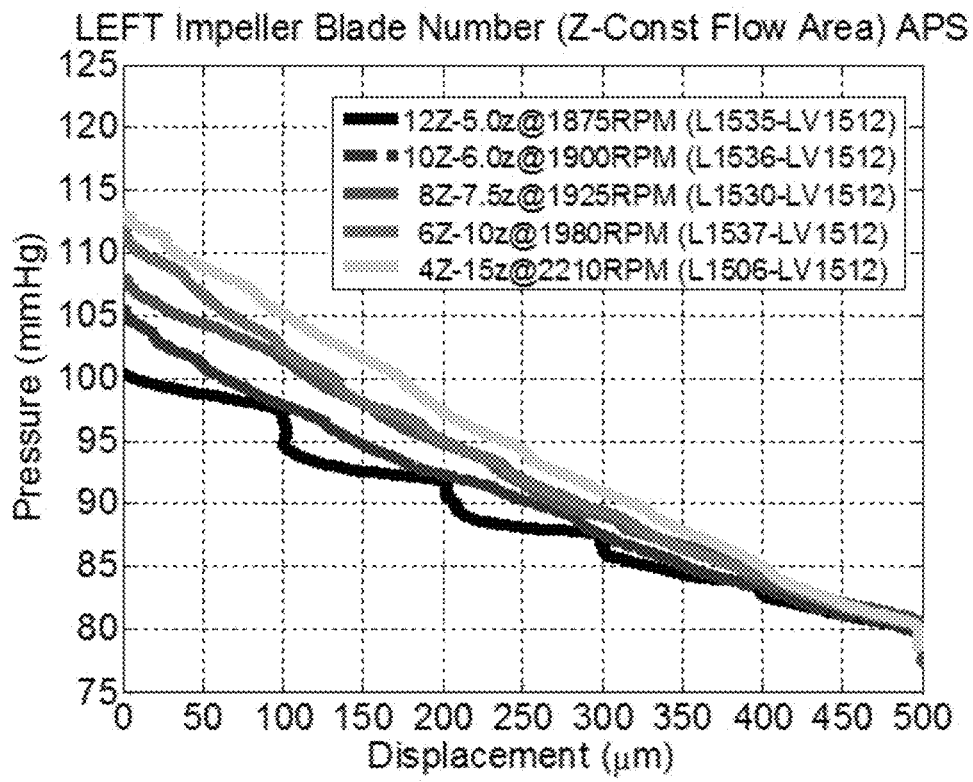
FIG. 8C is a graph showing examples of pressure variations based on impeller axial position for different numbers of vanes.
Figure 8D:
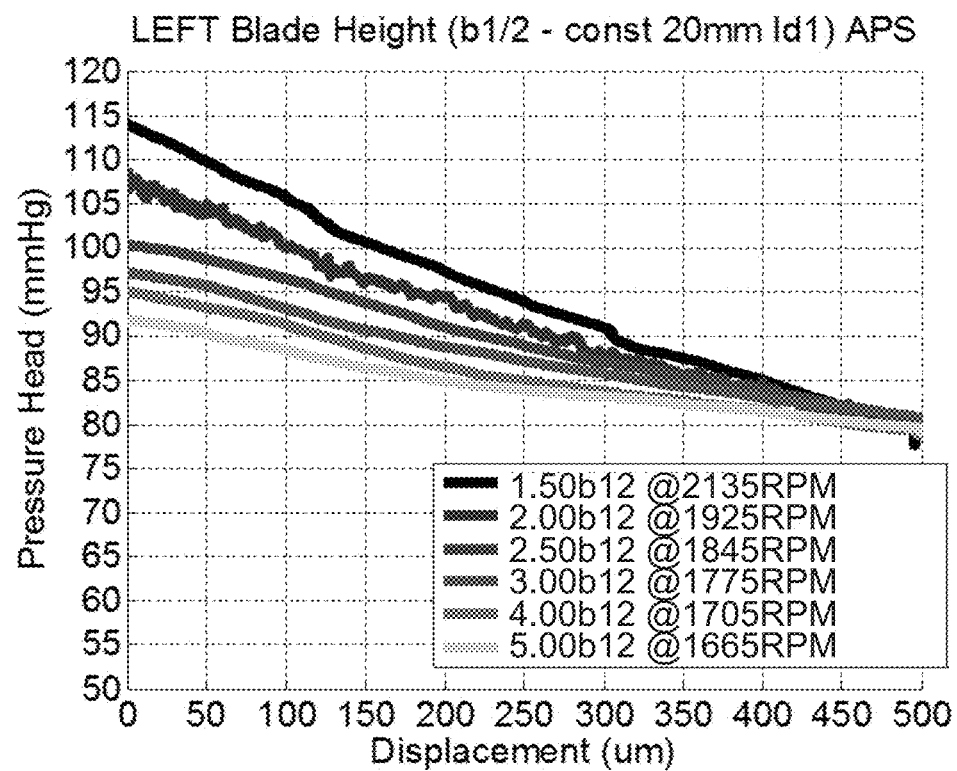
FIG. 8D is a graph showing examples of pressure variations based on impeller axial position for different vane heights for a constant impeller eye diameter.
Figure 8E:
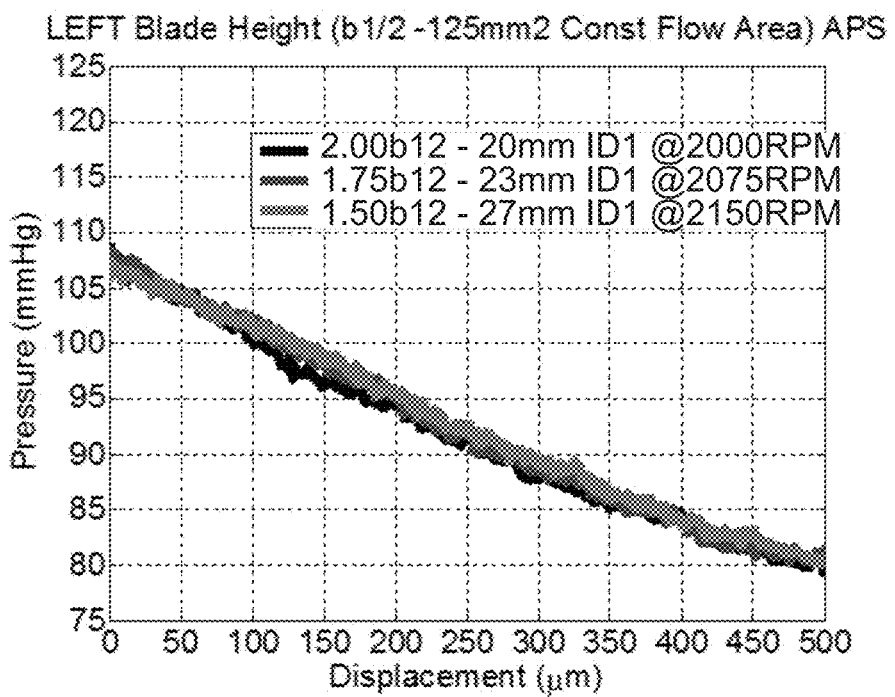
FIG. 8E is a graph showing examples of pressure variations based on impeller axial position for different vane heights for constant inflow and outflow areas.

A similar factor applies to the number of vanes. In this instance, as shown in FIG. 8C, decreasing the number of vanes leads to an increase in axial pressure, so fewer thicker vanes are more sensitive than a larger number of thin vanes.
Vane Height The height of the vane also contributes to axial pressure sensitivity, with a higher vane reducing the ability of blood to flow between the vane and housing and hence reducing axial pressure sensitivity, (whilst increasing outflow pressure sensitivity and efficiency). Examples of changes in sensitivity for different vane heights for constant impeller eye diameter ID1, and constant inlet and outlet areas are shown in FIGS. 8D and 8E respectively. From this, it is apparent that this sensitivity is insensitive to left vane height when the inlet (125 mm$^2$) and outlet (194 mm$^2$) flow areas of the impeller are maintained by increasing the inner eye diameter ID1 and reducing the outer diameter vane thickness $z_2$. However it is very sensitive to height when the inlet and outlet areas vary as a factor of the height.

Figure 8F:
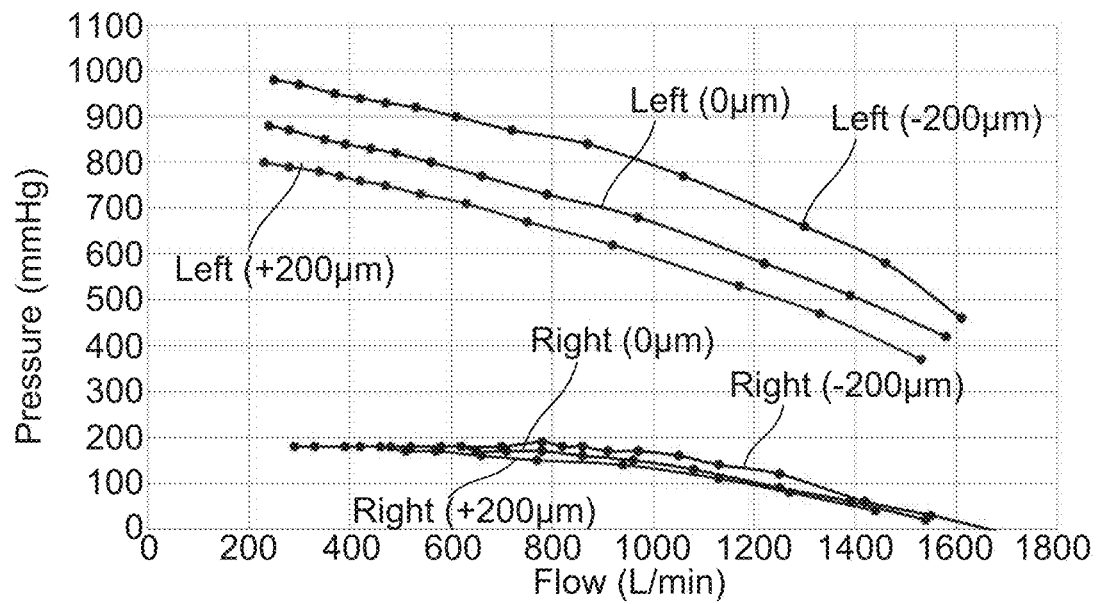
FIG. 8F is a graph showing examples of changes in the pump curve for left and right pumps for different axial impeller positions.

As previously described, the right hand pump impeller vane parameters are defined to flatten the pump curve as much as possible, in particular through the use of the large vane height and 90° vane angles. As a result, axial pressure sensitivity is minimised. In contrast, for the left hand pump, a degree of gradient is maintained for the pump curve due to the lower vane height, reduced vane outlet angle, and increased vane thickness, effectively sacrificing outflow pressure sensitivity in favour of axial pressure sensitivity. An example of this is shown in FIG. 8F, in which incremental movements of the impeller 120 within the cavity result in movement of the pump curve of the left hand pump, but less alteration for the right hand pump.

In practice for the left hand pump, a change in axial position of 200 μm causes a change in flow rate of at least one of at least 1 LPM, at least 2 LPM, less than 4 LPM and between 2 LPM and 3 LPM, whereas for the right hand pump, the change in flow rate is at least one of at least 0.2 LPM, at least 0.5 LPM, less than 2 LPM and between 0.5 LPM and 1.5 LPM.
Radial Stabilisation Radial destabilization forces arise from hydraulic force, rotor weight and shock disturbances. Hydraulic force is generated by the uneven pressure distribution of blood around the impeller periphery caused by acceleration and deceleration of fluid within the volutes leading to the outlets 112, 114. The direction and magnitude of this force is steady, and dependent on the volute type (circular, spiral, splitter) and varies according to operational flow rate. This force becomes unsteady in the case where the device is operated in pulsatile outflow mode by modulating the rotational speed, whereby the radial forces fluctuate with instantaneous outflow. This instantaneous outflow may exceed the average flow rate range required for circulatory support in humans (3-12 LPM), possibly reaching maximum instantaneous flow rates of 25 LPM. In contrast, the force generated by rotor weight and shock disturbances depends on the mass of the rotor and whilst the weight is steady in magnitude but varies in direction with patient position, the shock force and direction depends on the magnitude and direction of accelerations/decelerations applied to the device. Furthermore, the latter is generally considered an impulse disturbance and thus the damping of the fluid and surrounding bodily tissue helps to mitigate the magnitude of this force experienced by the system.

Accordingly, it is necessary to provide a mechanism for radial stabilisation that can accommodate these radial forces and prevent, or reduce the chance of impact between the impeller 120 and housing 110. In particular, to achieve non-contact suspension, the technique chosen for radial suspension must be able to generate sufficient forces to counteract hydraulic, gravitational and shock disturbances.

One technique to achieve radial suspension capacity involves the reduction of the radial clearance around the periphery of the rotor 121. This creates a hydrodynamic journal bearing, which essentially relies on the generation of high and low pressure zones around the rotor hub upon the onset of rotation. The force capacity and stability of the journal bearing is determined by a number of factors such as rotational speed, rotor diameter, rotor mass and fluid viscosity. Thus, radial clearance (often in the range of 50-150 μm) and the length of the journal (8-30 mm) are the main parameters remaining to alter to improve journal bearing performance. The addition of the inherently small clearance acts as a restriction to flow from the high pressure left chamber to the low pressure right.

Since there is only one rotating part and a full suspension is desired (no direct contact between the rotor and the casing), a leakage flow will form from the left to right cavity, driven by the pressure difference from the left to the right cavities. Whilst this has a negligible side effect for the patient, it is tended to lead traditional arrangements to implement a journal bearing and minimise separation between the rotor and housing.

However, this creates a region of high shear stresses, which in turn can case rupturing of red blood cells leading to hemolysis, activated platelets, and destruction of vonWillebrand Factor. Accordingly, it is desirable to provide an alternative mechanism for maintaining the impeller radial position. Furthermore, the hydraulic force and operating speed influence the function of the journal bearing, as such it is challenging to maintain functionality over the full range of flow rate and speeds required for the TAH application.
Magnetic Bearing Whilst not essential for a heart pump, magnetic suspension of a blood pump can significantly assist in improving biocompatibility. Suspending the rotor of the device with magnetic forces allows for larger clearance gaps between moving surfaces and thus lower shear stress exposure to the formed elements in the blood. Hence a lower degree of blood damage is expected.

In the current example pumps, active magnetic suspension is provided in the axial direction. However radial suspension is also required. To account for the anticipated radial hydraulic forces that are created from the pump configuration, a non-contact hydrodynamic journal bearing may conventionally be required. However the smaller gaps (50-150 μm) required for this bearing to function could potentially harm the formed elements of the blood.

The active axial magnetic bearing however can provide a (weaker) radial restoring force than a hydrodynamic bearing. However if the external radial forces can be reduced sufficiently over the operating flow range of the device, and the radial gap increased sufficiently, this solution suffices. A much larger gap (in the order of 2-4 mm) can then be utilized. Hence the design of the pump should attempt to minimize this radial hydraulic force over the operating flow range.

This criteria is not mutually exclusive to the requirement for improved outflow pressure sensitivity and improved hydraulic efficiency, and hence should be considered in the final selection of pump components.

Thus, some radial suspension capacity is provided by the axial magnetic bearing and motor system. The attractive force generated by the permanent magnets toward the stators of both motor and bearing also generate a 'passive' radial restoring reluctance force with rotor radial displacement.

Thus, at the same time that the bearing stabilizes the rotor axially, by balancing the attraction force from the motor and the resultant hydraulic forces acting on the rotor, it also generates a stable restoring radial force when the rotor is eccentric to the drive/bearing axis.

Figure 9A:
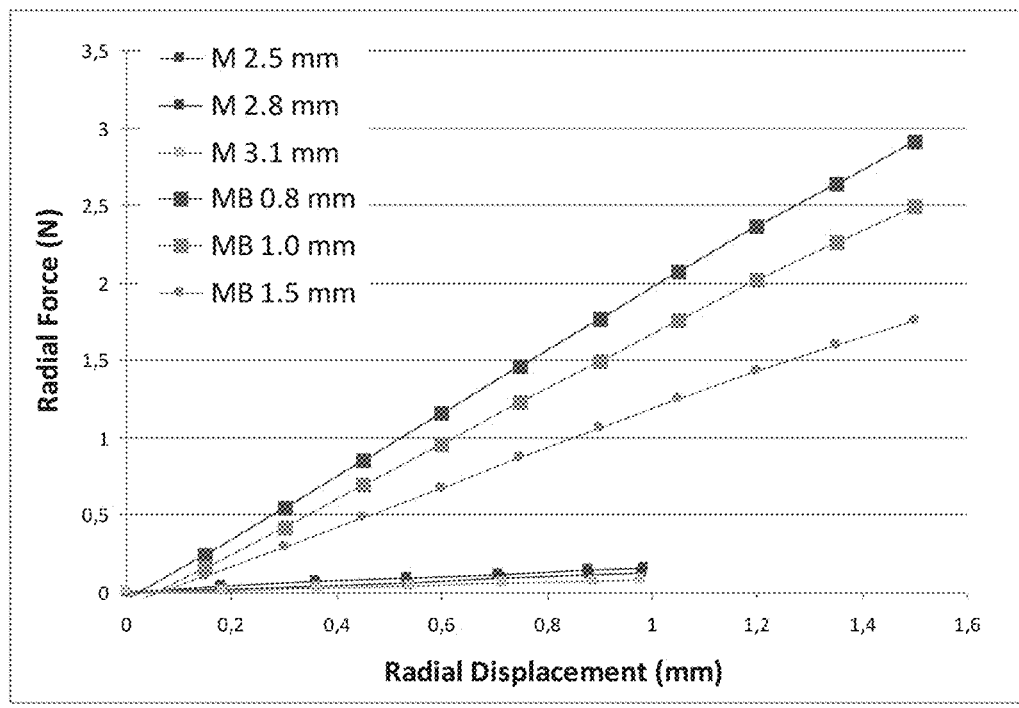
FIG. 9A is a graph showing examples of radial forces on the impeller for different radial displacements.

The radial force generated by the magnets is a function of the angle of the force vector resulting from the attraction between the bearing and motor stators and the rotor magnets. When there is no eccentricity between the rotor and the pump casing there is no radial force and the axial force is maximum. With increasing eccentricity the vector decomposes in the axial and radial direction, with small change in the force magnitude. This leads to a roughly linear increase in the radial force with increasing eccentricity. As eccentricity further increases, the favourable change in vector angle is compensated by a decrease in the vector magnitude and the slope of the radial force decreases with increasing eccentricity, as shown in FIG. 9A.

It is therefore apparent that the bearing configuration has the ability to provide at least some radial stability. Additionally, as the force increases with displacement, it is desirable to allow for greater radial movement of the impeller through the use of a larger radial gap compared to that provided for in journal bearing arrangements. This in turn can increase leakage between the left and right cavities. However, this can be compensated for by reducing the total axial movement of the rotor from 1 mm to 0.5-0.7 mm (typically 0.6 mm, but can be as low as 0.1 mm) and thus operating with comparatively lower axial gaps between the stepped face of the rotor and the casing.

In particular, the rotor typically has an outer circumferential wall spaced from an inner cavity wall by at least one of an average distance of at least 2 mm, an average distance of less than 8 mm, an average distance of less than 5 mm and an average distance of approximately 4 mm. This separation refers to a minimum distance between the rotor and the housing, which typically occurs between the rotor and BCD or cutwater. It will be appreciated that at other locations the spacing can be significantly larger, such as up to 8 mm In general the minimum spacing is dependent on the size and in particular the diameter of the impeller, and accordingly, the separation is typically at least 5% of the impeller rotor diameter, typically less than 40% and more typically approximately 16% of the impeller rotor diameter.

Shock disturbances are damped by the fluid viscosity in the gap, and this arrangement alone is sufficient to maintain bearing stability as long as hydraulic forces are minimised.

Figure 9B:
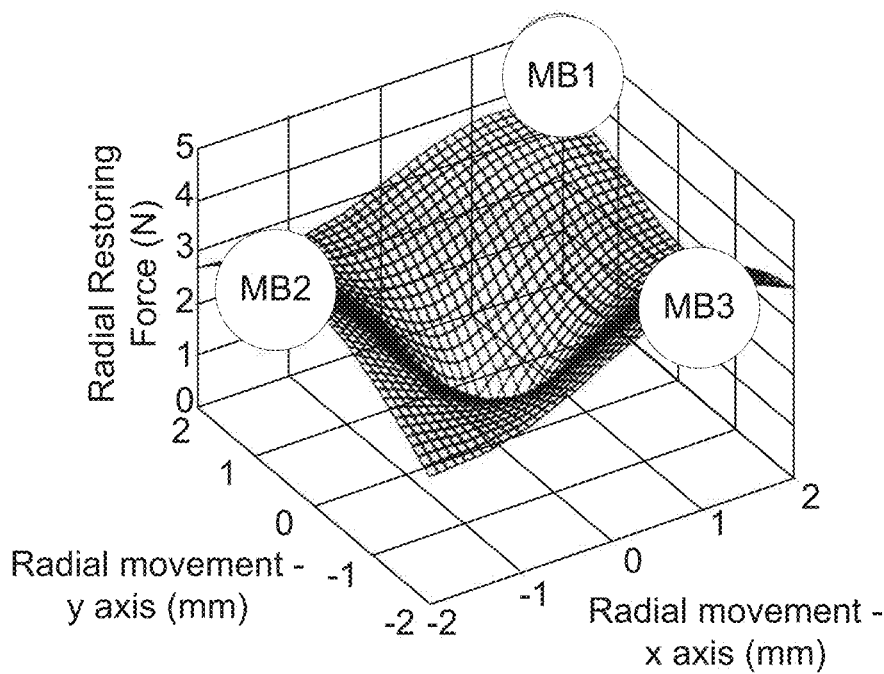
FIG. 9B is a graph showing examples of radial forces relative to the magnetic bearing stator locations.

Whilst the magnitude of the radial force directly contributes to the chance for the rotor to touchdown the casing in the radial direction, the direction of this force over the flow range can also assist when utilising the passive reluctance forces generated from an axial magnetic bearing. In this regard, the magnetic bearing system has an inherent passive radial restoring stiffness which increases when the force is acting directly towards a bearing stator. An example of the magnitude of the restoring force relative to the location of the bearing stators MB1, MB2, MB3 is shown in FIG. 9B.

From this it will be appreciated that it is desirable to manipulate the maximum radial force vectors at high and low flows to urge the rotor towards the bearing stators, thus enabling the system to take advantage of increased radial stiffness. Whilst the MB stator locations could then attempt to be adjusted to suit, it is more desirable to manipulate the force vector, which can be achieved through suitable selection of volute parameters, particularly cutwater angle, shape this force vector, as will now be described.

Volute Configuration

When considering volute configuration it is important to take into account the physical dimensions of the resulting pump. In this regard, the goal of an implantable heart pump is to minimize device implantation size to maximize the population that can receive circulatory support. The outer diameter OD3 of the volute casing is usually the largest radial dimension of the device, hence should be minimized without compromising performance.

It is known from turbo machinery theory that different volute collector profiles produce distinct pressure distributions around the impeller. More specifically, three types of volute are commonly employed in industry: circular, single and double or split volute. Whereas the circle volute is the simplest of all three, it generates an uneven pressure distribution and therefore comparatively higher radial forces, especially at higher flows.

Another volute type is a single/spiral type. The single volute has its cross-section increasing linearly (or as a function to conserve fluid angular momentum) around the circumference, therefore providing an efficient conversion from fluid velocity into pressure and, hence, an even pressure distribution around the impeller. Because the even pressure distribution is only occurring at the pump BEP, the use of the split volute is an effective way of balancing uneven pressure distribution, therefore generating lower radial forces for all operation points at the cost of larger viscous losses. In traditional single/spiral volute types, the cutwater angle CW is 0°. However, to allow for a sufficiently large throat area $A_{th}$, the outer diameter OD3, shown in FIG. 5F, must increase significantly, meaning the device may be too large to fit in smaller patients. This can be counteracted by increasing the CW angle, allowing OD3 to be reduced, allowing for a smaller overall device and allowing for a larger effective $A_{th}$.

To illustrate the effect of volute configurations, several configurations were systematically tested in a force test rig, whilst keeping the same rotor geometry, 10.6 mm length, for the sake of comparison. Among the configurations were circular volutes and single volutes, with parameter variations of base circle diameters (BCD), cutwater angles (CW), volute angles (VA) outer throat area wall diameters (D3) as well as throat areas ($A_{th}$) made up of variations in height (H) and width (W) to form different aspect ratios (AR). All configurations tested are listed in TABLE 1 below.

TABLE 1

| # | BCD BASE CIRCLE DIAMETER (mm) | OD3 OUTER DIAMETER3 (mm) | Ath THROAT AREA (mm$^2$) | W WIDTH (mm) | H HEIGHT (mm) | AR ASPECT RATIO | CW CUT-WATER ANGLE (°) | VA VOLUTE ANGLE (°) |
|---|---|---|---|---|---|---|---|---|
| V1 | 59 | 59 | 50 | 16.4 | 3.4 | 4.8 | 64 | 0 |
| LV1452 | 54 | 67 | 159.49 | 13.99 | 11.40 | 1.2 | 45.6 | 2.51 |

TABLE 1-continued

| # | BCD BASE CIRCLE DIAMETER (mm) | OD3 OUTER DIAMETER3 (mm) | Ath THROAT AREA (mm²) | W WIDTH (mm) | H HEIGHT (mm) | AR ASPECT RATIO | CW CUT-WATER ANGLE (°) | VA VOLUTE ANGLE (°) |
|---|---|---|---|---|---|---|---|---|
| LV1453 | 58 | 71 | 143.08 | 14.6 | 9.80 | 1.5 | 42 | 2.31 |
| LV1454 | 54 | 67 | 138.18 | 14.1 | 9.80 | 1.4 | 42 | 2.48 |
| LV1455 | 56 | 69 | 140.73 | 14.36 | 9.80 | 1.5 | 42 | 2.40 |
| LV1527 | 58 | 71 | 154.97 | 14.62 | 10.60 | 1.4 | 42 | 2.31 |
| LV1528 | 60 | 71 | 154.76 | 14.6 | 10.60 | 1.4 | 44.2 | 1.91 |
| LV1532 | 58 | 71 | 169.51 | 15.41 | 11.00 | 1.4 | 44.5 | 2.33 |
| LV1534 | 58 | 71 | 154.88 | 12.44 | 12.45 | 1.0 | 36 | 2.27 |
| LV1535 | 54 | 71 | 154.76 | 14.6 | 10.60 | 1.4 | 37 | 3.20 |
| LV1536 | 60 | 71 | 182.13 | 14.629 | 12.45 | 1.2 | 44.28 | 1.91 |
| LV1538 | 60 | 73 | 157.68 | 14.875 | 10.6 | 1.4 | 42.15 | 2.24 |
| LV1540 | 58 | 71 | 60.95 | 5.75 | 10.6 | 0.5 | 0 | 2.04 |
| LV1541 | 58 | 76 | 87.45 | 8.25 | 10.6 | 0.8 | 0 | 2.83 |
| LV1542 | 59 | 76 | 100.91 | 9.52 | 10.6 | 0.9 | 20 | 2.78 |
| LV1543 | 60 | 76 | 153.02 | 14.436 | 10.6 | 1.4 | 40 | 2.73 |
| LV1544 | 62 | 76 | 145.86 | 13.76 | 10.6 | 1.3 | 40 | 2.32 |

Figure 9C:
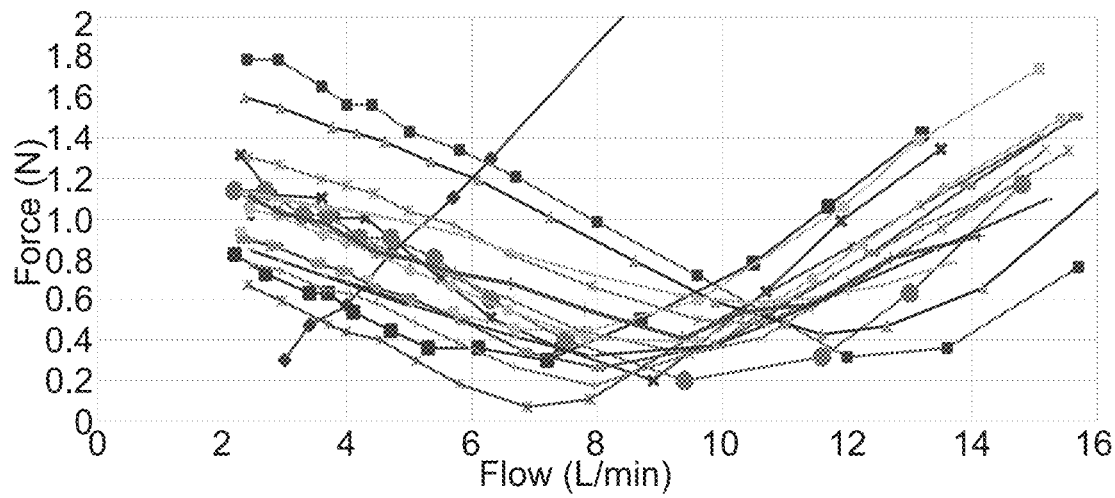
FIG. 9C is a graph showing examples of radial forces for different example pumps.
Figure 9D:
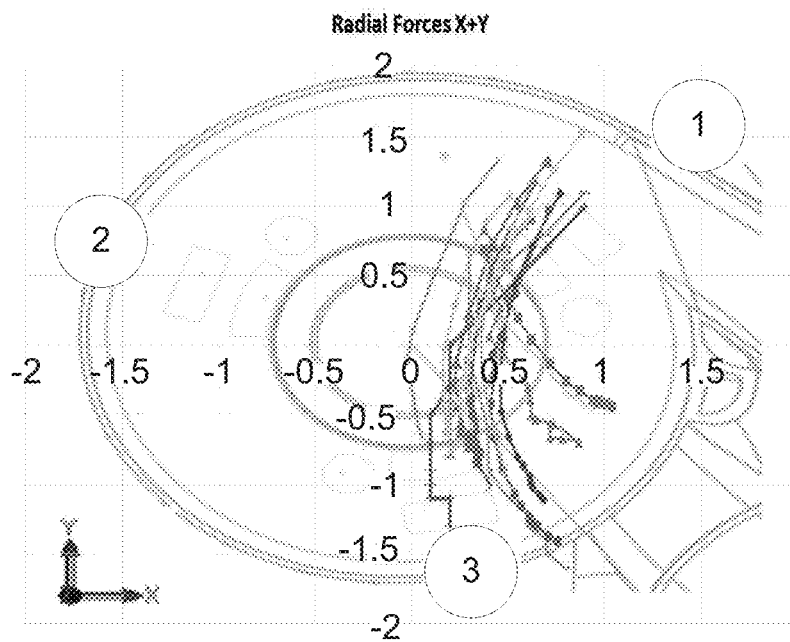
FIG. 9D is a graph showing examples of radial force components for different example pumps.
Figure 9E:
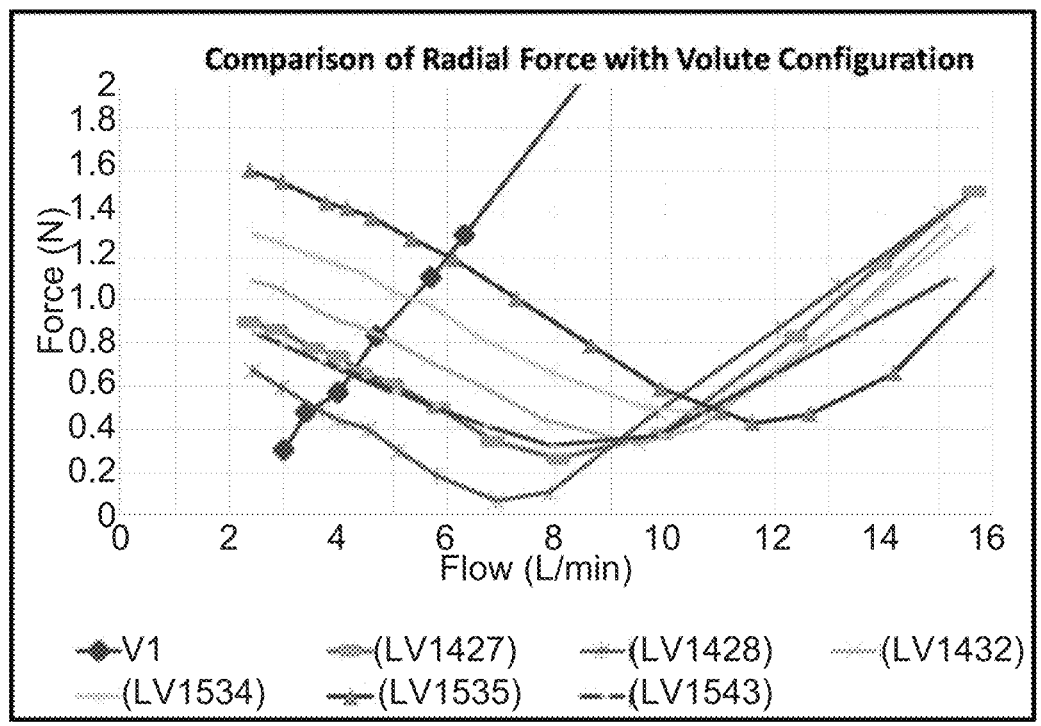
FIG. 9E is a graph showing examples of radial force components to illustrate the effect of different volute shapes.
Figure 9F:
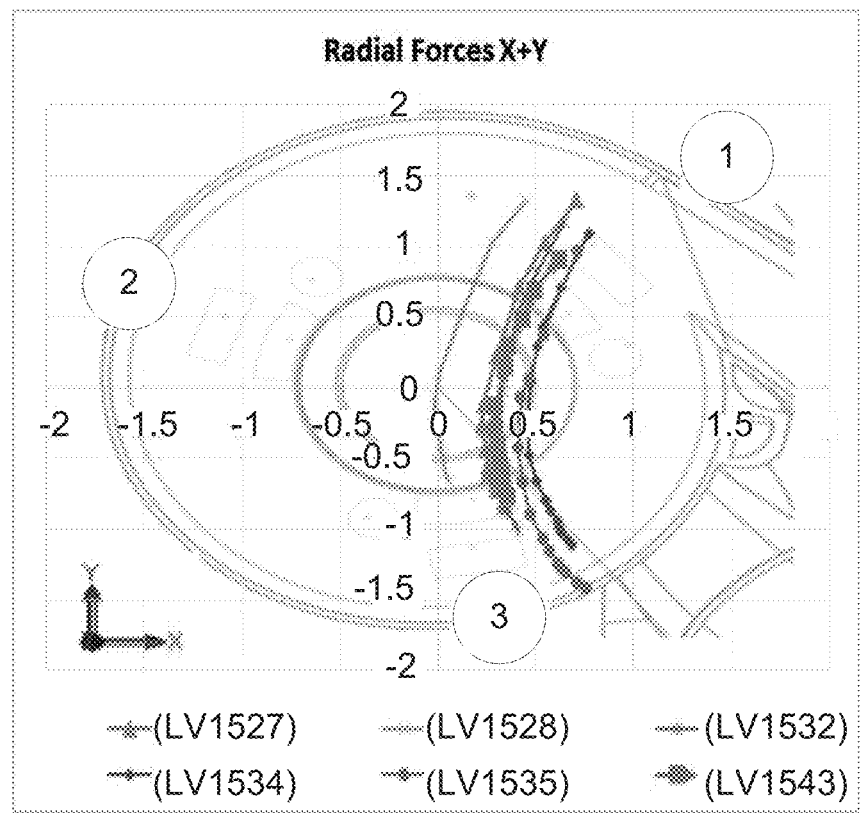
FIG. 9F is a graph showing examples of radial force components for different example pumps.
Figure 9G:
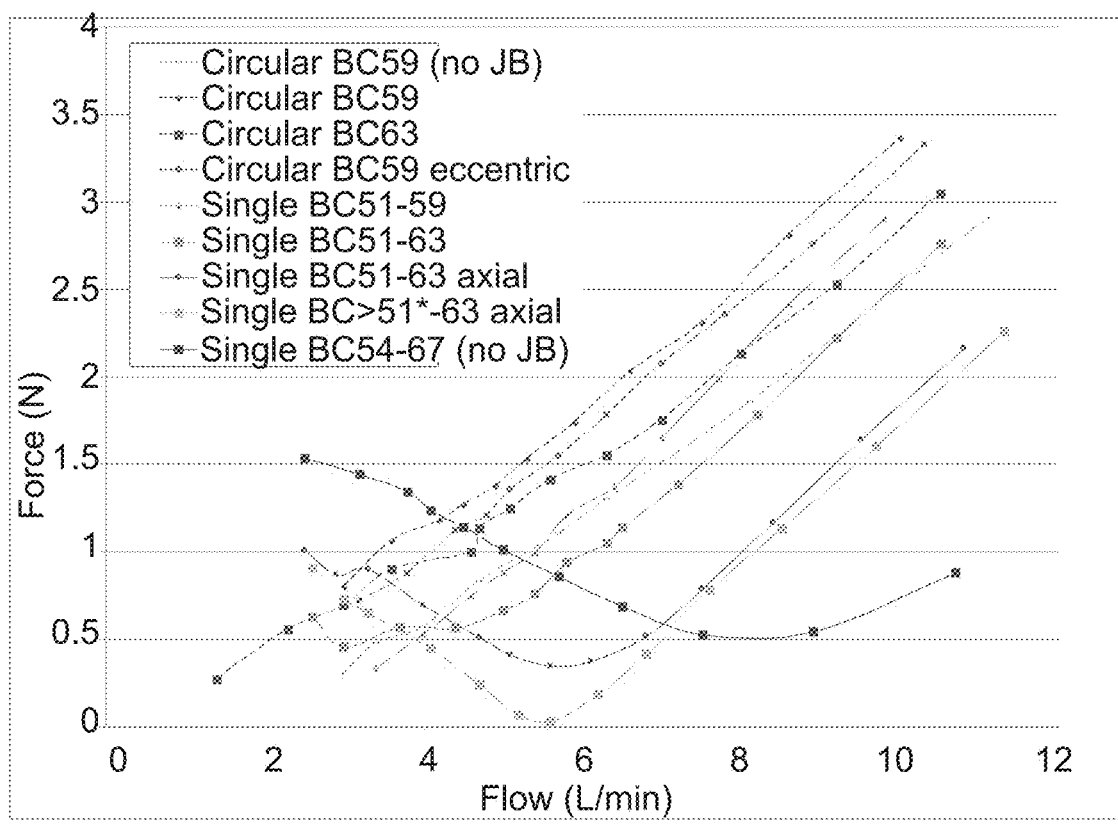
FIG. 9G is a graph showing further examples of radial force components to illustrate the effect of different volute shapes.
Figure 9H:
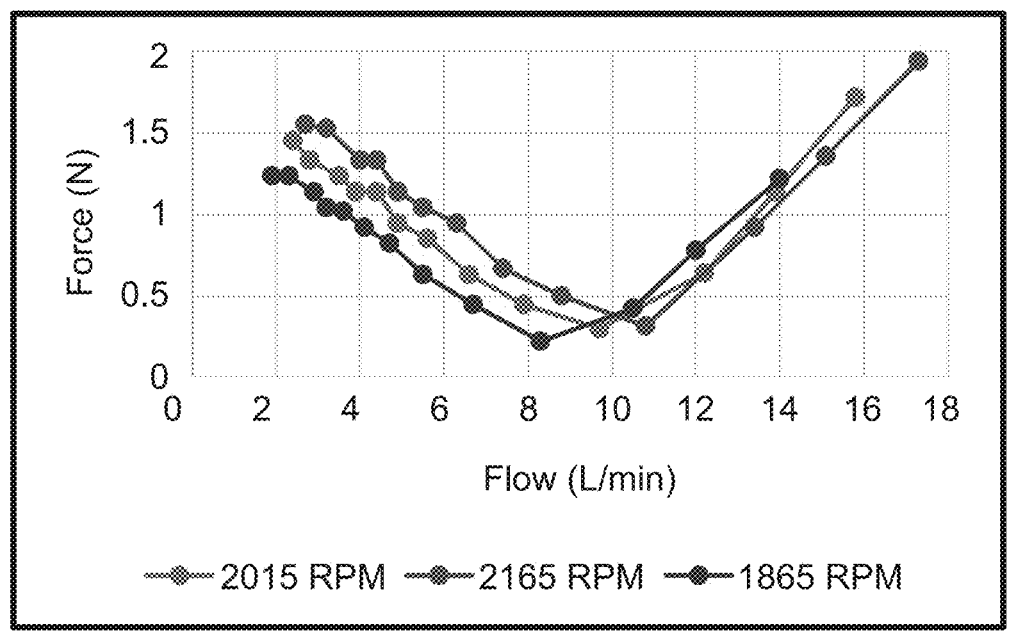
FIG. 9H is a graph showing examples of radial forces to illustrate the effect of different pump rotational speeds.
Figure 9I:
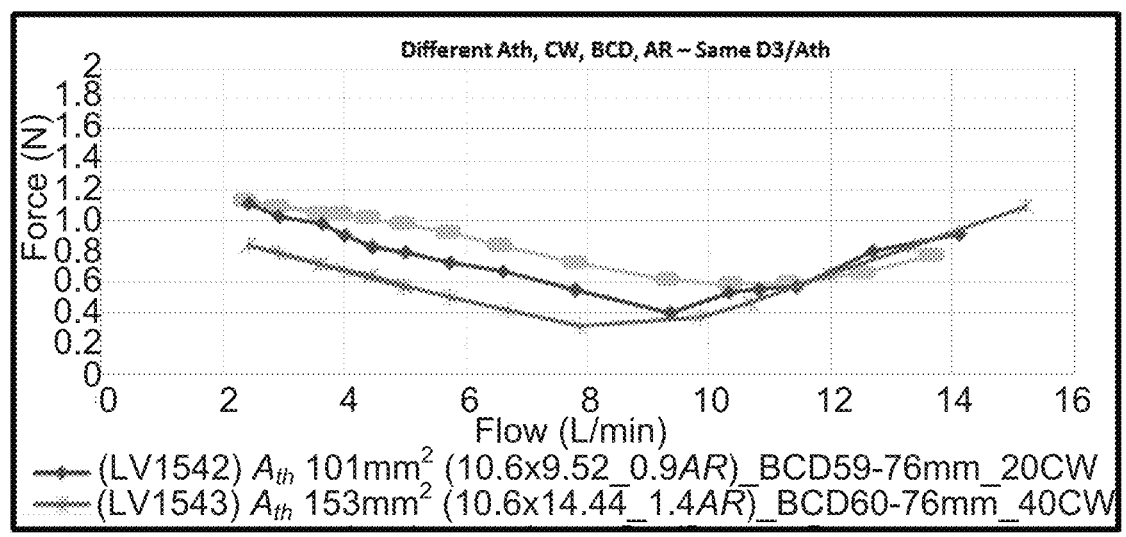
FIG. 9I is a graph showing examples of radial forces to illustrate the effect of different throat areas.
Figure 9J:
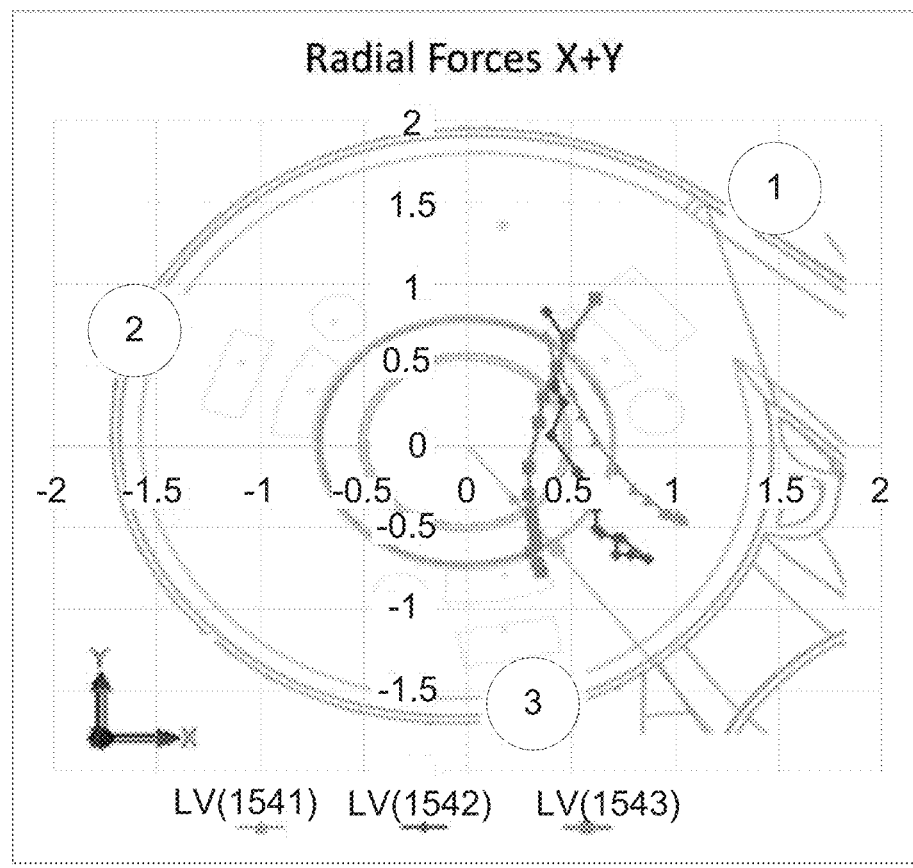
FIG. 9J is a graph showing examples of radial force components to illustrate the effect of different throat areas.
Figure 9K:
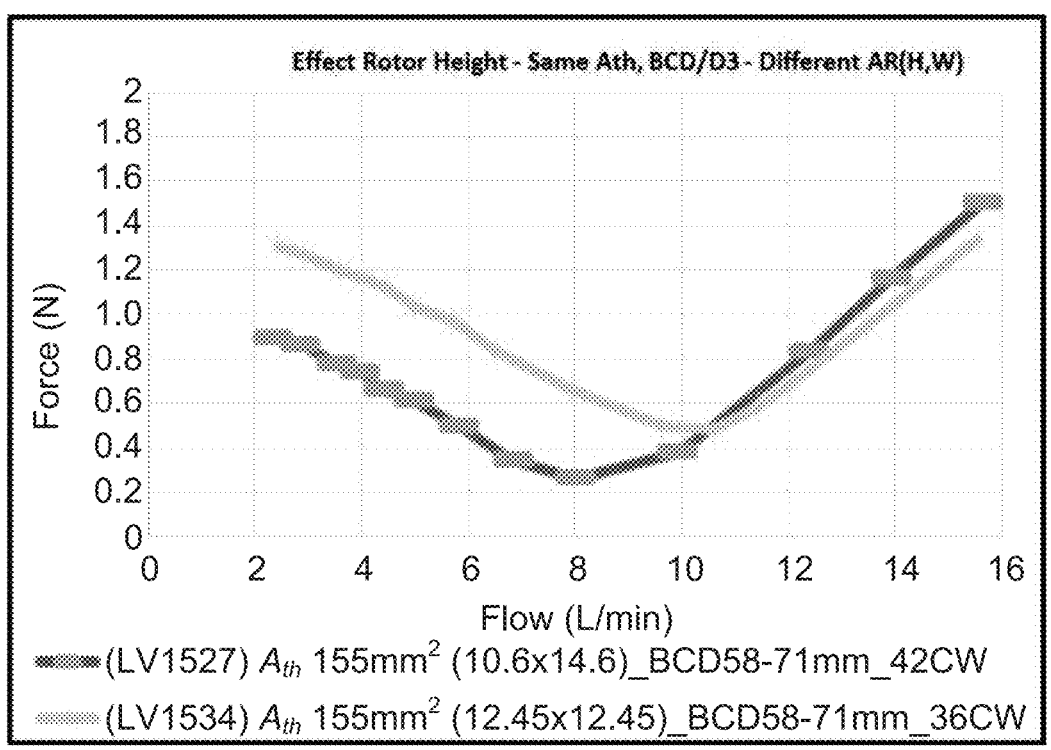
FIG. 9K is a graph showing examples of radial forces to illustrate the effect of different throat aspect ratios.
Figure 9L:
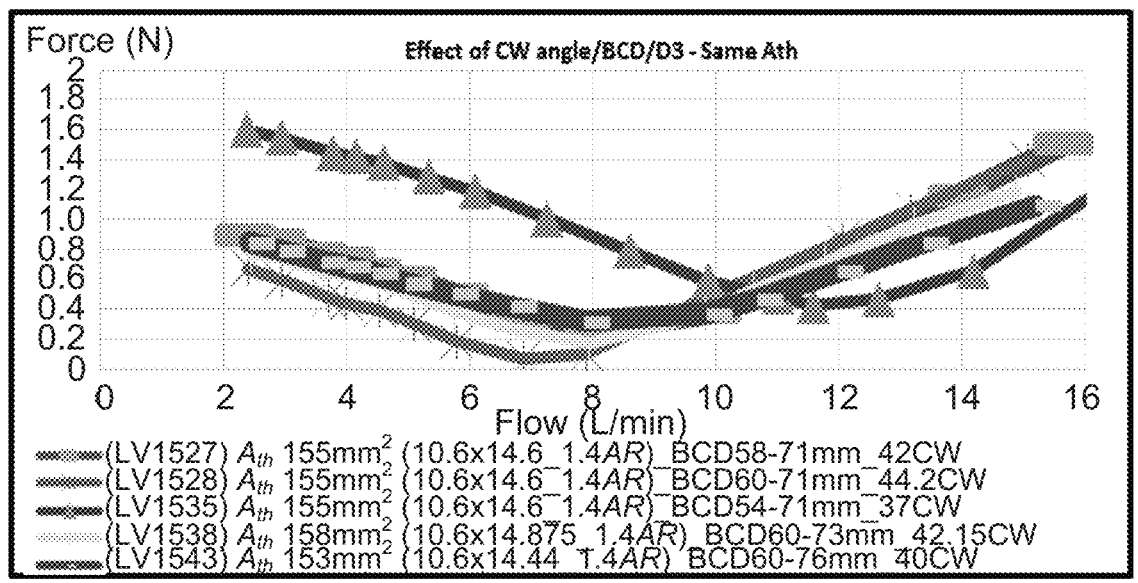
FIG. 9L is a graph showing first examples of radial forces to illustrate the effect of different cutwater angles.
Figure 9M:
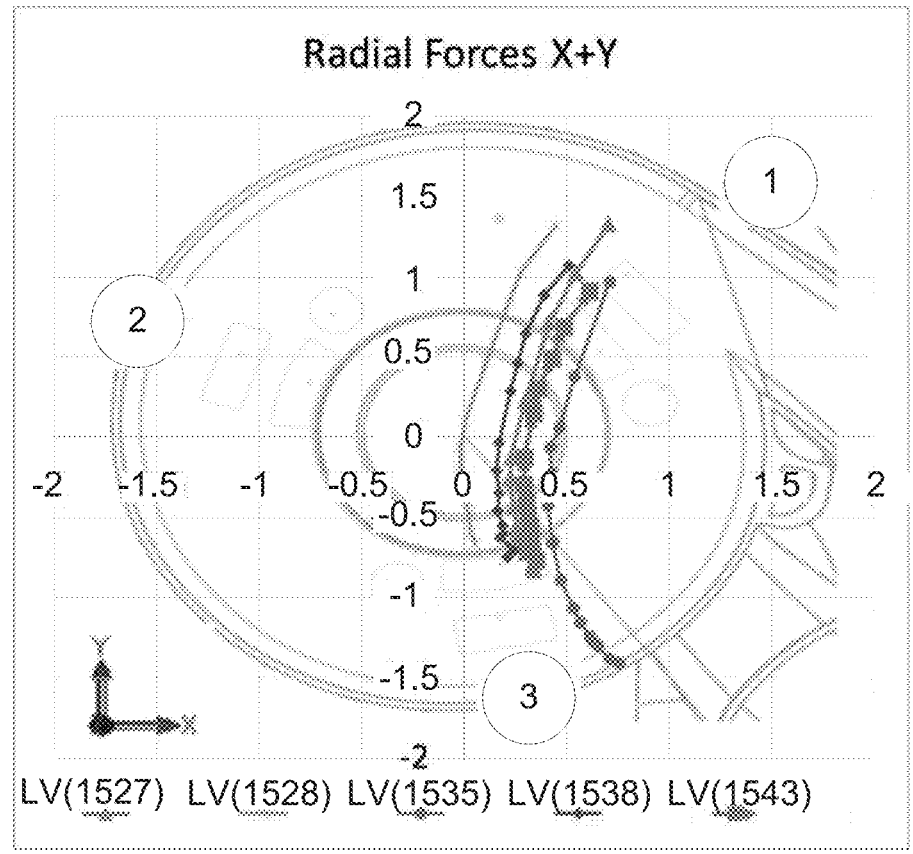
FIG. 9M is a graph showing first examples of radial force components to illustrate the effect of different cutwater angles.
Figure 9N:
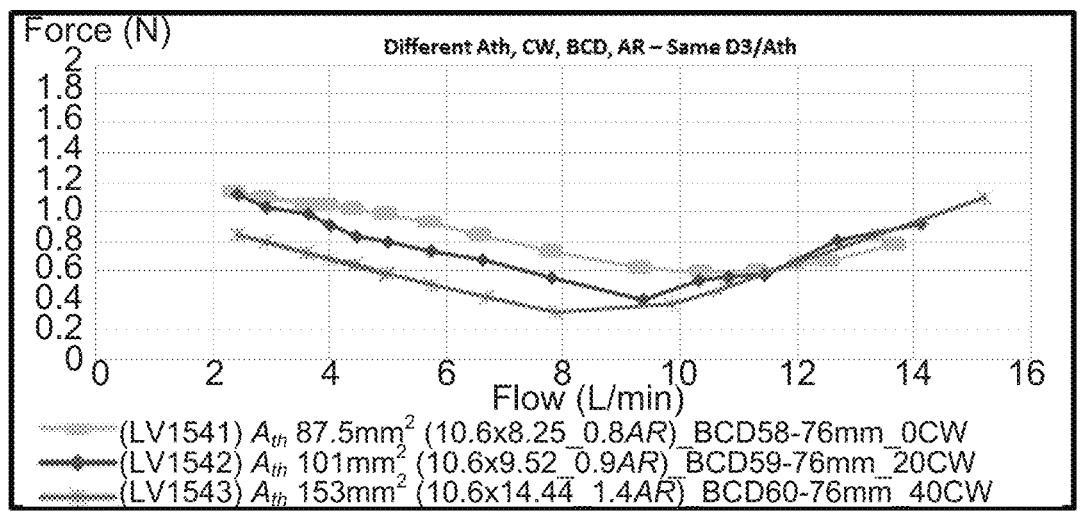
FIG. 9N is a graph showing second examples of radial forces to illustrate the effect of different cutwater angles.
Figure 9O:
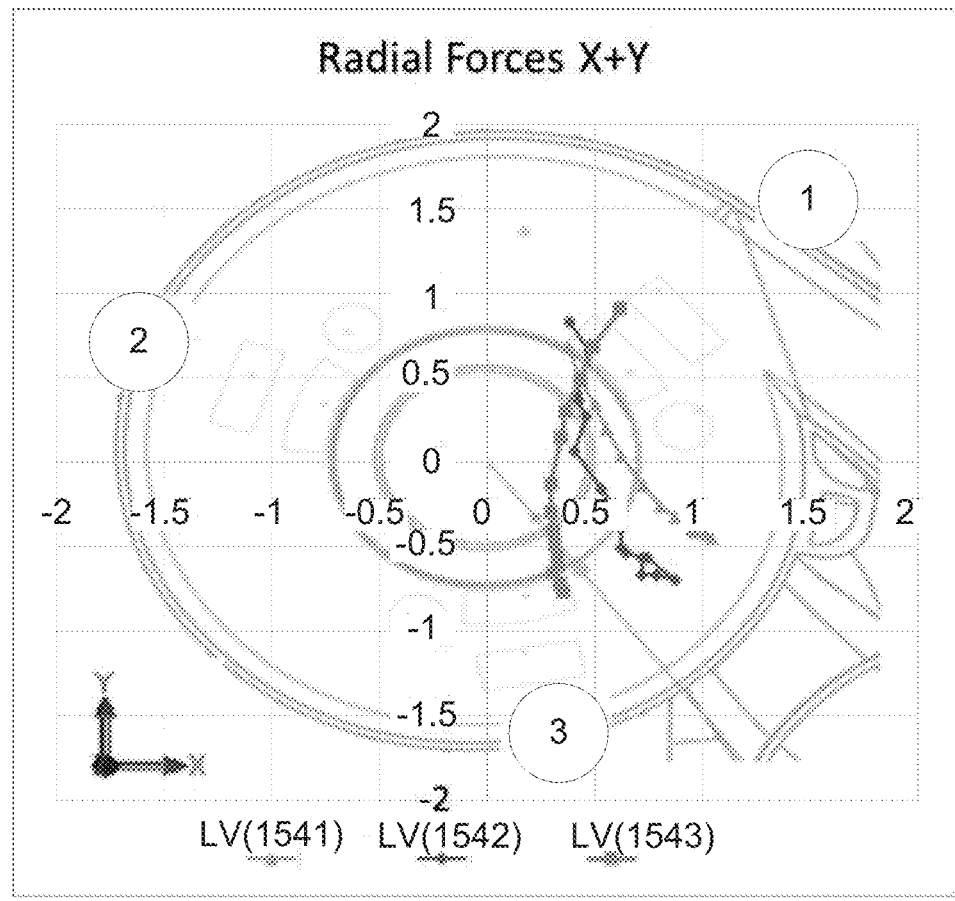
FIG. 9O is a graph showing second examples of radial force components to illustrate the effect of different cutwater angles.
Figure 9P:
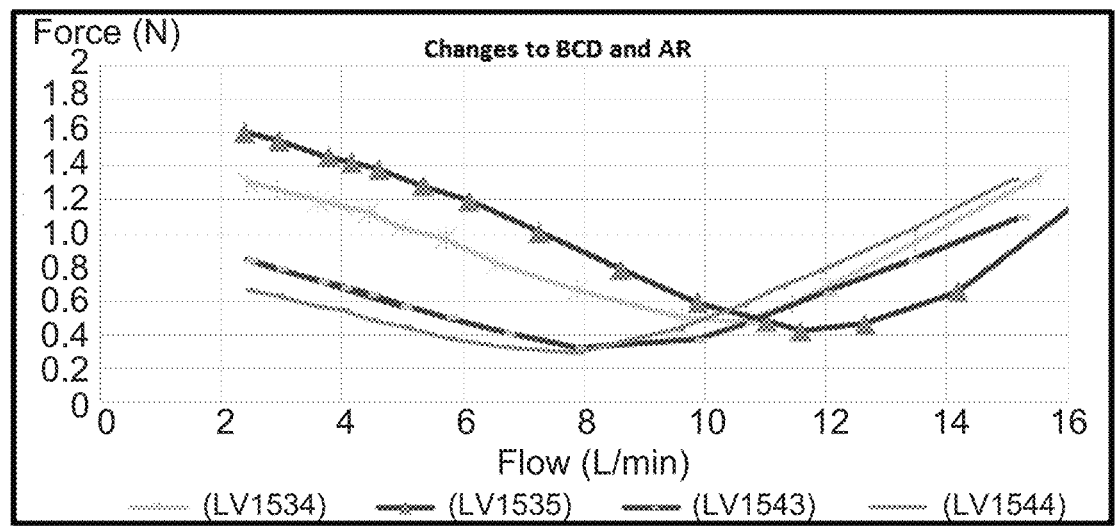
FIG. 9P is a graph showing examples of radial forces to illustrate the effect of different base circle diameters.
Figure 9Q:
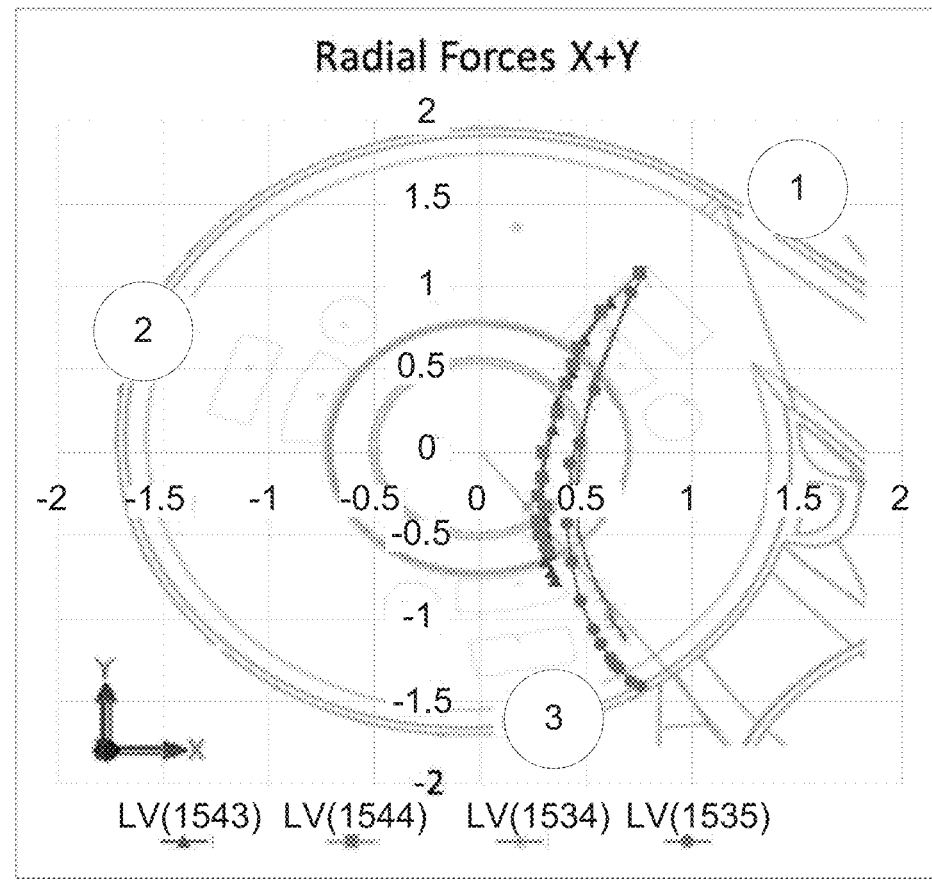
FIG. 9Q is a graph showing examples of radial force components to illustrate the effect of different base circle diameters.
Figure 9R:
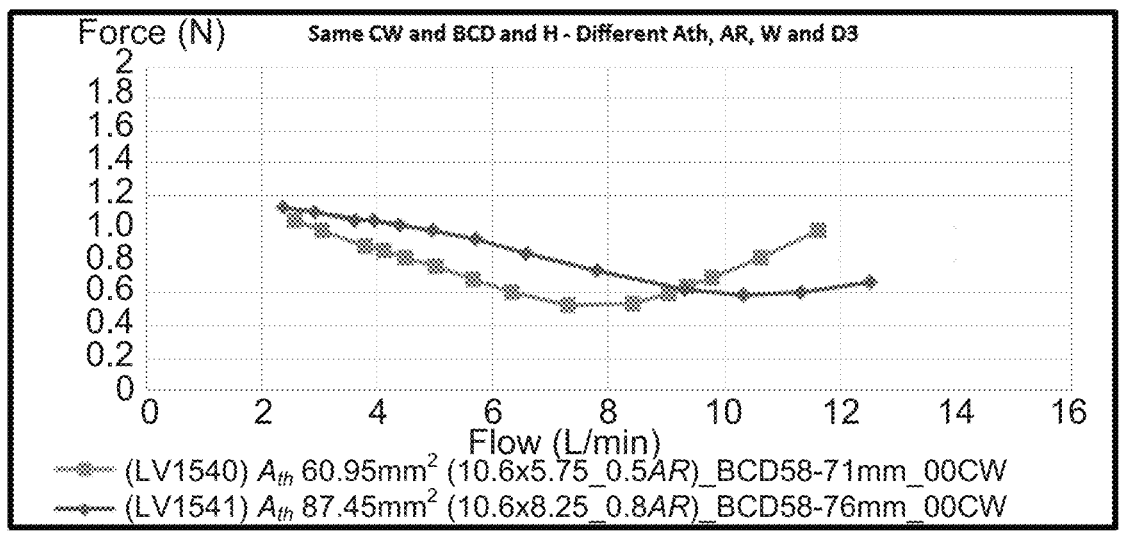
FIG. 9R is a graph showing examples of radial forces to illustrate the effect of different outer circle diameters.
Figure 9S:
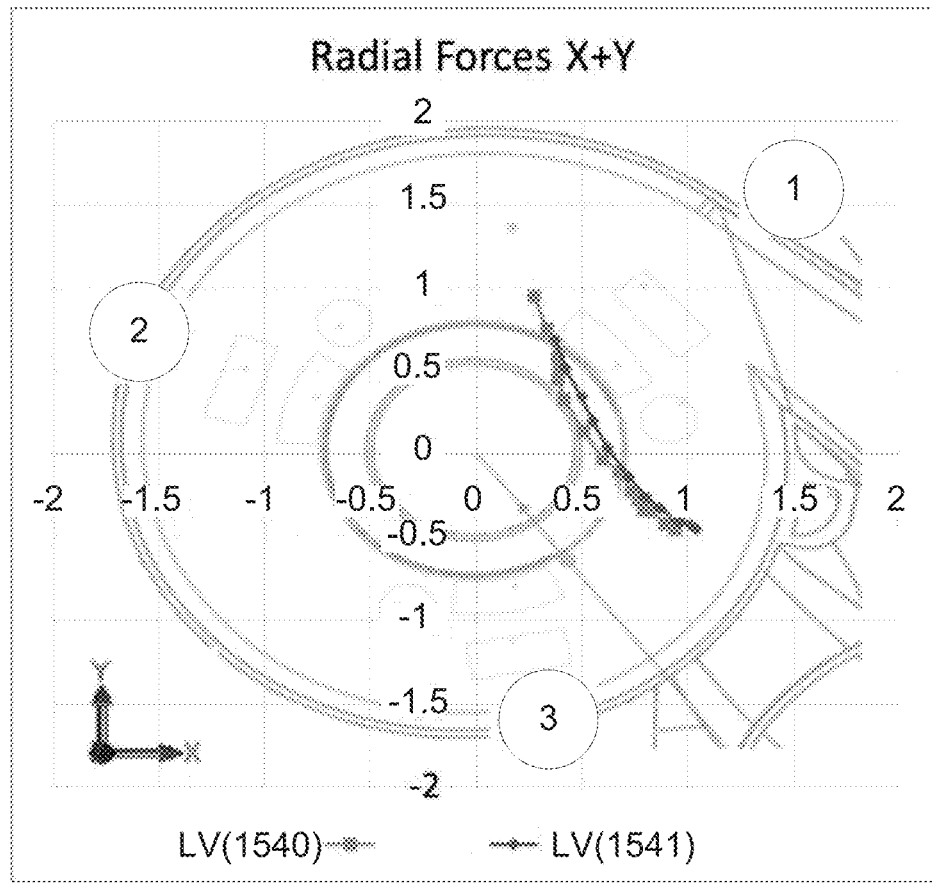
FIG. 9S is a graph showing examples of radial force components to illustrate the effect of different outer circle diameters.
Figure 9T:
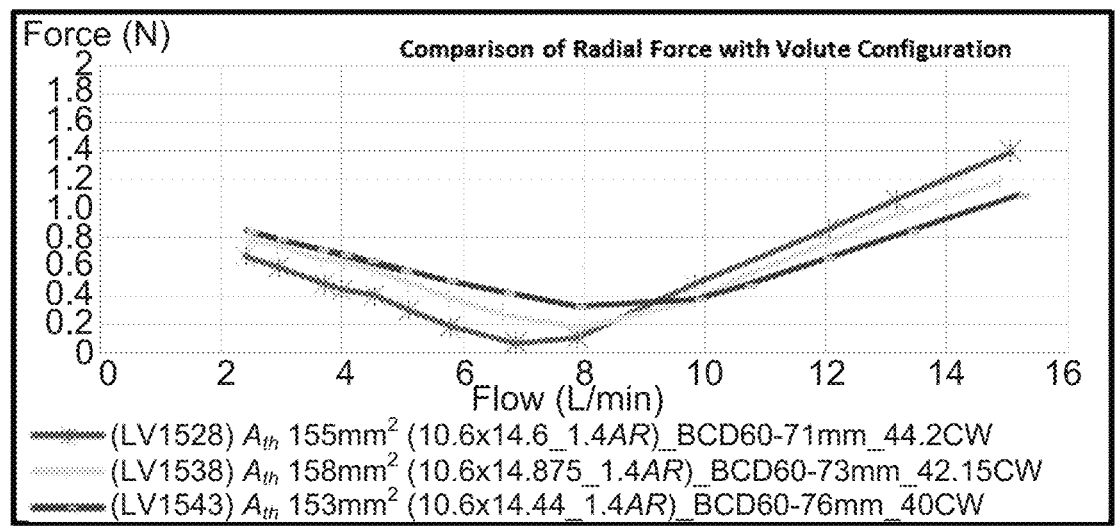
FIG. 9T is a graph showing examples of radial forces to illustrate the effect of different cutwater angles and outer circle diameters.
Figure 9U:
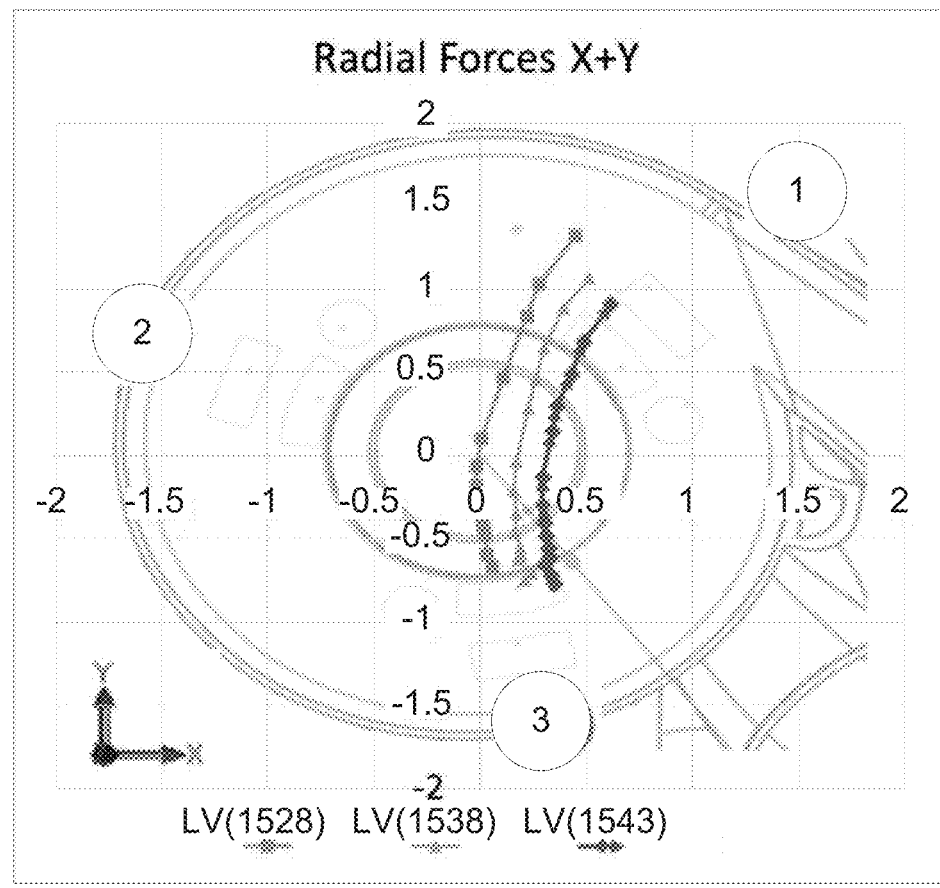
FIG. 9U is a graph showing examples of radial force components to illustrate the effect of cutwater angles and outer circle diameters.
Figure 9V:
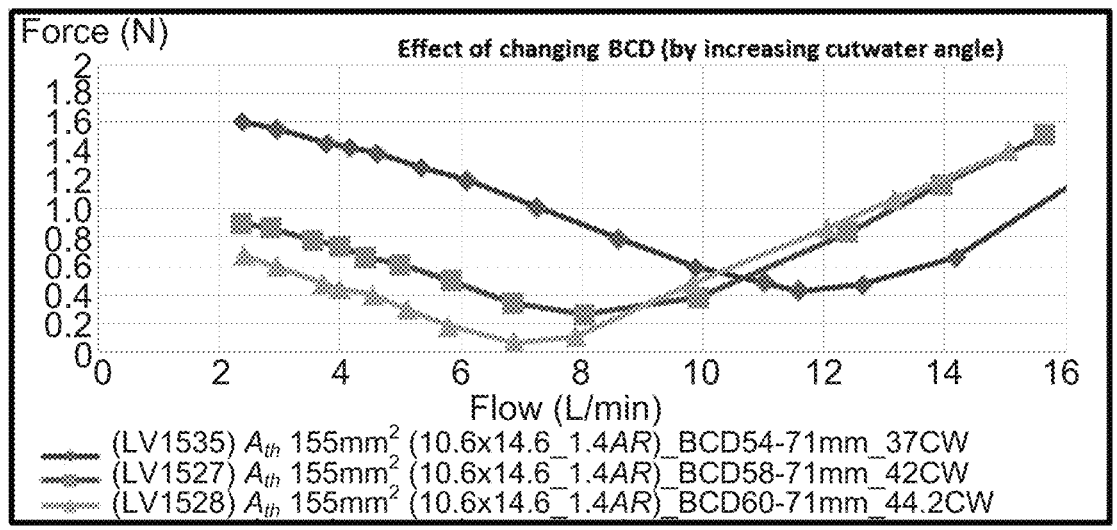
FIG. 9V is a graph showing examples of radial forces to illustrate the effect of different cutwater angles and base circle diameters.
Figure 9W:
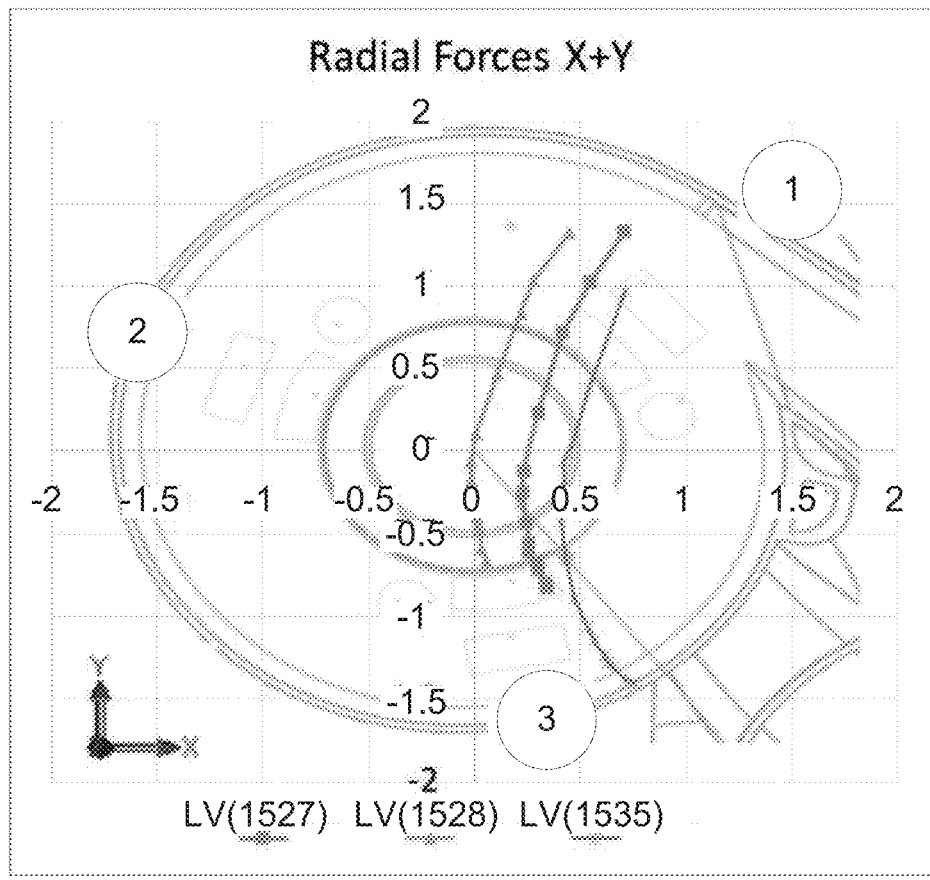
FIG. 9W is a graph showing examples of radial force components to illustrate the effect of cutwater angles and base circle diameters.
Figure 9X:
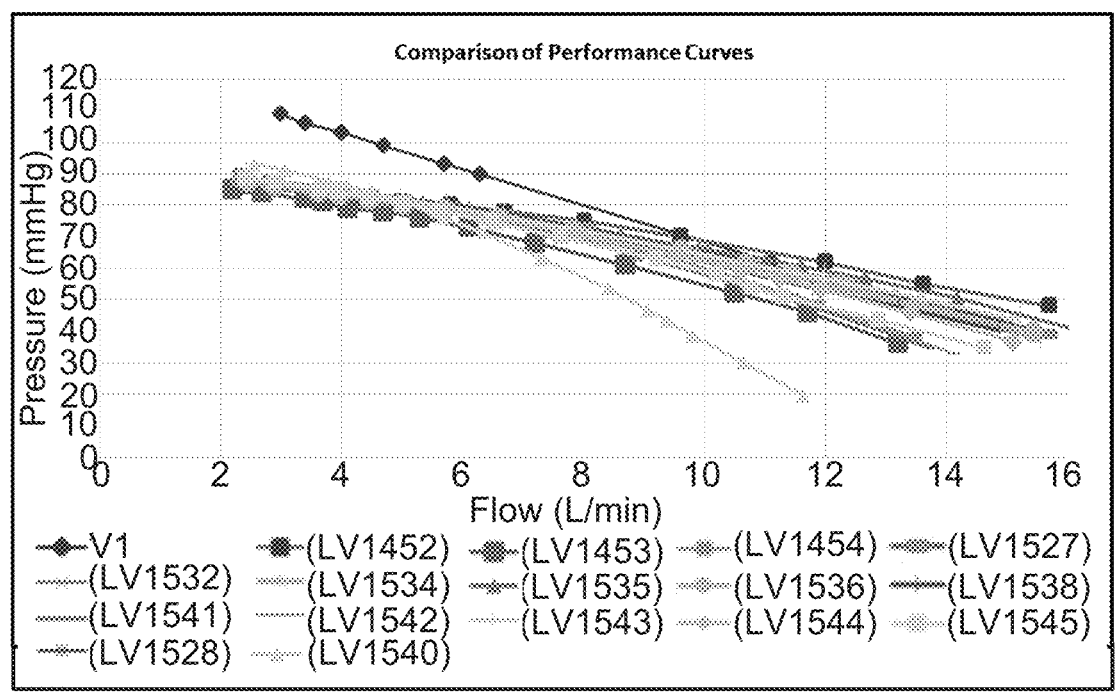
FIG. 9X is a graph showing examples of performance curves for different example pumps.
Figure 9Y:
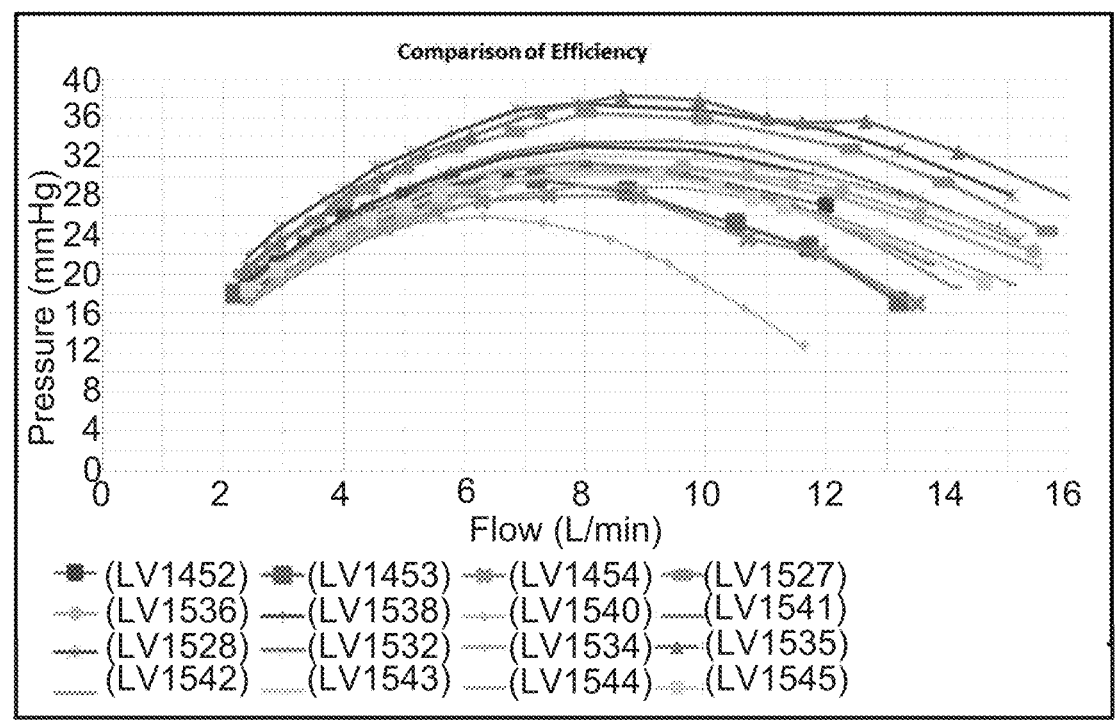
FIG. 9Y is a graph showing examples of efficiencies for different example pumps.

The results of all measured forces are shown in FIGS. 9C and 9D, with the pump performance curves and efficiencies being shown in FIGS. 9X and 9Y. The outcome of these results is discussed in more detail in the following sections.

Volute Shape

The effects of different volute shape on radial forces are shown in FIGS. 9E and 9F. This highlights that the circular volute (V1) produces unmanageable radial forces over the desired operating range of 3-12 LPM. Using a single volute with a large throat area designed for a BEP at 12 LPM flattens the pump curve, and also significantly reduces the forces at high flows, however raises them at lower flows due to fluid deceleration.

Further example circular and single volute configurations are shown in FIG. 9G. Whereas some designs were provided with a radial gap of the order of 0.1 mm to mimic the journal bearing influence, many designs of considerably larger radial gaps were tested for providing an idea about the forces the magnetic bearing system would have to passively overcome.

The first observation about the force curves is that higher forces are expected with increasing flow. This is valid for the circle volute in the whole tested range and for the single volutes after their turn over at the best efficiency point, where in both cases, fluid in the throat area region is required to accelerate. In addition, increasing the base circle diameter (BC) of either the circle or single volute decreases the forces, especially at higher flows (circular) and low flows (single). The circle volute geometry with the lowest force was the one with no journal bearing and thus a larger radial gap. In this volute, a 3 mm radial gap was left between rotor and volute wall, which effectively increased the volute cross-section area. This shows that not necessarily the base circle alone is a major determinant of the radial forces but the area where the rotor discharges the fluid pumped by the vanes (compare, for instance, circle BC 59 with circle BC59 (no journal bearing)), and the angle that the cutwater starts.

Secondly, single volutes produce, in general, less radial forces than circle volutes at design flows, with the rule of increasing the volute cross-section still holding. Moreover, increasing volute cross-section means an increase in throat area, altogether shifting the point of lowest force to higher flows. This result is in accordance with traditional turbo machinery theory. Furthermore, increasing the cross-section area yielded flatter force curves, effectively lowering the radial force, especially at high flows. This is of particular interest for the TAH application pump, since it enables stable operation at more demanding hemodynamic conditions like during exercise (flows about 12 LPM).

Accordingly, on left hand pumps, which tend to generate the greatest force, the casing may include a single volute, with this typically being configured to generate a maximum radial force of less than 1 N.

Rotational Speed

As shown in FIG. 9H, alterations in speed had minimal effect on the radial force shape/profile, rather shifting the minimum force point to the right as speed increased, This characteristic is of particular benefit when operating the device in a pulsatile outflow mode, whereby speed is increased to both increase outflow pressure and flow, resulting in lower forces at higher flow rates than would occur at a lower speed.

Effect of $A_{th}$ on Radial Force

The impact of throat area $A_{th}$ will now be described with reference to FIGS. 9I and 9J.

When comparing LV1527 and LV1532, whereby $A_{th}$ increases whilst AR, CW, BCD and D3 remain the same, a shift in minimum resultant radial force to higher flows is observed. Considering the individual X and Y force components, it can be observed that the larger $A_{th}$ translates to a lower +Y force, due to reduced acceleration in the throat and thus less reduction in pressure that would counteract unbalanced forces acting in this direction. Likewise, at low flows, the larger area at the throat produces larger fluid deceleration in this region and correspondingly raises the local pressure in this region, contribution to a larger force in the −Y direction. Minimal changes to X forces are observed with this configuration.

Despite the larger $A_{th}$ in LV1543 than LV1542 and LV1541 (153 mm² compared to 101 mm² and 87.5 mm²), increasing the BC from 58 mm to 59 mm to 60 mm and CW from 0° to 20° to 40°, increasing the AR from 0.8 to 0.9 to 1.4 (while maintaining H and OD3), significantly reduced forces at low flows and increased them slightly at flows above 12 LPM, resulting in the minimum force point reducing from 11 LPM to 8 LPM, and forces remaining below 0.8 N from 3-12 LPM. The deceleration of fluid at the cutwater at low flows due to a small $A_{th}$ and thus volume upstream of the cutwater dominates the production of part flow forces, particularly in the X direction opposing the cutwater.

Accordingly, this aligns with the preferred throat areas discussed previously.

Effect of Throat Geometry (AR) on Radial Force (H and W)

The impact of throat geometry, and in particular aspect ratio AR will now be described with reference to FIG. 9K.

When comparing LV1527 and LV1534, whereby AR and CW are both reduced, while $A_{th}$, BCD and OD3 are maintained. the minimum resultant force point is shifted to higher flows and increases in magnitude. In addition, resultant forces at low flows are increased, while forces at high flows are somewhat reduced.

A similar trend is observed with LV1528 and LV1536, and LV1543 and LV1527 whereby $A_{th}$ is increased and AR decreased by simply increasing the height (H) and maintaining CW, BCD/OD3 and throat width (W).

The throat geometry or aspect ratio in turn can set the rotor height. Examination of these results show that the ideal rotor height is approximately 10 mm, with smaller rotors resulting in a boundary layer blocking outflow at the throat and thus increase the radial force at high flows due to excessive fluid acceleration, whereas rotors taller than 11 mm lead to separation downstream of the higher volute cutwater wall becoming more significant and causing blockages at high flows, also resulting in acceleration of fluid and thus localized pressure drop and increased radial force.

Accordingly, the impeller includes a rotor having a height of at least one of at least 5 mm, less than 12 mm, between 6 mm and 10 mm and more typically approximately 10 mm, with the impeller height adding to the overall height.

Effect of Cutwater Angle CW

The impact of cutwater angle CW will now be described with reference to FIGS. 9L and 9M.

The cutwater angle influences the location within the casing that fluid is either diverted into the volute, or out of the pump through the throat.

When comparing LV1535, LV1543, LV1527, LV1538 and LV1528, whereby the cutwater angle increases from 37° to 44.2°, it can be observed that as cutwater increases, the minimum resultant force reduces in magnitude and shifts to lower flow rates. Furthermore when analyzing the X and Y component forces, and accounting for variations in other parameters, it is observed that the increasing CW effectively reduces the X force component away from the cutwater region.

Another way to describe this trend is to consider the distance between the BCD and the OD3. That is, as this value decreases, CW angle increases, and the forces in the X direction toward the cutwater region reduces as it is counteracted by forces generated from additional recirculating fluid past the cutwater.

When expanding the range of CW angles tested in LV1541, LV1542 and LV1543, a similar trend is observed whereby the minimum resultant force reduces in magnitude and shifts to lower flows as cutwater increases. Furthermore, as cutwater reduces through 20° to 0°, the X/Y force plot rotates anticlockwise by the same degree. Hence the cutwater angle can be used to orientate the force over the range of flow rates to correspond with the location of bearing stators.

Effect of BCD

The impact of BCD will now be described with reference to FIGS. 9N and 9O and FIGS. 9P and 9Q.

When comparing LV1534 an LV1535 in FIGS. 9N and 9O, increasing BCD and decreasing AR, but maintaining the CW angle, OD3 and $A_{th}$, shifts the minimum resultant radial force point to a lower flow. Regarding the force components, minimal influence is found on X forces, however Y forces are decreased at low flows, since fluid deceleration at the throat area is less since more fluid can recirculate between the cutwater and the impeller, thus maintaining velocity and converting less energy to pressure. Y forces are increased at high flows in this case, since pressure generation is reduced and thus cannot counteract the circumferential radial forces acting toward the +Y direction, due to the lower effective throat area caused by excessive blockage downstream of the cutwater due to a lower AR and thus larger $A_{th}$ (same H).

When comparing LV1543 and LV1544 in FIGS. 9P and 9Q, where again BCD is increased and AR is decreased and both CW and OD3 maintained, but this time $A_{th}$ is reduced, also $A_{th}$ shifts the minimum resultant radial force point to a lower flow. A similar trend is found with X and Y forces, whereas the larger Y forces at high flows is now simply attributed to the smaller $A_{th}$ causing additional fluid acceleration retarding pressure generation. This effect can also be observed when comparing LV1527, LV1528 and LV1535.

Effect of OD3

The impact of OD3 will now be described with reference to FIGS. 9R and 9S.

When comparing LV1540 and LV1541, an increase to OD3 as well as $A_{th}$ and AR (same H), whilst maintaining CW angle and BCD, shifts the resulting radial force minimum to a higher flow rate. Regarding the force components, minimal influence is found on X forces at all flow rates, and Y forces at low flow rates, however Y forces at high flow rates are reduced, due a lower requirement for fluid acceleration, since the larger OD3 increases the effective throat area by counteracting the blockage downstream of the cutwater caused by separation. This effect can also be observed when comparing LV1528 with LV1538 and LV1543.

Effect of CW and OD3

The impact of cutwater angle CW and outer circle diameter OD3 will now be described with reference to FIGS. 9T and 9U.

When comparing LV1543, LV1538 and LV1528, whereby CW is increased as OD3 decreases while all other parameters remain equal, it can be observed that the minimum force point of the resultant radial force shifts to lower flows, as well as reducing in magnitude. Regarding the force components, there is minimal influence on Y forces at low flows, however the increase in OD3 acts to decrease Y forces at high flows. Additionally, as CW increases, the force in the X direction decreases. This is due in part to a better matching of fluid velocity vectors interacting with the cutwater, creating less downstream blockage of the $A_{th}$ due to separation. The larger effective throat area results in increased fluid deceleration over the entire flow range, and thus raises the local pressure near the cutwater, which assists in counteracting unbalanced radial forces in the X direction.

Effect of CW and BCD

The impact of cutwater angle CW and base circle diameter BCD will now be described with reference to FIGS. 9V and 9W.

When comparing LV1535, LV1527 and LV1528, whereby CW is increased as BCD increases while all other parameters remain equal, it can be observed that the minimum force point of the resultant radial force also shifts to lower flows, as well as reducing in magnitude. As observed earlier, the influence on Y flows is dominated by the variations in BCD, with higher −Y forces experienced with lower BCDs, while the X forces again reduce as CW increases.

Taking the above into account, for the left pump the cutwater angle is typically at least one of between 0° and 70°, between 30° and 50°, between 40° and 45°, between 35° and 45°, between 45° and 50°, between 0° and 60° and approximately 45°. In contrast for the right pump the cutwater angle is typically between 90° and 180°, between 90° and 135°, between 0° and 90°, between 45° and 90°, between 45° and 135°, between 60° and 80° and approximately 70°.

Combined Effect

It will be appreciated that the above described variables need to be considered in conjunction, and their net combined effect is discussed below.

In this regard, effects of different volute configuration on radial forces are shown in FIGS. 9E and 9F. These highlights that the circular volute (V1) with a throat area in the traditional range for blood pumps of 50 mm$^2$ produces unmanageable radial forces over the desired operating range of 3-12 LPM.

Switching to a traditional single volute typical of a conventional blood pump with CW of 0° and a throat area of 61 mm$^2$ designed for a BEP around 6-7 LPM (LV1540), radial forces are reduced significantly, and sufficiently below 1.0 N over the range of 3-12 LPM. However, the pump characteristic curve is steep (−10 mmHg/LPM), and hydraulic efficiency whilst acceptable at 25% at BEP, is unacceptably poor at just 10% at 12 LPM. These characteristics, whilst arguably suitable for left ventricular assistance, are not appropriate for total ventricular replacement.

To provide improved performance over the flow range of 3-12 LPM, the throat area of the single volute was increased to 155 mm$^2$, corresponding to a BEP of >10 LPM. To minimize the total radial dimension of the device, the cutwater angle was also increased to 37°, creating an AR of 1.4. Not only does efficiency increase above 25% for the entire flow range, peaking at 38%, but the pump HQ curve returns a much flatter response (−3 mmHg/LPM). The increase in $A_{th}$ acts to shift the minimum resultant radial force to higher flows, and whilst the minimum radial force reduced to 0.4 N, this occurred at the upper limit of the range at 12 LPM, rising to an undesirable 1.5 N at 3 LPM.

To reduce the large radial force component at low flows, the volute configuration was modified to increase the BCD from 54 mm to 58 mm, whilst maintaining CW and $A_{th}$ by reducing the AR to 1.0 (LV1534). This reduces low flow radial forces by allowing the fluid decelerating into the $A_{th}$ an alternate recirculating pathway between the impeller and the cutwater, thus mitigating the level of deceleration and hence the conversion to pressure in this region, such that the force in the −Y direction is reduced. However, this configuration does not reduce the X force component. The result is a resultant force profile that has a minimum at 10 LPM, but still raises to 1.3 N at the lower 3 LPM range. Furthermore, hydraulic efficiency reduced by 8%.

To further reduce resultant radial forces at low flows whilst maintaining the same $A_{th}$, CW was increased further to 42.15° and AR increased back to 1.4 (LV1527), by reducing the H of $A_{th}$. This configuration shifted the minimum radial force to 8 LPM effectively achieving the goal of resultant radial force below 1.0 N for the entire flow range of 3-12 LPM, with comparable efficiency to LV535. The larger CW helps to reduce the effective area at the $A_{th}$, hence minimize the amount of fluid deceleration and thus raises localized pressure at the cutwater region, effectively counteracting the unbalanced forces toward this area. The increase in AR by reduction in throat H has a similar effect.

A further reduction in low flow forces can be achieved by expanding on values of the parameters identified above. Whilst again maintaining $A_{th}$, AR, the BC can be increased to 60 mm with a corresponding CW angle to 44.2° (LV1528). This configuration not only reduced the flow rate for which the minimum force occurred, but the magnitude of such force was reduced to 0.1 N, hence the maximum force over the desired flow range of 3-12 LPM was just 0.85 N. The already observed decrease in X force due to cutwater increase and reduction in −Y forces at low flows due to the increased BC we responsible for this improved performance at comparably high efficiency.

Finally, in the case where the device may be operated in pulsatile outflow mode, the range of flow for which the radial force should remain below 1.0 N may benefit from a higher limit of at least 15 LPM. Hence, while again maintaining $A_{th}$ and AR, a volute configuration was made whereby the OD3 was increased from 71 mm to 76 mm with a corresponding drop in CW to 40°. This increase in OD3 effectively reduced resultant radial forces to below 1.0 N from 3-15 PM by reducing radial Y forces at high flows. However the reduction in CW caused the X forces to increase, and hence low flow forces to increase slightly, which led to a slight drop in hydraulic efficiency by 5%.

Despite the changes in radial force profile, the performance curves for each volute configuration with an $A_{th}$>150 mm$^2$ were only marginally affected by the volute parameters.

Hence, it can be concluded that for a device operating between flow ranges of 3-12 LPM, the volute configuration LV1528 has superior resultant radial force profile, hydraulic efficiency, and pump curve gradient. Should the flow range need to be expanded to account for pulsatile outflow operation, the LV1543 configuration should be considered despite the reduction in efficiency. However increasing CW back to 45° or above can restore this.

Emboli Tolerant Right Pump

Emboli originating from the deep systemic veins may find their way into the right side of the blood pump. These naturally occurring emboli usually pass through the native right ventricle unimpeded and are filtered by the pulmonary network. Thus there is a requirement for the right pump to have large area flow paths to enable venous emboli to pass through the device.

In order to improve outflow pressure sensitivity, the cross-sectional area of flow paths through the right pump are maximised. These large passages reduce the characteristic resistance of the flow path allowing for the passing of these emboli through the right pump.

In one example, the heart pump includes a flow path having a cross-sectional area throughout the entire pump that is at least 50 mm$^2$, at least 100 mm$^2$, at least 125 mm$^2$ and more typically at least 140 mm$^2$. This includes inlet and outlet ports, inflow and outflow area of the impeller, and the volute throat area.

It will also be appreciated, that whilst less critical from the perspective emboli tolerance, the left pump can also include a similarly large cross-sectional flow path, in particular having a cross-sectional area throughout the entire pump that is at least 50 mm$^2$, at least 100 mm$^2$, at least 125 mm$^2$ and more typically at least 140 mm$^2$.

Left/Right Shunt Flow

As previously mentioned, the impeller rotor is radially separated from the cavity by a distance of between 2-4 mm. For a 50 mm diameter rotor, this leads to a cross-sectional flow path between the rotor and cavity of over 500 mm$^2$. Accordingly, in practice, the cross-sectional flow path between the right and left pumps is constrained by a separation between the right hand surface of the rotor and the cavity adjacent the magnetic bearing. In one example, this leads to a flow path cross-sectional area of at least 15 mm$^2$, no greater than 50 mm$^2$ and typically between 20-50 mm$^2$, depending on the relative position of the impeller rotor within the cavity.

Under normal flow conditions, the majority of blood flows within each pump, from the inlet to the outlet, meaning there is minimal leakage between the left and right pumps. Any such leakage is from the higher pressure left pump to the low pressure right pump, meaning oxygenated blood is shunted from the systemic to the pulmonary circulatory systems, which has minimal impact from a physiological perspective. This can also be beneficial during normal use as this helps prevent stagnation within the pump.

Additionally however the left/right shunt flow path can be utilised when implanting a heart pump in a subject. In this regard, during the implantation of the artificial heart, the circulation is supported by a cardiopulmonary bypass machine. In this mode, the lungs and heart are bypassed, and the pumping and oxygenation of the blood is assumed by the external pump and oxygenator. Therefore, the lungs are deflated, and depleted from blood flowing through the arterioles.

Traditionally, after the artificial heart is implanted, the bypass machine outflow is reduced (termed weaning) and the artificial heart is turned on so that it may provide the additional flow required by the circulatory system.

However, if the speed of the artificial heart is not sufficient to generate the same outflow pressure as the bypass machine, the blood will backflow through the artificial heart and enter the lungs, thus overloading them with blood and potentially causing edema and irreversible damage.

Therefore, the speed of the device needs to be high enough to generate sufficient pressure and also additional flow to compensate for the reduced flow from the bypass machine during the weaning procedure. However, this speed also results in a sudden return of perfusion to the lungs from the right side of the device.

This sudden reperfusion of de-oxygenated blood at a relatively high flow rate can cause the lung vessels to constrict, thus causing a high resistance state, limiting blood flow back to the left side of the artificial heart, and thus to the rest of the body for a period of time. To avoid this situation, the rate of blood reperfusion to the lungs should initially be low and then gradually increased.

An example process for implanting a heart pump will now be described with reference to FIGS. 13A to 13D, which show the status of the pump and circulatory parameters from data collected during a trial implantation process.

In this example, the heart pump is initially connected to the subject's pulmonary and systemic circulatory systems, but with the left pump outflow blocked, typically by clamping a cannula or the like. The pump is activated initially running at a low speed, such as 1000 RPM-1250 RPM, with blood being pumped from the right pump outlet, through the lungs, returning to the left pump inlet at a very low rate, typically lower than 0.5 LPM. As a result, the blood passes through the lung arterioles to collect oxygen, and returns to the left side of the pump. With the left outflow blocked, blood then flows through the left/right shunt flow path, before being returned to the lungs. In this regard, the left pump pressure is higher than the right pump pressure, due to the larger diameter of the impeller vanes on the left side of the rotor, thereby ensuring flow into the right pump.

The speed of the pump is gradually increased in a stepwise fashion, until the speed of the device is approximately 1800 RPM, which allows the blood flow rate though the lungs to increase to 2 LPM by creating a left side pressure of approximately 70 mmHg (that typically provided by cardiopulmonary bypass aortic pressure). This pressure is composed of a 10 mmHg left inlet pressure, and a 60 mmHg gradient created by the left impeller. The shunt flow rate is typically limited by the size of the cross sectional area of the left/right shunt flow path, which is typically 25 $mm^2$ for 2 LPM, but could increase to 50 $mm^2$ for 3 LPM-5 LPM of perfusion by moving the rotor axially away from the right side.

In this regard, it will be appreciated that the position of the impeller can be controlled in order to adjust the left/right shunt flow path cross-section, thereby providing control over the degree of shunt flow. For example, the pump can be finally operated with the impeller moved as far as possible into the left cavity, to thereby increase the separation between the impeller and the cavity housing in the right cavity, to thereby increase the flow path cross-sectional area.

It should be noted that if the left/right shunt flow path has a cross sectional area any smaller than 15 $mm^2$, which is typically observed with hydrodynamic bearings, this will result in a flow of less than 1 LPM, and possibly insufficient reperfusion, or a longer time on bypass as the lungs are reperfused.

As this process is performed, the blood passing through the lungs gathers more and more oxygen at each pass, thus helping to ease the lung restriction and resistance. This continues until the restriction in the lung passes, which typically takes between 5 and 10 mins, at which point the aortic cross clamp is removed. Backflow is prevented as the pressure in the pump left outflow already matches that in the aorta created by the bypass machine, hence the circulating flow through the lung continues.

Finally, the pump speed is gradually increased further as the bypass machine speed is reduced, thus allowing the artificial heart to assume the entire circulation, to both lung and body.

This procedure essentially prepares the lung circulation for full flow by gradually reperfusing the arterioles.

It is important however that this left/right shunt flow path is preferably no larger than 50 $mm^2$, since during normal operation, the shunt of flow from left to right may be deemed excessive. The left to right outflow ratio from the device should be maintained below 1(L):1.5(R), as experienced with clinical ventricular septal defects that do not manifest into clinical complications.

Accordingly, the above described approach provides a method of operating a biventricular heart pump during implantation, the method including connecting the heart pump to the pulmonary and systemic circulatory systems, blocking a left pump outflow to the system circulatory system, operating the pump so that blood flow recirculates through the lungs with blood flow received from the lungs via a left pump inlet being shunted to a right pump via a left/right shunt flow path so that blood is supplied to the lungs via a right pump outlet and once the lungs are perfused, unblocking the left pump outflow so that blood flows through the pulmonary and systemic circulatory systems.

This approach ensures the lungs are perfused prior to full speed operation of the device, which in turn assist in preventing lung damage.

Typically the method includes initially operating the pump at a rotational speed of between 1000 RPM and 1250 RPM or with a blood flow rate though the lungs of approximately 0.5 LPM. Following this the rotational speed of the pump is increased until the rotational speed is approximately 1800 RPM or the blood flow rate though the lungs increases to approximately 2 LPM.

Pumping of blood is then performed for between 5 minutes and 10 minutes or until lung resistance reduces, at which point the left pump outflow to the system circulatory system is unblocked.

Improved Inherent Left/Right Flow Balancing

The natural heart continuously balances systemic and pulmonary flow through ventricular interdependence and the Frank-Starling mechanism. When a rotary blood pump is used to replace or assist failing ventricles, the pump must provide or facilitate this functionality in order to meet the subject's physiological requirements.

For example, in the case of left ventricular assistance, if the device attached to the left ventricle is underperforming, pulmonary venous hypertension results, leading to compromised lung function. If however the left device is over performing, systemic hypertension can result in high systemic arterial pressure leading to the risk of haemorrhagic stroke. Conversely, the left pump may also remove excessive fluid from the left heart cavity leading to left intermittent or complete chamber collapse and cessation of forward flow.

In the case of biventricular support or replacement, if the pulmonary pump is under performing, systemic venous hypertension results with resultant peripheral oedema, and liver and kidney failure. In addition, the inadequate flow through the pulmonary circulation predisposes to suction events at the left pump inlet and hemodynamic collapse. Similarly, systemic pump hypo-function results in pulmonary hypertension, oedema, and lung failure as well as systemic hypotension and progressive shock. Maintaining flow balance is essential to avoid these potentially lethal hemodynamic states.

Currently rotary pumps do not automatically provide this functionality, and additional control mechanisms, such as speed control mechanisms are required.

The intrinsic ability of all rotary blood pumps to increase or decrease flow in response to changes in pressure differential is an attractive feature in that it might allow a rotary pumps configured for biventricular support to maintain some degree of balance without active pump speed and/or axial position management. Although integrated pumps are currently under development that use methods to assist this balance autonomously, the design of their respective left and right impeller can significantly expand the balance capability over a wide range of physiologic conditions. Furthermore the use of a dual pump necessitates that the speeds of the two pumps be precisely set to avoid systemic or pulmonary hypo-function. By choosing two impeller designs with the appropriate intrinsic pressure sensitivity, the demands of relying on the integrated pump's balancing methods, or indeed adjusting rotational pump speed of dual pumps moment by moment can be decreased.

The intrinsic pressure sensitivity of a rotary blood pump can be quantified, and an average pressure sensitivity of traditional pumps is 0.1 LPM/mmHg, which is roughly half to a third of what is observed in the 'unexcited' normal human heart at a given heart rate. As such, for every one-millimetre mercury increase in inlet pressure, there is an increase in pump output of one tenth of a litre per minute, without a change in rotational speed. Stated another way, as the inlet pressure of one pump starts to rise, as a result of pulmonary-systemic imbalance, that pump will autonomously begin to pump more without adjusting pump speed, autonomously bringing the pumps back into balance. By optimizing this functionality, the requirements for frequent and precise speed changes can be reduced. Eliminating the need to devise a complex system for sensing pump performance and managing speed changes may decrease developmental time, as well as device complexity, cost, and power consumption. When used together, an optimized hydraulic system can decrease the demands placed on an active control system and serve as backup in case of sensor failure or control system failure.

During everyday patient activities, such as changing posture and coughing, a heart pump is required to alter the relative outflow from the left and right pump chambers to keep flows balanced in the face of varying vascular resistances.

The shape of the left and right pump curve and their combination (relative left/right design pressure at a given flowrate and speed) dictates the ability for the TAH device to balance flows and thus maintain atrial pressure between 0-20 mmHg over a range of L/R resistance combinations.

To achieve the widest range of fluid balance, the right impeller should exhibit a flatter pump curve than the left. That is to say, the pressure sensitivity of the right impeller should be higher than the left, a phenomenon observed with the natural heart. The pressure sensitivity of conventional RBPs (0.05-0.1 LPM/mmHg) however is much lower than that of the natural heart (0.2-0.3 LPM/mmHg and up to 3-5 LPM/mmHg with excitation leading to heart rate changes). Thus it is desired to maximize the pressure sensitivity of the impellers, with particularly close attention to the right impeller.

The design point (ΔP) also significantly affects the range for which the device can balance flow whilst maintaining inflow pressures within a specified range. This is determined by the speed of the left pump to achieve 80 mmHg at 6 LPM and then, with this speed, determining the diameter of the right pump to achieve 20 mmHg at 6 LPM. This ratio of delta pressure (eg: 80 mmHg/20 mmHg) created by each side of the device also influences this range. A relatively stronger right pump to left will mean that higher pulmonary vascular resistance (PVR) can be accommodated prior to the transition of left atrial pressure below 0 mmHg. However the propensity for left atrial pressure (LAP) to rise above 20 mmHg increases at high systemic vascular resistance (SVR) and low pulmonary vascular resistance (PVR), although this can be accounted for by axial translation of the impeller to increase the performance of the left pump, or indeed by increasing impeller speed to increase both pump's performance.

The ability to axially translate the impeller, and maximizing its ability alter pressure for this movement (ie axial pressure sensitivity), creates alternate ratios of left/right design pressure, which widens the range of acceptable resistance combinations that may be encountered due to patient-to-patient resting variability, as well as those resistances presented during transient daily activities. Shifting the rotor toward the right chamber opens up the clearance above the left impeller, thus reducing outflow from the left side of the device. This produces a momentary shift in relative left and right chamber hydraulic performance, assisting to balance circulatory flows.

A typical ratio of resistances for a healthy patient at rest is SVR=1433±229 dyne·s·cm$^{-5}$ and PVR=85±33 dyne·s·cm$^{-5}$. A typical ratio of resistances for a heart failure patient (on medication) at rest is SVR=1127±390 dyne·s·cm$^{-5}$ and PVR=233±119 dyne·s·cm$^{-5}$.

A healthy patient might benefit from a L:R delta pressure ratio of 5.33:1 (LEFT 80 mmHg:15 mmHg RIGHT) whilst a HF patient with a rotary blood pump might benefit from a ratio of 4:1 (LEFT 80 mmHG:20 mmHg RIGHT) (ie relatively stronger right pump) to accommodate for relatively higher PVR and clinically preferred lower arterial pressure.

During everyday activities, these ranges may alter transiently. Whilst coughing or Valsalva, PVR alone can rise significantly up to +400% for a short period (up to 425 dyne·s·cm$^{-5}$). During a postural change, SVR alone can drop by −40% and then rise by +60% than settle to +30%. During a transition to exercise, SVR and PVR can both drop by up to −20 to −50% with a corresponding change in flow of >5 LPM.

With a left pump gradient of 50%, this change in flow of 5 LPM would result in a drop in aortic pressure of just 10 mmHg With a right pump gradient of 100%, a drop in pulmonary pressure of just 5 mmHg would result.

Since, during exercise, the skeletal muscle pump returns blood to the right atrium, and raises pressure (sometimes by 10 mmHg), these minor drops in left/right pump delta pressure could potentially reduce the incidence of arterial hypotension and associated syncope and dizziness.

Figure 10A:
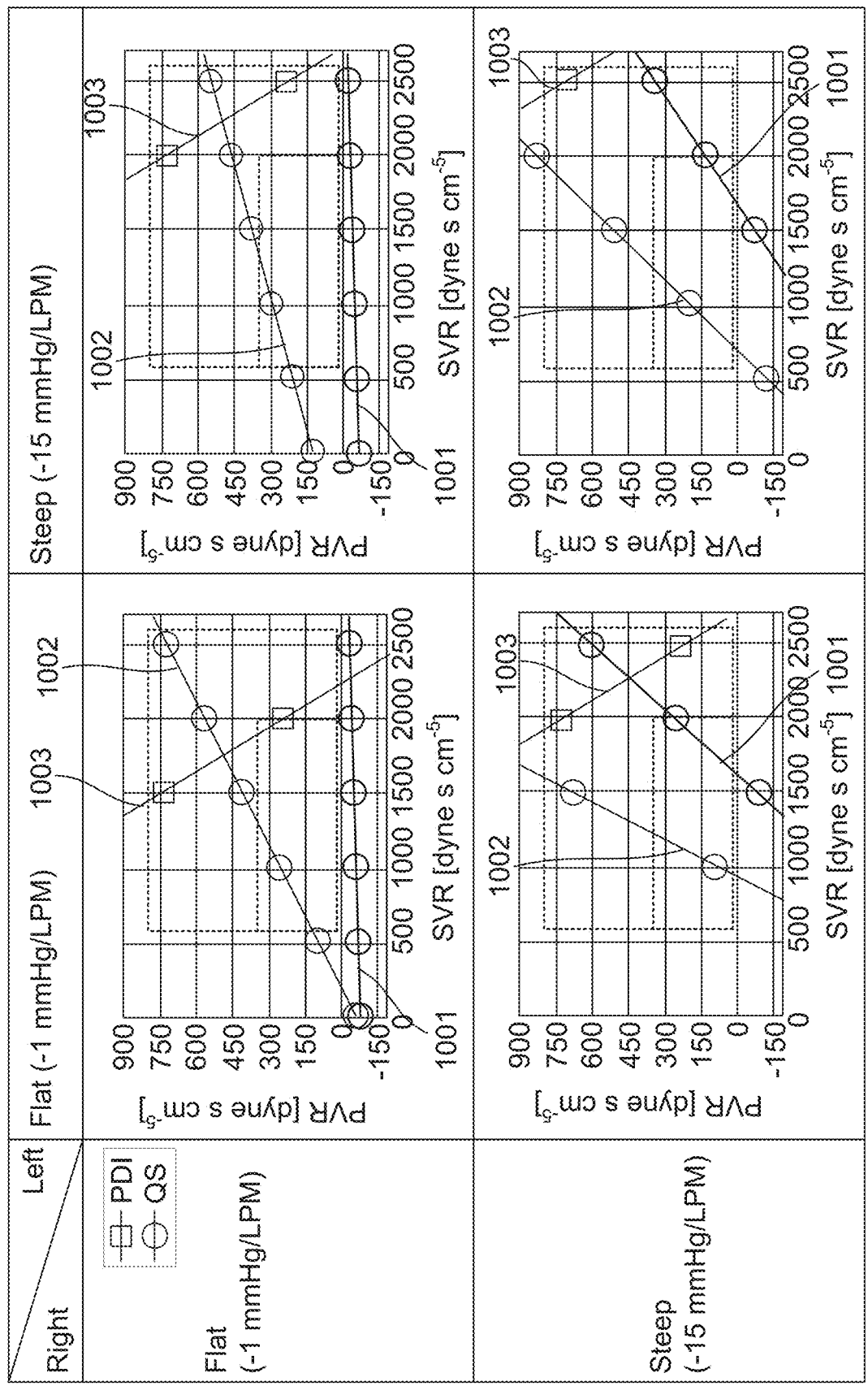
FIG. 10A is a series of graphs showing relationship between systemic and pulmonary vascular resistances for different pump curves.

An example of the capabilities of pumps having different pump curves is illustrated in FIG. 10A, with unbalanced (depicted as when inlet pressure reduces below 0 mmHg or rises above 20 mmHg) areas shaded grey. The resistance box composition is explained in the following by the example of the steep/steep combination.

With increasing SVR more volume is pooled in the left atrium and its pressure rises. At the same time right atrial pressure decreases so that the pressure difference between both atria (PDI) increases. If SVR keeps increasing, PDI will be above or below its predefined limits. Furthermore, total flow (Qs) will drop below a safe level (defined as 2 LPM). Consequently, any SVR-PVR combination below the line 1001 (LAP>20 mmHg), above the line 1001 (LAP<0 mmHG), or to the right of the line 1002 (Qs<2 LPM) is not considered in balance.

Figure 10B:
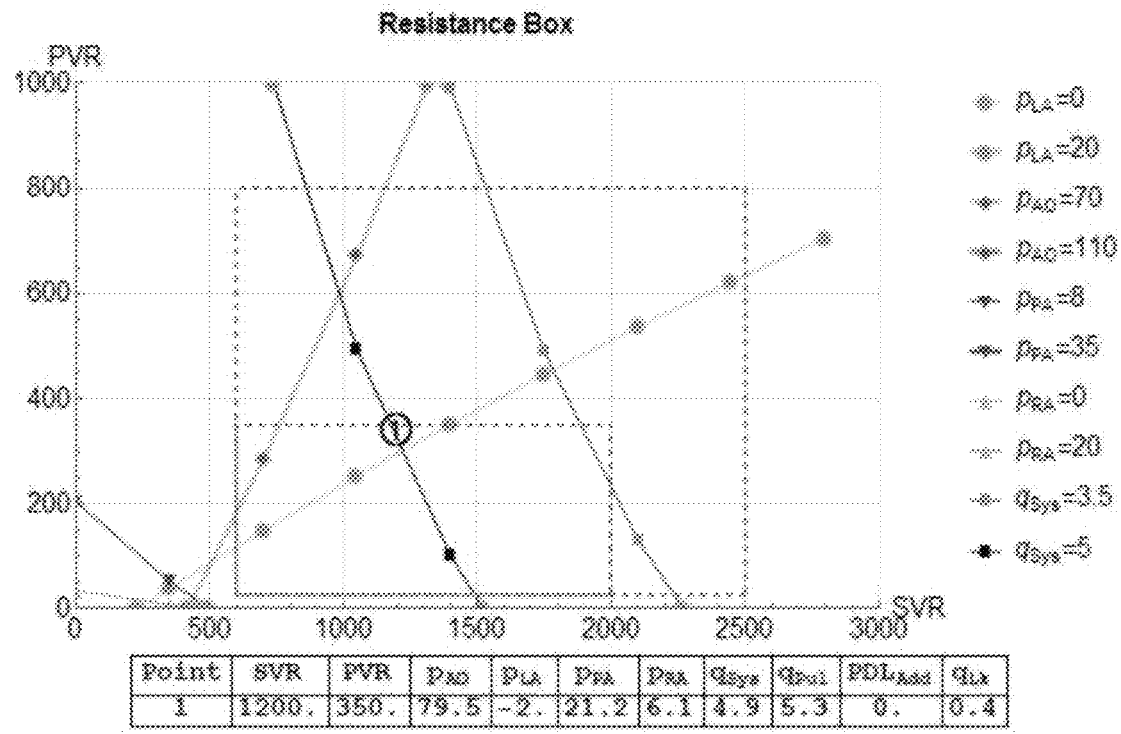
FIGS. 10B and 10C are graphs illustrating the effect of left/right design pressure.
Figure 10C:
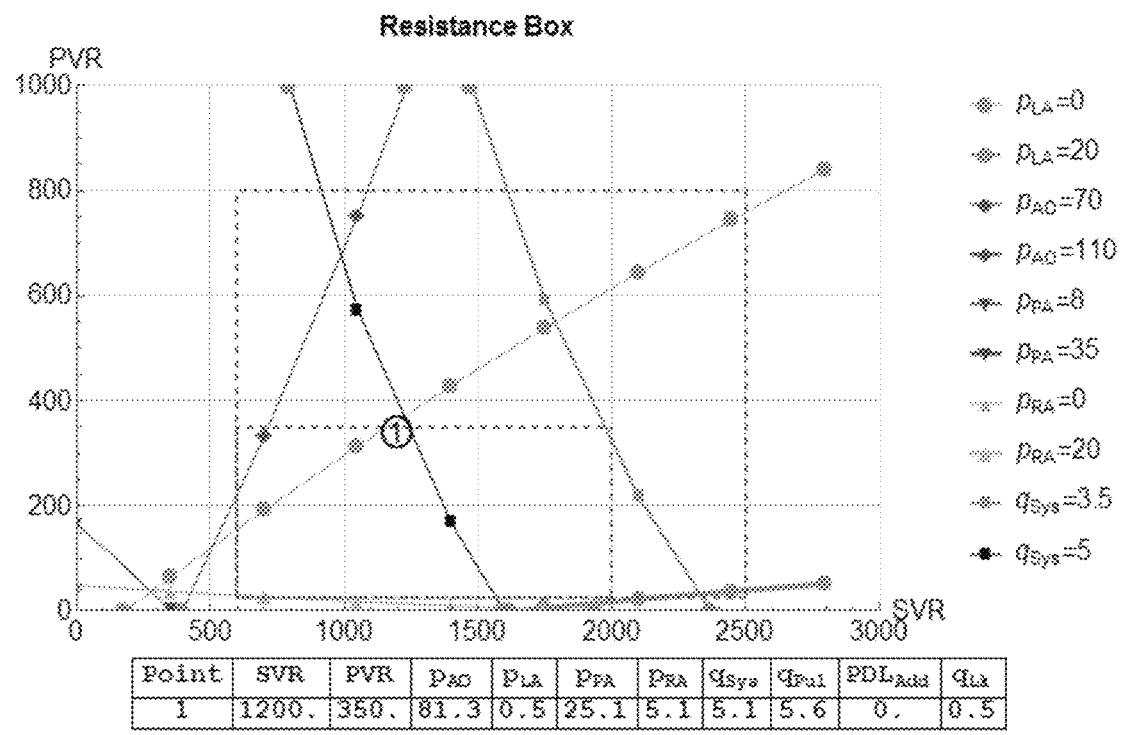

Additionally, the pump's left and right relative design pressure (delta pressure from measured from inlet to outlet at a given flow rate and rotational speed) affects the range of patient states for which the effective fluid balance can be maintained at a given rotational speed. This design pressure for the left pump is reached for a given pump design at a determined speed, and with this speed, the design pressure of the right pump is determined by the selection of the right pump design parameters (such as impeller vane outer diameter). The ratio of the resulting left and right design pressures at a given flow rate and speed is defined as the 'left/right design pressure ratio'. Examples, are shown in FIGS. 10B and 10C, which show the effect of left/right pressure design for pumps with left:right pressures of 80 mmHg:15 mmHg and 80 mmHg:20 mmHg at 2050 RPM, respectively. Here it can be seen that the smaller ratio (4:1) than (5.33:1) can lead to a larger window of balanced resistance conditions.

Figure 10D:
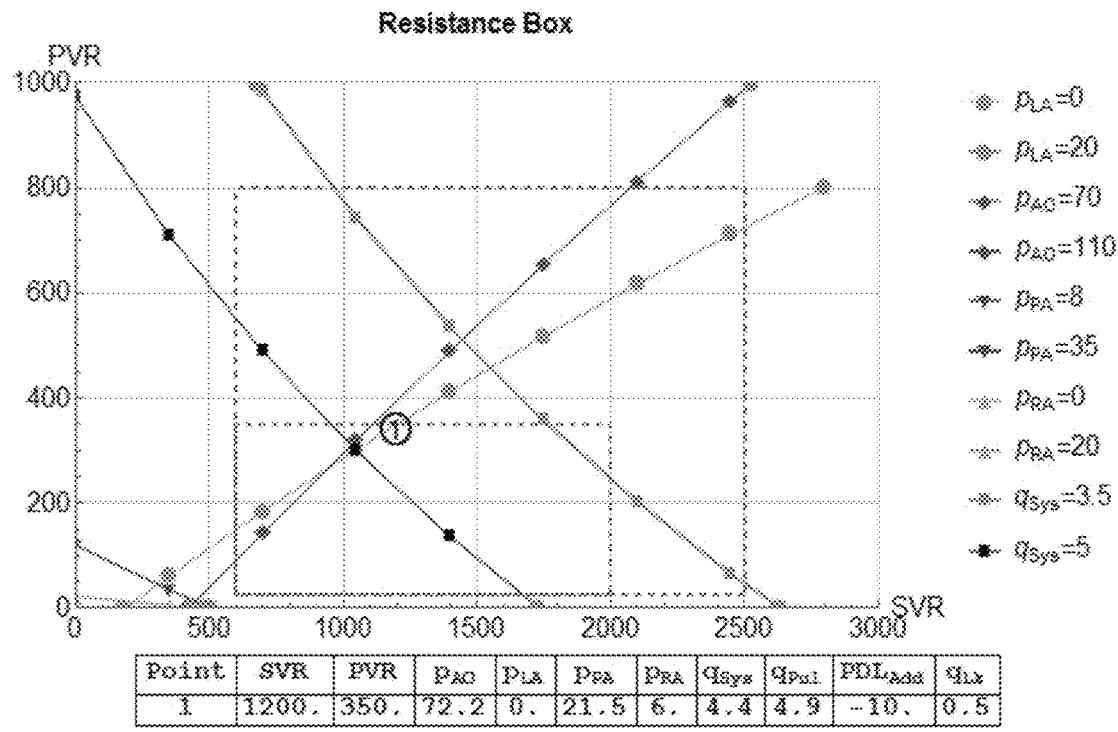
FIGS. 10D and 10E are graphs illustrating the effect of axial movement on balance range.
Figure 10E:
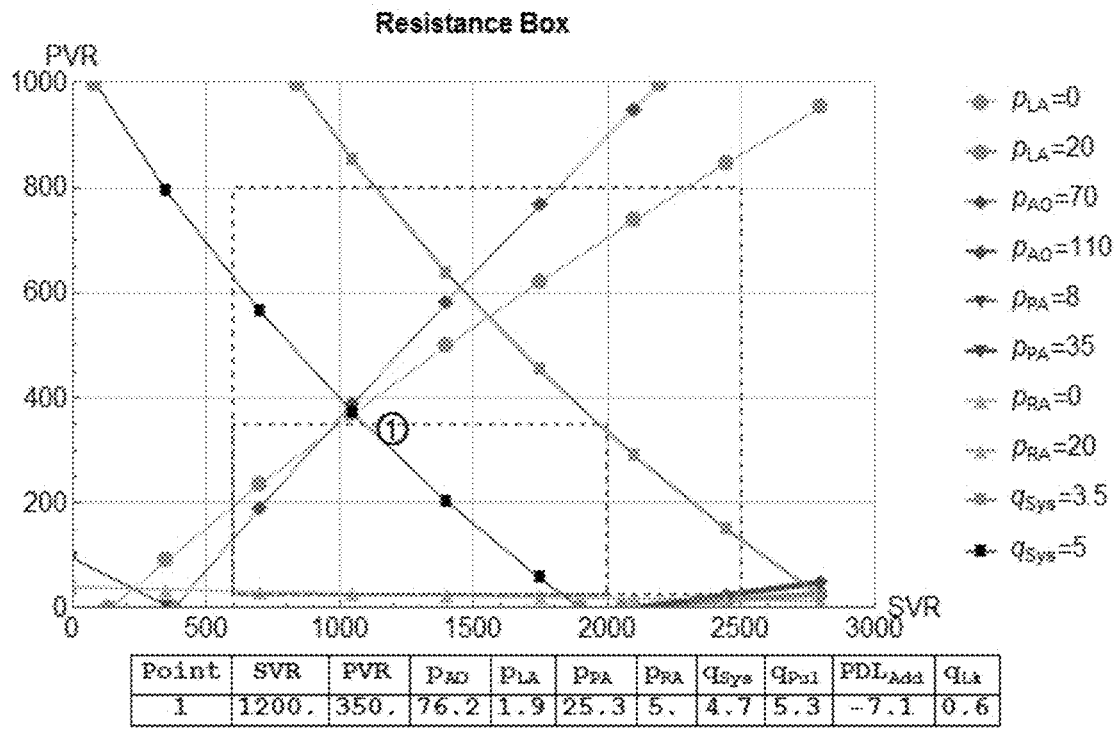

Furthermore, shifting the rotor axially within the pumping cavity can enhance the effect of alterations in left/right relative design pressure and axial pressure sensitivity (APS) of a RBP to help autonomously balance left and right outflows by altering the relative pumping capacity of each pump. For example, moving the rotor toward the right chamber opens up the clearance above the left impeller, thus reducing outflow and pressure from the left side of the device. This produces a momentary shift in relative left and right chamber hydraulic performance (altering the left/right design pressure ratio), assisting to balance a larger range of circulatory flows in a shorter period of time. This outcome can be likened to a change in relative rotational speed of the left and right impellers, however in this case speed is fixed. Examples of the effect of axial movement on balance range for different pumps are shown in FIGS. 10D and 10E, for cases of no axial movement and 200 μm movement that produces an APS of 60 mmHg/mm respectively. The axial movement increases the range of balanced conditions, effectively by altering the left/right design pressure ratio from 4:1 to 3.25:1 (rightward movement) and to 4.75:1 (leftward movement). The dotted circles represent hemodynamic data recovered from heart failure patients with previously implanted total artificial hearts.

It will be appreciated from this that when creating such heart pumps, the particular design of the pump can have a major impact on the pump performance curve and thus outflow pressure sensitivity of the heart pump. This affects the ability of the pump to pump blood at different flow rates at a given rotational speed, depending on the physiological requirements of the subject to which the pump is fitted.

Considering that in the TAH application, the left and right impellers are attached to a common rotating hub spinning one RPM, the delta pressure ratio is most influenced by the relative outer diameter of the left and right impeller vanes and the relative efficiency of each pump. Thus to reduce the left/right design pressure ratio generate would either require a) a larger diameter right impeller, or b) a relatively less efficient left impeller.

A larger diameter right impeller reduces area available for the magnetic bearing system to target, and as such would reduce its force capacity. Alternatively, a less efficient left impeller may be created by altering the parameters of the impeller design, which effectively reduces the hydraulic efficiency and thus pressure generation for a given rotational speed and flow rate.

Figure 10F:
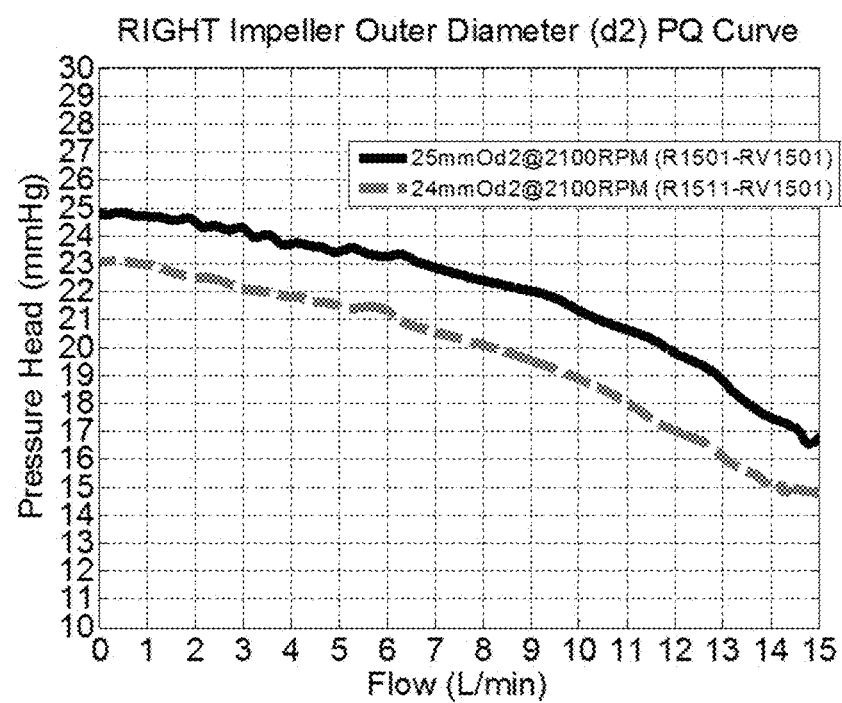
FIG. 10F is a graph illustrating examples of right pump curves for different right impeller outer diameter.

The effect of altering the right impeller diameter from 25 mm to 24 mm was to reduce design pressure by 2 mmHg at 5 LPM, down from 23.5 mmHg to 21.5 mmHg, as shown in FIG. 10F. The smaller diameter right impeller creates a larger gap (2 mm on the radius) between the outer circumference of the right impeller vanes and the base circle diameter of the stationary housing. Thus larger radial forces can be accommodated before potential touchdown. The smaller diameter also matches the selected left impellers to create a pressure ratio of 4:1 at a left/right vane tip gap of 300 μm.

Consideration however must be given to the effect altering pump parameters has on OPS and APS when meeting the left/right pressure ratio objectives, As seen in FIG. 10A, this is of particular importance for the right pump, whereby the flattest pump curve gradient (less negative) is desired. The left pump gradient is more forgiving, however too steep a gradient will limit the maximum outflow and pressure when systemic resistance drops (during transitions to exercise or upright posture) for a given rotational speed, potentially limiting patient quality of life.

As described in Stepanoff 1957, the pump performance curve gradient and thus OPS is linked heavily to the theoretical Euler head (dictated by selection of inlet and outlet vane angles), the fluid friction losses through the device (determined by the cross-sectional areas through the fluid path), hydraulic losses (determined in part by the mismatch of flow velocities and rotating/stationary vanes entering and exiting the pump) and recirculation losses (determined by the mismatch of flow rate, velocity and fluid path cross-sectional area). These parameters also influence the APS, with additional parameters such as vane height, angle, width and number having particular importance.

Generally speaking, improving both OPS and APS are competing objectives, and as such an optimum must be sought.

To obtain the flattest pump curve, pressure generation from the pump should be reduced at low flow and increased at high flow. This may however also come at the consequence of lower overall pressure generation and efficiency. For the right impeller, this means the speed would need to be higher to meet a certain design pressure, which means the left impeller would need to be even less efficient to maintain the targeted left/right design pressure ratio.

The trade of efficiency to create suitable left/right pump curve performance gradients however is considered important to provide correct balancing, which goes against conventional wisdom when designing blood pumps.

A weaker left pump can be achieved by choking forward flow with smaller fluid path areas, or utilizing a backward swept vane. These cause the pump curve to be steep and thus reduces outflow pressure sensitivity, however improve axial pressure sensitivity.

Alternatively, it was found that increasing the impeller inner eye diameter ID1 rapidly drops pressure from shutoff at low flows, but then maintains a flatter curve at higher flows. Thus a weaker impeller can be created without compromising outflow pressure sensitivity.

Maximizing the axial pressure sensitivity (particularly from the left impeller) can be influenced by altering the vane outlet angle (largest effect) and vane number and vane thickness/height:clearance ratio.

As described, flow path areas tend to influence the resistance of fluid to flow through the pump and thus outflow pressure sensitivity, with larger areas generally creating flatter pump curves.

However larger areas also tend to assist with device biocompatibility. Larger areas between the rotating impeller and the stationary casing result in smaller shear stresses in this region and thus reduced red blood cell lysis (haemolysis). However larger flow path areas are also suggested to reduce the incidence of vonWillebrand factor (vWF) degradation. Degradation of this molecule can lead to impaired ability for blood to clot, thus raising the risk of bleeding complications.

vWF degradation is often observed in patients implanted with rotary blood pumps. It is also observed in patients who suffer from aortic valve stenosis. In these situations, the peak blood velocity (10-20 LPM) ejected from the (often weakened) heart transverses through a narrowed orifice in the order of 10-12 mm in diameter (78.5-113.04 mm$^2$). Furthermore in the case of blood pumps, the smallest flow path area for which the entire flow rate must transverse may reduce to 60 mm$^2$ or lower.

This vWF degradation in both scenarios is reversed after heart transplantation, or in the case of valve stenosis, with the replacement of a mechanical heart valve (areas of 314-706 mm$^2$). However some vWF degradation remains when an undersized (smaller area) valve is implanted.

These observations suggest that raising the minimum blood flow area through the device to values greater than 60 mm$^2$ and even greater than 110 mm$^2$ may assist in reducing the severity of vWF degradation.

Figure 10G:
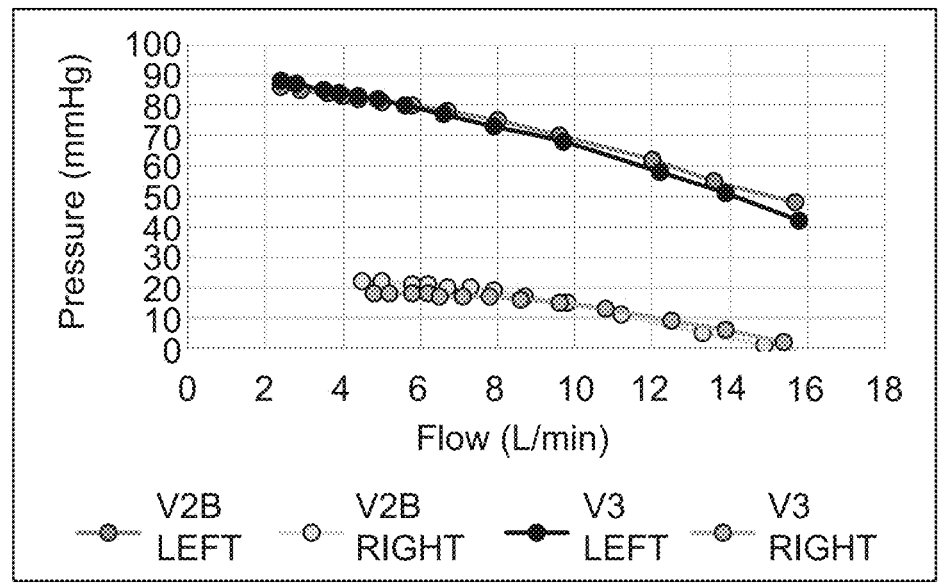
FIG. 10G is a graph showing examples of different pump curves for different pump configurations.

In the above described heart pump, the right pump curve is extremely flat (typically—1 mmHg/LPM), whilst the left pump curve is slightly steeper (typically −2 to −4 mmHg/LPM), as shown in FIG. 10G, helping provide automatic flow balancing.

Figure 10H:
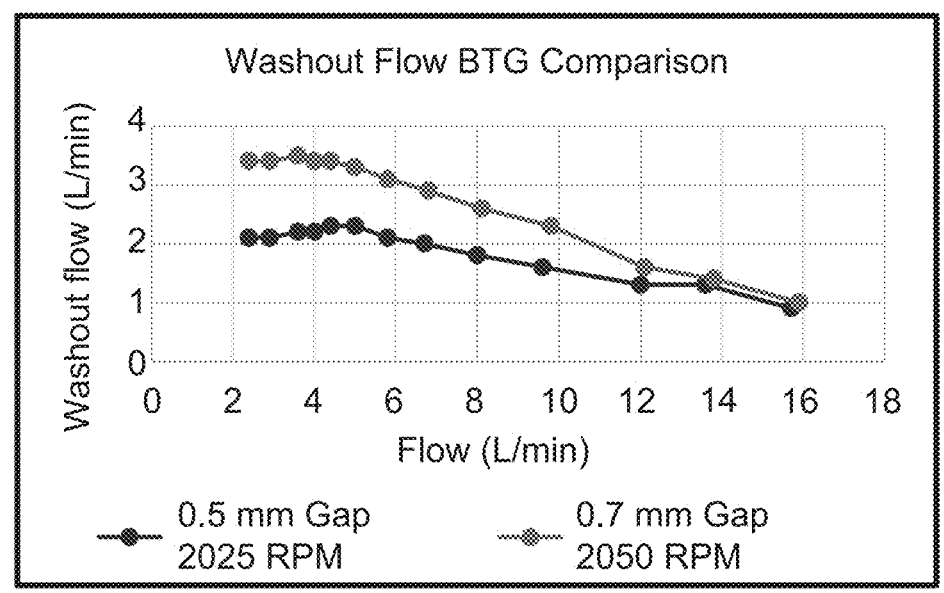
FIG. 10H is a graph showing examples of different pump curves for different pump configurations.

Additionally, since no radial journal bearing was used to further limit this shunt flow, total axial clearance was reduced from 1.2 mm to 0.7 mm to reduce the washout clearance. It was further reduced to 0.6 mm to minimize leakage, since the majority of the impeller axial pressure sensitivity (APS) occurs in the initial 0.5 mm of movement, as shown in FIG. 10H. The operating range of the impeller is restricted to +/−200 μm when operating in a total 0.6 mm clearance, so as to not allow the impeller to come with 100 μm of the stationary casing to assist with hemocompatibility. However the rotor may be able to come within 50 μm of the stationary casing at critical times to assist with flow balancing, effectively expanding the range of movement to +/−250 μm. It would be appreciated that these limits from the casing are fixed, resulting in a larger operating range as total clearance gap increases.

Accordingly, the above described blood pump provides improved characteristics including improved outflow pressure sensitivity, improved axial pressure sensitivity, reduced radial hydraulic forces over the desired flow range, emboli tolerance and improved inherent left/right flow balancing. These are achieved through a combination of pump parameters, including increasing the cross-sectional areas of flow paths (inlet and outlet port diameters) through the pump, reducing recirculation by increasing impeller vane height and/or thickness and adding secondary vanes, using a larger than normal throat area to provide a BEP at a higher flow rate, and selecting a volute design to minimize radial forces over a desired flow range.

Some example impeller configurations optimized for specific scenarios will now be described with reference to FIGS. 11A to 11L. Parameters for the respective impellers are shown in Table 2 below.

TABLE 2

|  | OPS Left TAH | Thrust Left TAH | APS Left TAH | OPS/APS Left TAH | OPS Left VAD | Right TAH |
|---|---|---|---|---|---|---|
| deltaP@2100 RPM @5 LPM | 80 | 80 | 74 | 81.5 | 80@1680 RPM | 20 |
| L/R Pressure ratio | (3.7)-4-(4.3):1 | (3.5)-4-(4.5):1 | (3)-3.6-(4.75):1 | (3.5)-4.1-(4.7):1 | N/A | N/A |
| Primary eye diameter ID1 (mm) | 30 | 25 | 25 | 30 | 25 | 16 |
| Secondary eye diameter ID2 (mm) | 35 | N/A | N/A | N/A | N/A | 19 |
| Rotor Diameter OD (mm) | 50 | 50 | 50 | 50 | 50 | 24 |
| Number of primary vanes | 4 | 4 | 4 | 8 | 10 | 4 |
| Number of secondary vanes | 4 | 0 | 0 | 0 | 0 | 4 |
| Vane outlet angle (°) | 80 | 80 | 20 | 40 | 80 | 90 |

TABLE 2-continued

|  | OPS Left TAH | Thrust Left TAH | APS Left TAH | OPS/APS Left TAH | OPS Left VAD | Right TAH |
|---|---|---|---|---|---|---|
| Vane inlet angle (°) | 84 | 84 | 64 | 64 | 84 | 90 |
| Vane height (mm) | 2.0 | 2.0 | 2.0 | 2.0 | 4.0 | 17.5 |
| Vane width (mm) | 7.5 | 18 | 15 | 15 | 1.0 | 1.5 |
| APS (mmHG) | 13 | 20 | 30 | 25 | 2 | N/A |
| OPS (mmHg/LPM) | −1.8 | −3.2 | −4 | −2.6 | −0.1 to −0.2 | −0.3 |
|  | 55% | 31.25% | 25% | 38% | 500-1000% | 333% |

Figure 11A:
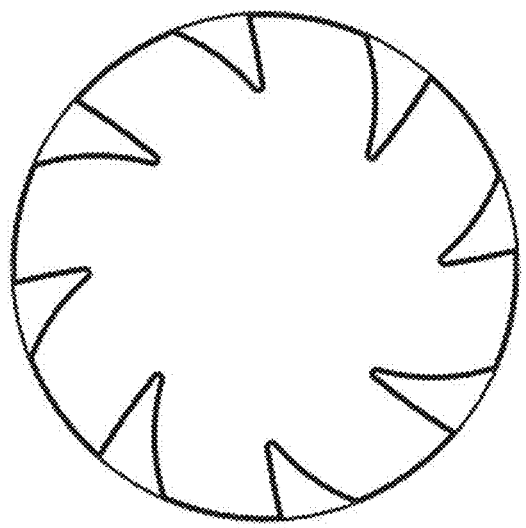
FIG. 11A is a schematic plan view of a first specific example impeller configuration.
Figure 11B:
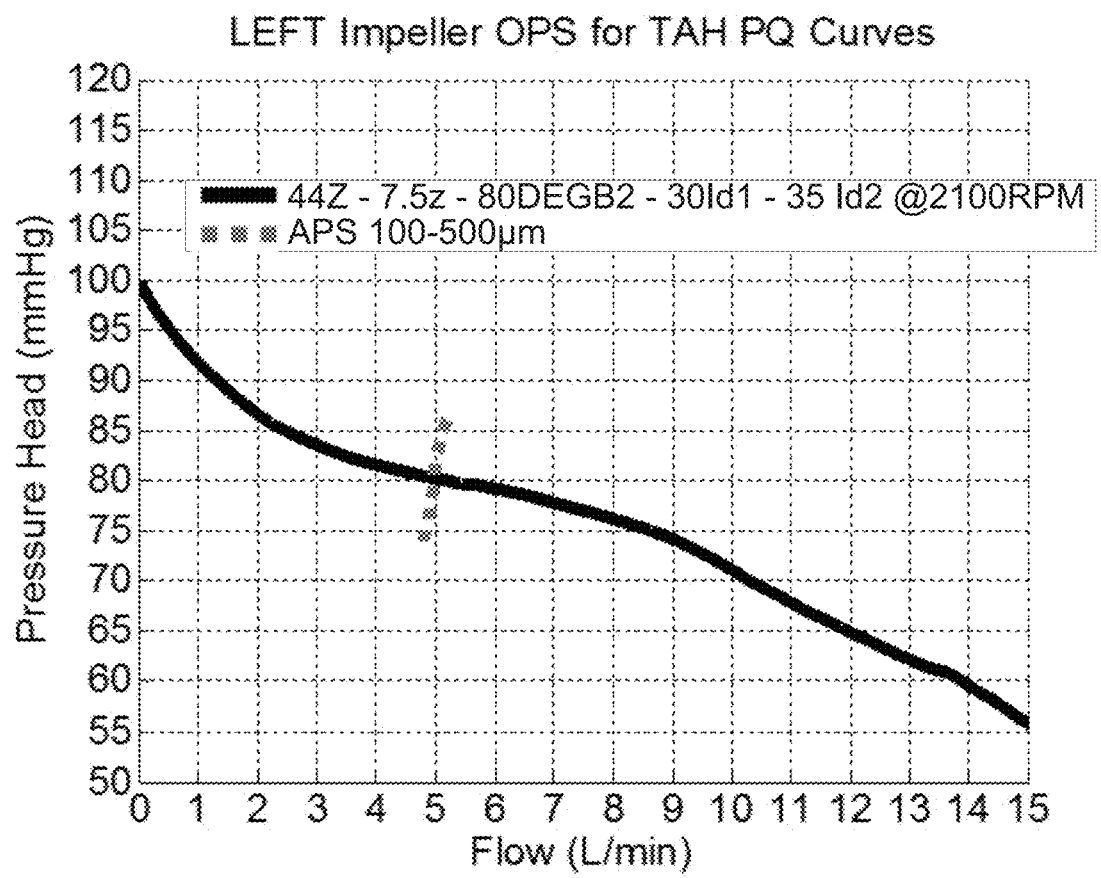
FIG. 11B is a graph illustrating a pump curve for the impeller configuration of FIG. 11A.

The OPS impeller is shown in FIG. 11A, with the performance curve being shown in FIG. 11B. The OPS impeller demonstrates characteristics for optimal OPS whilst still having some APS and creating the targeted L/R pressure ratio, and is characterized by the use of primary and secondary vanes with a large eye diameter and high inlet/outlet angle.

Figure 11C:
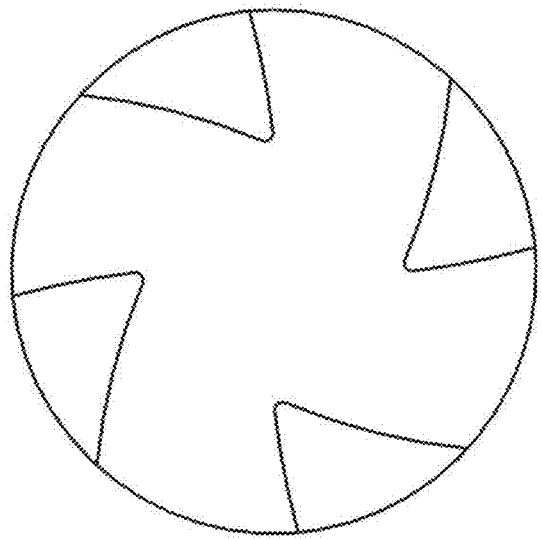
FIG. 11C is a schematic plan view of a second specific example impeller configuration.
Figure 11D:
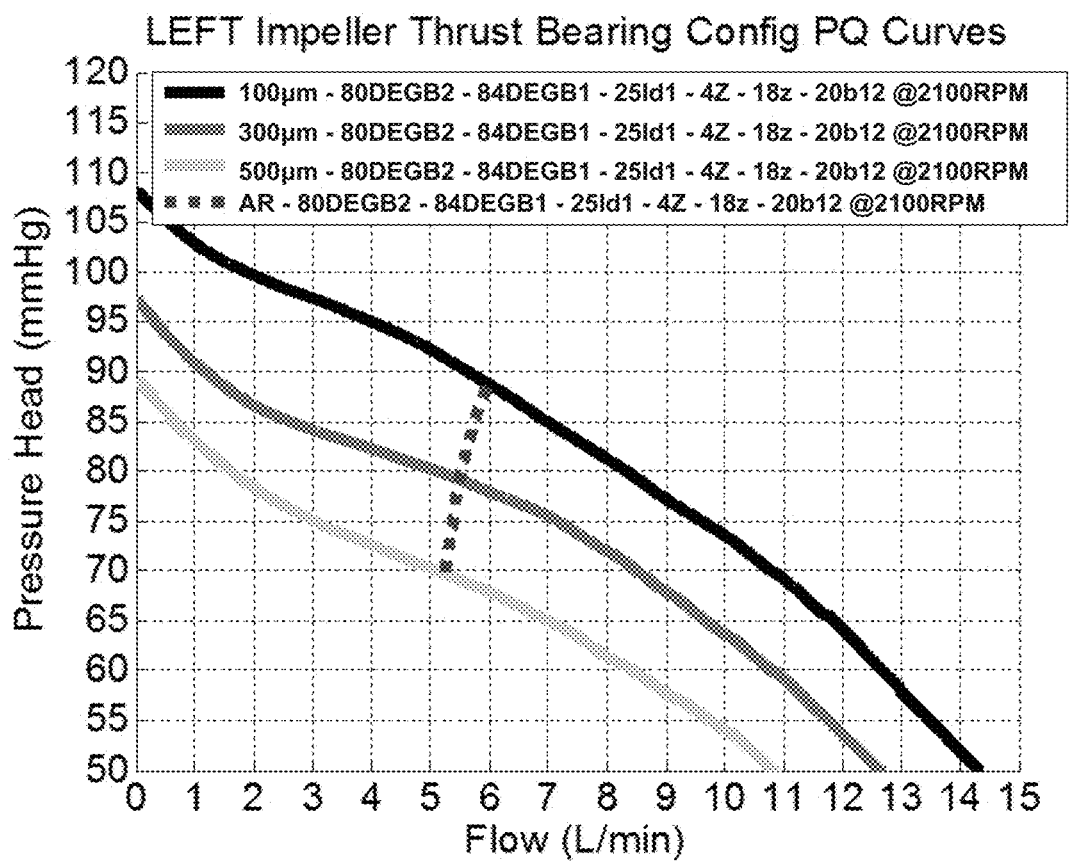
FIG. 11D is a graph illustrating a pump curve for the impeller configuration of FIG. 11C.

The thrust impeller is shown in FIG. 11C, with the performance curve being shown in FIG. 11D. The thrust impeller demonstrates characteristics for providing a backup thrust (hydrodynamic) axial bearing, and is characterized by the use of vanes having a thick outer edge to provide a high end surface area. The profile of the vane dictates that the leading edge is approx. 50-100 µm lower in the direction of the axis of rotation than the trailing edge of the vane.

Figure 11E:
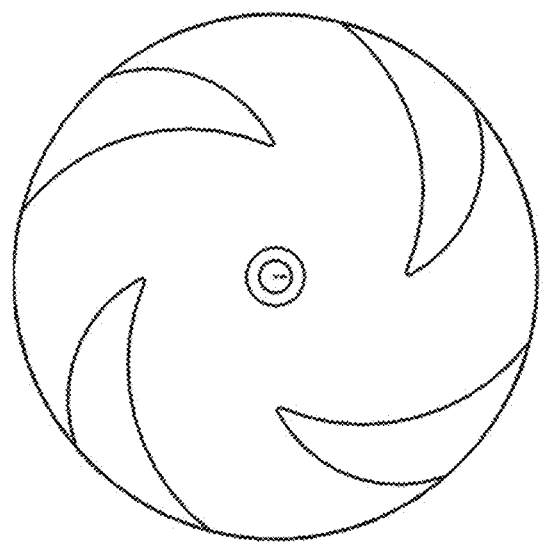
FIG. 11E is a schematic plan view of a third specific example impeller configuration.
Figure 11F:
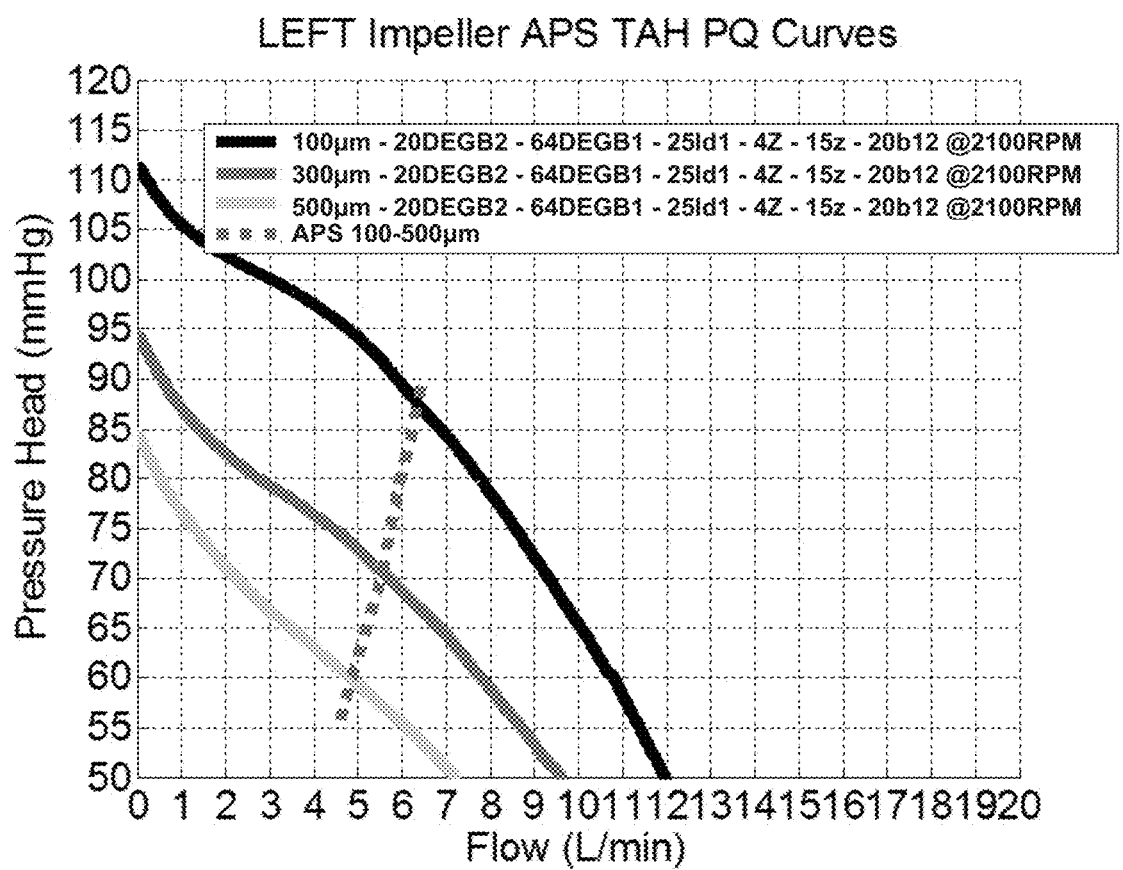
FIG. 11F is a graph illustrating a pump curve for the impeller configuration of FIG. 11E.

The APS impeller is shown in FIG. 11E, with the performance curve being shown in FIG. 11F. The APS impeller demonstrates characteristics for optimal APS, and is characterized by highly curved vanes with a small outlet angle.

Figure 11G:
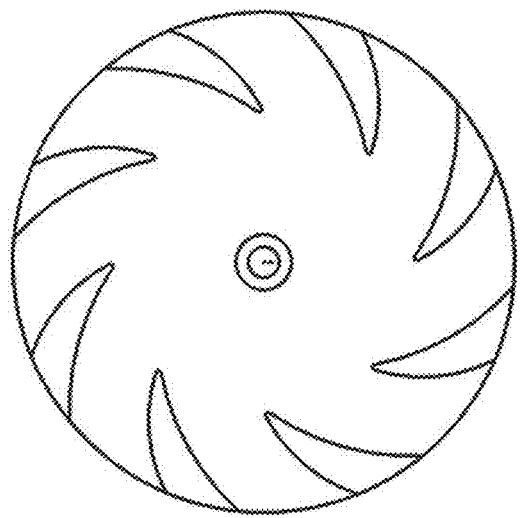
FIG. 11G is a schematic plan view of a fourth specific example impeller configuration.
Figure 11H:
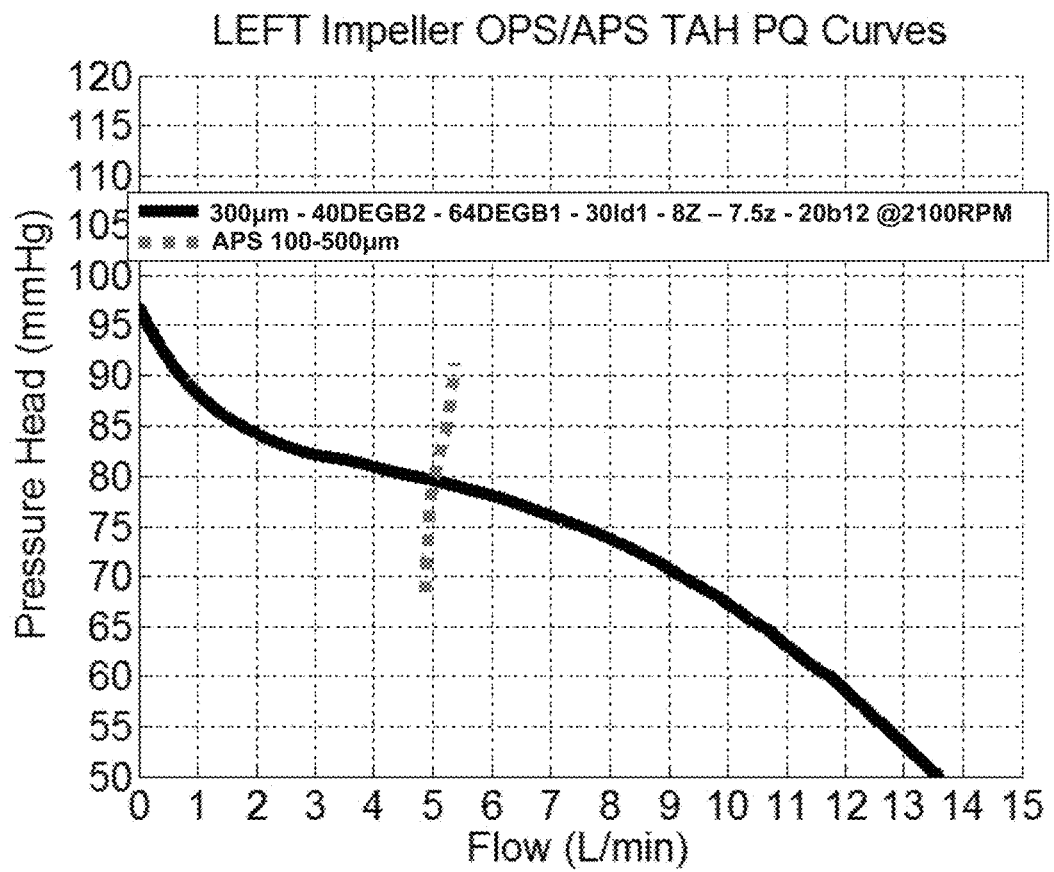

The OPS/APS impeller is shown in FIG. 11G, with the performance curve being shown in FIG. 11H. The OPS/APS impeller demonstrates a balance between OPS and APS making it the preferred impeller for TAH applications, and is characterized by the use of primary curved vanes with a medium-to-small outlet angle.

Figure 11I:
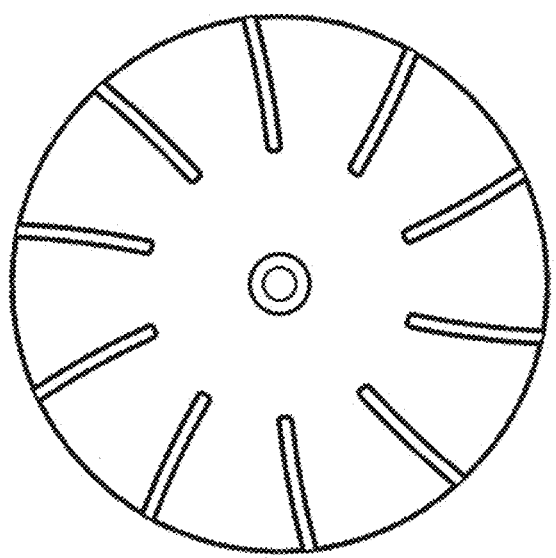
Figure 11J:
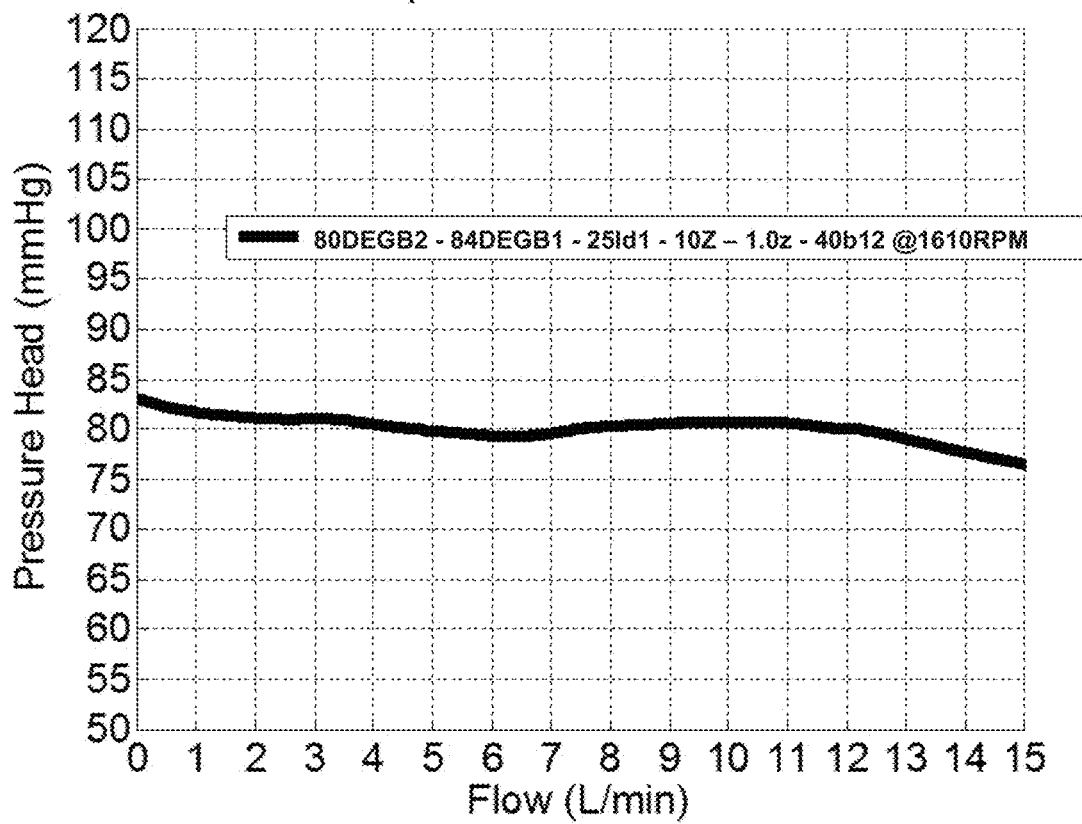

The OPS VAD impeller is shown in FIG. 11I, with the performance curve being shown in FIG. 11J. The OPS VAD impeller demonstrates extremely high OPS with minimal APS making it ideal for use in single VAD scenarios, and is characterized by the use of a large number of relatively high, thin vanes having large inlet/outlet angles.

Figure 11K:
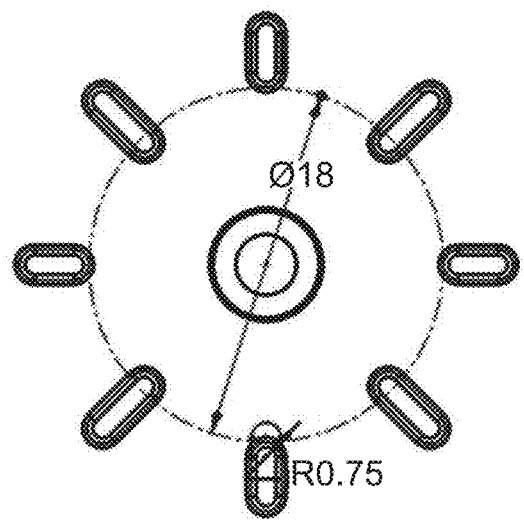
Figure 11L:
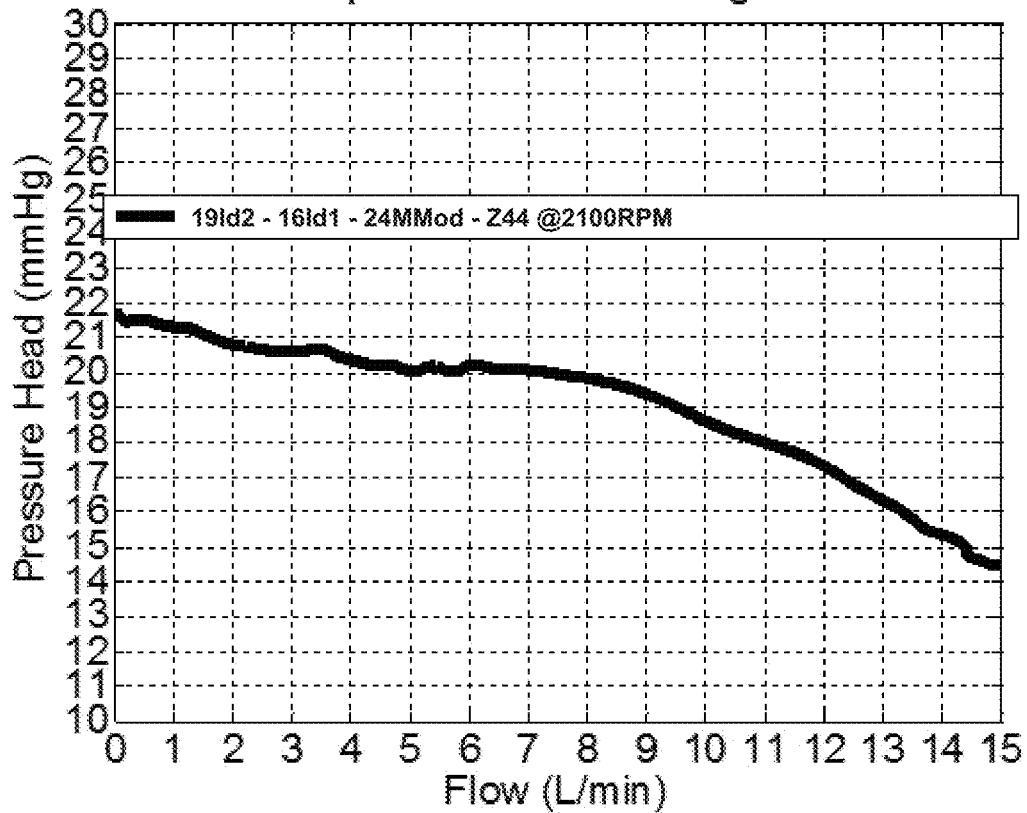

The RVAD impeller is shown in FIG. 11K, with the performance curve being shown in FIG. 11L. The RVAD impeller demonstrates high OPS with minimal APS and lower flow rates making it suitable for as an RVAD in TAH applications, and is characterized by the use of a number of extremely high primary and second vanes having steep inlet/outlet angles.

An example of a single VAD heart pump will now be described with reference to FIGS. 12A to 12F.

In this example, the heart pump 1200 includes a housing 1210 defining a cavity 1215. The housing can be of any suitable form but typically includes a main body, and left and right end caps which connect to the main body. The housing can be made of any suitable biocompatible material, and can be made of titanium, a polymer or the like.

The housing 1210 includes an inlet 1211, for connection to the left atrium/pulmonary vein or right atrium/vena cava, or left or right ventricle, and an outlet 1212 for connection to the aorta or pulmonary artery, respectively.

The heart pump 1200 includes an impeller 1220 provided within the cavity 1215. The impeller 1220 includes a rotor 1221 having vanes mounted thereon for urging fluid from the inlet 1211 to the outlet 1212 upon rotation of the impeller 1220. In this example, as the heart pump 1200 is a single ventricular assist device, the impeller includes a single set of vanes 1222 for urging fluid from the inlet 1211 to the outlet 1212. In this example, the vanes 1222 have a configuration similar to that described above with respect to FIGS. 11I and 11J, and these will not therefore be described in further detail, although it will be appreciated that other suitable vane configurations can be used. The impeller can also include an aperture 1224 extending therethrough to allow blood to flow around the rear surface of the impeller and thereby prevent stagnation and clotting of blood within the heart pump. Furthermore, the use of a magnetic bearing in this region allows for blood gaps in excess of 200-300 µm and up to 500 µm, which can both reduces shear stress and thus red cell lysis, as well as promote greater rates of washout flow than otherwise anticipated in gaps created by hydrodynamic bearings.

The heart pump 1200 further includes a drive 1230 that rotates the impeller 1220 within the cavity 1215. The drive 1230 can be of any appropriate form but typically includes a number of coils 1231, each wound on a respective stator 1232, supported by a mounting 1233, allowing the drive 1230 to be coupled to the housing 1210. The drive cooperates with magnetic material 1234 mounted in the rotor 1221, with the magnetic material being in the form of a number of circumferentially spaced permanent drive magnets arranged proximate an outer circumferential edge of the rotor 1221. In one example, the coils 1231 and stators 1232 are wedge shaped and circumferentially spaced around the mounting 1233, so as to provide twelve electromagnets radially aligned with the drive magnets 1234 in the rotor 1221, to thereby maximise a degree of magnetic coupling between the magnets in the rotor 1221 and the drive 1230.

The heart pump 1200 can further include a magnetic bearing 1240 including at least one bearing coil 1241 that controls an axial position of the impeller within the cavity 1215. In one particular example, shown in more detail in FIG. 12E, the magnetic bearing includes three bearing coils 1241, each of which is mounted on a first leg 1242.1 of respective U-shaped stators 1242, with a second leg 1242.2 being positioned radially inwardly of the first leg 1242.1. The stators 1242 are mounted to or integrally formed with a support 1243 and circumferentially spaced 120° apart around the housing so that the first and second legs 1242.1, 1242.2 align with respective magnetic material, such as bearing magnets 1244, 1245 within the impeller 1220, allowing an axial position of the impeller 1220 to be controlled.

In one particular example, the bearing rotor assembly includes ferromagnetic core target 1244 mounted in the rotor, proximate an outer circumferential edge of the rotor 1221, and a permanent bearing magnet or ferromagnetic material 1245 mounted radially inwardly of the first ferromagnetic core target 1244, so that the ferromagnetic core target and bearing magnets 1244, 1245 align with respective legs 1242.1, 1242.2 of the stators 1242. The ferromagnetic core target can be replaced with a second permanent magnet. However, the use of a magnetic bearing may not be required and can be replaced by a static physical bearing or hydrodynamic bearing, or the like.

Figure 12A:
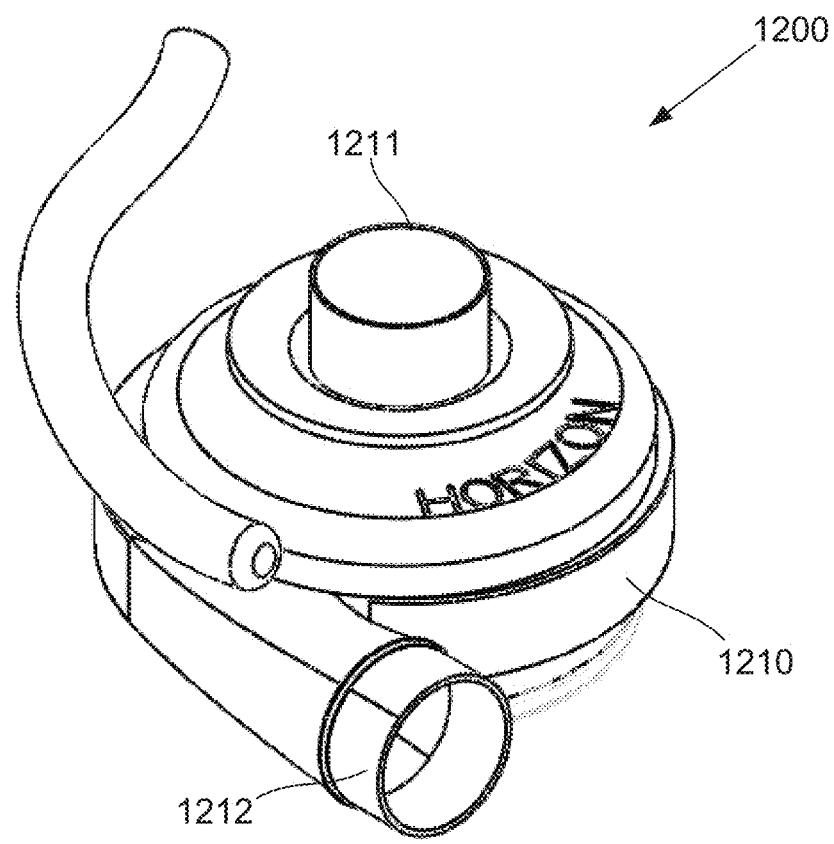
Figure 12B:
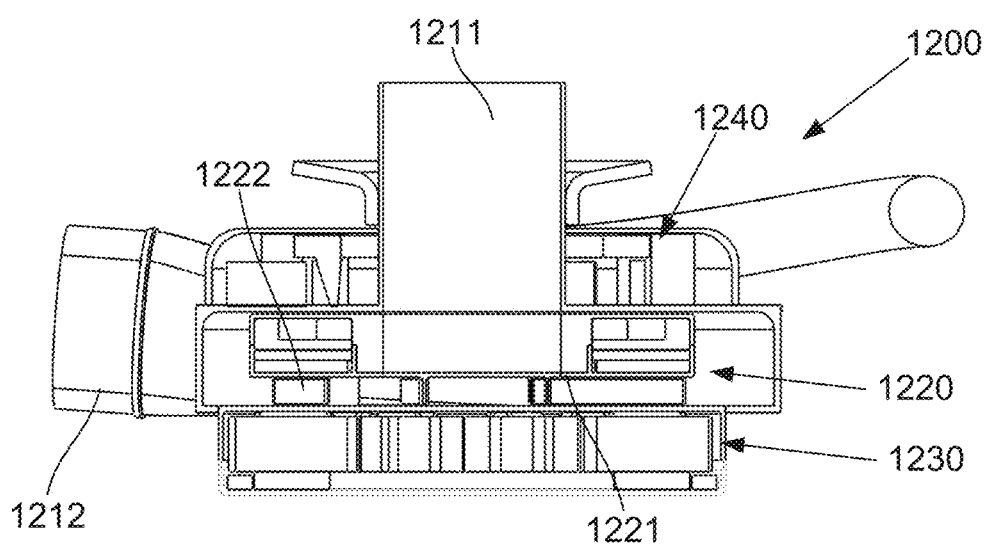
Figure 12C:
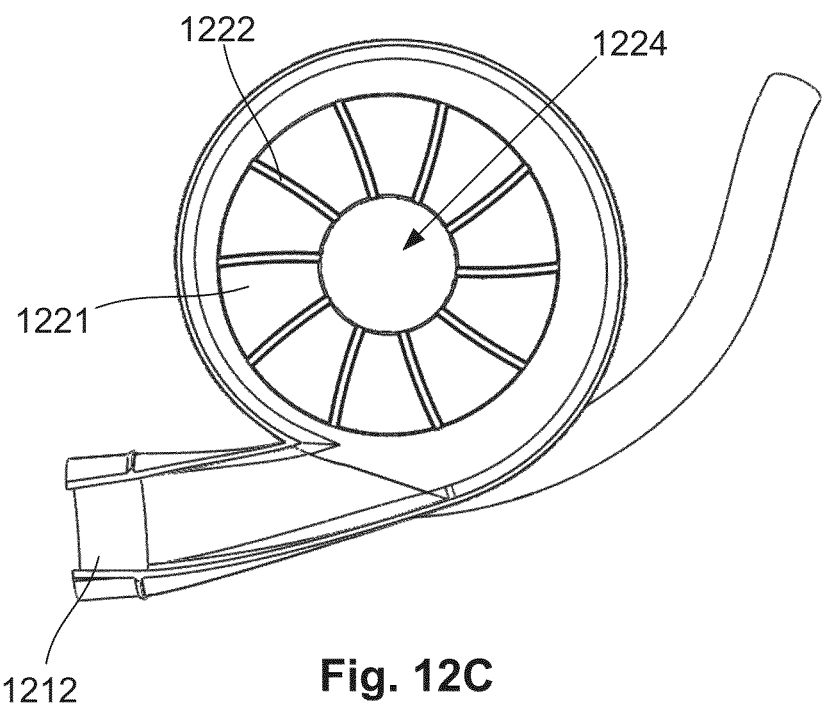
Figure 12D:
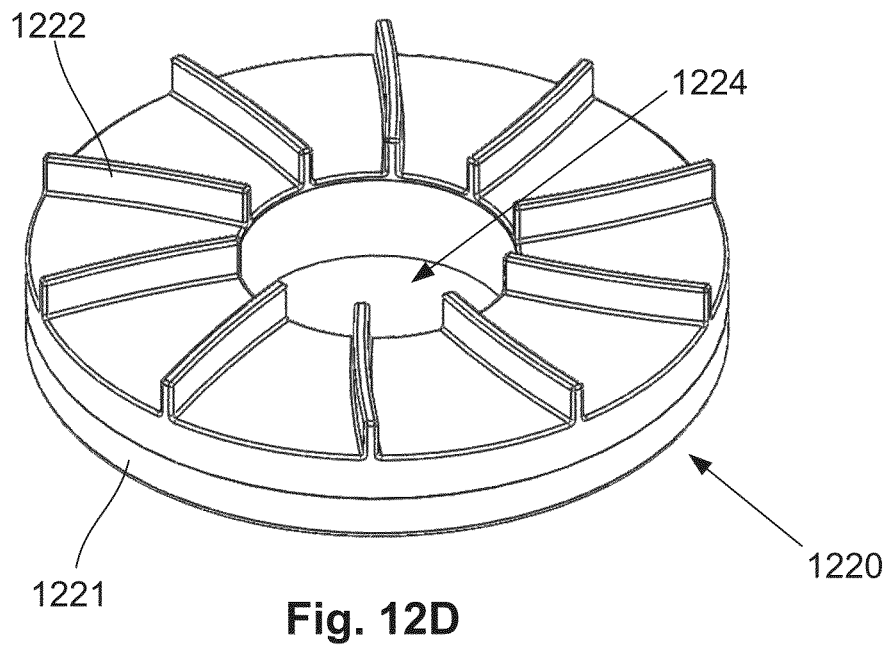
Figure 12E:
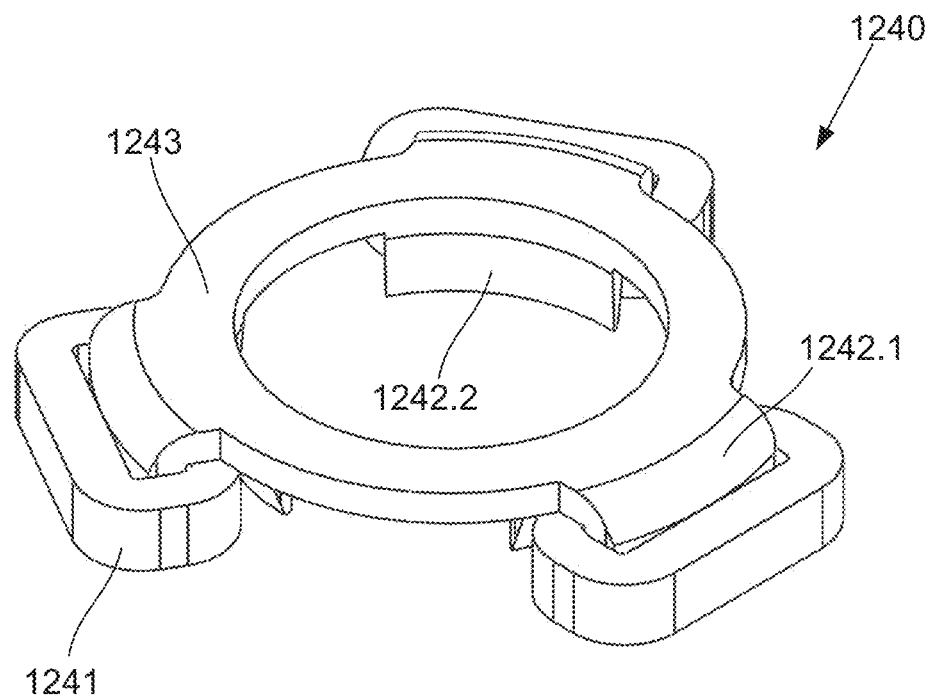
Figure 12F:
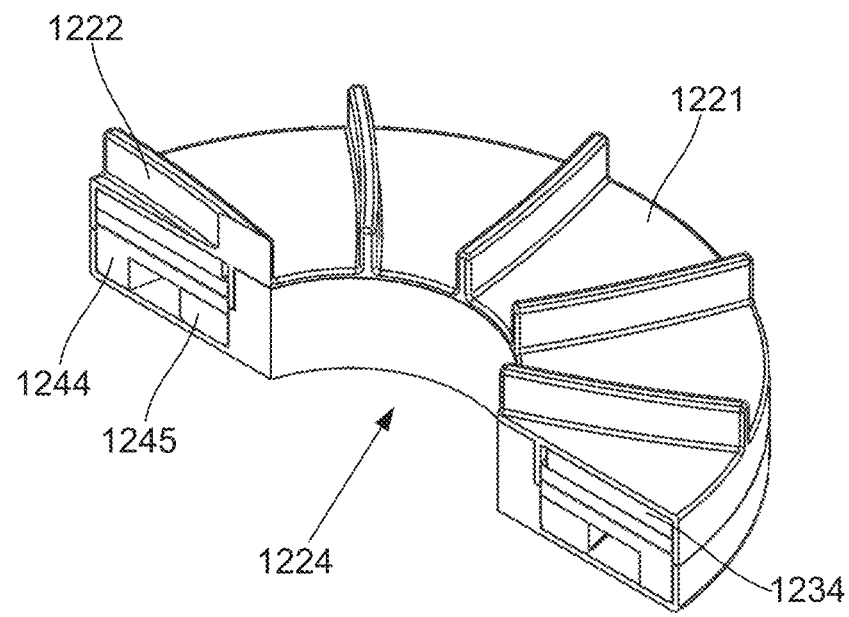

In this example, the drive 1230 and magnetic bearing 1240 are mounted at opposing ends of the housing 1210 so that the drive and bearing 1230, 1240 are provided proximate opposing surfaces of the rotor 1221 as shown for example in FIG. 12B. In the current example the drive 1230 is mounted adjacent the side of the impeller 1220 that includes vanes so as to maximise the blood gap between the rotor, vanes and the casing. That is to say, only the vane tips are in closer proximity to the casing, however this blood gap can still be in the order of 200-300 μm, and up to 500 μm. Additionally, bearing and drive are configured so that the magnetic forces inherent between the drive 1230 and impeller 1220, and between the magnetic bearing 1240 and impeller 1220 and the hydraulic forces on the impeller 1220 define a balance position within the cavity under conditions of normal flow. This minimises the bearing current required to maintain the position of the impeller 1220 within the cavity under nominal flow conditions.

It will be appreciated as in the previous example, the apparatus can further include a controller, and otherwise functions largely as previously described, and hence will not be described in further detail.

Some benefits of these arrangements include:

The ability to maintain passive radial suspension with just an axial magnetic bearing from 0-15 LPM without the need of journal bearing or other radial support bearings is achieved.

An increase in device outflow of up to 40% for a TAH and up to 50-100% for a VAD, with just a 15% reduction in arterial pressure during a transition from rest to exercise without a change in rotational speed.

Improved left impeller design to allow greater axial pressure sensitivity.

Improving the pulse pressure produced during pulsatile operation since smaller rotor RPM changes are required for larger changes in pressure.

Improved biocompatibility by removing the need for a journal bearing by enlarging the radial gap to >2 mm Allowing the native heart to transmit pressure and flow pulsatility (VAD only).

Reduction in diastolic pressure thus allowing the arterioles to rest which may reduce the incidence of aneurysm or GI bleed (VAD only).

The above described arrangement can be employed in wide range of circumstances and in different pump configurations. For example, this can be used when one or two pumps are used to provide assistance or replacement of the left or right ventricles, including in a TAH, when two rotary pumps to provide complete replacement of the native heart, in an LVAD/RVAD, when a single rotary pump is used to provide assistance to either the left or right ventricles, or in a BiVAD, when two rotary pumps to provide assistance to either the left or right ventricles.

The heart pump can be used with a controller and control process that uses an active magnetic bearing in conjunction with a zero power controller that controls the position of the rotor in response to a change of magnetic bearing current, or that uses speed control based on impeller position, for example in response to a perturbation in flow/bearing operation to provide an additional degree of control over flow.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers. As used herein and unless otherwise stated, the term "approximately" means±20%.

Whilst reference is made to absolute values of dimensions in the pump, it will be appreciated that these are for the purpose of illustrating a particular preferred embodiment. However, the pump is largely scalable, meaning that inter-related dimensions could be defined as percentages relative to one another, as long as these meet minimum requirements, such as the minimum flow part cross-sectional area requirements. For example, impeller dimensions for the left and right pumps could be defined relative to one another, so the left hand dimensions are a set percentage of the right hand dimensions. Similarly, the dimensions of the impeller, including the vane and rotor sizes could be defined relative to housing and cavity dimensions.

Persons skilled in the art will appreciate that numerous variations and modifications will become apparent. All such variations and modifications which become apparent to persons skilled in the art, should be considered to fall within the spirit and scope that the invention broadly appearing before described, including equivalents.

What is claimed is:

1. A heart pump including:
 a) a housing forming a cavity including:
  i) at least one inlet aligned with an axis of the cavity; and
  ii) at least one outlet provided in a circumferential outer wall of the cavity;
 b) an impeller provided within the cavity, the impeller including a disc-shaped rotor that rotates about an axis of rotation, the disc-shaped rotor having a face substantially perpendicular to the axis of rotation and having vanes that extend from the face in an axial direction parallel to the axis of rotation and that include a vane height in the axial direction of at least 10 mm and less than 30 mm, and wherein the vanes extend radially from an inner diameter of at least 10 mm so that fluid flowing through the inlet into a region radially inwardly of the vanes is urged radially outwardly to the outlet by the vanes; and
 c) a drive for rotating the impeller in the cavity.

2. A pump according to claim 1, wherein the pump generates a pressure head that is one of:
 a) between 60 mmHg and 100 mmHg at 6 LPM; or
 b) between 10 mmHg and 30 mmHg at 6 LPM.

3. A heart pump according to claim 1, wherein:
 a) the housing includes:
  i) a first cavity portion having a first inlet aligned with an axis of the first cavity portion and a first outlet provided in a circumferential outer wall of the first cavity portion; and
  ii) a second cavity portion having a second inlet aligned with an axis of the second cavity portion and a second outlet provided in a circumferential outer wall of the second cavity portion, the vanes that extend from the face of the rotor being provided within the second cavity portion; and
 b) the impeller includes:
  i) a first set of vanes being provided within the first cavity portion so as to define a first pump, wherein the first set of vanes extend from a first face of the rotor in a first axial direction parallel to the axis of rotation and include at least one of:
(1) a vane height in the first axial direction of at least 1.5 mm and less than 5 mm;
(2) a vane inlet angle of between 60° and 90°; or
(3) a vane outlet angle of less than 90° and greater than 200, and
ii) a second set of vanes being defined by the vanes of the second cavity portion so as to define a second pump, wherein the second set of vanes extend from a second face of the rotor in a second axial direction parallel to the axis of rotation.

4. A heart pump according to claim 3, wherein the pump includes a magnetic bearing including bearing coils and a controller adapted to monitor signals from a position sensor and control a current supplied to the bearing coils to control an axial position of the impeller within the cavity and wherein a change in an axial position of the impeller within the cavity controls in part a flow of fluid from the first inlet to the first outlet, and wherein a change in axial position of 200 µm causes at least one of:
a) a change in flow rate of at least 1 LPM and less than 4 LPM; or
b) a change in flow pressure of at least 5 mmHg.

5. A heart pump according to claim 3, wherein the first outlet at least one of:
a) has a throat area of between 60 mm$^2$ and 250 mm$^2$;
b) has a substantially rectangular cross-sectional shape and a width to height aspect ratio of between 1:2 and 2:1; or
c) defines a cutwater angle of between 0° and 70°.

6. A heart pump according to claim 3, wherein the first set of vanes of the impeller includes a number of primary vanes and a number of secondary vanes, the secondary vanes are smaller than the primary vanes, and at least one of:
a) the primary vanes have at least one of:
i) an inner diameter of at least 10 mm and less than 40 mm; or
ii) an outer thickness of at least 5 mm and less than 20 mm;
b) the secondary vanes have an inner diameter of at least 20 mm and less than 40 mm;
c) the primary and secondary vanes have an outer vane diameter of at least 20 mm and less than 60 mm;
d) there are an equal number of primary and secondary vanes; or
e) there are at least three and less than six of each of the primary and secondary vanes.

7. A heart pump according to claim 3, wherein in a region of an outlet volute of the first outlet the cavity has at least one of:
a) a base circle diameter of at least 40 mm and less than 100 mm; or
b) an outer wall diameter of at least 50 mm and less than 100 mm.

8. A heart pump according to claim 7, wherein over a defined flow range the volute generates a maximum radial force of less than 1.2 N, and wherein the defined flow range is at least 5 LPM to 8 LPM.

9. A heart pump according to claim 1, wherein the pump includes a magnetic bearing including bearing coils and a controller adapted to monitor signals from a position sensor and control a current supplied to the bearing coils to control an axial position of the impeller within the cavity and wherein a change in the axial position of the impeller within the cavity changes a flow of fluid from the inlet to the outlet, and wherein a change in axial position of 200 µm causes at least one of:
a) a change in flow rate of at least 0.2 LPM and less than 2 LPM; or
b) a change in flow pressure of at least 1 mmHg.

10. A heart pump according to claim 1, wherein the outlet at least one of:
a) has a throat area of at least 100 mm$^2$ and less than 250 mm$^2$;
b) has a substantially rectangular cross-sectional shape and a width to height aspect ratio of between 1:3 and 1:1; or
c) defines a cutwater angle that is between 0° and 180°.

11. A heart pump according to claim 1, wherein the impeller has at least one of:
a) a vane inlet angle of greater than 60° and less than 115°; or
b) a vane outlet angle of at least 60° and less than 115°.

12. A heart pump according to claim 1, wherein the impeller includes a number of primary vanes and a number of secondary vanes, the secondary vanes are smaller than the primary vanes, and at least one of:
a) the primary vanes have at least one of:
i) an inner diameter of at least 10 mm and less than 25 mm; or
ii) a thickness of at least 0.5 mm and less than 3.0 mm;
b) the secondary vanes have an inner diameter of at least 10 mm and less than 25 mm;
c) the primary and secondary vanes have an outer vane diameter of at least 15 mm and less than 40 mm;
d) there are an equal number of primary and secondary vanes;
e) there are between three and five primary vanes; or
f) there are between three and six secondary vanes.

13. A heart pump according to claim 1, wherein at least one of:
a) the inlet has a diameter of at least 10 mm and less than 30 mm; or
b) the cavity has a diameter of at least 20 mm and less than 40 mm.

14. A heart pump according to claim 1, wherein the rotor has at least one of:
a) a height in an axial direction of at least 5 mm and less than 15 mm; or
b) an outer circumferential wall spaced from an inner cavity wall by an average distance of at least 2 mm and less than 8 mm.

* * * * *